(12) United States Patent
Jones et al.

(10) Patent No.: US 10,202,391 B2
(45) Date of Patent: *Feb. 12, 2019

(54) CHEMICAL COMPOUNDS

(71) Applicant: AstraZeneca AB, Sodertalje (SE)

(72) Inventors: Clifford David Jones, Cheshire (GB); Richard Andrew Ward, Cambridge (GB); Mark Andrew Graham, Cheshire (GB); Steven Swallow, Cheshire (GB); Andrew Hornby Dobson, Cheshire (GB); James Francis McCabe, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/873,965

(22) Filed: Jan. 18, 2018

(65) Prior Publication Data

US 2018/0237443 A1    Aug. 23, 2018

Related U.S. Application Data

(63) Continuation of application No. 15/345,537, filed on Nov. 8, 2016, now Pat. No. 9,902,731.

(60) Provisional application No. 62/252,726, filed on Nov. 9, 2015, provisional application No. 62/401,351, filed on Sep. 29, 2016.

(51) Int. Cl.
  *C07D 487/04* (2006.01)
  *A61K 45/06* (2006.01)
  *A61K 31/506* (2006.01)
  *C07D 403/04* (2006.01)
  *A61K 31/416* (2006.01)

(52) U.S. Cl.
  CPC .......... *C07D 487/04* (2013.01); *A61K 31/416* (2013.01); *A61K 31/506* (2013.01); *A61K 45/06* (2013.01); *C07D 403/04* (2013.01); *C07B 2200/13* (2013.01)

(58) Field of Classification Search
  CPC .. C07B 2200/13; A61K 45/06; A61K 31/506; C07D 487/04
  See application file for complete search history.

(56) References Cited

U.S. PATENT DOCUMENTS 9,902,731 B2 * 2/2018 Jones .................. A61K 31/416

FOREIGN PATENT DOCUMENTS

| WO | 2007/042784 A2 | 4/2007 |
|---|---|---|
| WO | 2012085038 A1 | 6/2012 |
| WO | 2013/130976 A1 | 9/2013 |
| WO | 2015/032840 A1 | 3/2015 |
| WO | 2015/085007 A1 | 6/2015 |
| WO | 2015/103133 A1 | 7/2015 |
| WO | 2015/103137 A1 | 9/2015 |
| WO | 2015/154674 A1 | 10/2015 |
| WO | 2016/162325 A1 | 10/2016 |
| WO | 2016192063 A1 | 12/2016 |
| WO | 2016192064 A1 | 12/2016 |

OTHER PUBLICATIONS

Jeffrey T. Baganoff et al: "Tetrahydropyrrolo-diazepenones as inhibitors of ERK2 kinase", Bioorganic & Medicinal Chemistry Letters, vol. 25, No. 18, pp. 3788-3792.
Ward et al: "Structure-Guided Design of Highly Selective and Potent Covalent Inhibitors of ERK1/2", Journal of Medicinal Chemistry, 2015, 58(11), 4790-4801.
Yoon et al.: "The extracellular signal-regulated kinase: multiple substrates regulate diverse cellular functions"; Growth Factors 2006, 24, 21-44.
Vakiani E, Solit DB. KRAS and BRAF; drug targets and predictive biomarkers; Journal of Pathology 2011, 223, 219-29.

* cited by examiner

*Primary Examiner* — Alexander P Pagano
*Assistant Examiner* — Ebenezer O Sackey
(74) *Attorney, Agent, or Firm* — Meaghan Lynn Richmond

(57) ABSTRACT

The present disclosure concerns compounds of Formula (I)

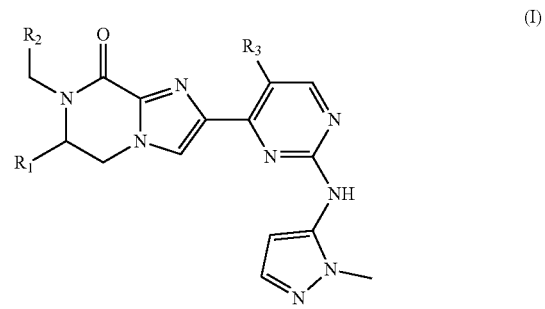

or pharmaceutically-acceptable salts thereof, wherein $R^1$, $R^2$ and $R^3$ have any of the meanings defined hereinbefore in the description; processes for their preparation, pharmaceutical compositions containing them and their use in the treatment of cancer.

3 Claims, 17 Drawing Sheets

CHEMICAL COMPOUNDS

This application is a continuation of U.S. application Ser. No. 15/345,537 filed on 8 Nov. 2016, which claims the benefit under 35 U.S.C. § 119(e) of Application No. 62/252,726 filed on 9 Nov. 2015 and Application No. 62/401,351 filed on 29 Sep. 2016.

The present disclosure relates to certain dihydroimidazopyrazinone derivatives and pharmaceutically-acceptable salts thereof that selectively inhibit ERK and possess anti-cancer activity. The present disclosure also relates to use of said dihydroimidazopyrazinone derivatives and pharmaceutically-acceptable salts thereof in methods of treatment of the human or animal body, for example in prevention or treatment of cancer. The present disclosure also relates to processes and intermediate compounds involved in the preparation of said dihydroimidazopyrazinone derivatives and to pharmaceutical compositions containing said dihydroimidazopyrazinone derivatives and pharmaceutically-acceptable salts thereof.

Protein kinases play a key regulatory role in almost every aspect of cell biology. The mammalian MAP kinases consist of cytoplasmic protein serine/threonine kinases that participate in the transduction of cellular signals from the plasma membrane to the nucleus. There are multiple MAPK signalling cascades each consisting of 3 components: a MAPK kinase (MAP3K), a MAPK kinase (MAP2K) and a MAPK. The activated MAP kinases phosphorylate numerous substrates including other protein kinases, protein phosphatases, transcription factors and other functional proteins. The RAS-RAF-MEK-ERK signalling cascade participates in the regulation of cell cycle progression, cell proliferation, survival, metabolism and transcription.

ERK1 and ERK2 are ubiquitously expressed MAPK kinases that participate in the RAS-RAF-MEK-ERK signalling cascade, which both contain unique N- and C-terminal extensions that provide signalling specificity, in addition to a 31-amino-acid-residue insertion within the kinase domain that provide additional functional specificity. ERK1 and ERK2 are activated in a wide variety of cell types by mitogenic and other stimuli, resulting in activation of multiple isoforms of RAS (HRAS, NRAS and KRAS). Activation of RAS leads to recruitment and activation of RAF isoforms (ARAF, BRAF and CRAF) and subsequent activation of MEK1 and MEK2, dual-specificity protein kinases that mediate the phosphorylation of tyrosine and threonine of ERK1 and ERK2. ERK1 and ERK2 have a large number of identified cytoplasmic and nuclear substrates (reference Yoon S, Seger R. The extracellular signal-regulated kinase: multiple substrates regulate diverse cellular functions; Growth Factors 2006, 24, 21-44).

The RAS-RAF-MEK-ERK signalling cascade is deregulated in a variety of diseases including brain injury, cancer, cardiac hypertrophy, diabetes and inflammation. Specifically in cancer, mutations in KRAS occur in approximately 58% of pancreatic, 33% of colorectal and 31% of biliary cancers, and NRAS mutations in 18% of melanomas. Oncogenic mutations in RAS result in elevated ERK activity across multiple tumours. In addition, BRAF mutations occur in approximately 40-60% of melanomas, 40% of thyroid cancers and 20% of colorectal cancers (reference Vakiani E, Solit D B. KRAS and BRAF; drug targets and predictive biomarkers; Journal of Pathology 2011, 223, 219-29). These observations indicate that the RAS-RAF-MEK-ERK signalling cascade is an attractive pathway for anti-cancer therapies across a broad range of human tumours.

We have found a series of chemical compounds which have selectivity for inhibition of ERK over other kinases on the same signalling cascade.

Where inhibition of ERK is referred to herein, it should be understood to mean inhibition of ERK1 and/or ERK2, particularly ERK2.

According to one aspect there is provided a compound of the Formula (I):

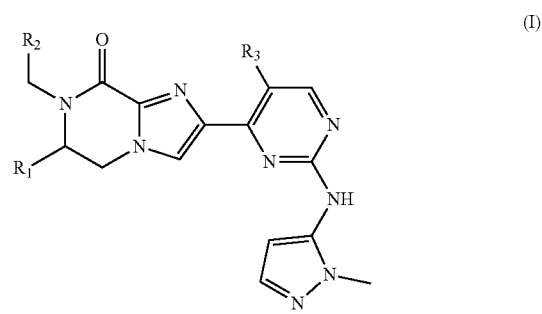

wherein:
$R^1$ is hydrogen, $C_{1-3}$ alkyl or —$CH_2OMe$;
$R^2$ is pyridinyl, optionally substituted on 1 ring carbon atom by a substituent independently selected from the group consisting of $C_{1-3}$ alkyl, difluoromethyl and trifluoromethyl; or
$R^2$ is pyrimidinyl, optionally substituted on 1 ring carbon atom by a substituent independently selected from the group consisting of $C_{1-3}$ alkyl, difluoromethyl and trifluoromethyl; or
$R^2$ is phenyl optionally substituted on 1 or 2 ring carbon atoms by a substituent independently selected from the group consisting of halo, difluoromethyl, trifluoromethyl, methoxy and —$OCHF_2$; and
$R^3$ is hydrogen, $C_{1-3}$ alkyl or chloro;
or a pharmaceutically-acceptable salt thereof.

In one embodiment there is provided a compound of Formula (I) as defined above.

In one embodiment there is provided a pharmaceutically-acceptable salt of a compound of Formula (I).

The term "optionally substituted" will be understood to mean "substituted or unsubstituted".

As used herein the term "alkyl" refers to both straight and branched chain saturated hydrocarbon radicals having the specified number of carbon atoms. References to individual alkyl groups such as "propyl" are specific for the straight chain version only and references to individual branched chain alkyl groups such as 'isopropyl' are specific for the branched chain version only.

Examples of $C_{1-3}$alkyl are methyl, ethyl, propyl and isopropyl.

Examples of $C_{1-4}$ alkyl include methyl, ethyl, propyl, isopropyl, butyl and tert-butyl.

The terms "halogen" or "halo," as used herein, refers to fluoro, chloro, bromo and iodo. In certain embodiments, the term "halo" may refer to fluoro, chloro, and bromo. In certain embodiments, the term "halo" may refer to fluoro and chloro. In certain embodiments, the term "halo" may refer to fluoro. In certain embodiments, the term "halo" may refer to chloro. In certain embodiments, the term "halo" may refer to bromo.

In one aspect $R^1$ is hydrogen, methyl or —$CH_2OMe$.
In one aspect $R^1$ is methyl or —$CH_2OMe$.
In one aspect, $R^1$ is hydrogen.

In one aspect, $R^1$ is methyl.

In one aspect, $R^1$ is —CH$_2$OMe.

In one aspect, $R^2$ is pyridinyl, optionally substituted on 1 ring carbon atom by a substituent independently selected from the group consisting of methyl, difluoromethyl and trifluoromethyl; or $R^2$ is pyrimidinyl, optionally substituted on 1 ring carbon atom by a substituent independently selected from the group consisting of methyl, difluoromethyl and trifluoromethyl; or $R^2$ is phenyl optionally substituted on 1 or 2 ring carbon atoms by a substituent independently selected from the group consisting of fluoro, chloro, difluoromethyl, trifluoromethyl, methoxy and —OCHF$_2$.

In one aspect, $R^2$ is pyridinyl, optionally substituted on 1 ring carbon atom by a substituent independently selected from the group consisting of methyl, difluoromethyl and trifluoromethyl; or $R^2$ is pyrimidinyl, optionally substituted on 1 ring carbon atom by trifluoromethyl; or $R^2$ is phenyl optionally substituted on 1 or 2 ring carbon atoms by a substituent independently selected from the group consisting of fluoro, chloro, difluoromethyl, trifluoromethyl, methoxy and —OCHF$_2$.

In one aspect, $R^2$ is pyridinyl, optionally substituted on 1 ring carbon atom by a substituent independently selected from the group consisting of methyl, difluoromethyl and trifluoromethyl; or $R^2$ is pyrimidinyl, optionally substituted on 1 ring carbon atom by trifluoromethyl; or $R^2$ is phenyl optionally substituted on 1 ring carbon atom by a substituent independently selected from the group consisting fluoro, chloro, difluoromethyl, trifluoromethyl, methoxy and —OCHF$_2$.

In one aspect, $R^2$ is pyridinyl, optionally substituted on 1 ring carbon atom by a substituent independently selected from the group consisting of methyl, difluoromethyl and trifluoromethyl; or $R^2$ is pyrimidinyl, optionally substituted on 1 ring carbon atom by trifluoromethyl; or $R^2$ is phenyl optionally substituted on 2 ring carbon atoms by a substituent independently selected from the group consisting of fluoro, chloro, difluoromethyl, trifluoromethyl, methoxy and —OCHF$_2$.

In one aspect, $R^2$ is pyridinyl, optionally substituted on 1 ring carbon atom by a substituent independently selected from the group consisting of methyl, difluoromethyl and trifluoromethyl; or $R^2$ is pyrimidinyl, optionally substituted on 1 ring carbon atom by trifluoromethyl; or $R^2$ is phenyl optionally substituted on 1 or 2 ring carbon atoms by a substituent independently selected from the group consisting of fluoro, chloro, difluoromethyl, methoxy and —OCHF$_2$.

In one aspect, $R^2$ is pyridinyl, optionally substituted on 1 ring carbon atom by difluoromethyl; or $R^2$ is phenyl optionally substituted on 1 or 2 ring carbon atoms by a substituent independently selected from the group consisting of fluoro and chloro.

In one aspect, $R^2$ is pyridinyl, optionally substituted on 1 ring carbon atom by a substituent independently selected from the group consisting of methyl, difluoromethyl and trifluoromethyl.

In one aspect, $R^2$ is pyridinyl, optionally substituted on 1 ring carbon atom by a methyl.

In one aspect, $R^2$ is pyridinyl, optionally substituted on 1 ring carbon atom by difluoromethyl.

In one aspect, $R^2$ is pyridinyl, optionally substituted on 1 ring carbon atom by trifluoromethyl.

In one aspect, $R^2$ is pyrimidinyl, optionally substituted on 1 ring carbon atom by a substituent independently selected from the group consisting of methyl, difluoromethyl or trifluoromethyl.

In one aspect, $R^2$ is pyrimidinyl, optionally substituted on 1 ring carbon atom by methyl.

In one aspect, $R^2$ is pyrimidinyl, optionally substituted on 1 ring carbon atom by difluoromethyl.

In one aspect, $R^2$ is pyrimidinyl, optionally substituted on 1 ring carbon atom by trifluoromethyl.

In one aspect, $R^2$ is phenyl optionally substituted on 1 or 2 ring carbon atoms by a substituent independently selected from the group consisting of fluoro, chloro, difluoromethyl, trifluoromethyl, methoxy and —OCHF$_2$.

In one aspect, $R^2$ is phenyl optionally substituted on 1 or 2 ring carbon atoms by a substituent independently selected from the group consisting of fluoro, chloro, difluoromethyl, methoxy and —OCHF$_2$.

In one aspect, $R^2$ is phenyl optionally substituted on 1 or 2 ring carbon atoms by a substituent independently selected from fluoro, chloro or methoxy.

In one aspect, $R^2$ is phenyl optionally substituted on 2 ring carbon atoms by a substituent independently selected from the group consisting of fluoro, chloro and methoxy.

In one aspect, $R^2$ is phenyl optionally substituted on 1 or 2 ring carbon atoms by a substituent independently selected from the group consisting fluoro, chloro and methoxy.

In one aspect, $R^2$ is phenyl optionally substituted on 1 or 2 ring carbon atoms by a substituent independently selected from the group consisting fluoro and chloro.

In one aspect, $R^2$ is phenyl optionally substituted on 1 ring carbon atom by a substituent independently selected from the group consisting of fluoro and chloro.

In one aspect, $R^2$ is phenyl optionally substituted on 2 ring carbon atoms by a substituent independently selected from the group consisting of fluoro and chloro.

In one aspect, $R^2$ is phenyl optionally substituted on 1 or 2 ring carbon atoms by a substituent independently selected from the group consisting fluoro and methoxy.

In one aspect, $R^2$ is phenyl optionally substituted on 2 ring carbon atoms by a substituent independently selected from the group consisting of fluoro and methoxy.

In one aspect, $R^2$ is phenyl optionally substituted on 1 or 2 ring carbon atoms by fluoro.

In one aspect, $R^2$ is phenyl optionally substituted on 1 or 2 ring carbon atoms by chloro.

In one aspect, $R^2$ is phenyl optionally substituted on 1 or 2 ring carbon atoms by difluoromethyl.

In one aspect, $R^2$ is phenyl optionally substituted on 1 or 2 ring carbon atoms by trifluoromethyl.

In one aspect, $R^2$ is phenyl optionally substituted on 1 or 2 ring carbon atoms by methoxy.

In one aspect, $R^2$ is phenyl optionally substituted on 1 or 2 ring carbon atoms by —OCHF$_2$.

In one aspect, $R^2$ is phenyl optionally substituted on 2 ring carbon atoms by fluoro.

In one aspect, $R^2$ is phenyl optionally substituted on 1 ring carbon atom by chloro.

In one aspect, $R^2$ is 6-methylpyridin-2-yl, 4-(difluoromethyl)pyridin-2-yl, 6-(difluoromethyl)pyridin-2-yl, 4-(trifluoromethyl)pyridin-2-yl, 6-(trifluoromethyl)pyridin-2-yl, 2-(trifluoromethyl)pyridin-4-yl, 2-(trifluoromethyl)pyrimidin-4-yl, 6-(trifluoromethyl)pyrimidin-4-yl, 3-chlorophenyl, 3,4-difluorophenyl, 3,5-difluorophenyl, 3-chloro-4-fluorophenyl, 3-(difluoromethoxy)phenyl, 3-(difluoromethyl)phenyl, 3-methoxyphenyl or 4-fluoro-3-methoxyphenyl.

In one aspect, $R^2$ is 6-(difluoromethyl)pyridin-2-yl, 3-chlorophenyl, 3,4-difluorophenyl or 3,5-difluorophenyl.

In one aspect, $R^2$ is 6-methylpyridin-2-yl.
In one aspect, $R^2$ is 4-(difluoromethyl)pyridin-2-yl.
In one aspect, $R^2$ is 6-(difluoromethyl)pyridin-2-yl.
In one aspect, $R^2$ is 4-(trifluoromethyl)pyridin-2-yl.
In one aspect, $R^2$ is 6-(trifluoromethyl)pyridin-2-yl.
In one aspect, $R^2$ is 2-(trifluoromethyl)pyridin-4-yl.
In one aspect, $R^2$ is 2-(trifluoromethyl)pyrimidin-4-yl.
In one aspect, $R^2$ is 6-(trifluoromethyl)pyrimidin-4-yl.
In one aspect, $R^2$ is 3-chlorophenyl.
In one aspect, $R^2$ is 3,4-difluorophenyl.
In one aspect, $R^2$ is 3,5-difluorophenyl.
In one aspect, $R^2$ is 3-chloro-4-fluorophenyl.
In one aspect, $R^2$ is 3-(difluoromethoxy)phenyl.
In one aspect, $R^2$ is 3-(difluoromethyl)phenyl.
In one aspect, $R^2$ is 3-methoxyphenyl.
In one aspect, $R^2$ is 4-fluoro-3-methoxyphenyl.
In one aspect, $R^3$ is hydrogen, methyl or chloro.
In one aspect, $R^3$ is hydrogen or methyl.
In one aspect, $R^3$ is hydrogen.
In one aspect, $R^3$ is methyl.
In one aspect, $R^3$ is chloro.

In a further aspect, there is provided a compound of formula (I) or a pharmaceutically-acceptable salt thereof, wherein:
$R^1$ is hydrogen, methyl or —CH$_2$OMe;
$R^2$ is pyridinyl, optionally substituted on 1 ring carbon atom by a substituent independently selected from the group consisting of methyl, difluoromethyl and trifluoromethyl; or
$R^2$ is pyrimidinyl, optionally substituted on 1 ring carbon atom by a substituent independently selected from the group consisting of methyl, difluoromethyl and trifluoromethyl; or
$R^2$ is phenyl optionally substituted on 1 or 2 ring carbon atoms by a substituent independently selected from the group consisting fluoro, chloro, difluoromethyl, trifluoromethyl, methoxy and —OCHF$_2$; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is pyridinyl, optionally substituted on 1 ring carbon atom by a substituent independently selected from the group consisting of methyl, difluoromethyl and trifluoromethyl; or
$R^2$ is pyrimidinyl, optionally substituted on 1 ring carbon atom by trifluoromethyl; or
$R^2$ is phenyl optionally substituted on 1 or 2 ring carbon atoms by a substituent independently selected from the group consisting of fluoro, chloro, difluoromethyl, trifluoromethyl, methoxy and —OCHF$_2$; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is pyridinyl, optionally substituted on 1 ring carbon atom by a substituent independently selected from the group consisting of methyl, difluoromethyl and trifluoromethyl; or
$R^2$ is pyrimidinyl, optionally substituted on 1 ring carbon atom by trifluoromethyl; or $R^2$ is phenyl optionally substituted on 1 carbon atom by a substituent independently selected from the group consisting of fluoro, chloro, difluoromethyl, trifluoromethyl, methoxy and —OCHF$_2$; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is pyridinyl, optionally substituted on 1 ring carbon atom by a substituent independently selected from the group consisting of methyl, difluoromethyl and trifluoromethyl; or
$R^2$ is pyrimidinyl, optionally substituted on 1 ring carbon atom by trifluoromethyl; or
$R^2$ is phenyl optionally substituted on 2 ring carbon atoms by a substituent independently selected from the group consisting of fluoro, chloro, difluoromethyl, trifluoromethyl, methoxy and —OCHF$_2$; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is pyridinyl, optionally substituted on 1 ring carbon atom by a substituent independently selected from the group consisting of methyl, difluoromethyl and trifluoromethyl; or
$R^2$ is pyrimidinyl, optionally substituted on 1 ring carbon atom by trifluoromethyl; or
$R^2$ is phenyl optionally substituted on 1 or 2 ring carbon atoms by a substituent independently selected from the group consisting of fluoro, chloro, difluoromethyl, methoxy and —OCHF$_2$; and
$R^3$ is hydrogen, methyl or chloro.

In a further aspect, there is provided a compound of formula (I) or a pharmaceutically-acceptable salt thereof, wherein:
$R^1$ is methyl or —CH$_2$OMe;
$R^2$ is pyridinyl, optionally substituted on 1 ring carbon atom by difluoromethyl; or
$R^2$ is phenyl optionally substituted on 1 or 2 ring carbon atoms by a substituent independently selected from the group consisting of fluoro and chloro; and
$R^3$ is hydrogen or methyl.

In a further aspect, there is provided a compound of formula (I) or a pharmaceutically-acceptable salt thereof, wherein:
$R^1$ is hydrogen, methyl or —CH$_2$OMe;
$R^2$ is pyridinyl, optionally substituted on 1 ring carbon atom by a substituent independently selected from the group consisting of methyl, difluoromethyl and trifluoromethyl; and
$R^3$ is hydrogen, methyl or chloro.

In a further aspect, there is provided a compound of formula (I) or a pharmaceutically-acceptable salt thereof, wherein:
$R^1$ is hydrogen, methyl or –CH$_2$OMe;
$R^2$ is pyridinyl, optionally substituted on 1 ring carbon atom by methyl; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is pyridinyl, optionally substituted on 1 ring carbon atom by difluoromethyl; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is pyridinyl, optionally substituted on 1 ring carbon atom by trifluoromethyl; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is pyrimidinyl, optionally substituted on 1 ring carbon atom by trifluoromethyl; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is phenyl optionally substituted on 1 or 2 ring carbon atoms by a substituent independently selected from the group consisting of fluoro, chloro, difluoromethyl, trifluoromethyl, methoxy and —OCHF$_2$; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is phenyl optionally substituted on 1 or 2 ring carbon atoms by a substituent independently selected from the group consisting of fluoro, chloro, difluoromethyl, trifluoromethyl, methoxy and —OCHF$_2$; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is phenyl optionally substituted on 1 or 2 ring carbon atoms by a substituent independently selected from the group consisting of fluoro, chloro, difluoromethyl and methoxy; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is phenyl optionally substituted on 1 or 2 ring carbon atoms by a substituent independently selected from the group consisting of fluoro, chloro and methoxy; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is phenyl optionally substituted on 2 ring carbon atoms by a substituent independently selected from the group consisting of fluoro, chloro and methoxy; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is phenyl optionally substituted on 1 or 2 ring carbon atoms by a substituent independently selected from the group consisting of fluoro and chloro; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is phenyl optionally substituted on 1 or 2 ring carbon atoms by a substituent independently selected from the group consisting of fluoro and methoxy; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is phenyl optionally substituted on 2 ring carbon atoms by a substituent independently selected from the group consisting of fluoro and chloro; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is phenyl optionally substituted on 2 ring carbon atoms by a substituent independently selected from the group consisting of fluoro and methoxy; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is 6-methylpyridin-2-yl, 4-(difluoromethyl)pyridin-2-yl, 6-(difluoromethyl)pyridin-2-yl, 4-(trifluoromethyl)pyridin-2-yl, 6-(trifluoromethyl)pyridin-2-yl, 2-(trifluoromethyl)pyridin-4-yl, 2-(trifluoromethyl)pyrimidin-4-yl, 6-(trifluoromethyl)pyrimidin-4-yl, 3-chlorophenyl, 3,4-difluorophenyl, 3,5-difluorophenyl, 3-chloro-4-fluorophenyl, 3-(difluoromethoxy)phenyl, 3-(difluoromethyl)phenyl, 3-methoxyphenyl or 4-fluoro-3-methoxyphenyl; and $R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is 6-(difluoromethyl)pyridin-2-yl, 3-chlorophenyl, 3,4-difluorophenyl or 3,5-difluorophenyl; and
$R^3$ is hydrogen, methyl or chloro.

In a further aspect, there is provided a compound of formula (I) or a pharmaceutically-acceptable salt thereof, wherein:
$R^1$ is methyl or —CH$_2$OMe;
$R^2$ is 6-(difluoromethyl)pyridin-2-yl, 3-chlorophenyl, 3,4-difluorophenyl or 3,5-difluorophenyl; and
$R^3$ is hydrogen or methyl.

In a further aspect, there is provided a compound of formula (I) or a pharmaceutically-acceptable salt thereof, wherein:
$R^1$ is hydrogen, methyl or —CH$_2$OMe;
$R^2$ is 6-(difluoromethyl)pyridin-2-yl; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is 3-chlorophenyl; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is 3,4-difluorophenyl; and
$R^3$ is hydrogen, methyl or chloro.

In a further aspect, there is provided a compound of formula (I) or a pharmaceutically-acceptable salt thereof, wherein:
$R^1$ is hydrogen, methyl or —CH$_2$OMe;
$R^2$ is 3,5-difluorophenyl; and
$R^3$ is hydrogen, methyl or chloro.

In a further aspect, there is provided a compound of formula (I) or a pharmaceutically-acceptable salt thereof, wherein:
$R^1$ is methyl or —CH$_2$OMe;
$R^2$ is 6-(difluoromethyl)pyridin-2-yl; and
$R^3$ is hydrogen or methyl.

In a further aspect, there is provided a compound of formula (I) or a pharmaceutically-acceptable salt thereof, wherein:
$R^1$ is methyl or —CH$_2$OMe;
$R^2$ is 3-chlorophenyl; and
$R^3$ is hydrogen or methyl.

In a further aspect, there is provided a compound of formula (I) or a pharmaceutically-acceptable salt thereof, wherein:
$R^1$ is methyl or —CH$_2$OMe;
$R^2$ is 3,4-difluorophenyl; and
$R^3$ is hydrogen or methyl.

In a further aspect, there is provided a compound of formula (I) or a pharmaceutically-acceptable salt thereof, wherein:
$R^1$ is methyl or —CH$_2$OMe;
$R^2$ is 3,5-difluorophenyl; and
$R^3$ is hydrogen or methyl.

In a further aspect, there is provided any one or more of the specific examples or a pharmaceutically-acceptable salt thereof. In a further aspect, there is provided the specific examples described herein or a pharmaceutically-acceptable salt thereof, wherein any one or more of the examples is excluded. In a further aspect, there is provided a compound selected from:

2-(2-((1-methyl-1H-pyrazol-5-yl)amino)pyrimidin-4-yl)-7-((6-methylpyridin-2-yl)methyl)-6,7-dihydroimidazo[1,2-a]pyrazin-8(5H)-one;

(S)-7-(3-chlorobenzyl)-6-methyl-2-(2-((1-methyl-1H-pyrazol-5-yl)amino)pyrimidin-4-yl)-6,7-dihydroimidazo[1,2-a]pyrazin-8(5H)-one;

(S)-7-(3-chloro-4-fluorobenzyl)-6-methyl-2-(2-((1-methyl-1H-pyrazol-5-yl)amino)pyrimidin-4-yl)-6,7-dihydroimidazo[1,2-a]pyrazin-8(5H)-one;

(S)-7-(3,4-difluorobenzyl)-6-methyl-2-(2-((1-methyl-1H-pyrazol-5-yl)amino)pyrimidin-4-yl)-6,7-dihydroimidazo[1,2-a]pyrazin-8(5H)-one;

2-(5-Methyl-2-((1-methyl-1H-pyrazol-5-yl)amino)pyrimidin-4-yl)-7-((6-(trifluoromethyl)pyridin-2-yl)methyl)pyridin-2-yl)methyl)-6,7-dihydroimidazo[1,2-a]pyrazin-8(5H)-one;

(S)-2-(5-chloro-2-((1-methyl-1H-pyrazol-5-yl)amino)pyrimidin-4-yl)-7-(3,4-difluorobenzyl)-6-methyl-6,7-dihydroimidazo[1,2-a]pyrazin-8(5H)-one;

(S)-2-(5-chloro-2-((1-methyl-1H-pyrazol-5-yl)amino)pyrimidin-4-yl)-7-(3-methoxybenzyl)-6-methyl-6,7-dihydroimidazo[1,2-a]pyrazin-8(5H)-one;

(S)-2-(5-chloro-2-((1-methyl-1H-pyrazol-5-yl)amino)pyrimidin-4-yl)-6-methyl-7-((2-(trifluoromethyl)pyrimidin-4-yl)methyl)-6,7-dihydroimidazo[1,2-a]pyrazin-8(5H)-one;

(S)-2-(5-chloro-2-((1-methyl-1H-pyrazol-5-yl)amino)pyrimidin-4-yl)-7-((6-(difluoromethyl)pyridin-2-yl)methyl)-6-methyl-6,7-dihydroimidazo[1,2-a]pyrazin-8(5H)-one;

(S)-2-(5-chloro-2-((1-methyl-1H-pyrazol-5-yl)amino)pyrimidin-4-yl)-6-methyl-7-((6-(trifluoromethyl)pyridin-2-yl)methyl)-6,7-dihydroimidazo[1,2-a]pyrazin-8(5H)-one;

(S)-2-(5-chloro-2-((1-methyl-1H-pyrazol-5-yl)amino)pyrimidin-4-yl)-6-methyl-7-((6-methylpyridin-2-yl)methyl)-6,7-dihydroimidazo[1,2-a]pyrazin-8(5H)-one;

7-(3-chloro-4-fluorobenzyl)-2-(5-methyl-2-((1-methyl-1H-pyrazol-5-yl)amino)pyrimidin-4-yl)-6,7-dihydroimidazo[1,2-a]pyrazin-8(5H)-one;

7-(3-chlorobenzyl)-2-(5-methyl-2-((1-methyl-1H-pyrazol-5-yl)amino)pyrimidin-4-yl)-6,7-dihydroimidazo[1,2-a]pyrazin-8(5H)-one;

7-(3-(difluoromethyl)benzyl)-2-(5-methyl-2-((1-methyl-1H-pyrazol-5-yl)amino)pyrimidin-4-yl)-6,7-dihydroimidazo[1,2-a]pyrazin-8(5H)-one;

7-((6-(difluoromethyl)pyridin-2-yl)methyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-7-((6-(difluoromethyl)pyridin-2-yl)methyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-7-(3-chlorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3-chlorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3,4-difluorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3-(difluoromethyl)benzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3,5-difluorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3-methoxybenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(4-fluoro-3-methoxybenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-((6-(difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-6-methyl-2-(5-methyl-2-((1-methyl-1H-pyrazol-5-yl)amino)pyrimidin-4-yl)-7-((2-(trifluoromethyl)pyrimidin-4-yl)methyl)-6,7-dihydroimidazo[1,2-a]pyrazin-8(5H)-one;

(S)-6-methyl-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one;

(S)-7-(3-(difluoromethoxy)benzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

is (S)-6-methyl-2-(5-methyl-2-((1-methyl-1H-pyrazol-5-yl)amino)pyrimidin-4-yl)-7-((4-(trifluoromethyl)pyridin-2-yl)methyl)-6,7-dihydroimidazo[1,2-a]pyrazin-8(5H)-one;

(S)-6-methyl-2-(5-methyl-2-((1-methyl-1H-pyrazol-5-yl)amino)pyrimidin-4-yl)-7-((2-(trifluoromethyl)pyridin-4-yl)methyl)-6,7-dihydroimidazo[1,2-a]pyrazin-8(5H)-one;

(S)-7-((4-(difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-6-methyl-2-(5-methyl-2-((1-methyl-1H-pyrazol-5-yl)amino)pyrimidin-4-yl)-7-((6-(trifluoromethyl)pyrimidin-4-yl)methyl)-6,7-dihydroimidazo[1,2-a]pyrazin-8(5H)-one;

7-(3,4-Difluorobenzyl)-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-6-Methyl-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one;

(R)-7-((6-(Difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(R)-7-(3-(difluoromethyl)benzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-6-(Methoxymethyl)-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one;

(R)-7-(3,5-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one; and (R)-7-(3-Methoxybenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

or a pharmaceutically-acceptable salt thereof.

In a further aspect, there is provided a compound selected from:

(R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct; and (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct.

In a further aspect, there is provided a compound selected from:

(S)-7-(3-chlorobenzyl)-6-methyl-2-(2-((1-methyl-1H-pyrazol-5-yl)amino)pyrimidin-4-yl)-6,7-dihydroimidazo[1,2-a]pyrazin-8(5H)-one;

(R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3,5-difluorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one; and (S)-7-((6-(difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

or a pharmaceutically-acceptable salt thereof.

In a further aspect, there is provided (S)-7-(3-chlorobenzyl)-6-methyl-2-(2-((1-methyl-1H-pyrazol-5-yl)amino)pyrimidin-4-yl)-6,7-dihydroimidazo[1,2-a]pyrazin-8(5H)-one; or a pharmaceutically-acceptable salt thereof.

In a further aspect, there is provided (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one; or a pharmaceutically-acceptable salt thereof.

In a further aspect, there is provided (S)-7-(3,5-difluorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one or a pharmaceutically-acceptable salt thereof.

In a further aspect, there is provided (S)-7-((6-(difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one; or a pharmaceutically-acceptable salt thereof.

In a further aspect there is provided the compound of Example 18 or a pharmaceutically-acceptable adduct thereof.

Some compounds of Formula (I) have a chiral centre and it will be recognised that such compound of Formula (I) may be prepared, isolated and/or supplied with or without the presence, in addition, of one or more of the other 2 possible enantiomeric isomers of the compound of Formula (I) in any relative proportions. The preparation of enantioenriched/enantiopure compounds may be carried out by standard techniques of organic chemistry that are well known in the art, for example by synthesis from enantioenriched or enantiopure starting materials, use of an appropriate enantioenriched or enantiopure catalyst during synthesis, and/or by resolution of a racemic or partially enriched mixture of stereoisomers, for example via chiral chromatography.

For use in a pharmaceutical context it may be preferable to provide the compound of Formula (I) or pharmaceutically-acceptable salt thereof without large amounts of the other stereoisomeric forms being present.

Accordingly, in one embodiment there is provided a composition comprising a compound of Formula (I) or a pharmaceutically-acceptable salt thereof, optionally together with one or more of the other stereoisomeric forms of the compound of Formula (I) or pharmaceutically-acceptable salt thereof, wherein the compound of Formula (I) or pharmaceutically-acceptable salt thereof is present within the composition with an enantiomeric excess (% ee) of ≥90%.

In a further embodiment the % ee in the above-mentioned composition is ≥95%.

In a further embodiment the % ee in the above-mentioned composition is ≥98%.

In a further embodiment the % ee in the above-mentioned composition is ≥99%.

In a further embodiment there is provided a pharmaceutical composition which comprises a compound of the Formula (I) or a pharmaceutically-acceptable salt thereof, in association with a pharmaceutically-acceptable diluent or carrier.

In one embodiment there is provided a pharmaceutical composition which comprises a compound of the Formula (I) or a pharmaceutically-acceptable salt thereof, in association with a pharmaceutically-acceptable diluent or carrier, optionally further comprising one or more of the other stereoisomeric forms of the compound of Formula (I) or pharmaceutically-acceptable salt thereof, wherein the compound of Formula (I) or pharmaceutically-acceptable salt thereof is present within the composition with an enantiomeric excess (% ee) of ≥90%.

In a further embodiment the % ee in the above-mentioned composition is ≥95%.

In a further embodiment the % ee in the above-mentioned composition is ≥98%.

In a further embodiment the % ee in the above-mentioned composition is ≥99%.

The compounds of Formula (I) and pharmaceutically-acceptable salts thereof may prepared, used or supplied in amorphous form, crystalline form, or semicrystalline form and any given compound of Formula (I) or pharmaceutically-acceptable salt thereof may be capable of being formed into more than one crystalline/polymorphic form, including hydrated (e.g. hemi-hydrate, a mono-hydrate, a di-hydrate, a tri-hydrate or other stoichiometry of hydrate) and/or solvated forms. It is to be understood that the present disclosure encompasses any and all such solid forms of the compound of Formula (I) and pharmaceutically-acceptable salts thereof.

In further embodiments there is provided a compound of Formula (I), which is obtainable by the methods described in the 'Examples' section hereinafter.

The present disclosure is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$.

A suitable pharmaceutically-acceptable salt of a compound of the Formula (I) is, for example, an acid addition salt.

A further suitable pharmaceutically-acceptable salt of a compound of the Formula (I) is, for example, a salt formed within the human or animal body after administration of a compound of the Formula (I) to said human or animal body.

A suitable pharmaceutically-acceptable salt of a compound of the Formula (I) may also be, for example, an acid-addition salt of a compound of the Formula (I), for example an acid-addition salt with a inorganic or organic acid such as hydrochloric acid, hydrobromic acid, sulphuric acid or trifluoroacetic acid. Pharmaceutically-acceptable salts of a compound of the Formula (I) may also be an acid-addition salt with an acid such as one of the following: acetic acid, adipic acid, benzene sulfonic acid, benzoic acid, cinnamic acid, citric acid, D,L-lactic acid, ethane disulfonic acid, ethane sulfonic acid, fumaric acid, L-tartaric acid, maleic acid, malic acid, malonic acid, methane sulfonic acid, napadisylic acid, phosphoric acid, saccharin, succinic acid or toluene sulfonic acid (such as p-toluenesulfonic acid). It is to be understood that a pharmaceutically-acceptable salt of a compound of the Formula (I) form an aspect of the present disclosure.

The compound of Formula (I) may be prepared as a co-crystal solid form. For the avoidance of doubt, a co-crystal refers to solids that are crystalline single-phase materials composed of a compound of Formula (I) and at least one other molecular and/or ionic compound, herein referred to as a co-former, generally in a stoichiometric ratio, which are neither solvates nor simple salts. Generally speaking, if the compound of Formula (I) and its coformer have a ΔpKa (pKa (base)−pKa (acid))>1, there will be substantial proton transfer resulting in ionization and potential formation of a salt as opposed to a co-crystal. On the other hand, if the compound of Formula (I) and its co-former have a ΔpKa (pKa (base)−pKa (acid))<1, there will be less than substantial proton transfer. If this criterion is met, the compound-co-former entity should be classified as a co-crystal. In a co-crystal, the compound and co-former molecules interact by hydrogen bonding and possibly other non-covalent interactions. It may be noted that a co-crystal may itself form solvates, including hydrates.

Pharmaceutically-acceptable co-crystals of a compound of the Formula (I) may be, for example, adipic acid or fumaric acid co-crystals. It is to be understood that a pharmaceutically-acceptable co-crystal of a compound of the Formula (I) forms another aspect of the present disclosure.

It is to be understood that the term "adduct", as herein described, covers both pharmaceutically-acceptable salts and pharmaceutically-acceptable co-crystals of a compound of the Formula (I). A skilled person would be able to determine whether a salt or a co-crystal is formed based on the difference in the pKa of the compound and its co-former as described hereinabove. In one aspect, an adduct is a salt. In another aspect, an adduct is a co-crystal.

Generally, reference herein to "a pharmaceutically-acceptable salt of a compound of Formula (I)" (or one or more of the Examples) in any embodiment or aspect is to be understood to include a compound of Formula (I) (or any one or more of the Examples respectively) presented as a pharmaceutically-acceptable co-crystal or more generally described as a (pharmaceutically-acceptable) adduct, unless the context demands otherwise.

The term "pharmaceutically-acceptable co-crystal of a compound of Formula (I)" is to be understood to refer to a co-crystal formed between the compound of Formula (I) and a pharmaceutically-acceptable counterion (co-former). Similarly, the term "pharmaceutically-acceptable adduct of a compound of formula (I)" is to be understood to refer to an adduct (salt or co-crystal) formed between the compound of Formula (I) and a pharmaceutically-acceptable counterion (co-former).

(R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, herein referred to as Form 1, is characterised in providing at least one of the following 2θ values measured using CuKα radiation: 23.3 and 16.7.

(R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, is characterised in providing an X-ray powder diffraction pattern, substantially as shown in FIG. 1. Ten X-Ray powder diffraction peaks are shown in Table 1:

TABLE 1

Ten X-Ray Powder Diffraction peaks for (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct Form 1

| Angle 2-Theta (2θ) | Intensity % |
|---|---|
| 23.3 | 100 |
| 16.7 | 72 |
| 21.6 | 67 |
| 13.6 | 67 |
| 7.3 | 47 |
| 19.6 | 37 |
| 25.8 | 33 |
| 28.1 | 32 |
| 14.5 | 25 |
| 11.0 | 24 |

According to the present disclosure there is provided a crystalline form of (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, which has an X-ray powder diffraction pattern with at least one specific peak at about 2-theta=23.3°.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, which has an X-ray powder diffraction pattern with at least one specific peak at about 2-theta=16.7°.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, which has an X-ray powder diffraction pattern with at least two specific peaks at about 2-theta=23.3° and 16.7°.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, which has an X-ray powder diffraction pattern with specific peaks at about 2-theta=23.3, 16.7, 21.6, 13.6, 7.3, 19.6, 25.8, 28.1, 14.5, 11.0°.

According to the present disclosure there is provided crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, which has an X-ray powder diffraction pattern substantially the same as the X-ray powder diffraction pattern shown in FIG. 1.

According to the present disclosure there is provided crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, which has an X-ray powder diffraction pattern with at least one specific peak at 2-theta=23.3° plus or minus 0.2° 2-theta.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, which has an X-ray powder diffraction pattern with at least one specific peak at 2-theta=16.7° plus or minus 0.2° 2-theta.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, which has an X-ray powder diffraction pattern with at least two specific peaks at 2-theta=23.3° and 16.7° wherein said values may be plus or minus 0.2° 2-theta.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, which has an X-ray powder diffraction pattern with specific peaks at 2-theta=23.3, 16.7, 21.6, 13.6, 7.3, 19.6, 25.8, 28.1, 14.5, 11.0° wherein said values may be plus or minus 0.2° 2-theta.

DSC analysis of (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, shows a melting endotherm with an onset of 203.8° C. and a peak at 204.6° C. (FIG. 2).

Thus DSC analysis shows (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, is a high melting solid with an onset of melting at about 203.8° C. and a peak at about 204.6° C.

(R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, herein referred to as Form 1, is characterised in providing at least one of the following 2θ values measured using CuKα radiation: 8.6 and 9.8.

(R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, is characterised in providing an X-ray powder diffraction pattern, substantially as shown in FIG. 3. Ten X-Ray powder diffraction peaks are shown in Table 2:

TABLE 2

Ten X-Ray Powder Diffraction peaks for (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct Form 1

| Angle 2-Theta (2θ) | Intensity % |
|---|---|
| 8.6 | 100 |
| 9.8 | 58 |
| 17.8 | 18 |
| 6.3 | 13 |
| 10.3 | 13 |
| 25.8 | 12 |
| 19.1 | 11 |
| 22.8 | 11 |
| 25.1 | 11 |
| 13.2 | 11 |

According to the present disclosure there is provided a crystalline form of (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, which has an X-ray powder diffraction pattern with at least one specific peak at about 2-theta=8.6°.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, which has an X-ray powder diffraction pattern with at least one specific peak at about 2-theta=9.8°.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, which has an X-ray powder diffraction pattern with at least two specific peaks at about 2-theta=8.6° and 9.8°.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, which has an X-ray powder diffraction pattern with specific peaks at about 2-theta=8.6, 9.8, 17.8, 6.3, 10.3, 25.8, 19.1, 22.8, 25.1, 13.2°.

According to the present disclosure there is provided crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, which has an X-ray powder diffraction pattern substantially the same as the X-ray powder diffraction pattern shown in FIG. 3.

According to the present disclosure there is provided crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, which has an X-ray powder diffraction pattern with at least one specific peak at 2-theta=8.6° plus or minus 0.2° 2-theta.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, which has an X-ray powder diffraction pattern with at least one specific peak at 2-theta=9.8° plus or minus 0.2° 2-theta.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, which has an X-ray powder diffraction pattern with at least two specific peaks at 2-theta=8.6° and 9.8° wherein said values may be plus or minus 0.2° 2-theta.

According to the present disclosure there is provided a crystalline form, (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, which has an X-ray powder diffraction pattern with specific peaks at 2-theta=8.6, 9.8, 17.8, 6.3, 10.3, 25.8, 19.1, 22.8, 25.1, 13.2° wherein said values may be plus or minus 0.2° 2-theta.

DSC analysis of (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, shows a melting endotherm with an onset of 185.4° C. and a peak at 186.2° C. (FIG. 4).

Thus DSC analysis shows (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, is a high melting solid with an onset of 185.4° C. and a peak at 186.2° C.

When it is stated that the present disclosure relates to a crystalline form of (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, and/or a crystalline form of (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, the degree of crystallinity is conveniently greater than about 60%, more conveniently greater than about 80%, preferably greater than about 90% and more preferably greater than about 95%. Most preferably, the degree of crystallinity is greater than about 98%.

The (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, provides X-ray powder diffraction patterns substantially the same as the X-ray powder diffraction patterns shown in FIG. 1 and has the ten (angle 2-theta values) shown in Table 1. The (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, provides X-ray powder diffraction patterns substantially the same as the X-ray powder diffraction patterns shown in FIG. 3 and has the ten (angle 2-theta values) shown in Table 2. It will be understood that the 2-theta values of the X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct, Form 1, of the present disclosure is not limited to the crystals that provide X-ray powder diffraction patterns identical to the X-ray powder diffraction pattern shown in FIG. 1, and any crystals providing X-ray powder diffraction patterns substantially the same as those shown in FIG. 1 fall within the scope of the present disclosure. In addition, it should be understood that the (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct, Form 1, of the present disclosure is not limited to the crystals that provide X-ray powder diffraction patterns identical to the X-ray powder diffraction pattern shown in FIG. 3, and any crystals providing X-ray powder diffraction patterns substantially the same as those shown in FIG. 3 fall within the scope of the present disclosure. A person skilled in the art of X-ray powder diffraction is able to judge the substantial identity of X-ray powder diffraction patterns.

Persons skilled in the art of X-ray powder diffraction will understand that the relative intensity of peaks can be affected by, for example, grains above 30 microns in size and non-unitary aspect ratios, which may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W.

(1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the X-ray powder diffraction pattern in FIG. 1 and when reading Table 1. Furthermore, it should be understood that intensities might fluctuate depending on experimental conditions and sample preparation (preferred orientation).

Any crystal form that provides a XRPD diffractogram or DSC thermogram substantially identical to those disclosed herein, fall within the scope of the present disclosures. One skilled in the art will have the ability to determine substantial identities of diffractograms, spectra and thermograms.

XRPD and DSC methodology conditions are herein described in the Examples.

It is to be understood that a suitable pharmaceutically-acceptable pro-drug of a compound of the Formula (I) also forms an aspect of the present disclosure. Accordingly, the compounds of the disclosure may be administered in the form of a pro-drug, which is a compound that is broken down in the human or animal body to release a compound of the disclosure. A pro-drug may be used to alter the physical properties and/or the pharmacokinetic properties of a compound of the present disclosure. A pro-drug can be formed when the compound of the present disclosure contains a suitable group or substituent to which a property-modifying group can be attached. Examples of pro-drugs include in-vivo cleavable ester or amide derivatives that may be formed at the carboxy group in a compound of the Formula (I).

Accordingly, one aspect of the present disclosure includes those compounds of Formula (I) as defined hereinbefore when made available by organic synthesis and when made available within the human or animal body by way of cleavage of a pro-drug thereof.

Accordingly, the present disclosure includes those compounds of the Formula (I) that are produced by organic synthetic means and also such compounds that are produced in the human or animal body by way of metabolism of a precursor compound, that is a compound of the Formula (I) may be a synthetically-produced compound or a metabolically-produced compound.

A suitable pharmaceutically-acceptable pro-drug of a compound of the Formula (I) one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula (I) that possesses a carboxy group is, for example, an in-vivo cleavable ester thereof. An in-vivo cleavable ester of a compound of the Formula (I) containing a carboxy group is, for example, a pharmaceutically-acceptable ester which is cleaved in the human or animal body to produce the parent acid. Suitable pharmaceutically-acceptable esters for a carboxy group include (1-6C)alkyl esters such as methyl, ethyl and tert-butyl, (1-6C)alkoxymethyl esters such as methoxymethyl esters, (1-6C)alkanoyloxymethyl esters such as pivaloyloxymethyl esters, 3-phthalidyl esters, (3-8C)cycloalkylcarbonyloxy-(1-6C)alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and (1-6C)alkoxycarbonyloxy-(1-6C)alkyl esters such as methoxycarbonyloxymethyl and 1-methoxycarbonyloxyethyl esters.

A suitable pharmaceutically-acceptable pro-drug of a compound of the Formula (I) which have a carboxy group is for example an in-vivo cleavable amide such as a N—$C_{1-6}$alkyl and N,N-di-($C_{1-6}$alkyl)amide such as N-methyl, N-ethyl, N-propyl, N,N-dimethyl, N-ethyl-N-methyl or N,N-diethylamide.

The in-vivo effects of a compound of the Formula (I) may be exerted in part by one or more metabolites that are formed within the human or animal body after administration of a compound of the Formula (I). As stated hereinbefore, the in-vivo effects of a compound of the Formula (I) may also be exerted by way of metabolism of a precursor compound (a pro-drug).

For the avoidance of doubt it is to be understood that where in this specification a group is qualified by 'hereinbefore defined' or 'defined herein' the said group encompasses the first occurring and broadest definition as well as each and all of the alternative definitions for that group.

Another aspect of the present disclosure provides a process for preparing a compound of the Formula (I), or a pharmaceutically-acceptable salt thereof. A suitable process is illustrated by the following representative process variants in which, unless otherwise stated $R^1$ to $R^3$ has any of the meanings defined hereinbefore. Necessary starting materials may be obtained by standard procedures of organic chemistry or are commercially available. The preparation of such starting materials is described in conjunction with the following representative process variants and within the accompanying Examples. Alternatively, necessary starting materials are obtainable by analogous procedures to those illustrated which are within the ordinary skill of an organic chemist.

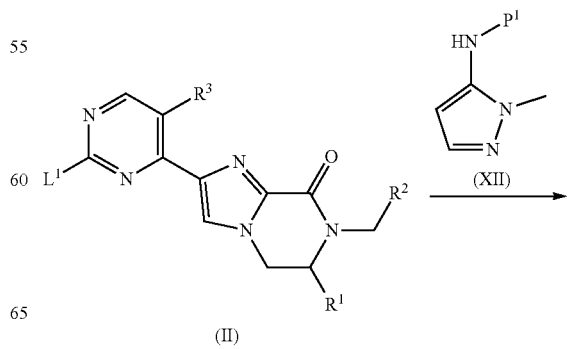

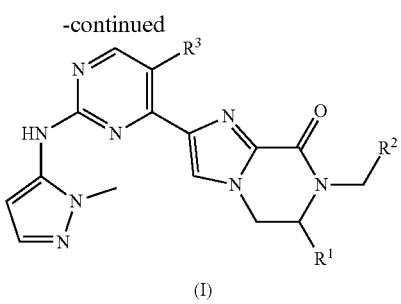

(I)

A compound of formula (I) may be prepared from a compound of formula (II), wherein $L^1$ is a suitable leaving group (such as halogen, or —$SO_2Me$, etc), by reaction with a compound of formula (XII), wherein $P^1$ is hydrogen, with a suitable base (such as NaH, $Na_2CO_3$, $Cs_2CO_3$ or $K_2CO_3$) in a suitable solvent (such as N,N-dimethylformamide or N,N-dimethylacetamide) or in the presence of a suitable Pd catalyst and phosphine ligand with a suitable base (e.g. $Cs_2CO_3$) in a suitable solvent (such as dioxane), under conditions of ambient or elevated temperatures (such as achieved by heating or by microwave irradiation). Alternatively, a compound of formula (I) may be prepared from a compound of formula (II), wherein $L^1$ is a suitable leaving group (such as halo, or —$SO_2Me$, etc.), by reaction with a compound of formula (XII), wherein $P^1$ is a suitable group other than hydrogen (such as formyl or trifluoroacetamide) with a suitable base (such as NaH, $Na_2CO_3$, $Cs_2CO_3$ or $K_2CO_3$) in a suitable solvent (such as N,N-dimethylformamide or N,N-dimethylacetamide) or in the presence of a suitable Pd catalyst and phosphine ligand with a suitable base (e.g. $Cs_2CO_3$) in a suitable solvent (such as dioxane), under conditions of elevated temperatures (such as achieved by heating or by microwave irradiation), followed by removal of the protecting group $P^1$ in the presence of a suitable base such as sodium hydroxide in a suitable solvent and water.

It will be appreciated that a compound of formula (I) may be transformed into another compound of formula (I) using conditions well known in the art.

Compounds of formula (XII) are either commercially available or well known in the art.

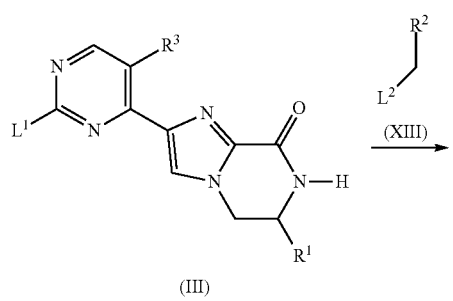

A compound of formula (II) may be prepared from a compound of formula (III), wherein $L^1$ is a suitable leaving group (such as Cl or —$SO_2Me$), by reaction with a compound of formula (XIII) wherein $L^2$ is a suitable leaving group (such as halogen, or —$OSO_2Me$, -Tos, etc), in the presence of a suitable base (such as sodium hydride or $K_2CO_3$) and a suitable solvent (such as N,N-dimethylformamide).

Compounds of formula (XIII) are either commercially available or well known in the art.

Alternatively compounds of formula (II) may be prepared from compounds of formula (VI), wherein $R^4$ is an alkyl group (such as methyl or ethyl), by the reaction with compounds of the formula (X) in the presence of suitable reducing reagent (such as $NaBH_3CN$) and a suitable solvent (such as tetrahydrofuran) followed by subsequent lactamisation conditions in a suitable solvent (such as MeOH) with a suitable base (such as ammonia), or with a Lewis acid catalyst (such as trimethylaluminium).

Compounds of formula (X) are either commercially available or well known in the art.

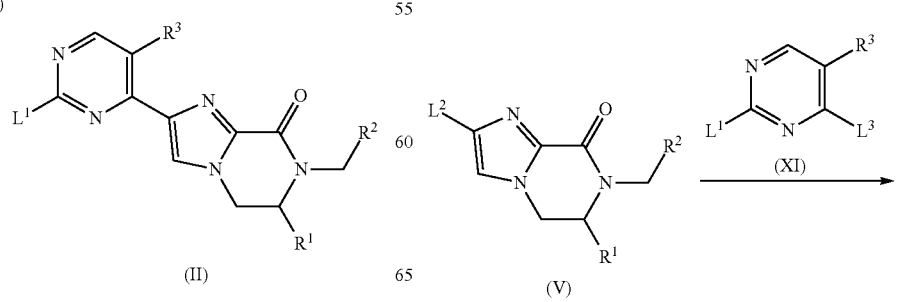

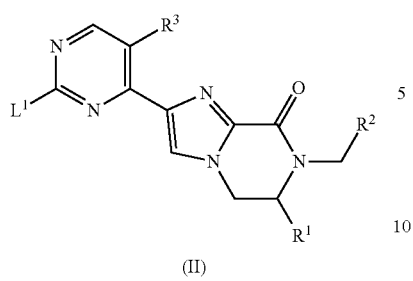

(II)

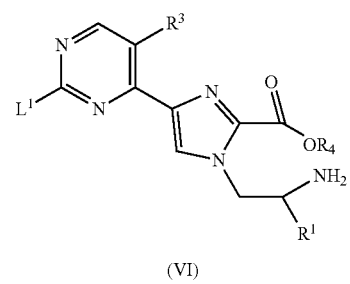

(VI)

A compound of formula (II) wherein $L^1$ is a pre-cursor to a suitable leaving group (such as —SMe, etc) may be prepared from a compound of formula (V), wherein $L^3$ is a suitable metal group (such as trimethyl stannane, etc), by reaction with a compound of formula (XI) wherein $L^2$ is a suitable leaving group (such as halo, or $OSO_2CF_3$), in the presence of a suitable Pd catalyst and phosphine ligand in a suitable solvent (such as a mixture of N,N-dimethylformamide, dimethoxyethane, water and ethanol) under suitable conditions such as heating thermally or in a microwave reactor.

Compounds of formula (XI) are either commercially available or well known in the art.

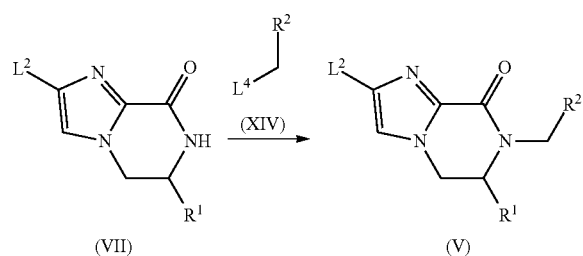

A compound of formula (V), wherein $R^1$ is hydrogen or an alkyl group (such as methyl), may be prepared from a compound of formula (VII), by reaction with a compound of formula (XIV) where $L^4$ is a suitable leaving group (such as halo, or $OSO_2CF_3$), in the presence of a suitable base (such as sodium hydride or $K_2CO_3$) and a suitable solvent (such as N,N-dimethylformamide or acetone).

Compounds of formula (XIV) are either commercially available or well known in the art.

A compound of formula (VI), wherein $R^4$ is an alkyl group (such as methyl or ethyl), may be prepared from a compound of formula (VIII), by reaction with either a compound of formula (XV), wherein $L^5$ is a suitable leaving group (such as halo, —$OSO_2Me$ or —$OSO_2CF_3$) and $P^3$ is a suitable protecting group (such as -Boc), or a compound of formula (XVI) wherein $P^3$ is a suitable protecting group (such as -Boc), in the presence of a suitable base (such as sodium hydride or $K_2CO_3$) in a suitable solvent (such as dioxane or MeCN) under conditions of ambient or elevated temperatures (such as achieved by heating or by microwave irradiation); In the case where compound of formula (XVI) is used it may be necessary to remove the intermediate sulfamic acid under conditions of aqueous acid (such as HCl) in a suitable solvent (such as ethanol). The protecting group $P^3$ can be removed from compounds of formula (XV) and (XVI) by the use of a suitable acid (such as HCl) in a suitable solvent (such as dioxane or ethanol), under conditions of ambient temperatures. A compound of formula (VI) may be isolated as a salt, such as a hydrochloride or dihydrochloride salt.

Compounds of formula (XV) and (XVI) are either commercially available or well known in the art.

The reaction of compound of formula (VIII) with a compound of formula (XVI) to prepare a compound of formula (VI) is novel and provides a further aspect of this present disclosure.

Therefore in a further aspect, there is provided a process for preparing a compound of formula (VI), said process comprising:

a) reaction of a compound of formula (VIII) with a compound of formula (XVI) in the presence of a suitable base in a suitable solvent, under conditions of ambient or elevated temperatures;

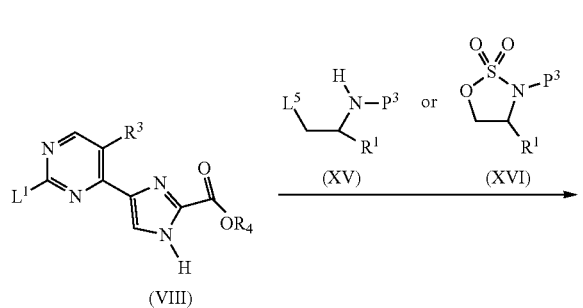

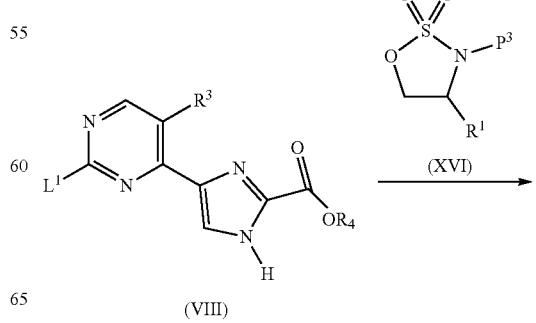

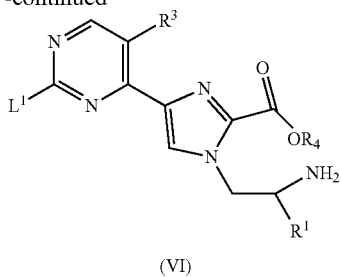

(VI)

wherein $R^1$ and $R^3$ are defined for compound of formula (I) hereinbefore;
$L^1$ is a leaving group or a pre-cursor to a leaving group;
$P^3$ is a protecting group; and
$R^4$ is an alkyl group; and
  b) optionally, an intermediate sulfamic acid is removed under conditions of aqueous acid in a suitable solvent; and
  c) removal of the protecting group $P^3$ in the presence of a suitable acid in a suitable solvent, under ambient temperatures.

In one embodiment, $L^1$ is —SMe or halogen.
In one embodiment, $L^1$ is —SMe or Cl.
In one embodiment, $R^4$ is an alkyl group.
In one embodiment, $R^4$ is $C_{1-4}$ alkyl.
In one embodiment, $R^4$ is methyl or ethyl.
In one embodiment, $R^4$ is methyl.
In one embodiment, $R^4$ is ethyl.
In one embodiment, a suitable base is sodium hydride or $K_2CO_3$.
In one embodiment, a suitable base is sodium hydride.
In one embodiment, reaction of a compound of formula (VIII) with a compound of formula (XVI) is performed in dioxane or MeCN.
In one embodiment, reaction of a compound of formula (VIII) with a compound of formula (XVI) is performed in dioxane.
In one embodiment, reaction of a compound of formula (VIII) with a compound of formula (XVI) is performed in MeCN.
In one embodiment, reaction of a compound of formula (VIII) with a compound of formula (XVI) is performed at temperatures at about 20° C.
In one embodiment, reaction of a compound of formula (VIII) with a compound of formula (XVI) is performed at temperatures of 18-25° C.
In one embodiment, reaction of a compound of formula (VIII) with a compound of formula (XVI) is performed at temperatures >20° C.
In one embodiment, reaction of a compound of formula (VIII) with a compound of formula (XVI) is performed at temperatures >50° C.
In one embodiment, reaction of a compound of formula (VIII) with a compound of formula (XVI) is performed at temperatures >80° C.
In one embodiment, reaction of a compound of formula (VIII) with a compound of formula (XVI) is performed at temperatures ≥85° C.
In one embodiment, reaction of a compound of formula (VIII) with a compound of formula (XVI) is performed at temperatures ≥85° C. and ≤100° C.
In one embodiment, reaction of a compound of formula (VIII) with a compound of formula (XVI) is performed at temperatures ≤100° C.

In one embodiment, reaction of a compound of formula (VIII) with a compound of formula (XVI) is performed at temperatures ≥80° C. and ≤110° C.
In one embodiment, reaction of a compound of formula (VIII) with a compound of formula (XVI) is performed at temperatures ≤110° C.
In one embodiment, a suitable aqueous acid is HCl.
In one embodiment, removal of intermediate sulfamic acid is performed in ethanol.
In one embodiment, $P^3$ is -Boc.
In one embodiment, a suitable base is $K_2CO_3$.
In one embodiment, a suitable acid is HCl.
In one embodiment, removal of the protecting group $P^3$ is performed in dioxane or ethanol.
In one embodiment, removal of the protecting group $P^3$ is performed in ethanol.
In one embodiment, removal of the protecting group $P^3$ is performed in dioxane.
In one embodiment, removal of the protecting group $P^3$ is at temperatures of 18-25° C.
In one embodiment, removal of the protecting group $P^3$ is at temperatures of 22-28° C.
In one embodiment, removal of the protecting group $P^3$ is at temperatures at about 20° C.
In one embodiment, removal of the protecting group $P^3$ is at temperatures at about

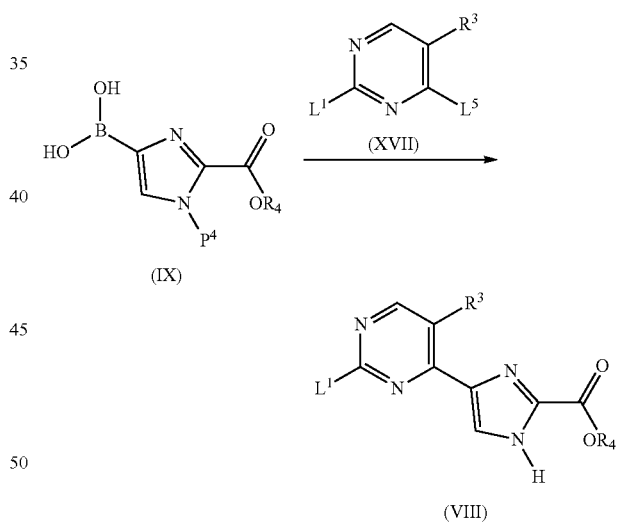

A compound of formula (VIII) wherein $L^1$ is a suitable leaving group (such as halogen, or —$SO_2Me$, etc) may be prepared from a compound of formula (IX), wherein $R^4$ is an alkyl group (such as methyl, etc) and $P^4$ is a protecting group (such as SEM) by reaction with a compound of formula (XVII) wherein $L^5$ is a suitable leaving group (such as halo, or $OSO_2CF_3$), in the presence of a suitable Pd catalyst and phosphine ligand, with a suitable base (such as caesium carbonate) in a suitable solvent (such as a mixture of dioxane and water), under suitable conditions (such as heating thermally or in a microwave reactor).

Compound of formula IX can be prepared by methods well known in the art.

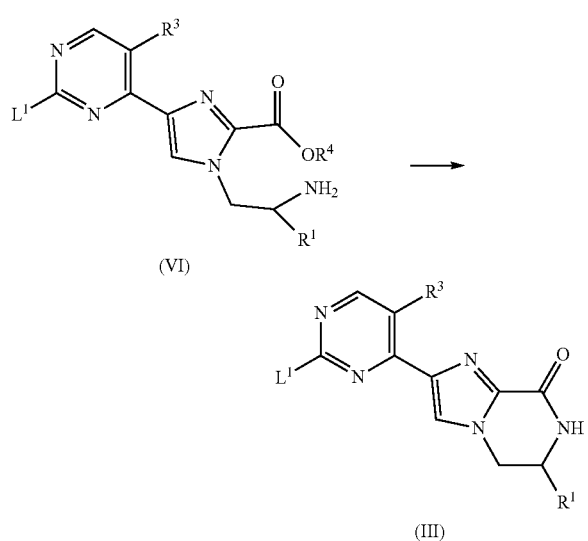

A compound of formula (III) may also be prepared from a compound of formula (VI) wherein $R^4$ is an alkyl group (such as methyl or ethyl) by treatment with a suitable base (such as ammonia) in a suitable solvent (such as MeOH).

When a pharmaceutically-acceptable salt of a compound of the Formula (I) is required it may be obtained by, for example, reaction of said compound with a suitable acid or suitable base.

When a pharmaceutically-acceptable pro-drug of a compound of the Formula (I) is required, it may be obtained using a conventional procedure. For example, an in-vivo cleavable ester of compound of the Formula (I) may be obtained by, for example, reaction of a compound of the Formula (I) containing a carboxy group with a pharmaceutically-acceptable alcohol. Further information on pro-drugs has been provided hereinbefore.

It will also be appreciated that, in some of the reactions mentioned hereinbefore, it may be necessary or desirable to protect any sensitive groups in the compounds. The instances where protection is necessary or desirable, and suitable methods for protection, are known to those skilled in the art. Conventional protecting groups may be used in accordance with standard practice (for illustration see T.W. Green, Protective Groups in Organic Synthesis, John Wiley and Sons, 1991). Thus, if reactants include groups such as amino, carboxy or hydroxy, it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain of the intermediates (for example, compounds of the Formulae II, III, IV, V, VI and VII, particularly Formulae II and VI) defined herein are novel and these are provided as a further features of the present disclosure.

Biological Assays

The following assays were used to measure the effects of the compounds of the present disclosure.

Compound Handling

All compounds or DMSO (dimethyl sulphoxide) for the ERK2 Mass Spectrometry and A375 phospho-p90RSK assays were dispensed from source plates containing compounds at 10 mM in 100% (v/v) DMSO or 100% DMSO, directly into assay plates using an Echo 555 Acoustic dispenser (Labcyte Inc™). Depending on the assay, two separate plate preparations were followed. In Workflow A, 10 mM compound stocks were diluted 1:100 using a fixed-tip 96-head Agilent VPrep liquid handler (Agilent Technologies, Santa Clara, Calif.) to give four intermediate dilutions (10 mM, 100 µM, 1 µM, 10 nM). In Workflow B, 10 mM compound stocks were diluted 1:10 using a Tecan Freedom Evo (Tecan Group Ltd., Switzerland), and then 1:100 using the Echo 555 and Labcyte LX to produce three intermediate dilutions across three Labcyte qualified source plates (1 mM, 10 µM, 100 nM). These intermediate dilution plates were then used by the Echo 555 to generate final assay-ready compound plates with a 12 point dose range (10, 3, 1, 0.25, 0.1, 0.03, 0.01, 0.0025, 0.001, 0.0003, 0.0001, 0.0000125 µM) in order to calculate compound $IC_{50}$s, with a total DMSO concentration in the assay of 1%. For the ERK2 Mass Spectrometry assay Workflow B was used. For the A375 phospho-p90RSK cell assay, the intermediate 1:100 dilution plate described in Workflow A was used by the Echo to dispense compounds and DMSO directly into the cell plates with a 12 point dose range (30, 10, 3.125, 1.25, 0.3, 0.1, 0.03125, 0.0125, 0.003, 0.001, 0.0003125, 0.00003 µM)

in order to calculate compound IC$_{50}$'s, with a total DMSO concentration in the assay of 0.3%.

ERK2 Rapidfire Mass Spectrometry Inhibition of Catalysis Assay

MEK U911-activated ERK2 protein was expressed and purified in-house. Enzyme and substrate solutions were made up in assay buffer consisting of 50 mM Tris (pH 7.5), 10 mM MgCl$_2$, 0.1 mM EGTA (ethylene glycol tetraacetic acid), 10 mM DTT (dithiothreitol) and 0.01% (v/v) CHAPS (3-[(3-Cholamidopropyl)dimethylammonio]-1-propanesulfonate). 1.2 nM ERK2 protein was prepared in assay buffer and 10 µl was dispensed into each well of a polypropylene, 384-well plate (#781201, Greiner) containing test and reference control compounds. Following a 15 minute pre-incubation of enzyme and compound at room temperature, 10 al of substrate solution was added consisting of 16 µM Erktide (IPTTPITTTYFFFK, #61777, AnaSpec) and 120 µM ATP (adenosine triphosphate) (measured Km) in assay buffer. The reaction was allowed to progress for 20 minutes at room temperature before being quenched by the addition of 80 al 1% (v/v) formic acid. The assay plates were then run on the RapidFire Mass Spectrometry platform (Agilent) to measure substrate (unphosphorylated Erktide) and product (phosphorylated Erktide) levels. Data was analysed and IC50's (half maximal inhibitory concentration) were calculated using Genedata Screener® software.

A375 Phospho-p90RSK Cellular Assay

The phospho-p90RSK cell assay was performed in the A375 cell line, a human malignant melanoma which has a BRAF mutation up-regulating the MAPK pathway and, hence, elevated endogenous levels of phospho-ERK and phospho-p90RSK. A375 cells were cultured in cell media composed of DMEM (Dulbecco's modified Eagle's medium), 10% (v/v) Foetal Calf Serum and 1% (v/v) L-Glutamine. After harvesting, cells were dispensed into black, 384-well Costar plates (#3712, Corning) to give 2400 cells per well in a total volume of 40 µl cell media, and were incubated overnight at 37° C., 90% relative humidity and 5% CO$_2$ in a rotating incubator. Test compounds and reference controls were dosed directly into the cell plates using a Labcyte Echo 555 acoustic dispenser. The cell plates were then incubated for 2 hours at 37° C. before being fixed by the addition of 20 µl 12% formaldehyde in PBS/A (4% final concentration), followed by a 20 minute room temperature incubation, and then a 2× wash with 150 µl PBS/A (phosphate buffered saline containing albumin) using a BioTek ELx405 platewasher. Cells were permeabilised with 20 µl 0.1% Triton X-100 in PBS/A for 20 minutes at room temperature, and then washed 1× with 100 µl PBS/A. Primary phospho-p90RSK (Thr359) (D1E9) rabbit monoclonal antibody (#8753, Cell Signaling Technology) was diluted 1:1000 in assay buffer (0.05% (v/v) Tween, 5% (v/v) Foetal Calf Serum, in PBS/A), 20 µl added per well, and plates were incubated at 4° C. overnight. Cell plates were washed 2× with 200 µl PBS/T (phosphate buffered saline containing Tween-20), then 20 µl 1:500 dilution in assay buffer of Alexa Fluor® 647 goat anti-rabbit IgG secondary antibody (#A31573, Molecular Probes, Life Technologies), with a 1:5000 dilution of Hoechst 33342, was added per well. Following a 90 minute incubation at room temperature, plates were washed 2× with 200 µl PBS/T, and 40 µl PBS/A was added per well. Stained cell plates were covered with black lid seals, and then read on a Cellomics ArrayScan™ VTI imaging platform (Thermo Scientific), using an XF53 filter with 10× objective, with a LED light source set-up to analyse nuclear staining with Hoechst 33342 (405 nm) and secondary antibody staining of phospho-p90RSK (647 nm). Data was analysed and IC50's were calculated using Genedata Screener® software.

Compounds as claimed herein generally have enzyme activity in the above assay of <0.5 mM, such as <0.2 mM.

The following data were generated for the Examples (the data below may be a result from a single experiment or an average of two or more experiments; variations from data presented in applications from which this application claims priority are due to further repetitions of the test causing slight changes in average values):

| Example | ERK2 Mass Spectrometry Enzyme IC$_{50}$ (µM) | p90RSK cell IC$_{50}$ (µM) |
| --- | --- | --- |
| 1 | 0.0174 | 17 |
| 2 | 0.0007 | 0.086 |
| 3 | 0.0005 | 0.081 |
| 4 | 0.0018 | 0.63 |
| 5 | 0.002 | 0.11 |
| 6 | 0.0006 | 0.025 |
| 7 | 0.0005 | 0.038 |
| 8 | 0.0011 | 0.21 |
| 9 | 0.0005 | 0.19 |
| 10 | 0.0011 | 0.055 |
| 11 | 0.0008 | 0.15 |
| 12 | 0.0006 | 0.003 |
| 13 | 0.0003 | 0.012 |
| 14 | 0.0003 | 0.024 |
| 15 | 0.0006 | 0.15 |
| 16 | 0.0011 | 0.12 |
| 17 | 0.0009 | 0.0052 |
| 18 | 0.0006 | 0.0057 |
| 18a | 0.0006 | 0.0074 |
| 19 | 0.0005 | 0.0053 |
| 20 | 0.0004 | 0.038 |
| 21 | 0.0006 | 0.011 |
| 22 | 0.0008 | 0.019 |
| 23 | 0.0006 | 0.04 |
| 24 | 0.0005 | 0.084 |
| 25 | 0.0007 | 0.13 |
| 26 | 0.0011 | 0.2 |
| 27 | 0.0008 | 0.077 |
| 28 | 0.0005 | 0.11 |
| 29 | 0.0009 | 0.13 |
| 30 | 0.0007 | 0.2 |
| 31 | 0.0008 | 0.14 |
| 32 | 0.0009 | 0.099 |
| 33 | 0.0008 | 0.031 |
| 35 | — | 0.093 |
| 36 | 0.0014 | 0.051 |
| 37 | 0.0007 | 0.064 |
| 38 | 0.0007 | 0.008 |
| 39 | 0.0018 | 0.070 |
| 40 | 0.0011 | 0.032 |
| 41 | 0.0015 | 0.130 |

Compounds of examples 1, 2, 3, 4, 6, 7, 9, 10, 11, 16, 17, 18, 19, 20, 21, 22, 23, 24, 25, 26, 27 and 28 have been shown to be at least 500 fold more selective for ERK2 over MEK in the MEK Autophosphorylation ADP-Glo Assay below.

MEK Autophosphorylation ADP-Glo Assay

Activated MEK protein was supplied by MRC-PPU (DU911, Dundee, UK) or expressed and purified in-house. The MEK assay was performed with the ADP-Glo™ Kinase Assay Kit (Promega, Madison, Wis., USA), in Greiner 384-well white low volume plates. 2 µl of 6 nM activated MEK protein, in assay buffer consisting of 50 mM Tris (pH 7.5), 10 mM DTT, 0.1 mM EGTA, 0.01% v/v Tween20 and 10 mM MgCl$_2$, was dispensed into each well of a plate containing test and reference control compounds. Following a 15 minute pre-incubation of enzyme and compound at room temperature, 2 µl of substrate solution was added consisting of 20 μM ATP ($K_{Mapp}^{ATP}$) in assay buffer. The assay reaction was allowed to proceed for 90 min at room temperature before stopping the reaction by the addition of 2 μl of ADP-Glo reagent. Plates were then covered and incubated for 40 min at room temperature. 4 μl Kinase Detection Reagent was then added and plates were incubated for 30 min, before the luminescence signal was read with a PHERAstar plate reader (BMG Labtech GmbH, Offenburg, Germany).

Combination Studies

Materials and Methods

A549 is a human non small cell lung cancer line carrying an oncogenic mutation in the KRAS gene (G12S). Female nude mice (Harlan, UK) were implanted subcutaneously (s.c.) on the left flank, with 5×10⁶ A549 cells (ATCC) per mouse.

Tumour growth was monitored by twice weekly calliper measurement and volumes calculated using elliptical formula (pi/6×width×width×length). Once tumours had reached a volume of ~200-300 mm³ animals were randomised into groups of 7-11 and were treated with a continuous combination schedule of selumetinib (ARRY-142886) 25 mg/kg BiD and Example 18a 25 mg/kg QD (four hours after first selumetinib dose), both were dosed by peroral route. Tumour volumes were measured twice weekly after dosing commenced.

Selumetinib was formulated in HPMC/Tween (0.5% Methocel [hydroxypropyl methocellulose]/0.1% Polysorbate 80), the suspension was stirred over night. Example 18a was formulated in 10% DMSO, 90% of a 40% kleptose solution (Kleptose is sourced from Roquette—Pharma [Trademarked] Hydroxypropyl betacyclodextrin—suitable for in-vivo use and formulations).

Tumour Growth Inhibition by Example 18a in Combination with MEK Inhibitor (Selumetinib)

Studies were performed in the A549 xenograft model. Selumetinib was dosed twice daily (BiD) 8 hours apart and Example 18a was dosed once daily (QD) 4 hours after the first selumetinib dose. Both compounds were dosed continuously for 3 weeks. Both vehicles were dosed in the vehicle group. Both selumetinib and Example 18a reduced tumour growth relative to vehicle only control (shown in FIG. 5). The combination of selumetinib plus Example 18a resulted in a further reduction in tumour growth, with evidence of regression in some animals.

Combination Studies—Cell Growth Inhibition

Cell Lines and Treatments

A549 is a human non small cell lung cancer line carrying an oncogenic mutation in the KRAS gene (G12S). H2122 is a human non small cell lung cancer line carrying an oncogenic mutation in the KRAS gene (G12C). H2009 is a human non small cell lung cancer line carrying an oncogenic mutation in the KRAS gene (G12A). Calu6 is a human non small cell lung cancer line carrying mutation in the KRAS (G13K) gene. All cell lines were obtained from the American Type Culture Collection.

All cell line were maintained at 37° C. and 5% $CO_2$ in a humidified atmosphere and grown in RPMI-1640 growth media supplemented with 10% FBS and 2 mmol/L glutamine. The identity of all cell lines was confirmed using short tandem repeat analysis as described previously (Davies B R, Greenwood H, Dudley P, et al: Preclinical pharmacology of AZD5363, an inhibitor of AKT: Pharmacodynamics, antitumor activity, and correlation of monotherapy activity with genetic background. Mol Cancer Ther 11(4):873-87, 2012). Compounds were dissolved in DMSO to a concentration of 10 mmol/L and stored under nitrogen.

Determination of Cell Growth

Cells were seeded in 384-well black, clear bottomed plates (Greiner Bio-One, Stonehouse, UK), cultured for 18-24 hours and treated with increasing concentrations of Example 18 and selumetinib (0-10 μmol/L) in a 6×6 dosing matrix. Cells were seeded at a concentration such that cells in untreated wells were approximately 80% confluent at the end of the assay. After 3 days of treatment, live cell number was determined using a Sytox Green endpoint as described previously ("Davies B R, Greenwood H, Dudley P, et al: Preclinical pharmacology of AZD5363, an inhibitor of AKT: Pharmacodynamics, antitumor activity, and correlation of monotherapy activity with genetic background. Mol Cancer Ther 11(4):873-87, 2012"). Briefly, Sytox Green nucleic acid dye (Invitrogen) diluted in TBS-EDTA buffer was added to cells at a final concentration of 0.13 μmol/L and the number of dead cells detected using an Acumen Explorer (TTP Labtech, Melbourn, UK). Cells were then permeabilised by the overnight addition of saponin (0.03% final concentration, diluted in TBS-EDTA buffer) and a total cell count measured. The live cell count was then determined by subtracting the number of dead cells per well from the total number of cells. Pre-dose measurements were made to indicate the number of live cells at the start of the experiment and thus an indication of whether the treatment regimen had resulted in cell death. The data is presented as % growth using the NCI formulas as follows;

$$\{[(Ti-Tz)/(C-Tz)]\times 100\}+100, \text{ for values for which } Ti >/= Tz$$

$$\{[(Ti-Tz)/Tz]\times 100\}+100, \text{ for concentrations for which } Ti < Tz$$

where, Tz represents the number of live cells at time zero, C represents the control growth and Ti represents the number of live cells in the presence of each drug regimen. This formula gives a percentage from 0% to 200%. Anti-proliferative effects are indicated by scores from 0% (no effect on cell growth) to 100% (complete inhibition of cell growth); cell killing is indicated by scores from 100% (no cell killing) to 200% (killing of all cells).

Analysis of Combination Activity

Combination activity (synergism), across the 6×6 dose matrix, was analysed in Genedata Screener12 (Genedata, Basel, Switzerland) using the Loewe dose-additivity model as described previously (Lehar J, Krueger A S, Avery W, et al: Synergistic drug combinations tend to improve therapeutically relevant selectivity. Nat Biotechnol 27(7):659-66, 2009 and Rickles R J, Tam W F, Giordano T P, 3rd, et al: Adenosine A2A and beta-2 adrenergic receptor agonists: Novel selective and synergistic multiple myeloma targets discovered through systematic combination screening. Mol Cancer Ther 11(7):1432-42, 201229). This model of additivity provides a null-reference that is predicted by the expected response if the two agents were the same drug. The 3-dimensional model surface, predicted from the two single-agent response curves, is subtracted from the experimentally-derived 3-dimensional dose effect surface to generate a difference volume. This excess matrix volume can be integrated to generate a synergy score. A synergy score cutoff >5 was used to identify combinations of interest in the initial high-throughput screen.

The results (shown in FIGS. 6-17) demonstrate that Example 18 can inhibit the growth of a panel of cancer cell lines with KRAS mutations as a monotherapy and this effect is synergistically enhanced by treatment with selumetinib. Synergy scores for each cell line are 25 (A549), 14.3

(H2122), 67.5 (H2009), and 3 (Calu6). The synergy scores above are an average of three or more independent experiments.

According to a further aspect of the present disclosure there is provided a pharmaceutical composition, which comprises a compound of the Formula (I), or a pharmaceutically-acceptable salt thereof, as defined hereinbefore in association with a pharmaceutically-acceptable diluent or carrier.

Suitable pharmaceutically-acceptable excipients for a tablet formulation include, for example, inert diluents, granulating and disintegrating agents, binding agents, lubricating agents, preservative agents and antioxidants. A further suitable pharmaceutically-acceptable excipient may be a chelating agent. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may alternatively be in the form of hard gelatin capsules in which the active ingredient is mixed with an inert solid diluent, or as soft gelatin capsules in which the active ingredient is mixed with water or an oil.

Aqueous suspensions generally contain the active ingredient in finely powdered form together with one or more suspending agents, dispersing or wetting agents. The aqueous suspensions may also contain one or more preservatives, anti-oxidants, colouring agents, flavouring agents, and/or sweetening agents.

Oily suspensions may be formulated by suspending the active ingredient in a vegetable oil or in a mineral oil. The oily suspensions may also contain a thickening agent. Sweetening agents such as those set out above, and flavouring agents may be added to provide a palatable oral preparation. These compositions may be preserved by the addition of an anti-oxidant.

Dispersible powders and granules suitable for preparation of an aqueous suspension by the addition of water generally contain the active ingredient together with a dispersing or wetting agent, suspending agent and one or more preservatives. Additional excipients such as sweetening, flavouring and colouring agents, may also be present.

The pharmaceutical compositions of the present disclosure may also be in the form of oil-in-water emulsions. The oily phase may be a vegetable oil or a mineral oil or a mixture of any of these. The emulsions may also contain sweetening, flavouring and preservative agents.

Syrups and elixirs may be formulated with sweetening agents, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent system.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient. Dry powder inhalers may also be suitable.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, oral administration to humans will generally require, for example, from 1 mg to 2 g of active agent (more suitably from 100 mg to 2 g, for example from 250 mg to 1.8 g, such as from 500 mg to 1.8 g, particularly from 500 mg to 1.5 g, conveniently from 500 mg to 1 g) to be administered compounded with an appropriate and convenient amount of excipients which may vary from about 3 to about 98 percent by weight of the total composition. It will be understood that, if a large dosage is required, multiple dosage forms may be required, for example two or more tablets or capsules, with the dose of active ingredient divided conveniently between them. Typically, unit dosage forms will contain about 10 mg to 0.5 g of a compound of this present disclosure, although a unit dosage form may contain up to 1 g. Conveniently, a single solid dosage form may contain between 1 and 300 mg of active ingredient.

The size of the dose for therapeutic or prophylactic purposes of compounds of the present disclosure will naturally vary according to the nature and severity of the disease state, the age and sex of the animal or patient and the route of administration, according to well known principles of medicine.

In using compounds of the present disclosure for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form.

In one aspect of the present disclosure, compounds of the present disclosure or pharmaceutically-acceptable salts thereof, are administered as tablets comprising 10 mg to 500 mg of the compound of Formula (I) (or a pharmaceutically-acceptable salt thereof), wherein one or more tablets are administered as required to achieve the desired dose.

As stated above, it is known that signalling through ERK causes tumourigenesis by one or more of the effects of mediating proliferation of cancer and other cells, mediating angiogenic events and mediating the motility, migration and invasiveness of cancer cells.

We have found that the compounds of the present disclosure possess potent anti-tumour activity which it is believed is obtained by way of inhibition of ERK that is involved in the signal transduction steps which lead to the proliferation and survival of tumour cells and the invasiveness and migratory ability of metastasising tumour cells.

Accordingly, the compounds of the present disclosure may be of value as anti-tumour agents, in particular as selective inhibitors of the proliferation, survival, motility, dissemination and invasiveness of mammalian cancer cells leading to inhibition of tumour growth and survival and to inhibition of metastatic tumour growth. Particularly, the compounds of the present disclosure may be of value as anti-proliferative and anti-invasive agents in the containment and/or treatment of solid tumour disease. Particularly, the compounds of the present disclosure may be useful in the prevention or treatment of those tumours which are sensitive to inhibition of ERK and that are involved in the signal transduction steps which lead to the proliferation and survival of tumour cells and the migratory ability and invasiveness of metastasising tumour cells. Further, the compounds of the present disclosure may be useful in the prevention or treatment of those tumours which are mediated alone or in part by inhibition of ERK, i.e. the compounds may be used to produce an ERK inhibitory effect in a warm-blooded animal in need of such treatment.

According to a further aspect there is provided a compound of the Formula (I), or a pharmaceutically-acceptable salt thereof, as defined hereinbefore for use as a medicament in a warm-blooded animal such as man.

According to a further aspect, there is provided a compound of the Formula (I), or a pharmaceutically-acceptable salt thereof, as defined hereinbefore for use in the production of an anti-proliferative effect in a warm-blooded animal such as man.

According to a further aspect there is provided a compound of the Formula (I), or a pharmaceutically-acceptable salt thereof, as defined hereinbefore for use in a warm-blooded animal such as man as an anti-invasive agent in the containment and/or treatment of solid tumour disease.

According to a further aspect there is provided the use of a compound of the Formula (I), or a pharmaceutically-acceptable salt thereof, as defined hereinbefore, for the production of an anti-proliferative effect in a warm-blooded animal such as man.

According to a further aspect there is provided the use of a compound of the Formula (I), or a pharmaceutically-acceptable salt thereof, as defined hereinbefore, in the manufacture of a medicament for use in the production of an anti-proliferative effect in a warm-blooded animal such as man.

According to a further aspect there is provided the use of a compound of the Formula (I), or a pharmaceutically-acceptable salt thereof, as defined hereinbefore, in the manufacture of a medicament for use in a warm-blooded animal such as man as an anti-invasive agent in the containment and/or treatment of solid tumour disease.

According to a further aspect there is provided a method for producing an anti-proliferative effect in a warm-blooded animal, such as man, in need of such treatment which comprises administering to said animal an effective amount of a compound of the Formula (I), or a pharmaceutically-acceptable salt thereof, as defined hereinbefore.

According to a further aspect there is provided a method for producing an anti-invasive effect by the containment and/or treatment of solid tumour disease in a warm-blooded animal, such as man, in need of such treatment which comprises administering to said animal an effective amount of a compound of the Formula (I), or a pharmaceutically-acceptable salt thereof, as defined hereinbefore.

According to a further aspect, there is provided a compound of the Formula (I), or a pharmaceutically-acceptable salt thereof, as defined hereinbefore, for use in the prevention or treatment of cancer in a warm-blooded animal such as man.

According to a further aspect there is provided the use of a compound of the Formula (I), or a pharmaceutically-acceptable salt thereof, as defined hereinbefore in the manufacture of a medicament for use in the prevention or treatment of cancer in a warm-blooded animal such as man.

According to a further aspect there is provided a method for the prevention or treatment of cancer in a warm-blooded animal, such as man, in need of such treatment which comprises administering to said animal an effective amount of a compound of the Formula (I), or a pharmaceutically-acceptable salt thereof, as defined hereinbefore.

According to a further aspect, there is provided a compound of the Formula (I), or a pharmaceutically-acceptable salt thereof, as defined hereinbefore for use in the prevention or treatment of solid tumour disease in a warm-blooded animal such as man.

According to a further aspect, there is provided the use of a compound of the Formula (I), or a pharmaceutically-acceptable salt thereof, as defined hereinbefore, in the manufacture of a medicament for use in the prevention or treatment of solid tumour disease in a warm-blooded animal such as man.

According to a further aspect, there is provided a method for the prevention or treatment of solid tumour disease in a warm-blooded animal, such as man, in need of such treatment which comprises administering to said animal an effective amount of a compound of the Formula (I), or a pharmaceutically-acceptable salt thereof, as defined hereinbefore.

According to a further aspect, there is provided a method for reducing the number of cancer cell in an individual in need of such treatment which comprises administering to said animal an effective amount of a compound of the Formula (I), or a pharmaceutically-acceptable salt thereof, as defined hereinbefore.

According to a further aspect, there is provided a method for reducing the size of a tumour in need of such treatment which comprises administering to said animal an effective amount of a compound of the Formula (I), or a pharmaceutically-acceptable salt thereof, as defined hereinbefore.

According to a further aspect, there is provided a method for reducing or inhibiting growth or proliferation of a tumour in need of such treatment which comprises administering to said animal an effective amount of a compound of the Formula (I), or a pharmaceutically-acceptable salt thereof, as defined hereinbefore.

According to a further aspect, there is provided a method for preventing metastasis or reducing the extent of metastasis in need of such treatment which comprises administering to said animal an effective amount of a compound of the Formula (I), or a pharmaceutically-acceptable salt thereof, as defined hereinbefore.

According to a further aspect, there is provided a method for extending the survival (including but not limited to progression free survival (PFS) or overall survival) in an individual having or at risk of having cancer in need of such treatment which comprises administering to said animal an effective amount of a compound of the Formula (I), or a pharmaceutically-acceptable salt thereof, as defined hereinbefore.

The phrase "effective amount" or "therapeutically-effective amount" means an amount that (i) treats the particular disease, condition or disorder, (ii) attenuates, ameliorates or eliminates one or more symptoms of the particular disease, condition or disorder, (iii) delays or prevents the onset of one or more symptoms of the particular disease, condition or disorder described herein. In the case of cancer, the effective amount may reduce the number of cancer cells; reduce the tumour size; inhibit (eg slow to some extent and preferably stop) infiltration of the cancer cells into peripheral organs; inhibit tumour metastasis; inhibit to some extent tumour growth; and/or relieve to some extent one or more of the symptoms associated with cancer. For cancer therapy, efficacy can be measure by assessing, for example the time to disease progression (TTP) and/or assessing the response rate (RR).

According to a further aspect there is provided a compound of the Formula (I), or a pharmaceutically-acceptable salt thereof, as defined hereinbefore, for use in the prevention or treatment of a hyperproliferative disease or disorder modulated by RAS/RAF/MEK/ERK kinases.

According to a further aspect there is provided the use of a compound of the Formula (I), or a pharmaceutically-acceptable salt thereof, as defined hereinbefore, in the manufacture of a medicament for use in the prevention or treatment of a hyperproliferative disease or disorder modulated by RAS/RAF/MEK/ERK kinases.

According to a further aspect there is provided a method for the prevention or treatment of a hyperproliferative disease or disorder modulated by RAS/RAF/MEK/ERK kinases which comprises administering to said animal an effective amount of a compound of the Formula (I), or a pharmaceutically-acceptable salt thereof, as defined hereinbefore.

According to a further aspect there is provided a compound of the Formula (I), or a pharmaceutically-acceptable salt thereof, as defined hereinbefore, for use in the prevention or treatment of a hyperproliferative disease or disorder mediated by ERK.

According to a further aspect there is provided the use of a compound of the Formula (I), or a pharmaceutically-acceptable salt thereof, as defined hereinbefore, in the manufacture of a medicament for use in the prevention or treatment of a hyperproliferative disease or disorder mediated by ERK.

According to a further aspect there is provided a method for the prevention or treatment of a hyperproliferative disease or disorder mediated by ERK which comprises administering to said animal an effective amount of a compound of the Formula (I), or a pharmaceutically-acceptable salt thereof, as defined hereinbefore.

According to a further aspect there is provided a compound of the Formula (I), or a pharmaceutically-acceptable salt thereof, as defined hereinbefore, for use in the prevention or treatment of those tumours which are sensitive to inhibition of ERK.

According to a further aspect there is provided the use of a compound of the Formula (I), or a pharmaceutically-acceptable salt thereof, as defined hereinbefore, in the manufacture of a medicament for use in the prevention or treatment of those tumours which is are sensitive to inhibition of ERK.

According to a further aspect there is provided a method for the prevention or treatment of those tumours which are sensitive to inhibition of ERK which comprises administering to said animal an effective amount of a compound of the Formula (I), or a pharmaceutically-acceptable salt thereof, as defined hereinbefore.

According to a further aspect there is provided a compound of the Formula (I), or a pharmaceutically-acceptable salt thereof, as defined hereinbefore for use in providing an inhibitory effect on ERK.

According to a further aspect there is provided the use of a compound of the Formula (I), or a pharmaceutically-acceptable salt thereof, as defined hereinbefore in the manufacture of a medicament for use in providing an inhibitory effect on ERK.

According to a further aspect there is also provided a method for providing an inhibitory effect on ERK which comprises administering an effective amount of a compound of the Formula (I), or a pharmaceutically-acceptable salt thereof, as defined hereinbefore.

According to a further aspect there is provided a compound of the Formula (I), or a pharmaceutically-acceptable salt thereof, as defined hereinbefore, for use in providing a selective inhibitory effect on ERK2.

According to a further aspect there is provided the use of a compound of the Formula (I), or a pharmaceutically-acceptable salt thereof, as defined hereinbefore, in the manufacture of a medicament for use in providing a selective inhibitory effect on ERK2.

According to a further aspect there is also provided a method for providing a selective inhibitory effect on ERK2 which comprises administering an effective amount of a compound of the Formula (I), or a pharmaceutically-acceptable salt thereof, as defined hereinbefore.

Compounds of Formula (I) may be effective in treating any cancer where the RAS/RAF/MEK/ERK kinase pathway is activated. Examples of cancers which have been reported to have such activation include acute myelogenous leukemia (AML), chronic myelomonocyic leukemia, multiple myeloma, chronic myelogenous leukemia, colorectal cancer (CRC), breast cancer, bladder cancer, head and neck cancer, brain cancer, glioblastoma, neuroblastoma, Non-Hodgkins lymphoma, pancreatic cancer, ovarian cancer, testicular cancer, thyroid cancer, non-small cell lung cancer (NSCLC), small cell lung cancer, melanoma, neurofibromatosis type 1 (NF1), biliary tract.

In one aspect, compounds may be effective in treating a cancer selected from NSCLC, pancreatic, CRC, melanoma, uveal melanoma, paediatric NF1, differentiated thyroid and biliary tract cancer.

In one aspect, compounds may be effective in treating KRAS or BRAF mutant cancers.

In one aspect, compounds may be effective in treating MAPK pathway dependent cancers such as NSCLC, pancreatic and CRC; in some embodiments such cancers are KRAS mutant cancers as described hereinafter.

In another aspect, compounds may be effective in treating BRAF mutant melanoma.

In a further aspect, compounds may be effective in treating a cancer selected from NRAS mutant melanoma, uveal melanoma, paediatric NF1, differentiated thyroid and biliary tract cancer.

According to a further aspect there is provided a compound of the Formula (I), or a pharmaceutically-acceptable salt thereof, as defined hereinbefore, for use in the treatment of NSCLC, pancreatic, CRC, melanoma, uveal melanoma, paediatric NF1, differentiated thyroid and biliary tract cancers.

According to a further aspect there is provided a compound of the Formula (I), or a pharmaceutically-acceptable salt thereof, as defined hereinbefore, for use in the treatment of NSCLC, pancreatic and CRC.

According to a further aspect there is provided a compound of the Formula (I), or a pharmaceutically-acceptable salt thereof, as defined hereinbefore, for use in the treatment of BRAF mutant melanoma.

According to a further aspect there is provided a compound of the Formula (I), or a pharmaceutically-acceptable salt thereof, as defined hereinbefore, for use in the treatment of NRAS mutant melanoma, uveal melanoma, paediatric NF1, differentiated thyroid and biliary tract cancer.

According to a further aspect there is provided a compound of the Formula (I), or a pharmaceutically-acceptable salt thereof, as defined hereinbefore, for use in the treatment of a cancer mediated by ERK, wherein the cancer has developed resistance to one or more other MAPK pathway inhibitors.

According to a further aspect there is provided a method for treating a cancer selected from NSCLC, pancreatic, CRC, melanoma, uveal melanoma, paediatric NF1, differentiated thyroid and biliary tract cancers, which comprises administering an effective amount of a compound of the Formula (I), or a pharmaceutically-acceptable salt thereof, as defined hereinbefore.

According to a further aspect there is provided a method for treating a cancer selected from NSCLC, pancreatic and CRC, which comprises administering an effective amount of a compound of the Formula (I), or a pharmaceutically-acceptable salt thereof, as defined hereinbefore.

According to a further aspect there is provided a method for treating BRAF mutant melanoma, which comprises administering an effective amount of a compound of the Formula (I), or a pharmaceutically-acceptable salt thereof, as defined hereinbefore.

According to a further aspect there is provided a method for treating a cancer selected from NRAS mutant melanoma, uveal melanoma, paediatric NF1, differentiated thyroid and biliary tract cancer, which comprises administering an effective amount of a compound of the Formula (I), or a pharmaceutically-acceptable salt thereof, as defined hereinbefore.

According to a further aspect there is provided a method for treating a cancer mediated by ERK, wherein the cancer has developed resistance to one or more other MAPK pathway inhibitors, which comprises administering an effective amount of a compound of the Formula (I), or a pharmaceutically-acceptable salt thereof, as defined hereinbefore.

According to a further aspect there is provided the use of a compound of the Formula (I), or a pharmaceutically-acceptable salt thereof, as defined hereinbefore, in the manufacture of a medicament for use in the treatment of a cancer selected from NSCLC, pancreatic, CRC, melanoma, uveal melanoma, paediatric NF1, differentiated thyroid and biliary tract cancers.

According to a further aspect there is provided the use of a compound of the Formula (I), or a pharmaceutically-acceptable salt thereof, as defined hereinbefore, in the manufacture of a medicament for use in the treatment of a cancer selected from NSCLC, pancreatic and CRC.

According to a further aspect there is provided the use of a compound of the Formula (I), or a pharmaceutically-acceptable salt thereof, as defined hereinbefore, in the manufacture of a medicament for use in the treatment of BRAF mutant melanoma.

According to a further aspect there is provided the use of a compound of the Formula (I), or a pharmaceutically-acceptable salt thereof, as defined hereinbefore, in the manufacture of a medicament for use in the treatment of NRAS mutant melanoma, uveal melanoma, paediatric NF1, differentiated thyroid and biliary tract cancer.

According to a further aspect there is provided the use of a compound of the Formula (I), or a pharmaceutically-acceptable salt thereof, as defined hereinbefore, in the manufacture of a medicament for use in the treatment of a cancer mediated by ERK, wherein the cancer has developed resistance to one or more other MAPK pathway inhibitors.

As stated hereinbefore, the in-vivo effects of a compound of the Formula (I) may be exerted in part by one or more metabolites that are formed within the human or animal body after administration of a compound of the Formula (I).

In the above compositions, methods and uses, particular compounds of Formula (I) are the compounds of the Examples, or pharmaceutically-acceptable salts thereof. Further illustrative examples for compositions, methods and uses are:

2-(2-((1-methyl-1H-pyrazol-5-yl)amino)pyrimidin-4-yl)-7-((6-methylpyridin-2-yl)methyl)-6,7-dihydroimidazo[1,2-a]pyrazin-8(5H)-one;

(S)-7-(3-chlorobenzyl)-6-methyl-2-(2-((1-methyl-1H-pyrazol-5-yl)amino)pyrimidin-4-yl)-6,7-dihydroimidazo[1,2-a]pyrazin-8(5H)-one;

(S)-7-(3-chloro-4-fluorobenzyl)-6-methyl-2-(2-((1-methyl-1H-pyrazol-5-yl)amino)pyrimidin-4-yl)-6,7-dihydroimidazo[1,2-a]pyrazin-8(5H)-one;

(S)-7-(3,4-difluorobenzyl)-6-methyl-2-(2-((1-methyl-1H-pyrazol-5-yl)amino)pyrimidin-4-yl)-6,7-dihydroimidazo[1,2-a]pyrazin-8(5H)-one;

2-(5-Methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one;

(S)-2-(5-chloro-2-((1-methyl-1H-pyrazol-5-yl)amino)pyrimidin-4-yl)-7-(3,4-difluorobenzyl)-6-methyl-6,7-dihydroimidazo[1,2-a]pyrazin-8(5H)-one;

(S)-2-(5-chloro-2-((1-methyl-1H-pyrazol-5-yl)amino)pyrimidin-4-yl)-7-(3-methoxybenzyl)-6-methyl-6,7-dihydroimidazo[1,2-a]pyrazin-8(5H)-one;

(S)-2-(5-chloro-2-((1-methyl-1H-pyrazol-5-yl)amino)pyrimidin-4-yl)-6-methyl-7-((2-(trifluoromethyl)pyrimidin-4-yl)methyl)-6,7-dihydroimidazo[1,2-a]pyrazin-8(5H)-one;

(S)-2-(5-chloro-2-((1-methyl-1H-pyrazol-5-yl)amino)pyrimidin-4-yl)-7-((6-(difluoromethyl)pyridin-2-yl)methyl)-6-methyl-6,7-dihydroimidazo[1,2-a]pyrazin-8(5H)-one;

(S)-2-(5-chloro-2-((1-methyl-1H-pyrazol-5-yl)amino)pyrimidin-4-yl)-6-methyl-7-((6-(trifluoromethyl)pyridin-2-yl)methyl)-6,7-dihydroimidazo[1,2-a]pyrazin-8(5H)-one;

(S)-2-(5-chloro-2-((1-methyl-1H-pyrazol-5-yl)amino)pyrimidin-4-yl)-6-methyl-7-((6-methylpyridin-2-yl)methyl)-6,7-dihydroimidazo[1,2-a]pyrazin-8(5H)-one;

7-(3-chloro-4-fluorobenzyl)-2-(5-methyl-2-((1-methyl-1H-pyrazol-5-yl)amino)pyrimidin-4-yl)-6,7-dihydroimidazo[1,2-a]pyrazin-8(5H)-one;

7-(3-chlorobenzyl)-2-(5-methyl-2-((1-methyl-1H-pyrazol-5-yl)amino)pyrimidin-4-yl)-6,7-dihydroimidazo[1,2-a]pyrazin-8(5H)-one;

7-(3-(difluoromethyl)benzyl)-2-(5-methyl-2-((1-methyl-1H-pyrazol-5-yl)amino)pyrimidin-4-yl)-6,7-dihydroimidazo[1,2-a]pyrazin-8(5H)-one;

7-((6-(difluoromethyl)pyridin-2-yl)methyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-7-((6-(difluoromethyl)pyridin-2-yl)methyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-7-(3-chlorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3-chlorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3,4-difluorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;
(S)-7-(3-(difluoromethyl)benzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;
(S)-7-(3,5-difluorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;
(S)-7-(3-methoxybenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;
(S)-7-(4-fluoro-3-methoxybenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;
(S)-7-((6-(difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;
(S)-6-methyl-2-(5-methyl-2-((1-methyl-1H-pyrazol-5-yl)amino)pyrimidin-4-yl)-7-((2-(trifluoromethyl)pyrimidin-4-yl)methyl)-6,7-dihydroimidazo[1,2-a]pyrazin-8(5H)-one;
(S)-6-methyl-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one;
(S)-7-(3-(difluoromethoxy)benzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;
(S)-6-methyl-2-(5-methyl-2-((1-methyl-1H-pyrazol-5-yl)amino)pyrimidin-4-yl)-7-((4-(trifluoromethyl)pyridin-2-yl)methyl)-6,7-dihydroimidazo[1,2-a]pyrazin-8(5H)-one;
(S)-6-methyl-2-(5-methyl-2-((1-methyl-1H-pyrazol-5-yl)amino)pyrimidin-4-yl)-7-((2-(trifluoromethyl)pyridin-4-yl)methyl)-6,7-dihydroimidazo[1,2-a]pyrazin-8(5H)-one;
(S)-7-((4-(difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;
(S)-6-methyl-2-(5-methyl-2-((1-methyl-1H-pyrazol-5-yl)amino)pyrimidin-4-yl)-7-((6-(trifluoromethyl)pyridin-4-yl)methyl)-6,7-dihydroimidazo[1,2-a]pyrazin-8(5H)-one;
7-(3,4-Difluorobenzyl)-2-(5-methyl-2-((1-methyl-1H-pyrazol-5-yl)amino)pyrimidin-4-yl)-6,7-dihydroimidazo[1,2-a]pyrazin-8(5H)-one;
(S)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;
(R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct;
(R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct;
(R)-6-Methyl-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one
(R)-7-((6-(Difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;
(R)-7-(3-(difluoromethyl)benzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;
(R)-6-(Methoxymethyl)-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one;
(R)-7-(3,5-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one; and
(R)-7-(3-Methoxybenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one.

The anti-cancer treatment defined herein may be applied as a sole therapy or may involve, in addition to the compounds of the present disclosure, conventional surgery or radiotherapy or chemotherapy. In certain embodiments, a compound of formula (I) is combined with another compound which has anti-hyperproliferative properties or that is useful in treating a hyperproliferative disorder. The additional compound may suitably have complementary activities to the compound of formula (I) such that they do not adversely affect each other. In some aspects such combination therapy may prevent or delay inherent or acquired resistance attributable to activation of the RAS/RAF/MEK/ERK pathway observed with MEK inhibition and to prevent or delay inherent or acquired resistance mediated via RAS pathway activation.

In addition to providing improved treatment for a given hyperproliferative disorder, administration of certain combinations may improve the quality of life of a patient compared to the quality of life experienced by the same patient receiving a different treatment. For example, administration of a combination to a patient may provide an improved quality of life compared to the quality of life the same patient would experience if they received only one of the individual agents as therapy. For example, a combined therapy may lower the dose of the therapeutic agents required. The combination may also cause reduced tumour burden and thereby reduce the associated adverse events.

Accordingly, in one embodiment there is provided a compound of Formula (I), or a pharmaceutically-acceptable salt thereof, and an additional anti-tumour substance for the conjoint treatment of cancer.

The anti-cancer treatment defined hereinbefore may be applied as a sole therapy or may involve, in addition to the compound of the present disclosure, conventional surgery or radiotherapy or chemotherapy. Such chemotherapy may include one or more of the following categories of anti-tumour agents:—

(i) antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) antihormonal agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) inhibitors of growth factor function and their downstream signalling pathways: included are Ab modulators of any growth factor or growth factor receptor targets, reviewed by Stern et al. *Critical Reviews in Oncology/Haematology*, 2005, 54, pp 1-29); also included are small molecule inhibitors of such targets, for example kinase inhibitors—examples include the anti-erbB2 antibody trastuzumab [Herceptin™], the anti-EGFR antibody panitumumab, the anti-EGFR antibody cetuximab [Erbitux, C225] and tyrosine kinase inhibitors including inhibitors of the erbB receptor family, such as epidermal growth factor family receptor (EGFR/erbB1) tyrosine kinase inhibitors such as gefitinib or erlotinib, erbB2 tyrosine kinase inhibitors such as lapatinib, and mixed erb1/2 inhibitors such as afatanib; similar strategies are available for other classes of growth factors and their receptors, for example inhibitors of the hepatocyte growth factor family or their receptors including c-met and ron; inhibitors of the insulin and insulin growth factor family or their receptors (IGFR, IR) inhibitors of the platelet-derived growth factor family or their receptors (PDGFR), and inhibitors of signalling mediated by other receptor tyrosine kinases such as c-kit, AnLK, and CSF-1R;

also included are modulators which target signalling proteins in the wider PI3-kinase signalling pathway, for example, inhibitors of other PI3-kinase isoforms such as PI3K-β, and ser/thr kinases such as AKT, mTOR, PDK, SGK, PI4K or PIP5K;

also included are inhibitors of serine/threonine kinases not listed above, for example raf inhibitors such as vemurafenib, MEK inhibitors such as selumetinib (AZD6244, ARRY-142886), cobimetinib or GDC-0623 (see for example WO2015/0832840), Abl inhibitors such as imatinib or nilotinib, Btk inhibitors such as ibrutinib, Syk inhibitors such as fostamatinib, aurora kinase inhibitors (for example AZD1152), inhibitors of other ser/thr kinases such as JAKs, STATs and IRAK4, and cyclin dependent kinase inhibitors;

iv) modulators of DNA damage signalling pathways, for example PARP inhibitors (e.g. Olaparib), ATR inhibitors or ATM inhibitors;

v) modulators of apoptotic and cell death pathways such as Bcl family modulators (e.g. ABT-263/Navitoclax, ABT-199);

(vi) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as sorafenib, axitinib, pazopanib, sunitinib and vandetanib (and compounds that work by other mechanisms (for example linomide, inhibitors of integrin αvβ3 function and angiostatin)];

(vii) vascular damaging agents, such as Combretastatin A4;

(viii) anti-invasion agents, for example c-Src kinase family inhibitors like (dasatinib, *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. Specific examples include monoclonal antibodies targeting PD-1 (e.g. BMS-936558), PDL-1 or CTLA4 (e.g. ipilimumab and tremelimumab);

(x) Antisense or RNAi based therapies, for example those which are directed to the targets listed.

(xi) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

According to this aspect there is provided a combination suitable for use in the treatment of cancer comprising a compound of Formula (I) as defined hereinbefore or a pharmaceutically-acceptable salt thereof and another anti-tumour agent, in particular any one of the anti tumour agents listed under (i)-(xi) above. In particular, the anti-tumour agent listed under (i)-(xi) above is the standard of care for the specific cancer to be treated; the person skilled in the art will understand the meaning of "standard of care".

Therefore in a further aspect there is provided a compound of Formula (I) or a pharmaceutically-acceptable salt thereof in combination with another anti-tumour agent, in particular an anti-tumour agent selected from one listed under (i)-(xi) herein above.

According to a further aspect there is provided a pharmaceutical composition which comprises a compound of Formula (I) or a pharmaceutically-acceptable salt thereof in combination with an anti-tumour agent selected from one listed under (i)-(xi) herein above, in association with a pharmaceutically-acceptable diluent or carrier.

According to a further aspect there is provided a pharmaceutical composition which comprises a compound of Formula (I) or a pharmaceutically-acceptable salt thereof in combination with an anti-tumour agent selected from one listed under (i)-(xi) herein above, in association with a pharmaceutically-acceptable diluent or carrier for use in treating cancer.

According to another feature there is provided the use of a compound of the Formula (I) or a pharmaceutically-acceptable salt thereof in combination with an anti-tumour agent selected from one listed under (i)-(xi) herein above, in the manufacture of a medicament for use in cancer in a warm-blooded animal, such as man.

According to another feature, there is provided a method of treating cancer in a warm-blooded animal, such as man, in need of such treatment which comprises administering to said animal an effective amount of a compound of Formula (I) or a pharmaceutically-acceptable salt thereof in combination with an anti-tumour agent selected from one listed under (i)-(xi) herein above.

In a further aspect there is provided a compound of Formula (I) or a pharmaceutically-acceptable salt thereof in combination with another anti-tumour agent, in particular an anti-tumour agent selected from one listed under (i) above.

In a further aspect there is provided a combination suitable for use in the treatment of cancer comprising a compound of Formula (I) as defined hereinbefore or a pharmaceutically-acceptable salt thereof and any one of the anti tumour agents listed under (i) above.

According to a further aspect there is provided a pharmaceutical composition which comprises a compound of Formula (I) or a pharmaceutically-acceptable salt thereof in combination with an anti-tumour agent selected from one listed under (i) herein above, in association with a pharmaceutically-acceptable diluent or carrier.

According to a further aspect there is provided a pharmaceutical composition which comprises a compound of Formula (I) or a pharmaceutically-acceptable salt thereof in combination with an anti-tumour agent selected from one listed under (i) herein above, in association with a pharmaceutically-acceptable diluent or carrier for use in treating cancer.

According to another feature there is provided the use of a compound of the Formula (I) or a pharmaceutically-acceptable salt thereof in combination with an anti-tumour agent selected from one listed under (i) herein above, in the manufacture of a medicament for use in cancer in a warm-blooded animal, such as man.

According to another feature, there is provided a method of treating cancer in a warm-blooded animal, such as man, in need of such treatment which comprises administering to said animal an effective amount of a compound of Formula (I) or a pharmaceutically-acceptable salt thereof in combination with an anti-tumour agent selected from one listed under (i) herein above.

In a further aspect there is provided a compound of Formula (I) or a pharmaceutically-acceptable salt thereof in combination with another anti-tumour agent, in particular an anti-tumour agent selected from one listed under (iii) above.

In a further aspect there is provided a combination suitable for use in the treatment of cancer comprising a compound of Formula (I) as defined hereinbefore or a pharmaceutically-acceptable salt thereof and any one of the anti tumour agents listed under (iii) above.

According to a further aspect there is provided a pharmaceutical composition which comprises a compound of Formula (I) or a pharmaceutically-acceptable salt thereof in combination with an anti-tumour agent selected from one listed under (iii) herein above, in association with a pharmaceutically-acceptable diluent or carrier.

According to a further aspect there is provided a pharmaceutical composition which comprises a compound of Formula (I) or a pharmaceutically-acceptable salt thereof in combination with an anti-tumour agent selected from one listed under (iii) herein above, in association with a pharmaceutically-acceptable diluent or carrier for use in treating cancer.

According to another feature there is provided the use of a compound of the Formula (I) or a pharmaceutically-acceptable salt thereof in combination with an anti-tumour agent selected from one listed under (iii) herein above, in the manufacture of a medicament for use in cancer in a warm-blooded animal, such as man.

According to another feature, there is provided a method of treating cancer in a warm-blooded animal, such as man, in need of such treatment which comprises administering to said animal an effective amount of a compound of Formula (I) or a pharmaceutically-acceptable salt thereof in combination with an anti-tumour agent selected from one listed under (iii) herein above.

In one aspect, suitable examples of anti tumour agents listed in (iii) above are those agents which also act on MAPK kinsases, particularly on the RAS-RAF-MEK-ERK signalling cascade such as MEK inhibitors.

In a further aspect there is provided a combination suitable for use in the treatment of cancer comprising a compound of Formula (I) as defined hereinbefore or a pharmaceutically-acceptable salt thereof and a MEK inhibitor, such as selumetinib (ARRY-142886).

In one aspect, the above combination of the compound of formula (I) and selumetinib (ARRY-142886) is suitable for use in the treatment of any cancer dependent on the MAPK pathway, such as NSCLC, pancreatic or CR cancer, optionally in combination with standard of care therapy.

The combination of a compound of Formula (I) and an anti-tumour agent listed in (iii) above, particularly another agent acting on MAPK kinases, particularly on the RAS-RAF-MEK-ERK signalling cascade such as MEK inhibitors/may be particularly useful in treating tumours with a higher prevalence of mutation in KRAS or BRAF.

Particular combinations of the present disclosure comprise any one of the compounds of the Examples herein (or a pharmaceutically-acceptable salt thereof) and a MEK inhibitor such as selumetinib (ARRY-142886) as described hereinabove. Further illustrative examples for combinations of the present disclosure and a MEK inhibitor such as selumetinib (ARRY-14288) are:

2-(2-((1-methyl-1H-pyrazol-5-yl)amino)pyrimidin-4-yl)-7-((6-methylpyridin-2-yl)methyl)-6,7-dihydroimidazo[1,2-a]pyrazin-8(5H)-one;

(S)-7-(3-chlorobenzyl)-6-methyl-2-(2-((1-methyl-1H-pyrazol-5-yl)amino)pyrimidin-4-yl)-6,7-dihydroimidazo[1,2-a]pyrazin-8(5H)-one;

(S)-7-(3-chloro-4-fluorobenzyl)-6-methyl-2-(2-((1-methyl-1H-pyrazol-5-yl)amino)pyrimidin-4-yl)-6,7-dihydroimidazo[1,2-a]pyrazin-8(5H)-one;

(S)-7-(3,4-difluorobenzyl)-6-methyl-2-(2-((1-methyl-1H-pyrazol-5-yl)amino)pyrimidin-4-yl)-6,7-dihydroimidazo[1,2-a]pyrazin-8(5H)-one;

2-(5-Methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one;

(S)-2-(5-chloro-2-((1-methyl-1H-pyrazol-5-yl)amino)pyrimidin-4-yl)-7-(3,4-difluorobenzyl)-6-methyl-6,7-dihydroimidazo[1,2-a]pyrazin-8(5H)-one;

(S)-2-(5-chloro-2-((1-methyl-1H-pyrazol-5-yl)amino)pyrimidin-4-yl)-7-(3-methoxybenzyl)-6-methyl-6,7-dihydroimidazo[1,2-a]pyrazin-8(5H)-one;

(S)-2-(5-chloro-2-((1-methyl-1H-pyrazol-5-yl)amino)pyrimidin-4-yl)-6-methyl-7-((2-(trifluoromethyl)pyrimidin-4-yl)methyl)-6,7-dihydroimidazo[1,2-a]pyrazin-8(5H)-one;

(S)-2-(5-chloro-2-((1-methyl-1H-pyrazol-5-yl)amino)pyrimidin-4-yl)-7-((6-(difluoromethyl)pyridin-2-yl)methyl)-6-methyl-6,7-dihydroimidazo[1,2-a]pyrazin-8(5H)-one;

(S)-2-(5-chloro-2-((1-methyl-1H-pyrazol-5-yl)amino)pyrimidin-4-yl)-6-methyl-7-((6-(trifluoromethyl)pyridin-2-yl)methyl)-6,7-dihydroimidazo[1,2-a]pyrazin-8(5H)-one;

(S)-2-(5-chloro-2-((1-methyl-1H-pyrazol-5-yl)amino)pyrimidin-4-yl)-6-methyl-7-((6-methylpyridin-2-yl)methyl)-6,7-dihydroimidazo[1,2-a]pyrazin-8(5H)-one;

7-(3-chloro-4-fluorobenzyl)-2-(5-methyl-2-((1-methyl-1H-pyrazol-5-yl)amino)pyrimidin-4-yl)-6,7-dihydroimidazo[1,2-a]pyrazin-8(5H)-one;

7-(3-chlorobenzyl)-2-(5-methyl-2-((1-methyl-1H-pyrazol-5-yl)amino)pyrimidin-4-yl)-6,7-dihydroimidazo[1,2-a]pyrazin-8(5H)-one;

7-(3-(difluoromethyl)benzyl)-2-(5-methyl-2-((1-methyl-1H-pyrazol-5-yl)amino)pyrimidin-4-yl)-6,7-dihydroimidazo[1,2-a]pyrazin-8(5H)-one;

7-((6-(difluoromethyl)pyridin-2-yl)methyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-7-((6-(difluoromethyl)pyridin-2-yl)methyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-7-(3-chlorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3-chlorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3,4-difluorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3-(difluoromethyl)benzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3,5-difluorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3-methoxybenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(4-fluoro-3-methoxybenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-7-((6-(difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-6-methyl-2-(5-methyl-2-((1-methyl-1H-pyrazol-5-yl)amino)pyrimidin-4-yl)-7-((2-(trifluoromethyl)pyrimidin-4-yl)methyl)-6,7-dihydroimidazo[1,2-a]pyrazin-8(5H)-one;

(S)-6-methyl-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one;

(S)-7-(3-(difluoromethoxy)benzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-6-methyl-2-(5-methyl-2-((1-methyl-1H-pyrazol-5-yl)amino)pyrimidin-4-yl)-7-((4-(trifluoromethyl)pyridin-2-yl)methyl)-6,7-dihydroimidazo[1,2-a]pyrazin-8(5H)-one;

(S)-6-methyl-2-(5-methyl-2-((1-methyl-1H-pyrazol-5-yl)amino)pyrimidin-4-yl)-7-((2-(trifluoromethyl)pyrimidin-4-yl)methyl)-6,7-dihydroimidazo[1,2-a]pyrazin-8(5H)-one;

(S)-7-((4-(difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(S)-6-methyl-2-(5-methyl-2-((1-methyl-1H-pyrazol-5-yl)amino)pyrimidin-4-yl)-7-((6-(trifluoromethyl)pyrimidin-4-yl)methyl)-6,7-dihydroimidazo[1,2-a]pyrazin-8(5H)-one;

7-(3,4-Difluorobenzyl)-2-(5-methyl-2-((1-methyl-1H-pyrazol-5-yl)amino)pyrimidin-4-yl)-6,7-dihydroimidazo[1,2-a]pyrazin-8(5H)-one;

(S)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct;

(R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct;

(R)-6-Methyl-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one;

(R)-7-((6-(Difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one;

(R)-7-(3-(difluoromethyl)benzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one;

(R)-6-(Methoxymethyl)-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one;

(R)-7-(3,5-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one; and (R)-7-(3-Methoxybenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one.

In all of the above combinations, it will be understood that the combination may also be dosed with standard of care treatment, as understood by the skilled person, such as other treatments from (i) to (xi) hereinbefore. In other aspects, suitably the standard of care may be selected from (i) above.

Therefore in a further aspect of the present disclosure, there is provided a triple combination suitable for use in the treatment of cancer
 a) a compound of formula (I) or a pharmaceutically-acceptable salt thereof;
 b) a compound selected from (iii) above (such as another compound acting on MAPK kinases) or a pharmaceutically-acceptable salt thereof; and
 c) standard of care therapy for the cancer to be treated.

Suitably standard of care therapy may be dosed according to its usual dosing regimen, as understood by the skilled person.

According to a further aspect there is provided a kit comprising a compound of Formula (I) or a pharmaceutically-acceptable salt thereof in combination with an anti-tumour agent selected from one listed under (i)-(xi) herein above.

According to a further aspect there is provided a kit comprising:
a) a compound of Formula (I) or a pharmaceutically-acceptable salt thereof in a first unit dosage form;
b) an anti-tumour agent selected from one listed under (i)-(xi) herein above in a second unit dosage form; and
c) container means for containing said first and second dosage forms.

According to a further aspect there is provided a kit comprising:
a) a compound of Formula (I) or a pharmaceutically-acceptable salt thereof in a first unit dosage form;
b) an anti-tumour agent selected from one listed under (i)-(xi) herein above in a second unit dosage form;
c) container means for containing said first and second dosage forms; and optionally
d) instructions for use.

Herein, where the term "combination" is used it is to be understood that this refers to simultaneous, separate or sequential administration. In one aspect of the present disclosure "combination" refers to simultaneous administration. In another aspect of the present disclosure "combination" refers to separate administration. In a further aspect of the present disclosure "combination" refers to sequential administration. Where the administration is sequential or separate, the delay in administering the second component should not be such as to lose the beneficial effect.

Although the compounds of the Formula (I) are primarily of value as therapeutic agents for use in warm-blooded animals (including man), they are also useful whenever it is required to inhibit ERK. Thus, they are useful as pharmacological standards for use in the development of new biological tests and in the search for new pharmacological agents.

Personalised Healthcare

Another aspect of the present disclosure is based on identifying a link between the status of the gene encoding KRAS and susceptibility to treatment with a compound of Formula (I). This therefore provides opportunities, methods and tools for selecting patients for treatment with a compound of Formula (I), particularly cancer patients, and/or avoiding treatment of patients less likely to respond therapeutically to the treatment thus avoiding unnecessary treatment and any side effects that may be associated with such ineffective treatment.

The present disclosure relates to patient selection tools and methods (including personalised medicine). The selection is based on whether the tumour cells to be treated possess wild-type or mutant KRAS gene. The KRAS gene status can therefore be used as a biomarker of susceptibility to treatment with an ERK inhibitor.

There is a clear need for biomarkers that will enrich for or select patients whose tumours will respond to treatment with an ERK inhibitor, such as a compound of Formula (I). Patient selection biomarkers that identify the patients most likely to respond to an agent are ideal in the treatment of cancer, since they reduce the unnecessary treatment of patients with non-responding tumours to the potential side effects of such agents.

A biomarker can be described as "a characteristic that is objectively measured and evaluated as an indicator of normal biologic processes, pathogenic processes, or pharmacologic responses to a therapeutic intervention". A biomarker is any identifiable and measurable indicator associated with a particular condition or disease where there is a correlation between the presence or level of the biomarker and some aspect of the condition or disease (including the presence of, the level or changing level of, the type of, the stage of, the susceptibility to the condition or disease, or the responsiveness to a drug used for treating the condition or disease). The correlation may be qualitative, quantitative, or both qualitative and quantitative. Typically a biomarker is a compound, compound fragment or group of compounds. Such compounds may be any compounds found in or produced by an organism, including proteins (and peptides), nucleic acids and other compounds.

Biomarkers may have a predictive power, and as such may be used to predict or detect the presence, level, type or stage of particular conditions or diseases (including the presence or level of particular microorganisms or toxins), the susceptibility (including genetic susceptibility) to particular conditions or diseases, or the response to particular treatments (including drug treatments). It is thought that biomarkers will play an increasingly important role in the future of drug discovery and development, by improving the efficiency of research and development programs. Biomarkers can be used as diagnostic agents, monitors of disease progression, monitors of treatment and predictors of clinical outcome. For example, various biomarker research projects are attempting to identify markers of specific cancers and of specific cardiovascular and immunological diseases. It is believed that the development of new validated biomarkers will lead both to significant reductions in healthcare and drug development costs and to significant improvements in treatment for a wide variety of diseases and conditions.

In order to optimally design clinical trials and to gain the most information from these trials, a biomarker may be required. The marker may be measurable in surrogate and tumour tissues. Ideally these markers will also correlate with efficacy and thus could ultimately be used for patient selection.

Thus, the technical problem underlying this aspect of the present disclosure is the identification of means for stratification of patients for treatment with a compound of Formula (I). The technical problem is solved by provision of the embodiments characterized in the claims and/or description herein.

The present disclosure provides a method of determining sensitivity of cells to a compound of Formula (I). The method comprises determining the status of KRAS gene in said cells. The cells are identified as likely to be sensitive to a compound of Formula I if the cells possess a mutated KRAS gene. Those patients with a mutated KRAS gene are therefore predicted to be particularly susceptible to treatment with a compound of Formula (I). A cell is defined as sensitive to a compound of Formula (I) if it inhibits the increase in cell number in a cell growth assay (either through inhibition of cell proliferation and/or through increased cell death). Methods of the present disclosure are useful for predicting which cells are more likely to respond to a compound of Formula (I) by growth inhibition.

The present disclosure is further based, in part, on methods that can be used to determine a patient's responsiveness to a compound of Formula (I) including determining whether to administer a compound of Formula (I). Specifically the methods of the present disclosure include the determination of the gene status of KRAS. The presence of a mutated KRAS gene indicates that the tumour cells are more likely to respond by growth inhibition when contacted with a compound of Formula (I). The KRAS gene status can therefore be used to select patients for treatment with a compound of Formula (I).

A sample "representative of the tumour" can be the actual tumour sample isolated, or may be a sample that has been further processed, e.g. a sample of PCR amplified nucleic acid from the tumour sample.

Definitions

In this Personalised Healthcare section:

"Allele" refers to a particular form of a genetic locus, distinguished from other forms by its particular nucleotide or amino acid sequence.

"Amplification reactions" are nucleic acid reactions which result in specific amplification of target nucleic acids over non-target nucleic acids. The polymerase chain reaction (PCR) is a well known amplification reaction.

"Cancer" is used herein to refer to neoplastic growth arising from cellular transformation to a neoplastic phenotype. Such cellular transformation often involves genetic mutation.

"Gene" is a segment of DNA that contains all the information for the regulated biosynthesis of an RNA product, including a promoter, exons, introns, and other sequence elements which may be located within 5' or 3' flanking regions (not within the transcribed portions of the gene) that control expression.

"Gene status" refers to whether the gene is wild type or not (i.e. mutant).

"Label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

"Non-synonymous variation" refers to a variation (variance) in or overlapping the coding sequence of a gene that result in the production of a distinct (altered) polypeptide sequence. These variations may or may not affect protein function and include missense variants (resulting in substitution of one amino acid for another), nonsense variants (resulting in a truncated polypeptide due to generation of a premature stop codon) and insertion/deletion variants.

"Synonymous variation" refers to a variation (variance) in the coding sequence of a gene that does not affect sequence of the encoded polypeptide. These variations may affect protein function indirectly (for example by altering expression of the gene), but, in the absence of evidence to the contrary, are generally assumed to be innocuous.

"Nucleic acid" refers to single stranded or double stranded DNA and RNA molecules including natural nucleic acids found in nature and/or modified, artificial nucleic acids having modified backbones or bases, as are known in the art.

"Primer" refers to a single stranded DNA oligonucleotide sequence capable of acting as a point of initiation for synthesis of a primer extension product which is complementary to the nucleic acid strand to be copied. The length and sequence of the primer must be such that they are able to prime the synthesis of extension products. A typical primer contains at least about 7 nucleotides in length of a sequence substantially complementary to the target sequence, but somewhat longer primers are preferred. Usually primers contain about 15-26 nucleotides, but longer or shorter primers may also be employed.

"Polymorphic site" is a position within a locus at which at least two alternative sequences are found in a population.

"Polymorphism" refers to the sequence variation observed in an individual at a polymorphic site. Polymorphisms include nucleotide substitutions, insertions, deletions and microsatellites and may, but need not, result in detectable differences in gene expression or protein function. In the absence of evidence of an effect on expression or protein function, common polymorphisms, including non-synonomous variants, are generally considered to be included in the definition of wild-type gene sequence. A catalog of human polymorphisms and associated annotation, including validation, observed frequencies, and disease association, is maintained by NCBI (dbSNP: http://www.ncbi.nlm.nih.gov/projects/SNP/). Please note that the term "polymorphism" when used in the context of gene sequences should not be confused with the term "polymorphism" when used in the context of solid state form of a compound, that is the crystalline or amorphous nature of a compound. The skilled person will understand the intended meaning by its context.

"Probe" refers to single stranded sequence-specific oligonucleotides which have a sequence that is exactly complementary to the target sequence of the allele to be detected.

"Response" is defined by measurements taken according to Response Evaluation Criteria in Solid Tumours (RECIST) involving the classification of patients into two main groups: those that show a partial response or stable disease and those that show signs of progressive disease.

"Stringent hybridisation conditions" refers to an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulphate, and 20 pg/ml denatured, sheared salmon sperm DNA, followed by washing the filters in 0.1×SSC at about 65° C.

"Survival" encompasses a patients' overall survival and progression-free survival.

"Overall survival" (OS) is defined as the time from the initiation of drug administration to death from any cause. "Progression-free survival" (PFS) is defined as the time from the initiation of drug administration to first appearance of progressive disease or death from any cause.

According to one aspect, the present disclosure provides a method for selecting a cancer patient suitable for treatment with a compound of Formula (I), the method comprising;

(a) testing a cancer patient to determine whether the KRAS gene in the patient's tumour is wild type or mutant; and selecting a patient for treatment with a compound of Formula (I) based thereon.

In one embodiment, the status of the KRAS gene in a patient's tumour is determining from a biological sample obtained from said patient In one embodiment the biological sample is a tumour cell containing sample. In one embodiment the biological sample is one that contains tumour DNA, such as a blood sample. According to one aspect of the present disclosure there is provided a method for selecting a patient for treatment with a compound of Formula (I), the method comprising obtaining a sample from a patient that comprises tumour cells or nucleic acid from the tumour cell; determining whether the KRAS gene in the patient's tumour cells is wild type or mutant; and selecting a patient for treatment with a compound of Formula (I) based thereon.

The method may include or exclude the actual patient sample isolation step. Thus, according to one aspect of the present disclosure there is provided a method for selecting a patient for treatment with a compound of Formula (I), the method comprising determining whether the KRAS gene in a tumour cell or nucleic acid containing sample previously isolated from the patient is wild type or mutant; and selecting a patient for treatment with a compound of Formula (I) based thereon.

In one embodiment, the patient is selected for treatment with a compound of Formula (I) if the tumour cell has a mutant KRAS gene.

According to another aspect of the present disclosure there is provided a method for predicting a patient's responsiveness to a compound of Formula (I), the method comprising determining whether the KRAS gene in the patient's tumour cells is wild type or mutant and based thereon, predicting a patient's responsiveness to treatment with a compound of Formula (I).

According to another aspect of the present disclosure there is provided a method for determining the likelihood of effectiveness of treatment with a compound of formula I in a human patient affected with cancer comprising: determining whether the KRAS gene(s) in the patient's tumour cells is wild type or mutant and based thereon, predicting a patient's responsiveness to treatment with a compound of Formula (I).

For the purpose of the present disclosure, a gene status of wild-type is meant to indicate normal or appropriate expression of the gene and normal function of the encoded protein. In contrast, mutant status is meant to indicate abnormal or inappropriate gene expression, or expression of a protein with altered function, consistent with the known roles of mutant KRAS in cancer (as described herein). Any number of genetic or epigenetic alterations, including but not limited to mutation, amplification, deletion, genomic rearrangement, or changes in methylation profile, may result in a mutant status. However, if such alterations nevertheless result in appropriate expression of the normal protein, or a functionally equivalent variant, then the gene status is regarded as wild-type. Examples of variants that typically would not result in a functional mutant gene status include synonomous coding variants and common polymorphisms (synonymous or non-synonymous). As discussed below, gene status can be assessed by a functional assay, or it may be inferred from the nature of detected deviations from a reference sequence.

In certain embodiments the wild-type or mutant status of the KRAS gene is determined by the presence or absence of non-synonymous nucleic acid variations in the genes. Observed non-synonymous variations corresponding to known common polymorphisms with no annotated functional effects do not contribute to a gene status of mutant.

KRAS Gene bank accession details: KRAS NM_004985

It will be apparent that the gene and mRNA sequences disclosed for KRAS and the KRAS protein sequence are each a representative sequence. In normal individuals there are two copies of each gene, a maternal and paternal copy, which will likely have some sequence differences, moreover within a population there will exist numerous allelic variants of the gene sequence. Other sequences regarded as wild type include those that possess one or more synonymous changes to the nucleic acid sequence (which changes do not alter the encoded protein sequence), non-synonymous common polymorphisms (e.g. germ-line polymorphisms) which alter the protein sequence but do not affect protein function, and intronic non-splice-site sequence changes.

According to another aspect of the present disclosure there is provided a method for determining the likelihood of effectiveness of treatment with a compound of Formula (I) in a human patient affected with cancer comprising: detecting the presence or absence of at least one non-synonymous nucleic acid variance in the KRAS gene of said patient relative to the wild type gene, wherein the presence of at least one somatic non-synonymous nucleic acid variance in the KRAS gene indicates that treatment with the compound of Formula (I) is likely to be effective.

According to another aspect of the present disclosure there is provided a method for assessing the susceptibility of an individual to treatment with a compound of Formula (I), which method comprises:
  (i) determining the non-synonymous mutation status of the KRAS gene in tumour cell nucleic acid from the individual; and,
  (ii) determining the likely susceptibility of the individual to treatment with a compound of Formula (I) by reference to the non-synonymous mutation status of the KRAS gene in the tumour cells.

There are numerous techniques available to the person skilled in the art to determine the gene status of KRAS. The gene status can be determined by determination of the nucleic acid sequence. This could be via direct sequencing of the full-length gene or analysis of specific sites within the gene, e.g. commonly mutated sites.

An alternative means for determining whether or not the KRAS gene is wild type or mutant is to assess the function of the transcribed gene. Functional mutation of this KRAS gene produces a protein that has impaired GTP hydrolysis capability. Mutant KRAS persists in an active, GTP-bound state, leading to constitutive and deregulated stimulation of downstream signalling of the pathway in cells, including but not limited to activation of Raf, PI3K and Ral pathways.

The assays to assess the functional status of KRAS variants when expressed in cells include but are not limited to:
  (i) increased binding to the Ras binding domain (RBD) of Raf1
  (ii) increased levels of phosphorylated ERK1/2, MEK1/2, or Akt;
  (iii) increased focus and colony formation of NIH-3T3 cells transfected with the variant of KRAS Samples The patient's sample to be tested for the gene status can be any tumour tissue, tumour-cell containing or tumour nucleic acid containing sample obtained or obtainable from the individual. The test sample is conveniently a sample of blood, mouth swab, biopsy, or other body fluid or tissue obtained from an individual. Particular examples include: circulating tumour cells, circulating DNA in the plasma or serum, cells isolated from the ascites fluid of ovarian cancer patients, lung sputum for patients with tumours within the lung, a fine needle aspirate from a breast cancer patient, urine, peripheral blood, a cell scraping, a hair follicle, a skin punch or a buccal sample.

It will be appreciated that the test sample may equally be a nucleic acid sequence corresponding to the sequence in the test sample, that is to say that all or a part of the region in the sample nucleic acid may firstly be amplified using any convenient technique e.g. polymerase chain reaction (PCR), before analysis. The nucleic acid may be genomic DNA or fractionated or whole cell RNA. In particular embodiments the RNA is whole cell RNA and is used directly as the template for labelling a first strand cDNA using random primers or poly A primers. The nucleic acid or protein in the test sample may be extracted from the sample according to standard methodologies (see Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.).

The diagnostic methods of the present disclosure can be undertaken using a sample previously taken from the individual or patient. Such samples may be preserved by freezing or fixed and embedded in formalin-paraffin or other media. Alternatively, a fresh tumour cell containing sample may be obtained and used.

The methods of the present disclosure can be applied using cells from any tumour. Suitable tumours for treatment with a compound of Formula (I) have been described hereinbefore.

Methods for Detection of Nucleic Acids

The detection of mutant KRAS nucleic acids can be employed, in the context of the present disclosure, to predict the response to drug treatment. Since mutations in these genes occur at the DNA level, the methods of the present disclosure can be based on detection of mutations or variances in genomic DNA, as well as transcripts and proteins themselves. It can be desirable to confirm mutations in genomic DNA by analysis of transcripts and/or polypeptides, in order to ensure that the detected mutation is indeed expressed in the subject.

It will be apparent to the person skilled in the art that there are a large number of analytical procedures which may be used to detect the presence or absence of variant nucleotides at one or more positions in a gene. In general, the detection of allelic variation requires a mutation discrimination technique, optionally an amplification reaction (such as one based on polymerase chain reaction) and optionally a signal generation system. There are a multitude of mutation detection techniques available in the art and these may be used in combination with a signal generation system, of which there are numerous available in the art. Many methods for the detection of allelic variation are reviewed by Nollau et al., *Clin. Chem.*, 1997, 43, 1114-1120; Anderson S M. *Expert Rev Mol Diagn.*, 2011, 11, 635-642; Meyerson M. et al., *Nat Rev Genet.*, 2010, 11, 685-696; and in standard textbooks, for example "*Laboratory Protocols for Mutation Detection*", Ed. by U. Landegren, Oxford University Press, 1996 and "PCR", $2^{nd}$ Edition by Newton & Graham, BIOS Scientific Publishers Limited, 1997.

As noted above, determining the presence or absence of a particular variance or plurality of variances in the KRAS gene in a patient with cancer can be performed in a variety of ways. Such tests are commonly performed using DNA or RNA collected from biological samples, e.g., tissue biopsies, urine, stool, sputum, blood, cells, tissue scrapings, breast aspirates or other cellular materials, and can be performed by a variety of methods including, but not limited to, PCR, hybridization with allele-specific probes, enzymatic mutation detection, chemical cleavage of mismatches, mass spectrometry or DNA sequencing, including minisequencing.

Suitable mutation detection techniques include amplification refractory mutation system (ARMS™), amplification refractory mutation system linear extension (ALEX™), competitive oligonucleotide priming system (COPS), Taqman, Molecular Beacons, restriction fragment length polymorphism (RFLP), and restriction site based PCR and fluorescence resonance energy transfer (FRET) techniques.

In particular embodiments the method employed for determining the nucleotide(s) within a biomarker gene is selected from: allele-specific amplification (allele specific PCR)—such as amplification refractory mutation system (ARMS), sequencing, allelic discrimination assay, hybridisation, restriction fragment length polymorphism (RFLP) or oligonucleotide ligation assay (OLA).

Generation of nucleic acids for analysis from samples generally requires nucleic acid amplification. Many amplification methods rely on an enzymatic chain reaction (such as a polymerase chain reaction, a ligase chain reaction, or a self-sustained sequence replication) or from the replication of all or part of the vector into which it has been cloned. Preferably, the amplification according to the present disclosure is an exponential amplification, as exhibited by for example the polymerase chain reaction.

Many target and signal amplification methods have been described in the literature, for example, general reviews of these methods in Landegren, U., et al., *Science*, 1988 242, 229-237 and Lewis, R., *Genetic Engineering News* 1990, 10, 54-55. These amplification methods can be used in the methods of the present disclosure, and include polymerase chain reaction (PCR), PCR in situ, ligase amplification reaction (LAR), ligase hybridisation, Qβ bacteriophage replicase, transcription-based amplification system (TAS), genomic amplification with transcript sequencing (GAWTS), nucleic acid sequence-based amplification (NASBA) and in situ hybridisation. Primers suitable for use in various amplification techniques can be prepared according to methods known in the art.

Polymerase Chain Reaction (PCR) PCR is a nucleic acid amplification method described inter alia in U.S. Pat. Nos. 4,683,195 and 4,683,202. PCR consists of repeated cycles of DNA polymerase generated primer extension reactions. The target DNA is heat denatured and two oligonucleotides, which bracket the target sequence on opposite strands of the DNA to be amplified, are hybridised. These oligonucleotides become primers for use with DNA polymerase. The DNA is copied by primer extension to make a second copy of both strands. By repeating the cycle of heat denaturation, primer hybridisation and extension, the target DNA can be amplified a million fold or more in about two to four hours. PCR is a molecular biology tool, which must be used in conjunction with a detection technique to determine the results of amplification. An advantage of PCR is that it increases sensitivity by amplifying the amount of target DNA by 1 million to 1 billion fold in approximately 4 hours. PCR can be used to amplify any known nucleic acid in a diagnostic context (Mok et al., *Gynaecologic Oncology*, 1994, 52: 247-252,).

An allele specific amplification technique such as Amplification Refractory Mutation System (ARMS™) (Newton et al., *Nucleic Acids Res.*, 1989, 17, 2503-2516) can also be used to detect single base mutations. Under the appropriate PCR amplification conditions a single base mismatch located at the 3'-end of the primer is sufficient for preferential amplification of the perfectly matched allele (Newton et al., 1989, supra), allowing the discrimination of closely related species. The basis of an amplification system using the primers described above is that oligonucleotides with a mismatched 3'-residue will not function as primers in the PCR under appropriate conditions. This amplification system allows genotyping solely by inspection of reaction mixtures after agarose gel electrophoresis.

Analysis of amplification products can be performed using any method capable of separating the amplification products according to their size, including automated and manual gel electrophoresis, mass spectrometry, and the like.

The methods of nucleic acid isolation, amplification and analysis are routine for one skilled in the art and examples of protocols can be found, for example, Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.) Particularly useful protocol source for methods used in PCR amplification is *PCR (Basics: From Background to Bench)* by M. J. McPherson, S. G. Mailer, R. Beynon, C. Howe, Springer Verlag; 1st edition (Oct. 15, 2000), ISBN: 0387916008.

According to another aspect of the present disclosure there is provided the use of a compound of Formula (I) to treat a cancer patient whose tumour cells have been identified as possessing a mutant KRAS gene.

According to another aspect of the present disclosure there is provided a compound of Formula (I) for treating cancers with tumour cells identified as harbouring mutant KRAS gene.

In still further embodiments, the present disclosure relates to pharmaceutical composition comprising a compound of Formula (I) for use in the prevention and treatment of cancer with tumour cells identified as harbouring a mutant KRAS gene.

For all the aspects above, mutant forms of KRAS determined/identified are at all positions across the gene.

In further aspects, compounds of the present disclosure may also be useful in treating BRAF mutant cancers. The information provided above within this personalised Healthcare section for KRAS mutant cancers may analogously be applied to BRAF resistant cancers, other than Gene Bank Accession details. BRAF gene bank accession details: BRAF NM_004333.

EXAMPLES

Figure 1:
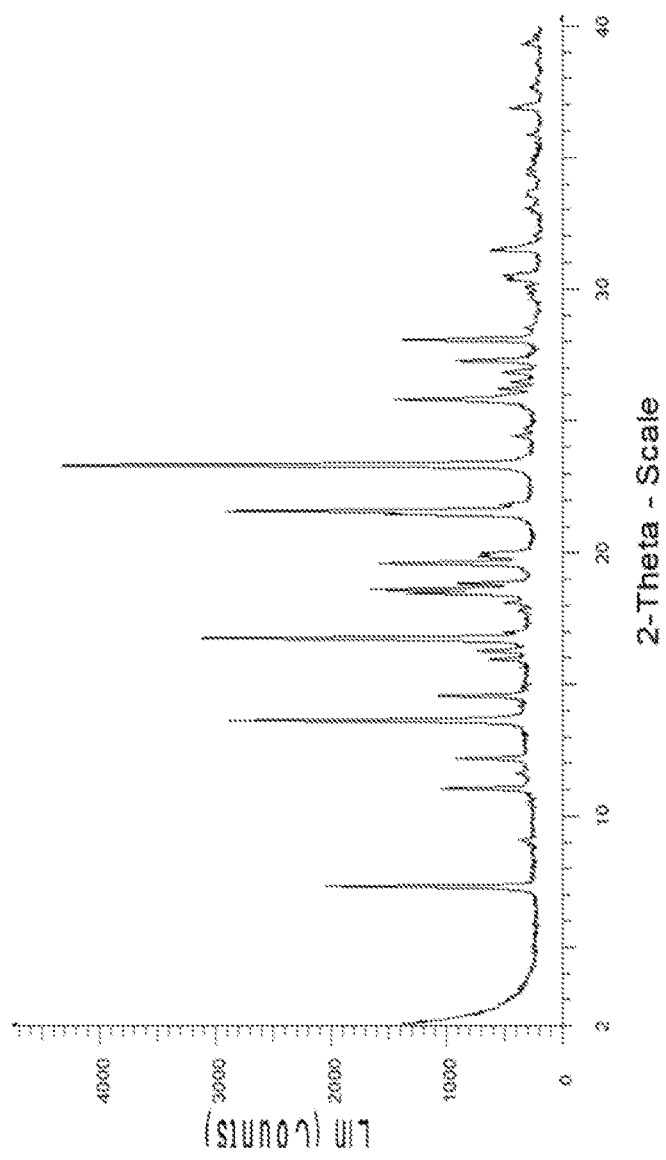
FIG. 1 shows the X-Ray Powder Diffraction Pattern of (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct Form 1 (Example 18a).

The present disclosure will now be illustrated in the following Examples in which, generally:
  (i) operations were carried out at ambient temperature, i.e. in the range 17 to 25° C. and under an atmosphere of an inert gas such as nitrogen unless otherwise stated;
  (ii) evaporations were carried out by rotary evaporation or utilising Genevac equipment or Biotage v10 evaporator in vacuo and work-up procedures were carried out after removal of residual solids by filtration;
  (iii) flash chromatography purifications were performed on an automated Teledyne Isco CombiFlash® Rf or Teledyne Isco CombiFlash® Companion® using pre-packed RediSep Rf Gold™ Silica Columns (20-40 m, spherical particles), GraceResolv™ Cartridges (Davisil® silica) or Silicycle cartridges (40-63 µm).
  (iv) preparative chromatography was performed on a Gilson prep HPLC instrument with UV collection;
  (v) chiral preparative chromatography was performed on a Gilson instrument with UV collection (233 injector/fraction collector, 333 & 334 pumps, 155 UV detector), or an Interchim PuriFlash 4250-250 system or a Novasep LC50 system with Knauer K2501 UV detector;
  (vi) yields, where present, are not necessarily the maximum attainable;
  (vii) in general, the structures of end-products of the Formula I were confirmed by nuclear magnetic resonance (NMR) spectroscopy; NMR chemical shift values were measured on the delta scale [proton magnetic resonance spectra were determined using a Bruker Avance 500 (500 MHz) or Bruker Avance 400 (400 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal; where "DMSO" is referred to as a solvent used in NMR it is understood to be d6-DMSO;
  (viii) in general, end-products of the Formula I were also characterised by mass spectroscopy following liquid chromatography (LCMS or UPLC); UPLC was carried out using a Waters UPLC fitted with Waters SQ mass spectrometer (Column temp 40, UV=220-300 nm, Mass Spec=ESI with positive/negative switching) at a flow rate of 1 ml/min using a solvent system of 97% A+3% B to 3% A to 97% B over 1.50 mins (total runtime with equilibration back to starting conditions etc 1.70 min), where A=0.1% formic acid in water (for acid work) or 0.1% ammonia in water (for base work) B=acetonitrile. For acid analysis the column used was Waters Acquity HSS T3 1.8™ 2.1×50 mm, for base analysis the column used was Waters Acquity BEH 1.7 µm 2×50 mm; LCMS was carried out using a Waters Alliance HT (2795) fitted with a Waters ZQ ESCi mass spectrometer and a Phenomenex Gemini-NX (50×2.1 mm 5 µm) column at a flow rate of 1.1 ml/min 95% A to 95% B over 4 min with a 0.5 min hold. The modifier is kept at a constant 5% C (50:50 acetonitrile:water 0.1% formic acid) or D (50:50 acetonitrile:water 0.1% ammonium hydroxide (0.88 SG) depending on whether it is an acidic or basic method.

(ix) ion exchange purification was generally performed using a SCX-2 (Biotage, Propylsulfonic acid functionalized silica. Manufactured using a trifunctional silane. Non end-capped) cartridge.

(x) intermediate purity was assessed by thin layer chromatographic, mass spectral, HPLC (high performance liquid chromatography) and/or NMR analysis.

(xi) X-Ray Powder Diffraction was performed using a Bruker D4. The X-ray powder diffractogram was determined by mounting a sample of the crystalline material on a Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 angstroms. The collimated X-ray source was passed through an automatic variable divergence slit set at V20 and the reflected radiation directed through a 5.89 mm anti scatter slit and a 9.55 mm detector slit. Samples were measured in reflection geometry in 0-2θ configuration over the scan range 2° to 40' 2θ with a nominal 0.12 second exposure per 0.02° increment. The instrument was equipped with a Position sensitive detector (Lynxeye). Persons skilled in the art of X-ray powder diffraction will understand that the relative intensity of peaks can be affected by, for example, grains above 30 microns in size and non-unitary aspect ratios that may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

(xii) Differential Scanning Calorimetry (DSC) was performed using a TA Instruments Q2000 DSC. Typically less than 5 mg of material contained in a standard aluminium pan fitted with a lid was heated over the temperature range 25° C. to 300° C. at a constant heating rate of 10° C. per minute. A purge gas using nitrogen was used—flow rate 50 ml per minute.

(xiii) the following abbreviations have been used:—

2nd Generation XantPhos precatalyst Chloro[(4,5-bis(diphenylphosphino)-9,9-dimethylxanthene)-2-(2'-amino-1,1'-biphenyl)]palladium(II)
18-crown-6 1,4,7,10,13,16-hexaoxacyclooctadecane
aq. Aqueous
atm a unit of atmospheric pressure
Boc tert-Butoxycarbonyl
BrettPhos 3rd generation precatalyst [2-(di-1-adamantylphosphino)-2',4',6'-triisopropyl-3,6-dimethoxybiphenyl][2-(2'-amino-1,1'-biphenyl)]palladium(II) methanesulfonate
CDCl$_3$ deutero-chloroform
DAST (diethylamino)sulfur trifluoride
DCM dichloromethane
DIEA N,N-diisopropylethylamine
DIPEA diisopropylethylamine
DMF dimethylformamide
DMSO dimethyl sulphoxide
DSC differential scanning calorimetry
EtOH ethanol
EtOAc ethyl acetate
IPA iso-propylalcohol
MeOH methanol
MeTHF rac-2-methyltetrahydrofuran
NBS N-bromosuccinimide
Pd$_2$dba$_3$ tris(dibenzylideneacetone)dipalladium(0)
rt/RT room temperature
sat. Saturated
SEM-Cl 2-(Trimethylsilyl)ethoxymethyl chloride
TEA triethylamine
THF tetrahydrofuran
Tos tosyl
XPhos 2nd generation precatalyst Chloro(2-dicyclohexylphosphino-2',4',6'-triisopropyl-1,1'-biphenyl) [2-(2'-amino-1,1'-biphenyl)]palladium(II)
XRPD X-Ray Powder Diffraction Example 1

2-(2-((1-Methyl-1H-pyrazol-5-yl)amino)pyrimidin-4-yl)-7-((6-methylpyridin-2-yl)methyl)-6,7-dihydroimidazo[1,2-a]pyrazin-8(5H)-one

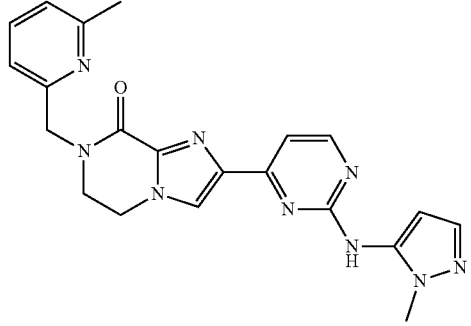 [SMILES: Cc1cccc(CN2CCn3cc(-c4ccnc(Nc5ccnn5C)n4)nc3C2=O)n1]

NaH (12.05 mg, 0.50 mmol) was added to 7-((6-methylpyridin-2-yl)methyl)-2-(2-(methylsulfonyl)pyrimidin-4-yl)-6,7-dihydroimidazo[1,2-a]pyrazin-8(5H)-one (Intermediate 1; 100 mg, 0.25 mmol) and N-(1-methyl-1H-pyrazol-5-yl)formamide (Intermediate 2; 94 mg, 0.75 mmol) in THF (1.5 mL) at 25° C. under nitrogen. The resulting solution was stirred at 25° C. for 3 hours. EtOH (2 mL) was added, and stirred for 10 min. The reaction mixture was quenched with water (50 mL) and extracted into EtOAc (30×25 mL), the organic layer was dried over Na$_2$SO$_4$, filtered and evaporated to afford crude product. The crude product was purified by preparative HPLC (Waters XBridge Prep C18 OBD column, 5µ silica, 19 mm diameter, 100 mm length), using decreasingly polar mixtures of water (containing 0.1% NH₄HCO₃) and MeCN as eluents. Fractions containing the desired compound were evaporated to dryness to afford 2-(2-((1-methyl-1H-pyrazol-5-yl)amino)pyrimidin-4-yl)-7-((6-methylpyridin-2-yl)methyl)-6,7-dihydroimidazo[1,2-a]pyrazin-8(5H)-one (Example 1; 40 mg, 38%) as a white solid. ¹HNMR (300 MHz, DMSO, 26° C.) δ 2.51 (3H, s), 3.70 (3H, s), 3.84-3.88 (2H, m), 4.40-4.44 (2H, m), 4.76 (2H, s), 6.30 (1H, s), 7.14-7.18 (2H, m), 7.32-7.35 (2H, m), 7.64-7.69 (1H, m), 7.93 (1H, s), 8.46 (1H, d), 9.38 (1H, s). m/z (ES+), [M+H]+=416.

Intermediate 1

7-((6-Methylpyridin-2-yl)methyl)-2-(2-(methylsulfonyl)pyrimidin-4-yl)-6,7-dihydroimidazo[1,2-a]pyrazin-8(5H)-one

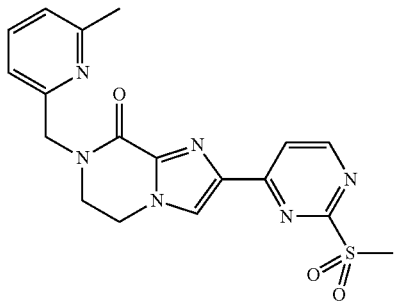 [SMILES: Cc1cccc(CN2CCn3cc(-c4ccnc(S(C)(=O)=O)n4)nc3C2=O)n1]

Potassium persulfate (1.01 g, 3.75 mmol) was added portionwise to 7-((6-methylpyridin-2-yl)methyl)-2-(2-(methylthio)pyrimidin-4-yl)-6,7-dihydroimidazo[1,2-a]pyrazin-8(5H)-one (Intermediate 3; 275 mg, 0.75 mmol) in MeOH (5 mL) at 25° C. under nitrogen. The resulting mixture was stirred at 25° C. for 12 hours. The reaction was then heated to 40° C. and stirred for a further 6 hours. The reaction mixture was then diluted with DCM (100 mL), and washed with water (25 mL×2). The organic layer was dried over Na₂SO₄, filtered and evaporated to afford crude product. The crude product was purified by flash silica chromatography, elution gradient 0 to 10% MeOH in DCM. Pure fractions were evaporated to dryness to afford 7-((6-methylpyridin-2-yl)methyl)-2-(2-(methylsulfonyl)pyrimidin-4-yl)-6,7-dihydroimidazo[1,2-a]pyrazin-8(5H)-one (Intermediate 1; 210 mg, 70%) as a white solid. ¹HNMR (300 MHz, DMSO, 26° C.) δ 2.50 (3H, s), 3.46 (3H, s), 3.85-3.95 (2H, m), 4.42-4.46 (2H, m), 4.86 (2H, s), 7.15-7.20 (2H, m), 7.64-7.69 (1H, m), 8.15 (1H, d), 8.40 (1H, s), 9.05 (1H, d). m/z (ES+), [M+H]+=399.

Intermediate 2

N-(1-Methyl-1H-pyrazol-5-yl)formamide

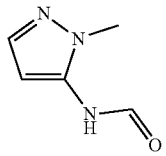

Formic acid (3.1 mL, 67.35 mmol) was added to acetic anhydride (7.7 mL, 75.42 mmol) to give a colourless solution. The resulting solution was stirred at 45° C. for 45 minutes. The reaction mixture was then cooled to 0° C. and 1-methyl-1H-pyrazol-5-amine (2 g, 20.59 mmol) was added. The resulting solution was stirred at 0° C. for 10 minutes. The reaction mixture was then poured into a mixture of water (50 mL) and EtOAc (50 mL) and the reaction mixture was adjusted to pH 8 with saturated K₂CO₃. The aqueous layer was extracted with EtOAc (6×50 mL) and washed with water (2×50 mL). The combined organic phases were dried over Na₂SO₄, filtered and evaporated to afford desired product N-(1-methyl-1H-pyrazol-5-yl)formamide (Intermediate 2; 1.21 g, 47%) as white solid. ¹H-NMR (300 MHz, CDCl₃, 26° C.) 3.80 (3H, s), 6.11 (1H, s), 7.44 (2H, s), 8.35 (1H, s). m/z (ES+), [M+H]+=126.

Intermediate 3

7-((6-Methylpyridin-2-yl)methyl)-2-(2-(methylthio)pyrimidin-4-yl)-6,7-dihydroimidazo[1,2-a]pyrazin-8(5H)-one

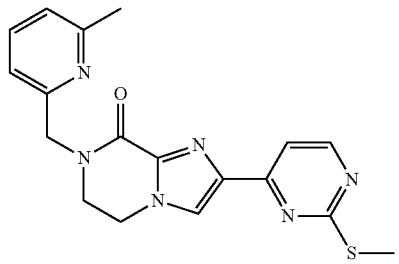 [SMILES: CSc1nccc(-c2cn3c(n2)C(=O)N(Cc2cccc(C)n2)CC3)n1]

4-Tributylstannyl-2-thiomethylpyrimidine (2.66 g, 6.41 mmol) was added to 2-bromo-7-((6-methylpyridin-2-yl)methyl)-6,7-dihydroimidazo[1,2-a]pyrazin-8(5H)-one (Intermediate 4; 1.87 g, 5.82 mmol) and Pd-118 ([1,1'-Bis(di-tert-butylphosphino)ferrocene]dichloropalladium(II)) (0.204 g, 0.29 mmol) in DMF (5 mL) under nitrogen. The resulting solution was stirred at 150° C. in a microwave reactor for 8 hours. The reaction mixture was filtered through celite, diluted with EtOAc (200 mL), and washed sequentially with water (50 mL×2). The combined organic layers were dried over Na₂SO₄, filtered and evaporated to afford crude product. The crude product was purified by C18-flash chromatography, elution gradient 0 to 50% MeCN in water. Pure fractions were evaporated to dryness to afford 7-((6-methylpyridin-2-yl)methyl)-2-(2-(methylthio)pyrimidin-4-yl)-6,7-dihydroimidazo[1,2-a]pyrazin-8(5H)-one (Intermediate 3; 0.28 g, 13%) as a grey solid. ¹H-NMR (400 MHz, CDCl₃, 22° C.) δ 2.50 (3H, s), 2.63 (3H, s), 3.85-3.89 (2H, m), 4.39-4.43 (2H, m), 4.85 (2H, s), 7.15-7.19 (2H, m), 7.59-7.69 (2H, m), 8.23 (1H, s), 8.63 (1H, d). m/z (ES+), [M+H]+=367.

Intermediate 4

2-Bromo-7-((6-methylpyridin-2-yl)methyl)-6,7-dihydroimidazo[1,2-a]pyrazin-8(5H)-one

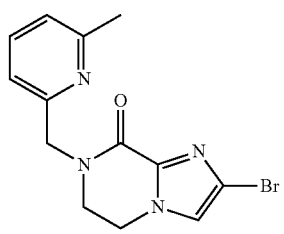 [SMILES: Cc1cccc(CN2CCn3cc(Br)nc3C2=O)n1]

Sodium acetate (3.24 g, 39.6 mmol) was added portionwise to ethyl 1-(2-aminoethyl)-4-bromo-1H-imidazole-2-carboxylate dihydrochloride (Intermediate 5; 5.3 g, 15.8 mmol) and 6-Methyl-2-pyridinecarboxaldehyde (1.92 g, 15.8 mmol) in MeOH (100 mL) cooled to 0° C. under nitrogen. The resulting solution was then stirred at 0° C. for 15 minutes. Sodium triacetoxyborohydride (10.1 g, 47.5 mmol) was added potionwise at 0° C. and the resulting solution was stirred at room temperature for 12 hours. The reaction mixture was then adjusted to pH 7-8 with saturated NaHCO₃ and diluted with DCM (250 mL). The DCM phase was then washed sequentially with water (50 mL×2). The combined organic phases were dried over Na₂SO₄, filtered and evaporated to afford crude product. The crude product was purified by flash silica chromatography, elution gradient 0 to 9% MeOH in DCM. Pure fractions were evaporated to dryness to afford 2-bromo-7-((6-methylpyridin-2-yl)methyl)-6,7-dihydroimidazo[1,2-a]pyrazin-8(5H)-one (Intermediate 4; 2.5 g, 49%) as a white solid. ¹H-NMR (300 MHz, DMSO, 27° C.) δ 2.44 (3H, s), 3.80-3.84 (2H, m), 4.28-4.32 (2H, m) 4.73 (2H, s), 7.13-7.16 (2H, m), 7.63-7.68 (1H, m), 7.96 (1H, s). m/z (ES+), [M+H]+=321.

Intermediate 5

Ethyl 1-(2-aminoethyl)-4-bromo-1H-imidazole-2-carboxylate dihydrochloride

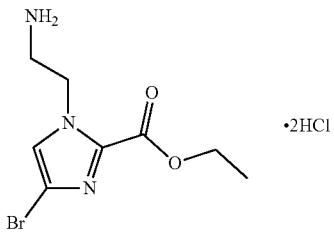

Ethyl 4-bromo-1-(2-((tert-butoxycarbonyl)amino)ethyl)-1H-imidazole-2-carboxylate (Intermediate 6; 4.6 g, 12.70 mmol) was added to HCl (excess) in 1,4-dioxane (40 mL) and the resulting solution stirred at room temperature for 2 hours. The solvent was removed under reduced pressure and the resulting solid was titrated with heptane and filtered to afford ethyl 1-(2-aminoethyl)-4-bromo-1H-imidazole-2-carboxylate (Intermediate 5; 5.30 g, 140%) as white solid. ¹H-NMR (300 MHz, DMSO, 25° C.) δ 1.33 (3H, t), 3.03-3.16 (2H, m), 4.35 (2H, q), 4.63 (2H, t), 7.34 (1H, s).

Intermediate 6

Ethyl 4-bromo-1-(2-((tert-butoxycarbonyl)amino)ethyl)-1H-imidazole-2-carboxylate

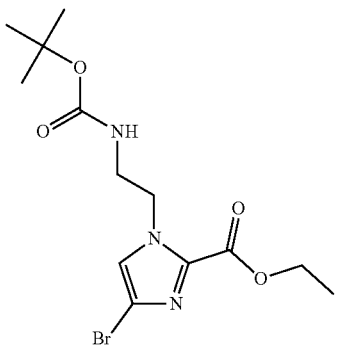 [SMILES: CCOC(=O)c1nc(Br)cn1CCNC(=O)OC(C)(C)C]

NBS (10.05 g, 56.5 mmol) was added portionwise to ethyl 1-(2-((tert-butoxycarbonyl)amino)ethyl)-1H-imidazole-2-carboxylate (Intermediate 7; 16 g, 56.5 mmol) in DCM (80 mL) and DMF (80 mL) at 0° C. under nitrogen. The resulting solution was then stirred at 0° C. temperature for 12 hours. The reaction mixture was diluted with DCM (300 mL), and washed sequentially with water (100 mL×2). The organic layer was dried over Na₂SO₄, filtered and evaporated to afford crude product. The crude product was purified by flash silica chromatography, elution gradient 0 to 20% EtOAc in DCM. Pure fractions were evaporated to dryness to afford ethyl 4-bromo-1-(2-((tert-butoxycarbonyl)amino)ethyl)-1H-imidazole-2-carboxylate (Intermediate 6; 4.60 g, 22.49%) as a white solid. ¹H-NMR (300 MHz, DMSO, 27° C.) δ 1.39-1.44 (12H, m), 3.47-3.53 (2H, m), 4.37-4.44 (2H, q), 4.53 (1H, s), 7.04 (1H, s). m/z (ES+), [M+H]+=362.

Intermediate 7

Ethyl 1-(2-((tert-butoxycarbonyl)amino)ethyl)-1H-imidazole-2-carboxylate

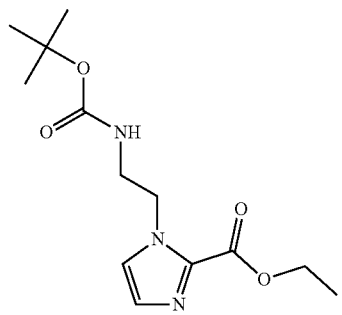 [SMILES: CCOC(=O)c1nccn1CCNC(=O)OC(C)(C)C]

tert-Butyl (2-bromoethyl)carbamate (17.59 g, 78.49 mmol) was added to ethyl 1H-imidazole-2-carboxylate (10 g, 71.36 mmol) and K₂CO₃ (11.83 g, 85.63 mmol) in DMF (200 mL) under nitrogen and the resulting mixture stirred at 80° C. for 8 hours. The reaction mixture was diluted with EtOAc (300 mL), and washed sequentially with water (50 mL×2). The aqueous layer was then further extracted with EtOAc (50 mL×5). The combined organic phases were dried over MgSO₄, filtered and evaporated to afford crude product. The crude product was purified by flash silica chromatography, elution gradient 0 to 100% EtOAc in petroleum ether. Pure fractions were evaporated to dryness to afford ethyl 1-(2-((tert-butoxycarbonyl)amino)ethyl)-1H-imidazole-2-carboxylate (Intermediate 7; 10.7 g, 53%) as a colourless liquid. ¹HNMR (400 MHz, DMSO, 21° C.) δ 1.20 (3H, t), 1.29 (9H, s), 3.26-3.34 (2H, m) 4.27 (2H, q), 4.32-4.40 (2H, m), 6.90 (1H, s), 7.06 (1H, s), 7.32 (1H, s).

Example 2

(S)-7-(3-Chlorobenzyl)-6-methyl-2-(2-((1-methyl-1H-pyrazol-5-yl)amino)pyrimidin-4-yl)-6,7-dihydroimidazo[1,2-a]pyrazin-8(5H)-one

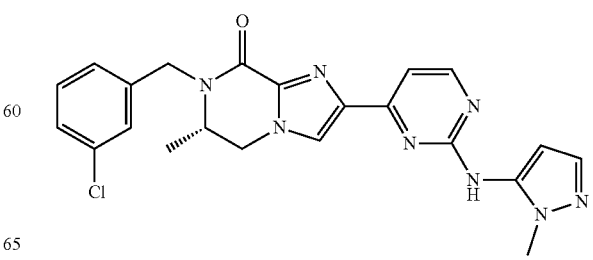

(S)-7-(3-Chlorobenzyl)-2-(2-chloropyrimidin-4-yl)-6-methyl-6,7-dihydroimidazo[1,2-a]pyrazin-8(5H)-one (Intermediate 8; 216 mg, 0.56 mmol), 1-methyl-1H-pyrazol-5-amine (59.4 mg, 0.61 mmol), cesium carbonate (363 mg, 1.11 mmol) and BrettPhos 3rd generation pre-catalyst (25.2 mg, 0.03 mmol) were suspended in tert-butanol (8 mL) and de-gassed with nitrogen for 10 minutes. The reaction was heated to 80° C. for 2 days under nitrogen. The reaction was then allowed to cool to room temperature, diluted with ethyl acetate (100 mL) and washed with saturated aqueous sodium bicarbonate (25 mL). The organic phases were dried over $Na_2SO_4$ and concentrated in vacuo to give a brown solid (250 mg). The solid was taken up in DMSO (5 mL) and filtered. The DMSO solution of crude product was then purified by preparative HPLC (Waters XBridge Prep C18 OBD column, 5μ silica, 30 mm diameter, 100 mm length), using decreasingly polar mixtures of water (containing 1% $NH_3$) and MeCN as eluents. Solvent was removed from the fractions containing product and the solid was dissolved in a mixture of DCM and methanol, then absorbed onto silica gel. The crude product was then purified by flash silica chromatography, elution gradient 0 to 15% MeOH in EtOAc. Pure fractions were evaporated to dryness to afford (S)-7-(3-chlorobenzyl)-6-methyl-2-(2-((1-methyl-1H-pyrazol-5-yl)amino)pyrimidin-4-yl)-6,7-dihydroimidazo[1,2-a]pyrazin-8(5H)-one (Example 2; 43 mg, 17.22%) as a white solid. $^1$H NMR (400 MHz, DMSO, 30° C.) 1.13 (3H, d), 3.71 (3H, s), 3.95-4.02 (1H, m), 4.28-4.45 (3H, m), 5.07 (1H, d), 6.31 (1H, d), 7.32-7.43 (5H, m), 7.46 (1H, s), 7.92 (1H, s), 8.48 (1H, d), 9.33 (1H, s). m/z: ES+[M+H]+ 449.

Intermediate 8

(S)-7-(3-Chlorobenzyl)-2-(2-chloropyrimidin-4-yl)-6-methyl-6,7-dihydroimidazo[1,2-a]pyrazin-8(5H)-one

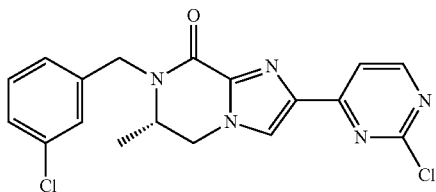 [SMILES: C[C@H]1Cn2cc(-c3ccnc(Cl)n3)nc2C(=O)N1Cc1cccc(Cl)c1]

Sodium hydride (60% dispersion) (25.03 mg, 0.63 mmol) was added to (S)-2-(2-chloropyrimidin-4-yl)-6-methyl-6,7-dihydroimidazo[1,2-a]pyrazin-8(5H)-one (Intermediate 9; 150 mg, 0.57 mmol) in DMF (12 mL) under nitrogen. The resulting suspension was stirred at 20° C. for 30 minutes. 3-Chlorobenzyl chloride (101 mg, 0.63 mmol) was added followed by tetrabutylammonium iodide (42.0 mg, 0.11 mmol) and the resulting solution stirred at 20° C. for 18 hours. The reaction mixture was poured into saturated aqueous $NH_4Cl$ (25 mL) and the aqueous phase extracted with EtOAc (75 mL). The organic phases were dried over $Na_2SO_4$ and concentrated in vacuo to give (S)-7-(3-chlorobenzyl)-2-(2-chloropyrimidin-4-yl)-6-methyl-6,7-dihydroimidazo[1,2-a]pyrazin-8(5H)-one (Intermediate 8; 221 mg, 100%) as a light brown solid. $^1$H NMR (400 MHz, DMSO, 21° C.) 1.13 (3H, d), 4.00 (1H, td), 4.27 (1H, dd), 4.38 (1H, d), 4.46 (1H, dd), 5.07 (1H, d), 7.36-7.4 (2H, m), 7.41 (1H, dd), 7.47 (1H, s), 7.93 (1H, d), 8.27 (1H, s), 8.75 (1H, d). m/z: ES+[M+H]+ 388.

Intermediate 9

(S)-2-(2-Chloropyrimidin-4-yl)-6-methyl-6,7-dihydroimidazo[1,2-a]pyrazin-8(5H)-one

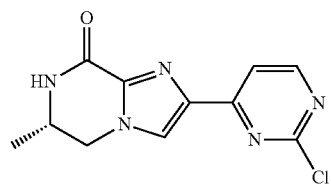 [SMILES: C[C@H]1Cn2cc(-c3ccnc(Cl)n3)nc2C(=O)N1]

A mixture of (S)-ethyl 1-(2-aminopropyl)-4-(2-chloropyrimidin-4-yl)-1H-imidazole-2-carboxylate.HCl (Intermediate 10; 2.16 g, 6.24 mmol) and 7N ammonia in methanol (107 ml, 748.7 mmol) was stirred under nitrogen at room temperature for 1 hour. The volatiles were removed under reduced pressure and the resulting solid was triturated with diethylether and DCM to afford an off white solid. The solid was further triturated with water and washed with diethylether and then absorbed on to silica from a DCM/methanol mixture. The crude product was purified by silica gel chromatography, eluting with 0-10% methanol in DCM. Pure fractions were combined and evaporated to afford a white solid, this was triturated with diethylether to afford (S)-2-(2-chloropyrimidin-4-yl)-6-methyl-6,7-dihydroimidazo[1,2-a]pyrazin-8(5H)-one (Intermediate 9; 0.6 g, 37%) as a white solid. $^1$H NMR (400 MHz, DMSO, 30° C.) 1.22 (3H, d), 3.93-4.08 (2H, m), 4.39 (1H, d), 7.89 (1H, d), 8.23 (1H, s), 8.36 (1H, s), 8.73 (1H, d). m/z: ES+[M+H]+ 264.

Intermediate 10

(S)-Ethyl 1-(2-aminopropyl)-4-(2-chloropyrimidin-4-yl)-1H-imidazole-2-carboxylate hydrochloride

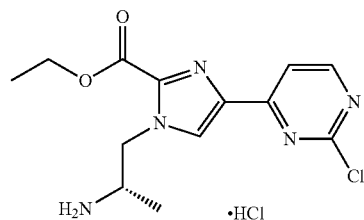 [SMILES: CCOC(=O)c1nc(-c2ccnc(Cl)n2)cn1C[C@H](C)N ; Cl]

To a solution of (S)-ethyl 1-(2-((tert-butoxycarbonyl)amino)propyl)-4-(2-chloropyrimidin-4-yl)-1H-imidazole-2-carboxylate (Intermediate 11; 2.56 g, 6.25 mmol) in 1,4-dioxane (50 mL) was added HCl (4N in 1,4-dioxane, 39 mL, 156.2 mmol) and reaction stirred at ambient temperature for 2 hours. The volatiles were removed under reduced pressure to afford (S)-ethyl 1-(2-aminopropyl)-4-(2-chloropyrimidin-4-yl)-1H-imidazole-2-carboxylate.HCl (Intermediate 10; 2.16 g) as a gum which was taken into the preparation of Intermediate 9 without further purification. m/z: ES+[M+H]+ 310.

Intermediate 11

(S)-Ethyl 1-(2-((tert-butoxycarbonyl)amino)propyl)-4-(2-chloropyrimidin-4-yl)-1H-imidazole-2-carboxylate

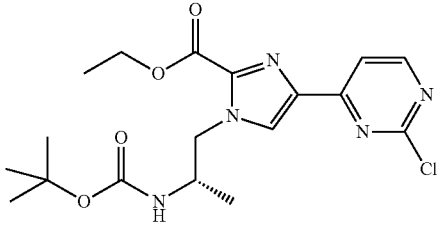 [SMILES: CCOC(=O)c1nc(-c2ccnc(Cl)n2)cn1C[C@H](C)NC(=O)OC(C)(C)C]

K$_2$CO$_3$ (4.32 g, 31.3 mmol) was added to (S)-tert-butyl 4-methyl-1,2,3-oxathiazolidine-3-carboxylate 2,2-dioxide (Intermediate 12; 2.23 g, 9.38 mmol), ethyl 4-(2-chloropyrimidin-4-yl)-1H-imidazole-2-carboxylate (Intermediate 14; 1.58 g, 6.25 mmol) and 1,4,7,10,13,16-hexaoxacyclooctadecane (0.413 g, 1.56 mmol) in 1,4-dioxane (50 mL) at 22° C. under nitrogen. The resulting mixture was stirred at 100° C. for 3 hours. Evaporation of the organic phase afforded a gum, which was suspended in dichloromethane and extracted with water and dried by passing through a phase separator cartridge. Evaporation afforded (S)-ethyl 1-(2-((tert-butoxycarbonyl)amino)propyl)-4-(2-chloropyrimidin-4-yl)-1H-imidazole-2-carboxylate (Intermediate 11; 2.56 g, 100%) as a solid. m/z: ES+[M+H]+ 410.

Intermediate 12

(4S)-tert-Butyl 4-methyl-1,2,3-oxathiazolidine-3-carboxylate 2,2-dioxide

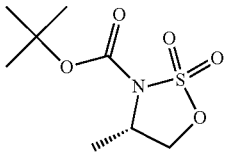

Ruthenium(III) chloride hydrate (0.062 g, 0.28 mmol) was added to a stirred mixture of tert-butyl (4S)-4-methyl-2-oxido-oxathiazolidin-2-ium-3-carboxylate (Intermediate 13; 87.36 g, 394.80 mmol) in acetonitrile (778 mL) and water (419 mL) at 15° C., followed by portionwise addition of sodium periodate (93 g, 434.29 mmol). The biphasic mixture was stirred at 20° C. for 1 hour. Water (600 mL) was added and the mixture extracted into ethyl acetate (3×600 mL). The combined organics were washed with water (500 mL), brine (250 mL), dried over MgSO$_4$, filtered and concentrated in vacuo to give (S)-tert-butyl 4-methyl-1,2,3-oxathiazolidine-3-carboxylate 2,2-dioxide (Intermediate 12; 84.3 g, 355 mmol, 90%) as an off-white solid. $^1$H NMR (400 MHz, CDCl$_3$, 30° C.) 1.51 (3H, d), 1.55 (9H, s), 4.19 (1H, dd), 4.37-4.46 (1H, m), 4.66 (1H, dd).

Intermediate 13 tert-Butyl (4S)-4-methyl-2-oxido-oxathiazolidin-2-ium-3-carboxylate

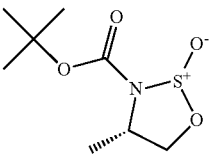

To a solution of 1H-imidazole (106 g, 1553.20 mmol) and triethylamine (124 mL, 893.09 mmol) in anhydrous dichloromethane (1427 mL) at −55° C. was added thionyl chloride (32.6 mL, 446.54 mmol) dropwise (exothermic, keeping T<−40° C.). The mixture was stirred for 5 minutes while cooling to −60° C. and a solution of (S)-tert-butyl 1-hydroxypropan-2-ylcarbamate (Sigma-Aldrich; 68.04 g, 388.30 mmol) in anhydrous dichloromethane (1427 mL) was added dropwise over 3.5 hours via a dropping funnel. The reaction mixture was stirred while warming to room temperature overnight. Water was added (750 mL) and the phases separated. The aqueous was further extracted into dichloromethane (500 mL). The combined organics were washed with water (250 mL), saturated brine (250 mL), dried over MgSO$_4$, filtered and concentrated in vacuo to give tert-butyl (4S)-4-methyl-2-oxido-oxathiazolidin-2-ium-3-carboxylate (Intermediate 13; 87.3 g, 395 mmol, 100%) as a pale oil. $^1$H NMR (400 MHz, CDCl$_3$, 30° C.) 1.50 (3H, d), 4.29 (1H, d), 4.68 (1H, t), 4.77 (1H, dd).

Intermediate 14

Ethyl 4-(2-chloropyrimidin-4-yl)-1H-imidazole-2-carboxylate

XPhos 2nd generation precatalyst (0.435 g, 0.55 mmol) was added to a degassed solution of ethyl 4-bromo-1-((2-(trimethylsilyl)ethoxy)methyl)-1H-imidazole-2-carboxylate (Intermediate 15; 3.86 g, 11.05 mmol), 4,4,4',4',5,5,5',5'-octamethyl-2,2'-bi(1,3,2-dioxaborolane) (4.21 g, 16.58 mmol) and KOAc (2.17 g, 22.10 mmol) in dioxane (100 mL) at ambient temperature under nitrogen and the resulting solution was heated to 85° C. for 3 hours. The reaction mixture was allowed to cool to 50° C. and cesium carbonate (7.20 g, 22.10 mmol), 2,4-dichloropyrimidine (1.646 g, 11.05 mmol) and water (20 mL) were added followed by Pd(PPh$_3$)$_4$ (0.638 g, 0.55 mmol) and the reaction mixture heated at 85° C. for 2 hours. The reaction mixture was then passed through celite and washed with MeOH and the volatiles removed under reduced pressure. Water and DCM were added and organic layer extracted and dried by passing through a phase separator cartridge. The volatiles were then removed under reduced pressure to afford an impure brown solid ethyl 4-(2-chloropyrimidin-4-yl)-1-((2-(trimethylsilyl)ethoxy)methyl)-1H-imidazole-2-carboxylate (4.24 g, 11.07 mmol). 2,2,2-trifluoroacetic acid (8.48 mL, 110.73 mmol) was added to ethyl 4-(2-chloropyrimidin-4-yl)-1-((2-(trimethylsilyl)ethoxy)methyl)-1H-imidazole-2-carboxylate (4.24 g, 11.07 mmol) in DCM (100 mL) and the resulting solution was stirred at ambient temperature for 2 hours and then left to stand at ambient temperature for 16 hours. The volatiles were removed under reduced pressure, the resultant solid was dissolved in DCM and water and filtered through a layer of celite. The aqueous layer was separated and basified with saturated sodium bicarbonate and extracted into DCM, then dried by passing through a phase separator cartridge and the solvent removed to afford a solid. The organic layer was passed through a phase separator cartridge, combined with the solid and pre-absorbed onto silica and subjected to silica chromatography eluting with 0-100% diethylether in DCM. Pure fractions were combined and evaporated to afford ethyl 4-(2-chloropyrimidin-4-yl)-1H-imidazole-2-carboxylate (Intermediate 14; 1.58 g, 57%) as a solid. $^1$H NMR (400 MHz, DMSO, 30° C.) 1.35 (3H, t), 4.38 (2H, q), 7.93 (1H, d), 8.19 (1H, s), 8.73 (1H, d), 13.95 (1H, s). m/z: ES+[M+H]+ 253.

Intermediate 15

Ethyl 4-bromo-1-((2-(trimethylsilyl)ethoxy)methyl)-1H-imidazole-2-carboxylate

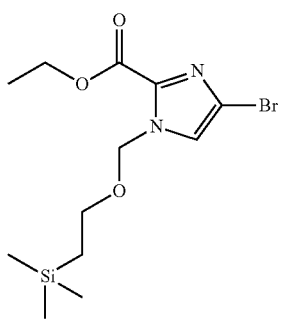 [SMILES: CCOC(=O)c1nc(Br)cn1COCC[Si](C)(C)C]

NBS (26.3 g, 147.93 mmol) was added to ethyl 1-((2-(trimethylsilyl)ethoxy)methyl)-1H-imidazole-2-carboxylate (Intermediate 16; 40 g, 147.93 mmol) in DMF (150 mL) under nitrogen and the resulting mixture stirred at 25° C. for 20 hours. The reaction mixture was quenched with water (200 mL), extracted with EtOAc (2×300 mL), the organic layers were washed with brine and dried over $Na_2SO_4$, filtered and evaporated to afford a yellow residue. The crude product was purified by flash silica chromatography, elution gradient 0 to 10% EtOAc in petroleum ether. Pure fractions were evaporated to dryness to afford ethyl 4-bromo-1-((2-(trimethylsilyl)ethoxy)methyl)-1H-imidazole-2-carboxylate (Intermediate 15; 21 g, 41%) as a colourless oil which solidified on standing. $^1$H NMR (400 MHz, CDCl$_3$, 25° C.) δ 0.02 (9H, s), 0.92-1.01 (2H, m), 1.45 (3H, t), 3.56-3.65 (2H, m), 4.45 (2H, q), 5.79 (2H, s), 7.28 (1H, s). m/z (ES+), [M+H]+=349/351.

Intermediate 16

Ethyl 1-((2-(trimethylsilyl)ethoxy)methyl)-1H-imidazole-2-carboxylate

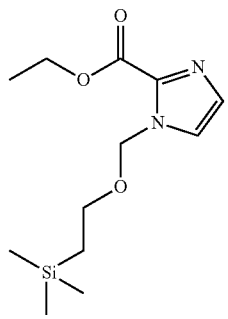 [SMILES: CCOC(=O)c1nccn1COCC[Si](C)(C)C]

SEM-Cl (18.98 mL, 107.04 mmol) was added to ethyl 1H-imidazole-2-carboxylate (10 g, 71.36 mmol) and NaH (4.28 g, 107 mmol) in DMF (50 mL) at 0° C. under nitrogen. The resulting mixture was then stirred at 25° C. for 12 hours. The reaction mixture was quenched with water (50 mL), extracted with EtOAc (2×100 mL), the organic layer was dried over $Na_2SO_4$, filtered and evaporated to afford a yellow residue. The crude product was purified by flash silica chromatography, elution gradient 30 to 70% EtOAc in petroleum ether. Pure fractions were evaporated to dryness to afford ethyl 1-((2-(trimethylsilyl)ethoxy)methyl)-1H-imidazole-2-carboxylate (Intermediate 16; 20 g, 100%) as a yellow oil. $^1$H NMR (400 MHz, DMSO, 30° C.) δ 0.00 (9H, s), 0.03-0.08 (2H, m), 1.37 (3H, t), 3.53-3.62 (2H, m), 4.37 (2H, q), 5.76 (2H, s), 7.18 (1H, d), 7.68 (1H, d). m/z: ES+[M+H]+ 271.

Example 3

(S)-7-(3-Chloro-4-fluorobenzyl)-6-methyl-2-(2-((1-methyl-1H-pyrazol-5-yl)amino)pyrimidin-4-yl)-6,7-dihydroimidazo[1,2-a]pyrazin-8(5H)-one

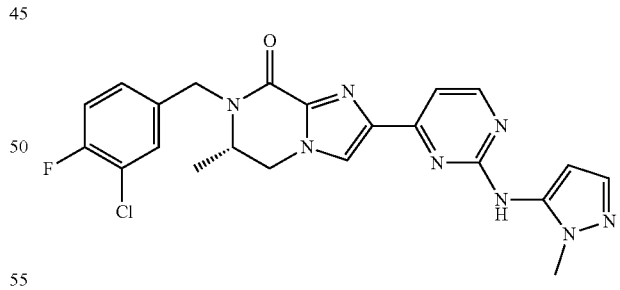

(S)-7-(3-Chloro-4-fluorobenzyl)-2-(2-chloropyrimidin-4-yl)-6-methyl-6,7-dihydroimidazo[1,2-a]pyrazin-8(5H)-one (Intermediate 17; 226 mg, 0.56 mmol), 1-methyl-1H-pyrazol-5-amine (59.4 mg, 0.61 mmol), cesium carbonate (363 mg, 1.11 mmol) and BrettPhos 3rd generation pre-catalyst (25.2 mg, 0.03 mmol) were suspended in tert-butanol (8 mL) and de-gassed with nitrogen for 10 minutes. The reaction was heated to 80° C. for 2 days under nitrogen. The reaction was then cooled to room temperature, diluted with ethyl acetate (100 mL) and the organic phase was washed with saturated aqueous sodium bicarbonate (25 mL), dried over Na₂SO₄ and concentrated in vacuo to give a brown gum. This gum was taken up in DMSO (5 mL) and filtered. The DMSO solution of crude product was then purified by preparative HPLC (Waters XBridge Prep C18 OBD column, 5μ silica, 19 mm diameter, 100 mm length), using decreasingly polar mixtures of water (containing 1% NH₃) and MeCN as eluents. Fractions containing the desired compound were evaporated to dryness to afford crude material. This was dissolved in a minimum of DCM, and absorbed onto silica gel by concentration under reduced pressure. The crude product was then further purified by flash silica chromatography, elution gradient 0 to 15% MeOH in EtOAc. Pure fractions were evaporated to dryness to afford (S)-7-(3-chloro-4-fluorobenzyl)-6-methyl-2-(2-((1-methyl-1H-pyrazol-5-yl)amino)pyrimidin-4-yl)-6,7-dihydroimidazo[1,2-a]pyrazin-8(5H)-one (Example 3; 40 mg, 15%) as an off white solid. ¹H NMR (400 MHz, DMSO, 30° C.) δ 1.13 (3H, d), 3.71 (3H, s), 3.96-4.03 (1H, m), 4.26-4.39 (2H, m), 4.41 (1H, dd), 5.04 (1H, d), 6.30 (1H, d), 7.35 (2H, dd), 7.39-7.44 (2H, m), 7.55-7.69 (1H, m), 7.92 (1H, s), 8.48 (1H, d), 9.33 (1H, s). m/z: ES+[M+H]+ 467.

Intermediate 17

(S)-7-(3-Chloro-4-fluorobenzyl)-2-(2-chloropyrimidin-4-yl)-6-methyl-6,7-dihydroimidazo[1,2-a]pyrazin-8(5H)-one

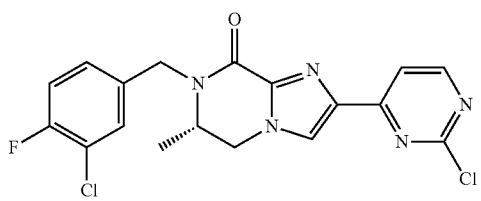 [SMILES: C[C@H]1Cn2cc(-c3ccnc(Cl)n3)nc2C(=O)N1Cc1ccc(F)c(F)c1]

Sodium hydride (60% dispersion, 25 mg, 0.63 mmol) was added to (S)-2-(2-chloropyrimidin-4-yl)-6-methyl-6,7-dihydroimidazo[1,2-a]pyrazin-8(5H)-one (Intermediate 9; 150 mg, 0.57 mmol) in DMF (12 mL) under nitrogen. The resulting suspension was stirred at 20° C. for 30 minutes. 2-Chloro-4-(chloromethyl)-1-fluorobenzene (112 mg, 0.63 mmol) was added followed by tetrabutylammonium iodide (42.0 mg, 0.11 mmol) and the resulting solution stirred at 20° C. for 18 hours. The reaction mixture was poured into saturated aqueous NH₄Cl (25 mL) and extracted with ethyl acetate (75 mL). The organic phases were dried over Na₂SO₄ and concentrated in vacuo to give (S)-7-(3-chloro-4-fluorobenzyl)-2-(2-chloropyrimidin-4-yl)-6-methyl-6,7-dihydroimidazo[1,2-a]pyrazin-8(5H)-one (Intermediate 17; 230 mg, 100%) as a light brown solid. ¹H NMR (400 MHz, DMSO, 33° C.) δ 1.13 (3H, d), 4.01 (1H, ddd), 4.26 (1H, dd), 4.36 (1H, d), 4.46 (1H, dd), 5.05 (1H, d), 7.39-7.41 (1H, m), 7.42 (1H, s), 7.59-7.66 (1H, m), 7.93 (1H, d), 8.27 (1H, s), 8.74 (1H, dd). m/z: ES+[M+H]+ 406.

Example 4

(S)-7-(3,4-Difluorobenzyl)-6-methyl-2-(2-((1-methyl-1H-pyrazol-5-yl)amino)pyrimidin-4-yl)-6,7-dihydroimidazo[1,2-a]pyrazin-8(5H)-one

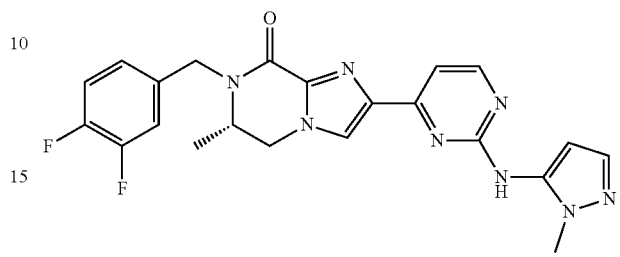

(S)-2-(2-Chloropyrimidin-4-yl)-7-(3,4-difluorobenzyl)-6-methyl-6,7-dihydroimidazo[1,2-a]pyrazin-8(5H)-one (Intermediate 18; 218 mg, 0.56 mmol), 1-methyl-1H-pyrazol-5-amine (59.7 mg, 0.62 mmol), cesium carbonate (364 mg, 1.12 mmol) and BrettPhos 3rd generation pre-catalyst (25.3 mg, 0.03 mmol) were suspended in tert-butanol (8 mL) and de-gassed with nitrogen for 10 minutes. The reaction was heated to 80° C. for 18 hours under nitrogen. The reaction was cooled to room temperature, diluted with ethyl acetate (100 mL) and washed with saturated aqueous NaHCO₃ (25 mL), dried over Na₂SO₄ and concentrated in vacuo to give a brown solid. The crude material was dissolved in DCM, concentrated in vacuo and adsorbed onto silica. The crude product was purified by flash silica chromatography, elution gradient 0 to 15% MeOH in EtOAc. Pure fractions were evaporated to dryness to afford (S)-7-(3,4-difluorobenzyl)-6-methyl-2-(2-((1-methyl-1H-pyrazol-5-yl)amino)pyrimidin-4-yl)-6,7-dihydroimidazo[1,2-a]pyrazin-8(5H)-one (Example 4; 88 mg, 34.9%) as an off white solid. ¹H NMR (400 MHz, DMSO, 30° C.) δ 1.13 (3H, d), 3.71 (3H, s), 3.96-4.03 (1H, m), 4.27-4.38 (2H, m), 4.43 (1H, dd), 5.05 (1H, d), 6.30 (1H, d), 7.22-7.28 (1H, m), 7.35 (2H, dd), 7.37-7.5 (2H, m), 7.92 (1H, s), 8.47 (1H, d), 9.33 (1H, s). m/z: ES+[M+H]+ 451.

Intermediate 18

(S)-2-(2-Chloropyrimidin-4-yl)-7-(3,4-difluorobenzyl)-6-methyl-6,7-dihydroimidazo[1,2-a]pyrazin-8(5H)-one

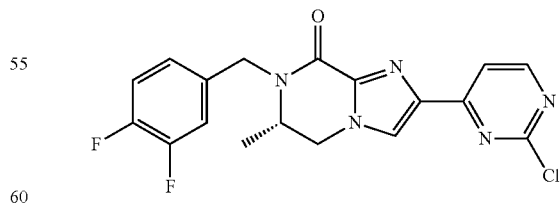

Sodium hydride (60% dispersion) (25.03 mg, 0.63 mmol) was added to (S)-2-(2-chloropyrimidin-4-yl)-6-methyl-6,7-dihydroimidazo[1,2-a]pyrazin-8(5H)-one (Intermediate 9; 150 mg, 0.57 mmol) in DMF (12 mL) under nitrogen. The resulting suspension was stirred at 20° C. for 30 minutes. 4-(bromomethyl)-1,2-difluorobenzene (130 mg, 0.63 mmol)

was added followed by tetrabutylammonium iodide (42.0 mg, 0.11 mmol) and the resulting solution stirred at 20° C. for 18 hours. The reaction mixture was poured into saturated aqueous NH$_4$Cl (25 mL) and extracted with ethyl acetate (75 mL). The organic phases were dried over Na$_2$SO$_4$ and concentrated in vacuo to give (S)-2-(2-chloropyrimidin-4-yl)-7-(3,4-difluorobenzyl)-6-methyl-6,7-dihydroimidazo[1,2-a]pyrazin-8(5H)-one (Intermediate 18; 222 mg, 100%) as a brown gum. $^1$H NMR (400 MHz, DMSO, 30° C.) δ 1.14 (3H, d), 3.94-4.07 (1H, m), 4.27 (1H, dd), 4.36 (1H, d), 4.47 (1H, dd), 5.06 (1H, d), 7.26 (1H, s), 7.37-7.51 (2H, m), 7.93 (1H, d), 8.26 (1H, s), 8.74 (1H, d). m/z: ES+[M+H]+ 390.

Example 5

2-(5-Methyl-2-((1-methyl-1H-pyrazol-5-yl)amino) pyrimidin-4-yl)-7-((6-(trifluoromethyl)pyridin-2-yl) methyl)-6,7-dihydroimidazo[1,2-a]pyrazin-8(5H)-one

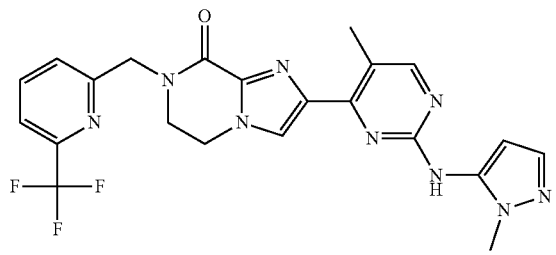 [SMILES: Cc1cnc(Nc2ccnn2C)nc1-c1cn2c(n1)C(=O)N(Cc1cccc(C(F)(F)F)n1)CC2]

3rd Generation BrettPhos precatalyst (10.72 mg, 0.01 mmol) was added to 2-(2-chloro-5-methylpyrimidin-4-yl)-7-((6-(trifluoromethyl)pyridin-2-yl)methyl)-6,7-dihydroimidazo[1,2-a]pyrazin-8(5H)-one (Intermediate 19; 50 mg, 0.12 mmol), 1-methyl-1H-pyrazol-5-amine (22.97 mg, 0.24 mmol) and Cs$_2$CO$_3$ (96 mg, 0.30 mmol) in 1,4-dioxane (3 mL) at 25° C. under nitrogen. The resulting solution was stirred at 120° C. for 8 hours. The solvent was removed by distillation under vacuum. The crude product was purified by flash silica chromatography, elution gradient 3 to 4% MeOH in DCM. Pure fractions were evaporated to dryness to afford crude product. The crude product was further purified by preparative HPLC (XSelect CSH Prep C18 OBD column, 5μ silica, 19 mm diameter, 150 mm length), using decreasingly polar mixtures of water (containing 0.05% NH$_4$HCO$_3$) and MeCN as eluents. Fractions containing the desired compound were evaporated to dryness to afford 2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one (Example 5; 23.5 mg, 41%) as a white solid. $^1$H NMR (400 MHz, DMSO, 20.1° C.) δ 2.51 (3H, s), 3.70 (3H, s), 3.90-3.98 (2H, m), 4.43-4.51 (2H, m), 4.91 (2H, s), 6.31 (1H, d), 7.34 (1H, d), 7.76 (1H, d), 7.84 (1H, d), 7.95 (1H, s), 8.10 (1H, t), 8.33 (1H, s), 9.24 (1H, s). m/z (ES+), [M+H]+=484.

Intermediate 19

2-(2-Chloro-5-methylpyrimidin-4-yl)-7-((6-(trifluoromethyl)pyridin-2-yl)methyl)-6,7-dihydroimidazo [1,2-a]pyrazin-8(5H)-one

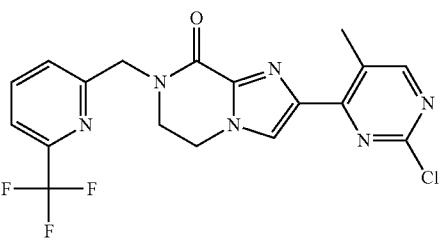 [SMILES: Cc1cnc(Cl)nc1-c1cn2c(n1)C(=O)N(Cc1cccc(C(F)(F)F)n1)CC2]

NH$_3$ (7N in MeOH, 3 mL) was added to ethyl 4-(2-chloro-5-methylpyrimidin-4-yl)-1-(2-(((6-(trifluoromethyl)pyridin-2-yl)methyl)amino)ethyl)-1H-imidazole-2-carboxylate (Intermediate 20; 60 mg, 0.13 mmol) at 25° C. under air and the resulting solution was stirred at 50° C. for 12 hours. The solvent was removed by distillation under vacuum to afford 2-(2-chloro-5-methylpyrimidin-4-yl)-7-((6-(trifluoromethyl)pyridin-2-yl)methyl)-6,7-dihydroimidazo[1,2-a]pyrazin-8(5H)-one (Intermediate 19; 50 mg, 92%) as a white solid. m/z (ES+), [M+H]+=423.

Intermediate 20

Ethyl 4-(2-chloro-5-methylpyrimidin-4-yl)-1-(2-(((6-(trifluoromethyl)pyridin-2-yl)methyl)amino) ethyl)-1H-imidazole-2-carboxylate

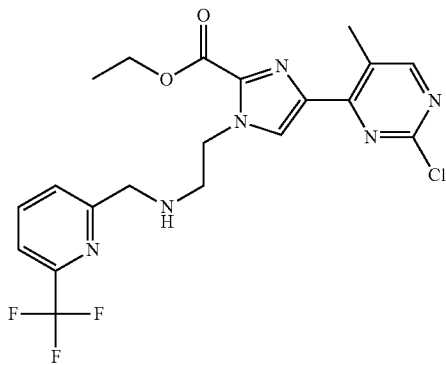 [SMILES: CCOC(=O)c1nc(-c2nc(Cl)ncc2C)cn1CCNCc1cccc(C(F)(F)F)n1]

6-(trifluoromethyl)picolinaldehyde (114 mg, 0.65 mmol) was added to ethyl 1-(2-aminoethyl)-4-(2-chloro-5-methylpyrimidin-4-yl)-1H-imidazole-2-carboxylate dihydrochloride (Intermediate 21; 250 mg, 0.65 mmol) in DCM (10 mL) at 25° C. under air. The resulting solution was stirred at 40° C. for 3 hours. Sodium triacetoxyborohydride (415 mg, 1.96 mmol) was added to reaction mixture at 25° C. and the resulting solution was stirred at 25° C. for 12 hours. The reaction mixture was quenched with water (10 mL) and extracted with DCM (3×15 mL). The organic layers were combined and washed with brine (15 mL), dried over Na$_2$SO$_4$, filtered and the volatiles removed under reduced pressure. The crude product was purified by flash silica chromatography, elution gradient 2 to 5% MeOH in DCM.

Pure fractions were evaporated to dryness to afford ethyl 4-(2-chloro-5-methylpyrimidin-4-yl)-1-(2-(((6-(trifluoromethyl)pyridin-2-yl)methyl)amino)ethyl)-1H-imidazole-2-carboxylate (Intermediate 20; 60 mg, 19.6%) as a white solid. m/z (ES+), [M+H]+=469.

Intermediate 21

1-(2-Aminoethyl)-4-(2-chloro-5-methylpyrimidin-4-yl)-1H-imidazole-2-carboxylate

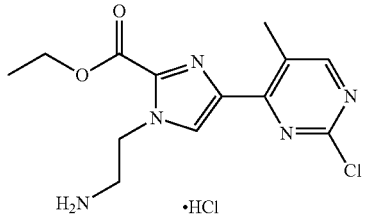 [SMILES: CCOC(=O)c1nc(-c2nc(Cl)ncc2C)cn1CCN ; Cl]

HCl (4N in 1,4-dioxane, 50 mL) was added to ethyl 1-(2-((tert-butoxycarbonyl)amino)ethyl)-4-(2-chloro-5-methylpyrimidin-4-yl)-1H-imidazole-2-carboxylate (Intermediate 22; 3.2 g, 7.81 mmol) at 25° C. under air and the resulting solution was stirred at 25° C. for 12 hours. The solvent was removed by distillation under vacuum and the crude residue was triturated with EtOAc to give a solid which was collected by filtration and dried under vacuum to give ethyl 1-(2-aminoethyl)-4-(2-chloro-5-methylpyrimidin-4-yl)-1H-imidazole-2-carboxylate.HCl (Intermediate 21; 2.90 g, 97%) as a white solid. $^1$H NMR (400 MHz, DMSO, 20.1° C.) δ 1.35 (3H, t), 2.60-2.65 (3H, m), 4.38 (2H, q), 4.75 (2H, t), 8.37 (3H, s), 8.46 (1H, s), 8.63 (1H, d), 10.17 (2H, s). m/z (ES+), [M+H]+=310.

Intermediate 22

Ethyl 1-(2-((tert-butoxycarbonyl)amino)ethyl)-4-(2-chloro-5-methylpyrimidin-4-yl)-1H-imidazole-2-carboxylate

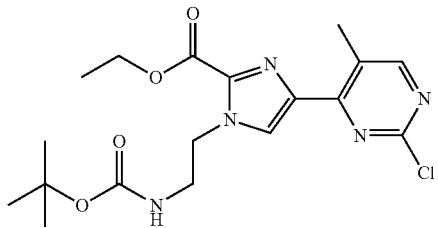 [SMILES: CCOC(=O)c1nc(-c2nc(Cl)ncc2C)cn1CCNC(=O)OC(C)(C)C]

tert-Butyl 1,2,3-oxathiazolidine-3-carboxylate 2,2-dioxide (2.76 g, 12.37 mmol) was added portionwise to ethyl 4-(2-chloro-5-methylpyrimidin-4-yl)-1H-imidazole-2-carboxylate (Intermediate 23; 3.0 g, 11.25 mmol), K$_2$CO$_3$ (4.66 g, 33.75 mmol) and 18-crown-6 ether (0.595 g, 2.25 mmol) in 1,4-dioxane (60 mL) at 100° C. under air. The resulting solution was stirred at 100° C. for 2 hours. The mixture was cooled, filtered and the resulting solid was washed with ethyl acetate. The filtrate was then concentrated under reduced pressure. The crude product was purified by flash silica chromatography, elution gradient 25 to 30% EtOAc in petroleum ether. Pure fractions were evaporated to dryness to afford ethyl 1-(2-((tert-butoxycarbonyl)amino)ethyl)-4-(2-chloro-5-methylpyrimidin-4-yl)-1H-imidazole-2-carboxylate (Intermediate 22; 3.20 g, 69.4%) as a white solid. $^1$H NMR (400 MHz, DMSO, 20.2° C.) δ 1.25 (9H, s), 1.35 (3H, t), 2.62 (3H, s), 3.35 (2H, dd), 4.37 (2H, q), 4.49 (2H, t), 6.93 (1H, t), 8.18 (1H, s), 8.61 (1H, s). m/z (ES+), [M+H]+=410.

Intermediate 23

Ethyl 4-(2-chloro-5-methylpyrimidin-4-yl)-1H-imidazole-2-carboxylate

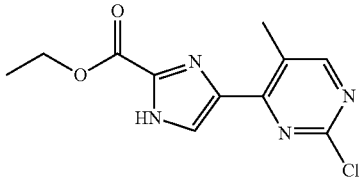 [SMILES: CCOC(=O)c1nc(-c2nc(Cl)ncc2C)c[nH]1]

Trifluoroacetic acid (20 mL, 259.60 mmol) was added to ethyl 4-(2-chloro-5-methylpyrimidin-4-yl)-1-((2-(trimethylsilyl)ethoxy)methyl)-1H-imidazole-2-carboxylate (Intermediate 24; 5.6 g, 14.11 mmol) in DCM (20 mL) at 25° C. and the resulting mixture was stirred at 25° C. for 12 hours. The volatiles were then removed under reduced pressure and the reaction mixture was basified with saturated NaHCO$_3$. The resulting precipitate formed was collected by filtration, washed with water (100 mL) and dried under vacuum to afford ethyl 4-(2-chloro-5-methylpyrimidin-4-yl)-1H-imidazole-2-carboxylate (Intermediate 23; 3.50 g, 93%) as a white solid. $^1$H NMR (400 MHz, DMSO, 23° C.) δ 1.35 (3H, t), 2.62 (3H, s), 4.37 (2H, q), 8.13 (1H, s), 8.62 (1H, s), NH not observed. m/z (ES+), [M+H]+=267.

An alternative method for the preparation of Intermediate 23:

Ethyl 4-(2-chloro-5-methylpyrimidin-4-yl)-1-((2-(trimethylsilyl)ethoxy)methyl)-1H-imidazole-2-carboxylate (Intermediate 24; 176 g, 443.38 mmol) was added to TFA (500 mL, 6489.91 mmol) in DCM (500 mL). The resulting reaction mixture was stirred at room temperature for 16 hours. The volatiles were then removed under reduced pressure. Excess saturated aqueous Na$_2$CO$_3$ was added and the resulting precipitate was collected by filtration, washed with water (1 L) and dried under vacuum. The crude solid was triturated with MeCN to give a solid which was collected by filtration and dried under vacuum to give ethyl 4-(2-chloro-5-methylpyrimidin-4-yl)-1H-imidazole-2-carboxylate (Intermediate 23; 106 g, 90%) as a white solid. $^1$H NMR (300 MHz, DMSO, 19.7° C.) δ 1.34 (3H, t), 2.61 (3H, s), 4.33-4.41 (2H, m), 8.13 (1H, s), 8.61 (1H, s), 13.99 (1H, s). m/z (ES+), [M+H]+=267.

An alternative method for one pot synthesis of Intermediate 23:

Step 1:

To a stirred solution of 3,4,7,8-Tetramethyl-1,10-phenanthroline (3.72 g, 15.41 mmol) and Di-mu-methoxobis(1,5-cyclooctadiene)diiridium (I) (5.21 g, 7.71 mmol) in anhydrous MeTHF (900 mL) were added successively bis (pinacolato)diboron (108 g, 423.86 mmol) and a solution of ethyl 1-((2-(trimethylsilyl)ethoxy)methyl)-1H-imidazole-2-carboxylate (114.5 g, 385.33 mmol) in MeTHF (100 mL) under nitrogen atmosphere. The resulting mixture was degassed 3 times under nitrogen, heated to 70° C. and stirred for 3 hours. The reaction mixture was quenched with water (25 mL), the organic phase separated and concentrated to 500 mL. This solution was used directly in Step 2 without purification.

Step 2:

The MeTHF (500 mL) solution produced in Step 1 was added slowly to a stirred mixture of aqueous K$_2$CO$_3$ (161 g, 1156 mmol) in water (500 mL), 2,4-dichloro-5-methylpyrimidine (77 g, 462.4 mmol) and 1,1'-Bis(diphenylphosphino) ferrocene dichloropalladium (II) dichloromethane adduct (9.44 g, 15.56 mmol) in MeTHF (500 mL) at 40° C. over 3 hours. After complete addition, the layers were separated and the organic layer was washed with water (500 mL) and concentrated to 500 mL. This was used directly in Step 3 without purification.

Step 3:

HCl in iso-propylalcohol (5-6 N, 116 mL, 578 mmol) was a added to the solution produced in Step 2 at room temperature and stirred for 30 minutes. The reaction mixture was then diluted with water (500 mL). The aqueous layer was extracted with MeTHF (500 mL) and combined organic layers were washed with aqueous sodium bicarbonate (4% w/w solution, 500 mL) and water (200 mL). The organic phase was concentrated to half and stirred with heptane (1000 mL). The resulting precipitate was filtered, washed with a MeTHF/heptane mixture (1:4, 500 mL) and dried under vacuum to afford ethyl 4-(2-chloro-5-methylpyrimidin-4-yl)-1H-imidazole-2-carboxylate as a solid (Intermediate 23, 60.5 g, 59%, overall yield over 3 Steps). $^1$H NMR (400 MHz, DMSO, 23° C.) δ 1.35 (3H, t), 2.62 (3H, s), 4.37 (2H, q), 8.13 (1H, s), 8.62 (1H, s), NH not observed. m/z (ES+), [M+H]+=267.

Intermediate 24

Ethyl 4-(2-chloro-5-methylpyrimidin-4-yl)-1-((2-(trimethylsilyl)ethoxy)methyl)-1H-imidazole-2-carboxylate

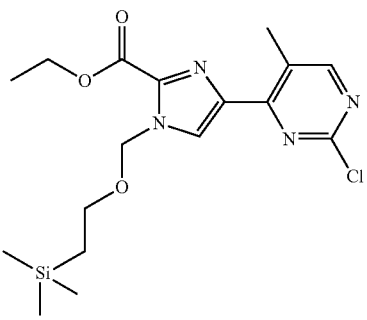

Pd(Ph$_3$P)$_4$ (1.158 g, 1.00 mmol) was added to (2-(ethoxycarbonyl)-1-((2-(trimethylsilyl)ethoxy)methyl)-1H-imidazol-4-yl)boronic acid (Intermediate 25; 6.3 g, 20.05 mmol), 2,4-dichloro-5-methylpyrimidine (3.27 g, 20.05 mmol) and Cs$_2$CO$_3$ (13.07 g, 40.10 mmol) in 1,4-dioxane (120 mL) and water (20 mL) at 25° C. under nitrogen and the resulting mixture was stirred at 85° C. for 2 hours. The reaction mixture was poured into water (200 mL), extracted with DCM (2×250 mL), the organic layer was dried over Na$_2$SO$_4$, filtered and evaporated. The crude product was purified by flash silica chromatography, elution gradient 0 to 10% EtOAc in petroleum ether. Pure fractions were evaporated to dryness to afford ethyl 4-(2-chloro-5-methylpyrimidin-4-yl)-1-((2-(trimethylsilyl)ethoxy)methyl)-1H-imidazole-2-carboxylate (Intermediate 24; 5.60 g, 70.4%) as a pale yellow solid. $^1$H NMR (400 MHz, CDCl$_3$, 23° C.) δ 0.02 (9H, s), 0.93-1.03 (2H, m), 1.48 (3H, t), 2.71-2.76 (3H, m), 3.59-3.69 (2H, m), 4.48 (2H, q), 5.85 (2H, s), 8.16 (1H, s), 8.42-8.47 (1H, m). m/z (ES+), [M+H]+=397.

An alternative method for the preparation of Intermediate 24:

Batch 1: Pd(Ph$_3$P)$_4$ (1.655 g, 1.43 mmol) was added to (2-(ethoxycarbonyl)-1-((2-(trimethylsilyl)ethoxy)methyl)-1H-imidazol-4-yl)boronic acid (Intermediate 25; 9 g, 28.64 mmol), 2,4-dichloro-5-methylpyrimidine (4.67 g, 28.64 mmol) and Cs$_2$CO$_3$ (28.0 g, 85.93 mmol) in 1,4-dioxane (80 mL) and water (20 mL) under nitrogen. The reaction mixture was then stirred at 85° C. for 2 hour and then cooled to room temperature.

Batch 2: Pd(Ph$_3$P)$_4$ (24.82 g, 21.48 mmol) was added to 2,4-dichloro-5-methylpyrimidine (70.0 g, 429.64 mmol), (2-(ethoxycarbonyl)-1-((2-(trimethylsilyl)ethoxy)methyl)-1H-imidazol-4-yl)boronic acid (Intermediate 25; 135 g, 429.64 mmol) and Cs$_2$CO$_3$ (420 g, 1288.91 mmol) in 1,4-dioxane (2000 mL) and water (400 mL) under nitrogen. The reaction mixture was then stirred at 85° C. for 2 hour and then cooled to room temperature. Batches 1 and 2 above were combined and evaporated to dryness. The residue was dissolved in EtOAc (2 L) and washed sequentially with saturated aqueous NaHCO$_3$ (450 mL), water (300 mL) and brine (350 mL). The organic phase was dried over Na$_2$SO$_4$, filtered and the volatiles removed under reduced pressure. The crude product was purified by flash column chromatography, elution gradient 0 to 5% EtOAc in petroleum ether. Pure produce containing fractions were evaporated to dryness to afford ethyl 4-(2-chloro-5-methylpyrimidin-4-yl)-1-((2-(trimethylsilyl)ethoxy)methyl)-1H-imidazole-2-carboxylate (Intermediate 24; 123 g, 67.4%) as a solid. $^1$H NMR (400 MHz, CDCl$_3$, 23° C.) δ 0.02 (9H, s), 0.93-1.03 (2H, m), 1.48 (3H, t), 2.71-2.76 (3H, m), 3.59-3.69 (2H, m), 4.48 (2H, q), 5.85 (2H, s), 8.16 (1H, s), 8.42-8.47 (1H, m). m/z (ES+), [M+H]+=397.

Intermediate 25

Ethyl 4-(2,5-dichloropyrimidin-4-yl)-1-((2-(trimethylsilyl)ethoxy)methyl)-1H-imidazole-2-carboxylate

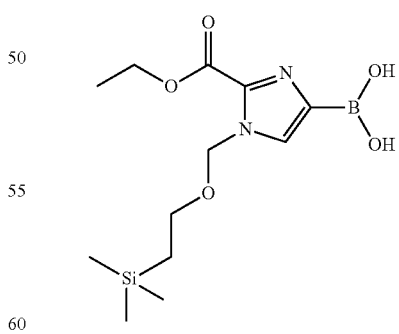

2nd Generation XPhos precatalyst (0.788 g, 1.00 mmol) was added to ethyl 4-bromo-1-((2-(trimethylsilyl)ethoxy)methyl)-1H-imidazole-2-carboxylate (Intermediate 25a, also commercially available; 7 g, 20.04 mmol), 4,4,4',4',5,5',5'-octamethyl-2,2'-bi(1,3,2-dioxaborolane) (7.63 g, 30.06 mmol) and KOAc (3.93 g, 40.08 mmol) in 1,4- dioxane (100 mL) at 25° C. under nitrogen. The resulting mixture was then stirred at 85° C. for 3 hours. The reaction mixture was filtered and the filtrate was used in the next step directly without further purification. m/z (ES+), [M+H]+=315.

Alternative method to prepare Intermediate 25:

2-Dicyclohexylphosphino-2',4',6'-tri-iso-propyl-1,1'-biphenyl (12.28 g, 25.77 mmol) was added to tris(dibenzylideneacetone)dipalladium(0)-chloroform adduct (11.11 g, 10.74 mmol) in 1,4-dioxane (2000 mL) at room temperature under nitrogen. The resulting mixture was stirred then stirred at room temperature for 45 hours. Ethyl 4-bromo-1-((2-(trimethylsilyl)ethoxy)methyl)-1H-imidazole-2-carboxylate (150 g, 429.43 mmol), bis(pinacolato)diboron (131 g, 515.32 mmol) and potassium acetate (126 g, 1288.29 mmol) were added at room temperature under nitrogen. The resulting mixture was stirred at 80° C. for 8 hours. The reaction mixture was then filtered through celite. The solvent was removed under reduced pressure to afford (2-(ethoxycarbonyl)-1-((2-(trimethylsilyl)ethoxy)methyl)-1H-imidazol-4-yl)boronic acid (Intermediate 25; 135 g, 100%) as a yellow oil. m/z (ES+), [M+H]+=315.

Intermediate 25a

Ethyl 4-Bromo-1-((2-(trimethylsilyl)ethoxy)methyl)-1H-imidazole-2-carboxylate

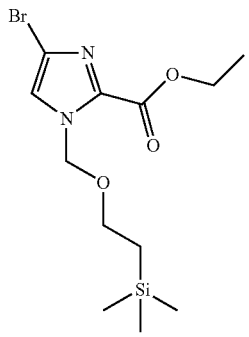 [SMILES: CCOC(=O)c1nc(Br)cn1COCC[Si](C)(C)C]

NBS (158 g, 887.56 mmol) was added portionwise to ethyl 1-((2-(trimethylsilyl)ethoxy)methyl)-1H-imidazole-2-carboxylate (Intermediate 25b; 160 g, 591.71 mmol) in DMF (1200 mL) and DCM (1300 mL) at 0° C. The resulting reaction was stirred at 25° C. for 48 hours. The volatiles were removed under reduced pressure and EtOAc (7 L) was added. The organic phase was then washed sequentially with saturated NaHCO$_3$ (1 L), water (1 L), and saturated brine (750 mL). The organic layer was dried over Na$_2$SO$_4$, filtered and evaporated to afford the crude product which was purified by flash silica chromatography, elution gradient 0 to 4% EtOAc in petroleum ether. Pure fractions were evaporated to dryness to afford ethyl 4-bromo-1-((2-(trimethylsilyl)ethoxy)methyl)-1H-imidazole-2-carboxylate (Intermediate 25a; 106 g, 51.3%) as a pale yellow oil which solidified on standing. $^1$H NMR (300 MHz, DMSO) δ—0.07 (9H, s), 0.77-0.85 (2H, m), 1.29 (3H, t), 3.53 (2H, t), 4.30 (2H, q), 5.66 (2H, s), 7.83 (1H, s). m/z (ES+), [M+H]+=349/351.

Intermediate 25b

Ethyl 1-((2-(trimethylsilyl)ethoxy)methyl)-1H-imidazole-2-carboxylate

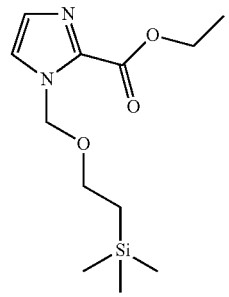 [SMILES: CCOC(=O)c1nccn1COCC[Si](C)(C)C]

SEM-Cl (286 g, 1712.55 mmol) was added dropwise to ethyl 1H-imidazole-2-carboxylate (200 g, 1427.12 mmol) and K$_2$CO$_3$ (592 g, 4281.37 mmol) in acetone (3 L) at 0° C. The resulting mixture was stirred at ambient temperature for 16 hours. The resulting precipitate was removed by filtration and washed with EtOAc (1 L). The combined organic layers were then dried over Na$_2$SO$_4$ and the volatiles removed under reduced pressure. The result crude material was purified by flash silica chromatography, elution gradient 0 to 30% EtOAc in petroleum ether. Pure fractions were evaporated to dryness to afford ethyl 1-((2-(trimethylsilyl)ethoxy)methyl)-1H-imidazole-2-carboxylate (Intermediate 25b; 328 g, 85%) as a pale yellow oil. $^1$H NMR (300 MHz, CDCl$_3$) δ −0.01 (9H, s), 090-0.97 (2H, m), 1.45 (3H, t), 3.50-3.63 (2H, m), 4.43 (2H, q), 5.81 (2H, s), 7.22 (1H, s), 7.28 (1H, s). m/z (ES+), [M+H]+=271.

Example 6

(S)-2-(5-Chloro-2-((1-methyl-1H-pyrazol-5-yl)amino)pyrimidin-4-yl)-7-(3,4-difluorobenzyl)-6-methyl-6,7-dihydroimidazo[1,2-a]pyrazin-8(5H)-one

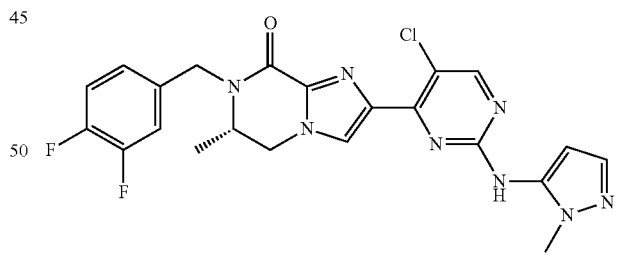

2nd Generation XantPhos precatalyst (20.95 mg, 0.02 mmol) was added to (S)-2-(2,5-dichloropyrimidin-4-yl)-7-(3,4-difluorobenzyl)-6-methyl-6,7-dihydroimidazo[1,2-a]pyrazin-8(5H)-one (Intermediate 26; 100 mg, 0.24 mmol), 1-methyl-1H-pyrazol-5-amine (Intermediate 26; 57.2 mg, 0.59 mmol) and Cs$_2$CO$_3$ (154 mg, 0.47 mmol) in 1,4-dioxane (5 mL) at 25° C. under nitrogen and the resulting mixture was stirred at 100° C. for 8 hours. The volatiles were removed under reduced pressure and the crude product was purified by flash silica chromatography, elution gradient 0 to 6% MeOH in DCM. Pure fractions were evaporated to dryness to afford a yellow residue. The product was further purified by preparative HPLC (XSelect CSH Prep C18 OBD column, 5μ silica, 19 mm diameter, 150 mm length), using decreasingly polar mixtures of water (containing 0.03% NH₃) and MeCN as eluents. Fractions containing the desired compound were evaporated to dryness to afford (S)-2-(5-chloro-2-((1-methyl-1H-pyrazol-5-yl)amino)pyrimidin-4-yl)-7-(3,4-difluorobenzyl)-6-methyl-6,7-dihydroimidazo[1,2-a]pyrazin-8(5H)-one (Example 6; 16.00 mg, 14%) as a white solid. $^1$H NMR (400 MHz, DMSO, 22° C.) δ 1.15 (3H, d), 3.71 (3H, s), 4.00 (1H, s), 4.34 (2H, d), 4.47 (1H, dd), 5.07 (1H, d), 6.32 (1H, s), 7.27 (1H, s), 7.35 (1H, d), 7.38-7.51 (2H, m), 8.19 (1H, s), 8.54 (1H, s), 9.73 (1H, s). m/z (ES+), [M+H]+=485.

Intermediate 26

(S)-2-(2,5-Dichloropyrimidin-4-yl)-7-(3,4-difluorobenzyl)-6-methyl-6,7-dihydroimidazo[1,2-a]pyrazin-8(5H)-one

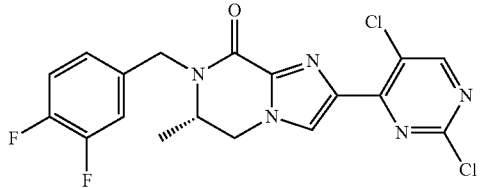 [SMILES: C[C@H]1Cn2cc(-c3nc(Cl)ncc3Cl)nc2C(=O)N1Cc1ccc(F)c(F)c1]

A solution of (S)-ethyl 4-(2,5-dichloropyrimidin-4-yl)-1-(2-((3,4-difluorobenzyl)amino)propyl)-1H-imidazole-2-carboxylate (Intermediate 27; 200 mg, 0.43 mmol) in NH₃ (7N in MeOH, 5 mL, 35.00 mmol) was stirred at 50° C. for 2 hours. The solvent was then removed under reduced pressure. The crude product was then purified by flash silica chromatography, elution gradient 0 to 5% MeOH in DCM. Pure fractions were evaporated to dryness to afford (S)-2-(2,5-dichloropyrimidin-4-yl)-7-(3,4-difluorobenzyl)-6-methyl-6,7-dihydroimidazo[1,2-a]pyrazin-8(5H)-one (Intermediate 26; 100 mg, 55.4%) as a yellow solid. m/z (ES+), [M+H]+=424.

Intermediate 27

(S)-Ethyl 4-(2,5-dichloropyrimidin-4-yl)-1-(2-((3,4-difluorobenzyl)amino)propyl)-1H-imidazole-2-carboxylate

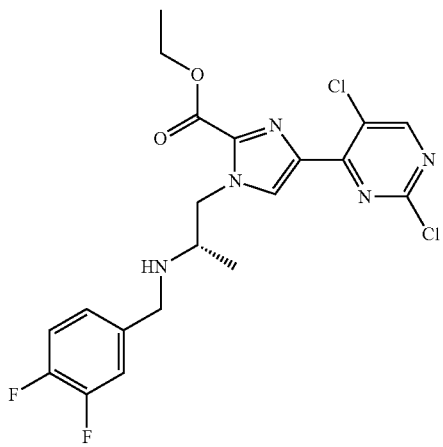 [SMILES: CCOC(=O)c1nc(-c2nc(Cl)ncc2Cl)cn1C[C@H](C)NCc1ccc(F)c(F)c1]

3,4-Difluorobenzaldehyde (74.9 mg, 0.53 mmol) was added to (S)-ethyl 1-(2-aminopropyl)-4-(2,5-dichloropyrimidin-4-yl)-1H-imidazole-2-carboxylate dihydrochloride (Intermediate 28; 200 mg, 0.48 mmol) in DCM (10 mL) at 25° C. under nitrogen. After stirring at 40° C. for 3 hours, sodium triacetoxyborohydride (305 mg, 1.44 mmol) was added and the resulting mixture was stirred at 25° C. for 3 hours. The reaction mixture was then quenched with saturated NaHCO₃ (20 mL), extracted with DCM (2×50 mL), the organic layer was dried over Na₂SO₄, filtered and evaporated to afford the crude product (S)-ethyl 4-(2,5-dichloropyrimidin-4-yl)-1-(2-((3,4-difluorobenzyl)amino)propyl)-1H-imidazole-2-carboxylate (Intermediate 27; 200 mg, 89%) as a yellow solid. The product was used in the next step directly without further purification. m/z (ES+), [M+H]+=470.

Intermediate 28

(S)-Ethyl 1-(2-aminopropyl)-4-(2,5-dichloropyrimidin-4-yl)-1H-imidazole-2-carboxylate dihydrochloride

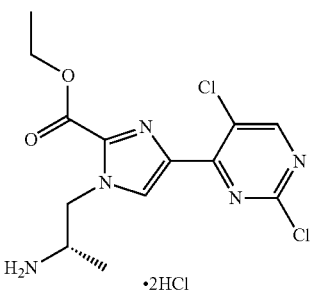 [SMILES: CCOC(=O)c1nc(-c2nc(Cl)ncc2Cl)cn1C[C@H](C)N ; "·2HCl"]

A solution of (S)-ethyl 1-(2-((tert-butoxycarbonyl)amino)propyl)-4-(2,5-dichloropyrimidin-4-yl)-1H-imidazole-2-carboxylate (Intermediate 29; 2.8 g, 6.30 mmol) in HCl (4N in 1,4-dioxane, 20 mL) was stirred at 25° C. overnight. The precipitate was collected by filtration, washed with EtOAc (20 mL) and dried under vacuum to afford (S)-ethyl 1-(2-aminopropyl)-4-(2,5-dichloropyrimidin-4-yl)-1H-imidazole-2-carboxylate (Intermediate 28; 2.50 g, 95%) as a white solid. $^1$H NMR (400 MHz, DMSO, 24° C.) δ 1.26 (3H, d), 1.37 (3H, t), 3.75 (1H, s), 4.40 (2H, d), 4.63 (2H, d), 8.05 (3H, s), 8.61 (1H, s), 8.94 (1H, s). m/z (ES+), [M+H]+=344.

Intermediate 29

(S)-Ethyl 1-(2-((tert-butoxycarbonyl)amino)propyl)-4-(2,5-dichloropyrimidin-4-yl)-1H-imidazole-2-carboxylate

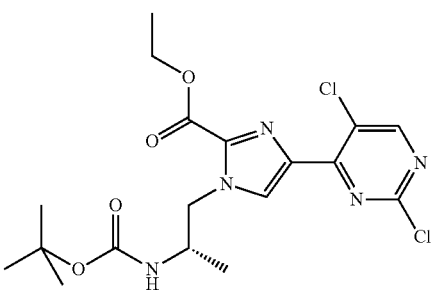 [SMILES: CCOC(=O)c1nc(-c2nc(Cl)ncc2Cl)cn1C[C@H](C)NC(=O)OC(C)(C)C]

1M HCl (20 mL, 20.00 mmol) was added to (S)-(tert-butoxycarbonyl)(1-(4-(2,5-dichloropyrimidin-4-yl)-2-(ethoxycarbonyl)-1H-imidazol-1-yl)propan-2-yl)sulfamic acid (Intermediate 30; 6 g, 11.44 mmol) in EtOH (20 mL) at 25° C. under air. The resulting mixture was stirred at 50° C. for 20 minutes. The reaction mixture was quenched with saturated NaHCO$_3$ (50 mL), extracted with DCM (3×100 mL), the organic layer was dried over Na$_2$SO$_4$, filtered and evaporated to afford yellow residue. The crude product was purified by flash silica chromatography, elution gradient 0 to 30% EtOAc in petroleum ether. Pure fractions were evaporated to dryness to afford (S)-ethyl 1-(2-((tert-butoxycarbonyl)amino)propyl)-4-(2,5-dichloropyrimidin-4-yl)-1H-imidazole-2-carboxylate (Intermediate 29; 2.80 g, 55.1%) as a white solid. $^1$H NMR (300 MHz, CDCl$_3$, 27° C.) δ 1.24 (3H, d), 1.35 (9H, s), 1.46 (2H, t), 4.03-4.17 (1H, m), 4.46 (2H, q), 4.58-4.69 (2H, m), 5.30 (1H, s), 8.08 (1H, s), 8.58 (1H, s). m/z (ES+), [M+H]+=444.

Intermediate 30

(S)-(tert-Butoxycarbonyl)(1-(4-(2,5-dichloropyrimidin-4-yl)-2-(ethoxycarbonyl)-1H-imidazol-1-yl)propan-2-yl)sulfamic acid

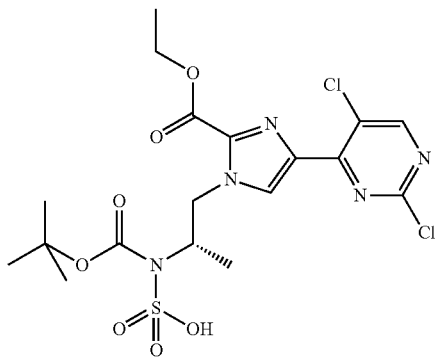 [SMILES: CCOC(=O)c1nc(-c2nc(Cl)ncc2Cl)cn1C[C@H](C)N(C(=O)OC(C)(C)C)S(=O)(=O)O]

(S)-tert-butyl 4-methyl-1,2,3-oxathiazolidine-3-carboxylate 2,2-dioxide (Intermediate 12; 4.59 g, 19.33 mmol) was added portionwise to ethyl 4-(2,5-dichloropyrimidin-4-yl)-1H-imidazole-2-carboxylate (Intermediate 31; 3.7 g, 12.89 mmol) and K$_2$CO$_3$ (5.34 g, 38.66 mmol) in acetonitrile (30 mL) at 80° C. under nitrogen. The resulting mixture was stirred at 85° C. for 12 hours. The reaction mixture was then filtered and washed with MeCN. The solvent was removed under reduced pressure to afford the desired product (S)-(tert-butoxycarbonyl)(1-(4-(2,5-dichloropyrimidin-4-yl)-2-(ethoxycarbonyl)-1H-imidazol-1-yl)propan-2-yl)sulfamic acid (Intermediate 30; 6.00 g, 89%) as a yellow oil. The product was used in the next step directly without further purification. m/z (ES+), [M+H]+=524.

Intermediate 31

Ethyl 4-(2,5-dichloropyrimidin-4-yl)-1H-imidazole-2-carboxylate

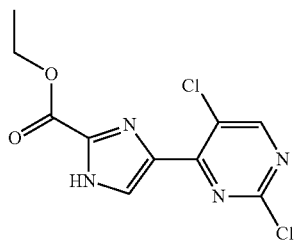 [SMILES: CCOC(=O)c1nc(-c2nc(Cl)ncc2Cl)c[nH]1]

Trifluoroacetic acid (20 mL, 259.60 mmol) was added to ethyl 4-(2,5-dichloropyrimidin-4-yl)-1-((2-(trimethylsilyl)ethoxy)methyl)-1H-imidazole-2-carboxylate (Intermediate 32; 5.6 g, 13.42 mmol) in DCM (20 mL) at 25° C. The resulting mixture was stirred at 25° C. for 12 hours. The solvent was removed under reduced pressure and the reaction mixture was basified with excess saturated NaHCO$_3$. The resulting precipitate formed was collected by filtration, washed with water (100 mL) and dried under vacuum to afford ethyl 4-(2,5-dichloropyrimidin-4-yl)-1H-imidazole-2-carboxylate (Intermediate 31; 3.70 g, 96%) as a white solid. $^1$H NMR (400 MHz, DMSO, 25° C.) δ 1.36 (3H, t), 4.39 (2H, q), 7.59 (1H, s), 8.32 (1H, s), 8.90 (1H, s). m/z (ES+), [M+H]+=287.

Intermediate 32

Ethyl 4-(2,5-dichloropyrimidin-4-yl)-1-((2-(trimethylsilyl)ethoxy)methyl)-1H-imidazole-2-carboxylate

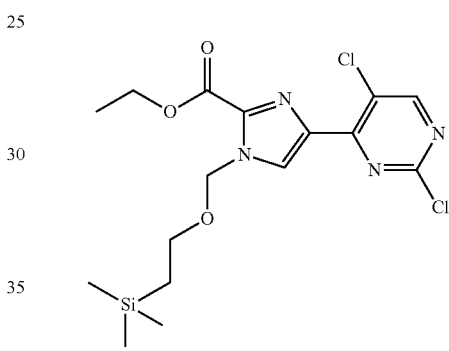

Pd(Ph$_3$P)$_4$ (1.14 g, 0.99 mmol) was added to (2-(ethoxycarbonyl)-1-((2-(trimethylsilyl)ethoxy)methyl)-1H-imidazol-4-yl)boronic acid (Intermediate 25; 6.2 g, 19.73 mmol), 2,4,5-trichloropyrimidine (3.62 g, 19.73 mmol) and Cs$_2$CO$_3$ (9.64 g, 29.60 mmol) in 1,4-dioxane (160 mL) and water (40 mL) at 25° C. under nitrogen. The resulting mixture was stirred at 85° C. for 2 hours. The reaction mixture was poured into water (150 mL), extracted with DCM (2×250 mL), the organic layers were dried over Na$_2$SO$_4$, filtered and evaporated to afford a yellow residue. The crude product was purified by flash silica chromatography, elution gradient 0 to 10% EtOAc in petroleum ether. Pure fractions were evaporated to dryness to afford ethyl 4-(2,5-dichloropyrimidin-4-yl)-1-((2-(trimethylsilyl)ethoxy)methyl)-1H-imidazole-2-carboxylate (Intermediate 32; 5.60 g, 68%) as a white solid. $^1$H NMR (400 MHz, CDCl$_3$, 25° C.) δ 0.01 (9H, s), 0.93-1.02 (2H, m), 1.48 (3H, t), 3.60-3.69 (2H, m), 4.48 (2H, q), 5.89 (2H, s), 8.29 (1H, s), 8.63 (1H, s). m/z (ES+), [M+H]+=417.

Example 7

(S)-2-(5-Chloro-2-((1-methyl-1H-pyrazol-5-yl)amino)pyrimidin-4-yl)-7-(3-methoxybenzyl)-6-methyl-6,7-dihydroimidazo[1,2-a]pyrazin-8(5H)-one

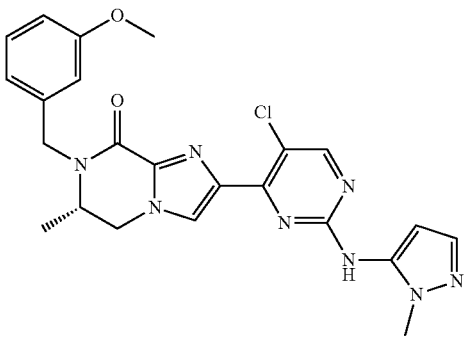 [SMILES: COc1cccc(CN2C(=O)c3nc(-c4nc(Nc5ccnn5C)ncc4Cl)cn3C[C@@H]2C)c1]

2nd Generation XantPhos precatalyst (31.9 mg, 0.04 mmol) was added to (S)-2-(2,5-dichloropyrimidin-4-yl)-7-(3-methoxybenzyl)-6-methyl-6,7-dihydroimidazo[1,2-a]pyrazin-8(5H)-one (Intermediate 33; 150 mg, 0.36 mmol), 1-methyl-1H-pyrazol-5-amine (87 mg, 0.90 mmol) and Cs$_2$CO$_3$ (234 mg, 0.72 mmol) in 1,4-dioxane (5 mL) at 25° C. under nitrogen. The resulting mixture was stirred at 100° C. for 8 hours. The solvent was then removed under reduced pressure and the crude product was purified by flash silica chromatography, elution gradient 0 to 6% MeOH in DCM. Pure fractions were evaporated to dryness to afford a yellow residue. The residue was further purified by preparative HPLC (XSelect CSH Prep C18 OBD column, 5μ silica, 19 mm diameter, 150 mm length), using decreasingly polar mixtures of water (containing 0.03% NH$_3$) and MeCN as eluents. Fractions containing the desired compound were evaporated to dryness to afford (S)-2-(5-chloro-2-((1-methyl-1H-pyrazol-5-yl)amino)pyrimidin-4-yl)-7-(3-methoxybenzyl)-6-methyl-6,7-dihydroimidazo[1,2-a]pyrazin-8(5H)-one (Example 7; 31.0 mg, 18.05%) as a white solid. $^1$H NMR (400 MHz, DMSO, 20° C.) δ 1.13 (3H, d), 3.71 (3H, s), 3.76 (3H, s), 3.96 (1H, d), 4.26-4.36 (2H, m), 4.41 (1H, dd), 5.09 (1H, d), 6.32 (1H, s), 6.84-6.91 (1H, m), 6.96 (2H, d), 7.24-7.38 (2H, m), 8.20 (1H, s), 8.54 (1H, s), 9.74 (1H, s). m/z (ES+), [M+H]+=479.

Intermediate 33

(S)-2-(2,5-Dichloropyrimidin-4-yl)-7-(3-methoxybenzyl)-6-methyl-6,7-dihydroimidazo[1,2-a]pyrazin-8(5H)-one

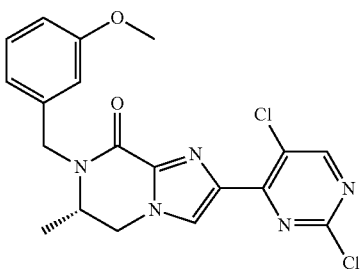 [SMILES: COc1cccc(CN2C(=O)c3nc(-c4nc(Cl)ncc4Cl)cn3C[C@@H]2C)c1]

TEA (0.162 mL, 1.16 mmol) was added to (S)-ethyl 4-(2,5-dichloropyrimidin-4-yl)-1-(2-((3-methoxybenzyl)amino)propyl)-1H-imidazole-2-carboxylate (Intermediate 34; 180 mg, 0.39 mmol) in toluene (8 mL) at 25° C. under air. The resulting mixture was stirred at 140° C. for 8 hours. The solvent was then removed under reduced pressure and the crude product was purified by flash silica chromatography, elution gradient 0 to 3% MeOH in DCM. Pure fractions were evaporated to dryness to afford (S)-2-(2,5-dichloropyrimidin-4-yl)-7-(3-methoxybenzyl)-6-methyl-6,7-dihydroimidazo[1,2-a]pyrazin-8(5H)-one (Intermediate 33; 150 mg, 93%) as a yellow solid. m/z (ES+), [M+Na]+=418. (S)-2-(2,5-dichloropyrimidin-4-yl)-7-(3-methoxybenzyl)-6-methyl-6,7-dihydroimidazo[1,2-a]pyrazin-8(5H)-one (Intermediate 33) was used in the next step without further purification.

Intermediate 34

(S)-Ethyl 4-(2,5-dichloropyrimidin-4-yl)-1-(2-((3-methoxybenzyl)amino)propyl)-1H-imidazole-2-carboxylate

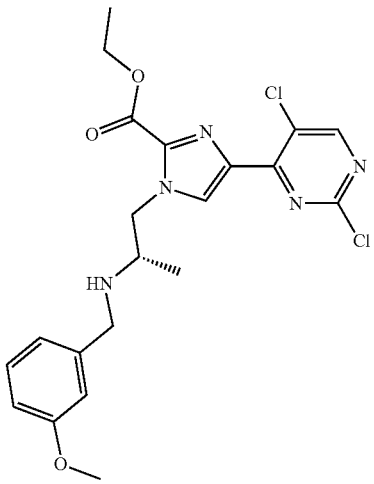 [SMILES: CCOC(=O)c1nc(-c2nc(Cl)ncc2Cl)cn1C[C@H](C)NCc1cccc(OC)c1]

3-methoxybenzaldehyde (71.8 mg, 0.53 mmol) was added to (S)-ethyl 1-(2-aminopropyl)-4-(2,5-dichloropyrimidin-4-yl)-1H-imidazole-2-carboxylate dihydrochloride (Intermediate 28; 200 mg, 0.48 mmol) in DCM (10 mL) at 25° C. under nitrogen. After stirring at 40° C. for 3 hours, sodium triacetoxyborohydride (305 mg, 1.44 mmol) was added and the resulting mixture was stirred at 25° C. for 3 hours. The reaction mixture was quenched with saturated NaHCO$_3$ (20 mL), extracted with DCM (2×50 mL), the organic layers were dried over Na$_2$SO$_4$, filtered and evaporated to afford a yellow residue. The crude product was purified by flash silica chromatography, elution gradient 0 to 5% MeOH in DCM. Pure fractions were evaporated to dryness to afford (S)-ethyl 4-(2,5-dichloropyrimidin-4-yl)-1-(2-((3-methoxybenzyl)amino)propyl)-1H-imidazole-2-carboxylate (Intermediate 34; 180 mg, 81%) as a yellow solid. m/z (ES+), [M+H]+=464.

Example 8

(S)-2-(5-chloro-2-((1-methyl-1H-pyrazol-5-yl)amino)pyrimidin-4-yl)-6-methyl-7-((2-(trifluoromethyl)pyrimidin-4-yl)methyl)-6,7-dihydroimidazo[1,2-a]pyrazin-8(5H)-one

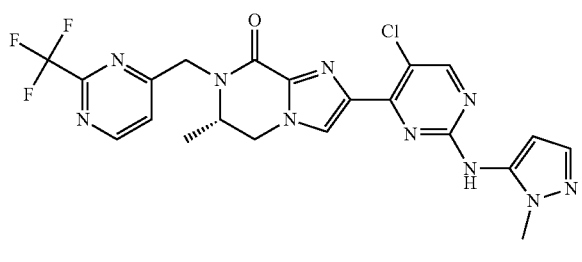 [SMILES: C[C@H]1Cn2cc(-c3nc(Nc4ccnn4C)ncc3Cl)nc2C(=O)N1Cc1ccnc(C(F)(F)F)n1]

2nd Generation XantPhos precatalyst (12.41 mg, 0.01 mmol) was added to (S)-2-(2,5-dichloropyrimidin-4-yl)-6-methyl-7-((2-(trifluoromethyl)pyrimidin-4-yl)methyl)-6,7-dihydroimidazo[1,2-a]pyrazin-8(5H)-one (Intermediate 35; 64 mg, 0.14 mmol), 1-methyl-1H-pyrazol-5-amine (33.9 mg, 0.35 mmol) and $Cs_2CO_3$ (91 mg, 0.28 mmol) in 1,4-dioxane (5 mL) at 25° C. under nitrogen and the resulting mixture was stirred at 100° C. for 8 hours. The solvent was then removed under reduced pressure. The crude product was purified by flash silica chromatography, elution gradient 0 to 6% MeOH in DCM. Pure fractions were evaporated to dryness to afford a yellow residue. This residue was further purified by preparative HPLC (XSelect CSH Prep C18 OBD column, 5μ silica, 19 mm diameter, 150 mm length), using decreasingly polar mixtures of water (containing 0.03% $NH_3$) and MeCN as eluents. Fractions containing the desired compound were evaporated to dryness to afford (S)-2-(5-chloro-2-((1-methyl-1H-pyrazol-5-yl)amino)pyrimidin-4-yl)-6-methyl-7-((2-(trifluoromethyl)pyrimidin-4-yl)methyl)-6,7-dihydroimidazo[1,2-a]pyrazin-8(5H)-one (Example 8; 15.2 mg, 21%) as a white solid. $^1$H NMR (400 MHz, DMSO, 20.1° C.) δ 1.25 (3H, d), 3.71 (3H, s), 4.18 (1H, ddd), 4.42 (1H, dd), 4.60-4.69 (2H, m), 5.23 (1H, d), 6.32 (1H, d), 7.35 (1H, d), 7.94 (1H, s), 8.25 (1H, s), 8.55 (1H, s), 9.03 (1H, d), 9.74 (1H, s). m/z (ES+), [M+H]+=519.

Intermediate 35

(S)-2-(2,5-dichloropyrimidin-4-yl)-6-methyl-7-((2-(trifluoromethyl)pyrimidin-4-yl)methyl)-6,7-dihydroimidazo[1,2-a]pyrazin-8(5H)-one

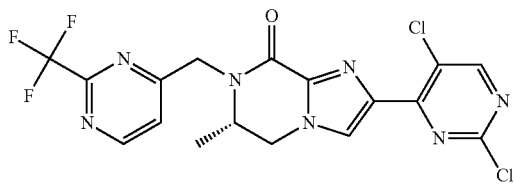 [SMILES: C[C@H]1Cn2cc(-c3nc(Cl)ncc3Cl)nc2C(=O)N1Cc1ccnc(C(F)(F)F)n1]

TEA (0.129 mL, 0.93 mmol) was added to (S)-ethyl 4-(2,5-dichloropyrimidin-4-yl)-1-(2-(((2-(trifluoromethyl)pyrimidin-4-yl)methyl)amino)propyl)-1H-imidazole-2-carboxylate (Intermediate 36; 156 mg, 0.31 mmol) in toluene (3 mL) at 25° C. under air. The resulting mixture was stirred at 140° C. for 4 hours. The solvent was then removed under reduced pressure. The crude product was purified by flash silica chromatography, elution gradient 3 to 4% MeOH in DCM. Pure fractions were evaporated to dryness to afford (S)-2-(2,5-dichloropyrimidin-4-yl)-6-methyl-7-((2-(trifluoromethyl)pyrimidin-4-yl)methyl)-6,7-dihydroimidazo[1,2-a]pyrazin-8(5H)-one (Intermediate 35; 64.0 mg, 45.2%) as a yellow solid. m/z (ES+), [M+H]+=458.

Intermediate 36

(S)-Ethyl 4-(2,5-dichloropyrimidin-4-yl)-1-(2-(((2-(trifluoromethyl)pyrimidin-4-yl)methyl)amino)propyl)-1H-imidazole-2-carboxylate

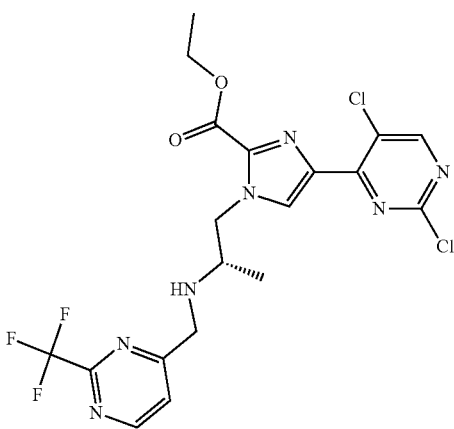 [SMILES: CCOC(=O)c1nc(-c2nc(Cl)ncc2Cl)cn1C[C@H](C)NCc1ccnc(C(F)(F)F)n1]

2-(Trifluoromethyl)pyrimidine-4-carbaldehyde (127 mg, 0.72 mmol) was added to (S)-ethyl 1-(2-aminopropyl)-4-(2,5-dichloropyrimidin-4-yl)-1H-imidazole-2-carboxylate dihydrochloride (Intermediate 28; 300 mg, 0.72 mmol) in DCM (10 mL) at 25° C. under air. The resulting solution was stirred at 40° C. for 3 hours. Sodium triacetoxyborohydride (457 mg, 2.16 mmol) was added to reaction mixture at 25° C. The resulting solution was stirred at 25° C. for 12 hours. The reaction mixture was quenched with water (10 mL) and extracted with DCM (3×15 mL). The organic layers were combined and washed with brine (15 mL), dried over $Na_2SO_4$, filtered and evaporated to afford yellow oil. The crude product was purified by flash silica chromatography, elution gradient 2 to 3% MeOH in DCM. Pure fractions were evaporated to dryness to afford (S)-ethyl 4-(2,5-dichloropyrimidin-4-yl)-1-(2-(((2-(trifluoromethyl)pyrimidin-4-yl)methyl)amino)propyl)-1H-imidazole-2-carboxylate (Intermediate 36; 156 mg, 43%) as a yellow oil. $^1$H NMR (400 MHz, CDCl$_3$, 20.2° C.) δ 1.26-1.38 (3H, m), 1.44 (3H, t), 2.85 (1H, s), 4.01 (2H, q), 4.33-4.51 (2H, m), 4.55-4.70 (1H, m), 4.92 (2H, s), 7.65 (1H, d), 8.65 (1H, d), 8.74-8.85 (1H, m), 8.91 (1H, d). m/z (ES+), [M+H]+=504.

Example 9

(S)-2-(5-Chloro-2-((1-methyl-1H-pyrazol-5-yl)amino)pyrimidin-4-yl)-7-((6-(difluoromethyl)pyridin-2-yl)methyl)-6-methyl-6,7-dihydroimidazo[1,2-a]pyrazin-8(5H)-one

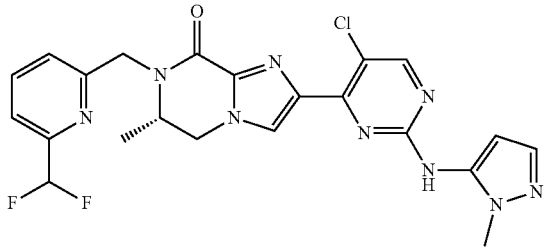 [SMILES: C[C@H]1Cn2cc(-c3nc(Nc4ccnn4C)ncc3Cl)nc2C(=O)N1Cc1cccc(C(F)F)n1]

2nd Generation XantPhos precatalyst (24.28 mg, 0.03 mmol) was added to (S)-2-(2,5-dichloropyrimidin-4-yl)-7-((6-(difluoromethyl)pyridin-2-yl)methyl)-6-methyl-6,7-dihydroimidazo[1,2-a]pyrazin-8(5H)-one (Intermediate 37; 120 mg, 0.27 mmol), 1-methyl-1H-pyrazol-5-amine (66.3 mg, 0.68 mmol) and Cs$_2$CO$_3$ (178 mg, 0.55 mmol) in 1,4-dioxane (5 mL) at 25° C. under nitrogen. The resulting mixture was stirred at 100° C. for 8 hours. The solvent was then removed under reduced pressure and the crude product was purified by flash silica chromatography, elution gradient 0 to 6% MeOH in DCM. Pure fractions were evaporated to dryness to afford a yellow residue. This residue was further purified by preparative HPLC (XSelect CSH Prep C18 OBD column, 5μ silica, 19 mm diameter, 150 mm length), using decreasingly polar mixtures of water (containing 0.03% NH$_3$) and MeCN as eluents. Fractions containing the desired compound were evaporated to dryness to afford (S)-2-(5-chloro-2-((1-methyl-1H-pyrazol-5-yl)amino)pyrimidin-4-yl)-7-((6-(difluoromethyl)pyridin-2-yl)methyl)-6-methyl-6,7-dihydroimidazo[1,2-a]pyrazin-8(5H)-one (Example 9; 27 mg, 19.8%) as a white solid. $^1$H NMR (400 MHz, DMSO, 23° C.) δ 1.21 (3H, d), 3.71 (3H, s), 4.12 (1H, s), 4.38 (1H, d), 4.48-4.63 (2H, m), 5.22 (1H, d), 6.32 (1H, s), 6.97 (1H, t), 7.35 (1H, d), 7.59-7.67 (2H, m), 8.00 (1H, t), 8.23 (1H, s), 8.54 (1H, s), 9.72 (1H, s). m/z (ES+), [M+H]+=500.

Intermediate 37

(S)-2-(2,5-Dichloropyrimidin-4-yl)-7-((6-(difluoromethyl)pyridin-2-yl)methyl)-6-methyl-6,7-dihydroimidazo[1,2-a]pyrazin-8(5H)-one

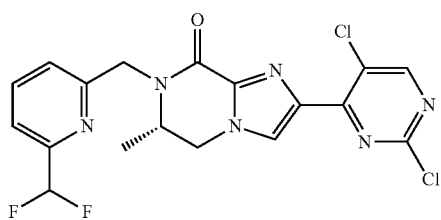 [SMILES: C[C@H]1Cn2cc(-c3nc(Cl)ncc3Cl)nc2C(=O)N1Cc1cccc(C(F)F)n1]

A solution of (S)-ethyl 4-(2,5-dichloropyrimidin-4-yl)-1-(2-(((6-(difluoromethyl)pyridin-2-yl)methyl)amino)propyl)-1H-imidazole-2-carboxylate (Intermediate 38; 200 mg, 0.41 mmol) in NH$_3$ (7N in MeOH, 5 mL, 35.00 mmol) was stirred at 50° C. for 2 hours. The solvent was then removed under reduced pressure and the crude product was purified by flash silica chromatography, elution gradient 0 to 5% MeOH in DCM. Pure fractions were evaporated to dryness to afford (S)-2-(2,5-dichloropyrimidin-4-yl)-7-((6-(difluoromethyl)pyridin-2-yl)methyl)-6-methyl-6,7-dihydroimidazo[1,2-a]pyrazin-8(5H)-one (Intermediate 37; 120 mg, 66.3%) as a yellow solid. m/z (ES+), [M+H]+=439.

Intermediate 38

(S)-Ethyl 4-(2,5-dichloropyrimidin-4-yl)-1-(2-(((6-(difluoromethyl)pyridin-2-yl)methyl)amino)propyl)-1H-imidazole-2-carboxylate

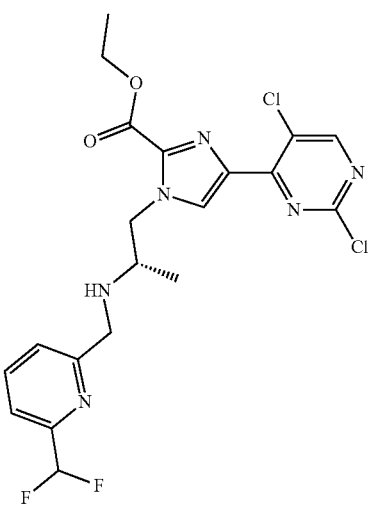 [SMILES: CCOC(=O)c1nc(-c2nc(Cl)ncc2Cl)cn1C[C@H](C)NCc1cccc(C(F)F)n1]

6-(difluoromethyl)picolinaldehyde (Intermediate 39; 226 mg, 1.44 mmol) was added to (S)-ethyl 1-(2-aminopropyl)-4-(2,5-dichloropyrimidin-4-yl)-1H-imidazole-2-carboxylate dihydrochloride (Intermediate 28; 200 mg, 0.48 mmol) in DCM (15 mL) at 25° C. under nitrogen. After stirring at 40° C. for 3 hours, sodium triacetoxyborohydride (305 mg, 1.44 mmol) was added and the resulting mixture was stirred at 25° C. for 3 hours. The reaction mixture was quenched with saturated NaHCO$_3$ (20 mL) and extracted with DCM (2×50 mL). The combined organic layers was dried over Na$_2$SO$_4$, filtered and evaporated to afford the desired product (S)-ethyl 4-(2,5-dichloropyrimidin-4-yl)-1-(2-(((6-(difluoromethyl)pyridin-2-yl)methyl)amino)propyl)-1H-imidazole-2-carboxylate (Intermediate 38; 200 mg, 86%) as a yellow solid. m/z (ES+), [M+H]+=485.

Intermediate 39

6-(Difluoromethyl)picolinaldehyde

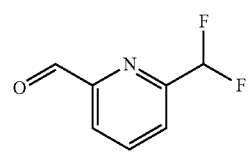 [SMILES: O=Cc1cccc(C(F)F)n1]

LiAlH$_4$ (1.141 g, 30.07 mmol) was added to 6-(difluoromethyl)-N-methoxy-N-methylpicolinamide (Intermediate 40; 5 g, 23.13 mmol) in THF (80 mL) cooled to −78° C. under nitrogen and the resulting solution was stirred at −78° C. for 1 hour. The reaction was diluted EtOAc (6 mL), then quenched with water (1 mL) at −78° C. NaOH (15% aqueous, 3.0 mL) and water (1.0 mL) were added and the resulting solids were filtered off. The filtrate was dried over Na$_2$SO$_4$, filtered and evaporated to afford 6-(difluoromethyl)picolinaldehyde (Intermediate 39; 3.60 g, 99%) as a yellow oil. The product was used in the next step without further purification. m/z (ES+), [M+H]+=158.

Intermediate 40

6-(Difluoromethyl)-N-methoxy-N-methylpicolinamide

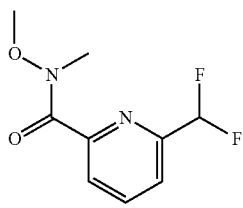

Oxalyl dichloride (7.92 g, 62.39 mmol) was added dropwise to 6-(difluoromethyl)picolinic acid (Intermediate 41; 5.4 g, 31.19 mmol) and DMF (0.242 mL, 3.12 mmol) in DCM (30 mL) at 25° C. under nitrogen. The resulting mixture was stirred at 25° C. for 2 hours. The solvent was then removed under reduced pressure to afford the desired product 6-(difluoromethyl)picolinoyl chloride (6.00 g, 100%) as a yellow oil which was used immediately. N,O-dimethylhydroxylamine hydrochloride (4.58 g, 46.98 mmol) was added portionwise to 6-(difluoromethyl)picolinoyl chloride (6.0 g, 31.32 mmol) and TEA (17.46 mL, 125.29 mmol) in DCM (50 mL) at 25° C. under nitrogen. The resulting mixture was then stirred at 25° C. for 12 hours. The reaction mixture was quenched with water (50 mL), extracted with DCM (2×100 mL), the organic layers were dried over Na$_2$SO$_4$, filtered and evaporated to afford yellow residue. The crude product was purified by flash silica chromatography, elution gradient 0 to 30% EtOAc in petroleum ether. Pure fractions were evaporated to dryness to afford 6-(difluoromethyl)-N-methoxy-N-methylpicolinamide (Intermediate 40; 5.00 g, 73.8%) as a yellow liquid. $^1$H NMR (400 MHz, CDCl$_3$, 20° C.) δ 3.42 (3H, s), 3.80 (3H, s), 6.68 (1H, t), 7.74 (2H, d), 7.98 (1H, t). m/z (ES+), [M+H]+=217.

Intermediate 41

6-(Difluoromethyl)picolinic acid

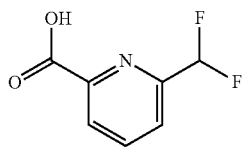 [SMILES: O=C(O)c1cccc(C(F)F)n1]

A solution of methyl 6-(difluoromethyl)picolinate (Intermediate 42; 6.2 g, 33.13 mmol) in HCl (30 mL, 360.00 mmol) was heated at 90° C. for 8 hours. The solvent was removed under reduced pressure to afford the desired product 6-(difluoromethyl)picolinic acid (Intermediate 41; 5.40 g, 94%) as a white solid. $^1$H NMR (400 MHz, DMSO, 20° C.) δ 7.05 (1H, t), 7.94 (1H, t), 8.16-8.22 (2H, m), 13.56 (1H, s). m/z (ES+), [M+H]+=174.

Intermediate 42

Methyl 6-(difluoromethyl)picolinate

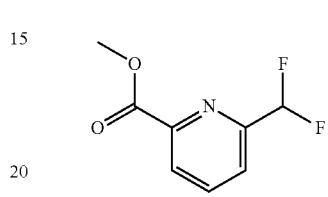

2-bromo-6-(difluoromethyl)pyridine (Intermediate 43; 8.5 g, 40.86 mmol), potassium acetate (8.02 g, 81.73 mmol) and Pd(dppf)Cl$_2$ (1.495 g, 2.04 mmol) in MeOH (100 mL) were stirred under an atmosphere of CO at 10 atm at 70° C. for 6 hours. The reaction mixture was then filtered and the filtrate was evaporated under reduced pressure. The crude product was purified by flash silica chromatography, elution gradient 0 to 20% EtOAc in petroleum ether. Pure fractions were evaporated to dryness to afford methyl 6-(difluoromethyl)picolinate (Intermediate 42; 6.20 g, 81%) as a colourless liquid. $^1$H NMR (400 MHz, CDCl$_3$, 20° C.) δ 4.06 (3H, s), 6.79 (1H, t), 7.89 (1H, d), 8.05 (1H, t), 8.24-8.31 (1H, m). m/z (ES+), [M+H]+=188.

Intermediate 43

2-Bromo-6-(difluoromethyl)pyridine

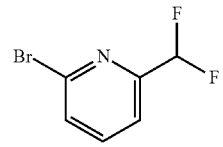

DAST (17.76 mL, 134.40 mmol) was added dropwise to 6-bromopicolinaldehyde (10 g, 53.76 mmol) in DCM (150 mL) cooled to 0° C. over a period of 10 minutes. The resulting mixture was stirred at 25° C. for 12 hours. The reaction mixture was quenched with water (20 mL) and basified by the addition of NaHCO$_3$ (sat. aq.). The aqueous phase was extracted with DCM (3×150 mL), the organic layer was dried over Na$_2$SO$_4$, filtered and evaporated to afford a brown liquid. The crude product was purified by flash silica chromatography, elution gradient 0 to 8% EtOAc in petroleum ether. Pure fractions were evaporated to dryness to afford 2-bromo-6-(difluoromethyl)pyridine (Intermediate 43; 9.00 g, 80%) as a colourless liquid. $^1$H NMR (400 MHz, CDCl$_3$, 22° C.) δ 6.59 (1H, t), 7.58-7.65 (2H, m), 7.71 (1H, t). m/z (ES+), [M+H]+=208/210.

Example 10

(S)-2-(5-Chloro-2-((1-methyl-1H-pyrazol-5-yl)amino)pyrimidin-4-yl)-6-methyl-7-((6-trifluoromethyl)pyridin-2-yl)methyl)-6,7-dihydroimidazo[1,2-a]pyrazin-8(5H)-one

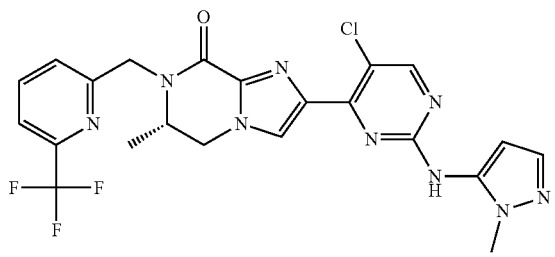 [SMILES: C[C@H]1Cn2cc(-c3nc(Nc4ccnn4C)ncc3Cl)nc2C(=O)N1Cc1cccc(C(F)(F)F)n1]

2nd Generation XantPhos precatalyst (14.97 mg, 0.02 mmol) was added to (S)-2-(2,5-dichloropyrimidin-4-yl)-6-methyl-7-((6-(trifluoromethyl)pyridin-2-yl)methyl)-6,7-dihydroimidazo[1,2-a]pyrazin-8(5H)-one (Intermediate 44; 77 mg, 0.17 mmol), 1-methyl-1H-pyrazol-5-amine (40.9 mg, 0.42 mmol) and $Cs_2CO_3$ (110 mg, 0.34 mmol) in 1,4-dioxane (3 mL) at 25° C. under nitrogen. The resulting mixture was stirred at 100° C. for 6 hours. The solvent was removed under reduced pressure and the crude product was purified by flash silica chromatography, elution gradient 5 to 6% MeOH in DCM. Pure fractions were evaporated to dryness to afford a yellow crude product. This crude product was further purified by preparative HPLC (XSelect CSH Prep C18 OBD column, 5μ silica, 19 mm diameter, 150 mm length), using decreasingly polar mixtures of water (containing 0.03% $NH_3$) and MeCN as eluents. Fractions containing the desired compound were evaporated to dryness to afford (S)-2-(5-chloro-2-((1-methyl-1H-pyrazol-5-yl)amino)pyrimidin-4-yl)-6-methyl-7-((6-(trifluoromethyl)pyridin-2-yl)methyl)-6,7-dihydroimidazo[1,2-a]pyrazin-8(5H)-one (Example 10; 18.5 mg, 21%) as a white solid. $^1$H NMR (400 MHz, DMSO, 23.0° C.) δ 1.22 (3H, d), 3.71 (3H, s), 4.15 (1H, ddd), 4.40 (1H, dd), 4.53-4.64 (2H, m), 5.23 (1H, d), 6.32 (1H, d), 7.35 (1H, d), 7.75-7.87 (2H, m), 8.10 (1H, t), 8.23 (1H, s), 8.54 (1H, s), 9.73 (1H, s). m/z (ES+), [M+H]+=518.

Intermediate 44

(S)-2-(2,5-Dichloropyrimidin-4-yl)-6-methyl-7-((6-(trifluoromethyl)pyridin-2-yl)methyl)-6,7-dihydroimidazo[1,2-a]pyrazin-8(5H)-one

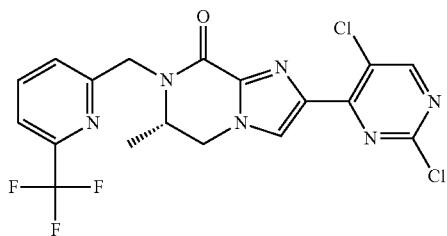 [SMILES: C[C@H]1Cn2cc(-c3nc(Cl)ncc3Cl)nc2C(=O)N1Cc1cccc(C(F)(F)F)n1]

$NH_3$ (7N in MeOH, 3 mL) was added to (S)-ethyl 4-(2,5-dichloropyrimidin-4-yl)-1-(2-(((6-(trifluoromethyl)pyridin-2-yl)methyl)amino)propyl)-1H-imidazole-2-carboxylate (Intermediate 45; 98 mg, 0.19 mmol). The resulting solution was stirred at 50° C. for 2 hours. The solvent was removed by distillation under vacuum to afford (S)-2-(2,5-dichloropyrimidin-4-yl)-6-methyl-7-((6-(trifluoromethyl)pyridin-2-yl)methyl)-6,7-dihydroimidazo[1,2-a]pyrazin-8(5H)-one (Intermediate 44; 77 mg, 86%) as a colourless oil. The product was used in the next step directly without further purification. m/z (ES+), [M+H]+=457.

Intermediate 45

(S)-Ethyl 4-(2,5-dichloropyrimidin-4-yl)-1-(2-(((6-(trifluoromethyl)pyridin-2-yl)methyl)amino)propyl)-1H-imidazole-2-carboxylate

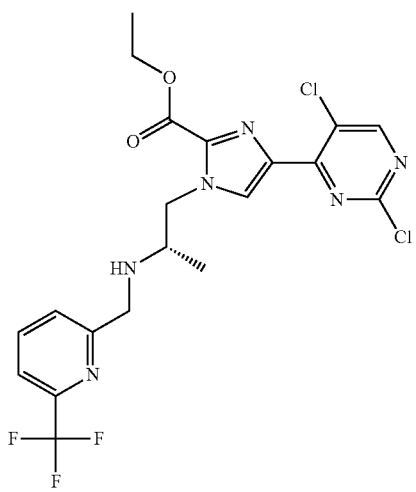 [SMILES: CCOC(=O)c1nc(-c2nc(Cl)ncc2Cl)cn1C[C@H](C)NCc1cccc(C(F)(F)F)n1]

6-(trifluoromethyl)picolinaldehyde (115 mg, 0.66 mmol) was added to (S)-ethyl 1-(2-aminopropyl)-4-(2,5-dichloropyrimidin-4-yl)-1H-imidazole-2-carboxylate dihydrochloride (Intermediate 28; 250 mg, 0.60 mmol) in DCM (10 mL) at 20° C. under nitrogen. The resulting solution was stirred at 40° C. for 4 hours. Sodium triacetoxyborohydride (254 mg, 1.20 mmol) was then added at 20° C. and the resulting solution was stirred at 20° C. for 12 hours. The reaction mixture was quenched with water (10 mL), extracted with DCM (3×15 mL). The combined organic layers were washed with brine (15 mL), dried over $Na_2SO_4$, filtered and evaporated to afford a yellow oil. The crude product was purified by flash silica chromatography, elution gradient 2 to 2.5% MeOH in DCM. Pure fractions were evaporated to dryness to afford (S)-ethyl 4-(2,5-dichloropyrimidin-4-yl)-1-(2-(((6-(trifluoromethyl)pyridin-2-yl)methyl)amino)propyl)-1H-imidazole-2-carboxylate (Intermediate 45; 98 mg, 32.5%) as a yellow oil. m/z (ES+), [M+H]+=503.

Example 11

(S)-2-(5-chloro-2-((1-methyl-1H-pyrazol-5-yl)amino)pyrimidin-4-yl)-6-methyl-7-((6-methylpyridin-2-yl)methyl)-6,7-dihydroimidazo[1,2-a]pyrazin-8(5H)-one

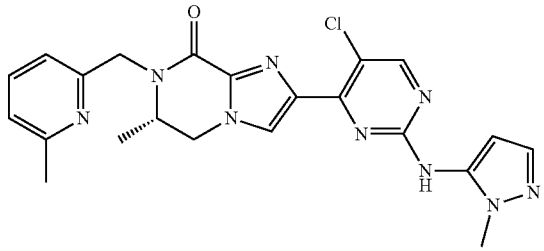 [SMILES: Cc1cccc(CN2C(=O)c3nc(-c4nc(Nc5ccnn5C)ncc4Cl)cn3C[C@@H]2C)n1]

2nd Generation XantPhos precatalyst (26.4 mg, 0.03 mmol) was added to (S)-2-(2,5-dichloropyrimidin-4-yl)-6-methyl-7-((6-methylpyridin-2-yl)methyl)-6,7-dihydroimidazo[1,2-a]pyrazin-8(5H)-one (Intermediate 46; 120 mg, 0.30 mmol), 1-methyl-1H-pyrazol-5-amine (72.2 mg, 0.74 mmol) and $Cs_2CO_3$ (194 mg, 0.60 mmol) in 1,4-dioxane (8 mL) at 25° C. under nitrogen. The resulting mixture was stirred at 100° C. for 8 hours. The solvent was then removed under reduced pressure. The crude product was purified by flash silica chromatography, elution gradient 0 to 6% MeOH in DCM. Pure fractions were evaporated to dryness to afford a yellow residue. This residue was further purified by preparative HPLC (XSelect CSH Prep C18 OBD column, 5μ silica, 19 mm diameter, 150 mm length), using decreasingly polar mixtures of water (containing 0.03% $NH_3$) and MeCN as eluents. Fractions containing the desired compound were evaporated to dryness to afford (S)-2-(5-chloro-2-((1-methyl-1H-pyrazol-5-yl)amino)pyrimidin-4-yl)-6-methyl-7-((6-methylpyridin-2-yl)methyl)-6,7-dihydroimidazo[1,2-a]pyrazin-8(5H)-one (Example 11; 50 mg, 36.2%) as a white solid. $^1$H NMR (400 MHz, DMSO, 22° C.) δ 1.19 (3H, d), 2.47 (3H, s), 3.70 (3H, s), 4.08 (1H, d), 4.32-4.43 (2H, m), 4.53 (1H, dd), 5.15 (1H, d), 6.31 (1H, d), 7.21 (2H, dd), 7.34 (1H, d), 7.68 (1H, t), 8.21 (1H, s), 8.53 (1H, s), 9.72 (1H, s). m/z (ES+), [M+H]+=464.

Intermediate 46

(S)-2-(2,5-Dichloropyrimidin-4-yl)-6-methyl-7-((6-methylpyridin-2-yl)methyl)-6,7-dihydroimidazo[1,2-a]pyrazin-8(5H)-one

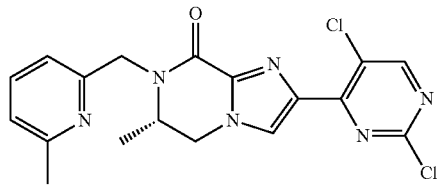 [SMILES: Cc1cccc(CN2C(=O)c3nc(-c4nc(Cl)ncc4Cl)cn3C[C@@H]2C)n1]

Sodium acetate (118 mg, 1.44 mmol) was added to (S)-ethyl 1-(2-aminopropyl)-4-(2,5-dichloropyrimidin-4-yl)-1H-imidazole-2-carboxylate dihydrochloride (Intermediate 28; 200 mg, 0.48 mmol) and 6-methylpicolinaldehyde (63.9 mg, 0.53 mmol) in MeOH (10 mL) at 20° C. under nitrogen. The resulting mixture was stirred at 25° C. for 30 minutes. Sodium triacetoxyborohydride (203 mg, 0.96 mmol) was added and the reaction mixture was stirred at 25° C. for 18 hours. The reaction was quenched with saturated aqueous $NaHCO_3$ (25 mL) and the aqueous phase was extracted with DCM (3×50 mL). The combined organic phases were dried over $Na_2SO_4$, filtered and evaporated to afford yellow residue. The crude product was purified by flash silica chromatography, elution gradient 0 to 5% MeOH in DCM. Pure fractions were evaporated to dryness to afford (S)-2-(2,5-dichloropyrimidin-4-yl)-6-methyl-7-((6-methylpyridin-2-yl)methyl)-6,7-dihydroimidazo[1,2-a]pyrazin-8(5H)-one (Intermediate 46; 120 mg, 62.1%) as a white solid. $^1$H NMR (400 MHz, CDCl$_3$, 24° C.) δ 1.33 (3H, d), 2.60 (3H, s), 4.09 (1H, d), 4.19-4.46 (2H, m), 4.52 (1H, d), 5.42 (1H, d), 7.15 (1H, s), 7.34 (1H, s), 7.63 (1H, s), 8.02 (1H, s), 8.61 (1H, s). m/z (ES+), [M+H]+=403.

Example 12

7-(3-Chloro-4-fluorobenzyl)-2-(5-methyl-2-((1-methyl-1H-pyrazol-5-yl)amino)pyrimidin-4-yl)-6,7-dihydroimidazo[1,2-a]pyrazin-8(5H)-one

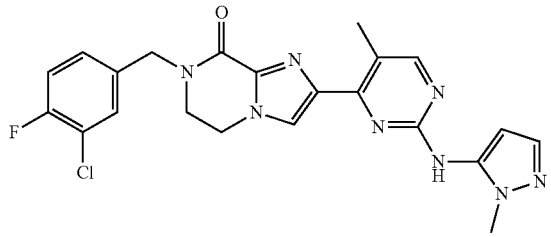

2nd Generation XantPhos precatalyst (63.9 mg, 0.07 mmol) was added to 7-(3-chloro-4-fluorobenzyl)-2-(2-chloro-5-methylpyrimidin-4-yl)-6,7-dihydroimidazo[1,2-a]pyrazin-8(5H)-one (Intermediate 47; 292 mg, 0.72 mmol), 1-methyl-1H-pyrazol-5-amine (140 mg, 1.44 mmol) and $Cs_2CO_3$ (585 mg, 1.80 mmol) in 1,4-dioxane (3 mL) at 25° C. under nitrogen. The resulting solution was stirred at 100° C. for 4 hours. The solvent was removed by distillation under vacuum and the crude product was purified by flash silica chromatography, elution gradient 0 to 7% MeOH in DCM. Product containing fractions were evaporated to dryness to afford crude product. This crude product was purified further by preparative HPLC (XSelect CSH Prep C18 OBD column, 5μ silica, 19 mm diameter, 150 mm length), using decreasingly polar mixtures of water (containing 0.05% $NH_4HCO_3$) and MeCN as eluents. Fractions containing the desired compound were evaporated to dryness to afford 7-(3-chloro-4-fluorobenzyl)-2-(5-methyl-2-((1-methyl-1H-pyrazol-5-yl)amino)pyrimidin-4-yl)-6,7-dihydroimidazo[1,2-a]pyrazin-8(5)-one (Example 12; 59.7 mg, 17.79%) as a white solid. $^1$H NMR (400 MHz, CDCl$_3$, 20.1° C.) δ 2.70 (3H, s), 3.72 (2H, dd), 3.81 (3H, s), 4.26-4.34 (2H, m), 4.77 (2H, s), 6.31 (1H, d), 6.98 (1H, s), 7.15 (1H, t), 7.23-7.32 (1H, m), 7.45 (1H, dd), 7.49 (1H, d), 7.73 (1H, s), 8.30 (1H, s). m/z (ES+), [M+H]+=467.

Intermediate 47

7-(3-Chloro-4-fluorobenzyl)-2-(2-chloro-5-methyl-pyrimidin-4-yl)-6,7-dihydroimidazo[1,2-a]pyrazin-8(5H)-one

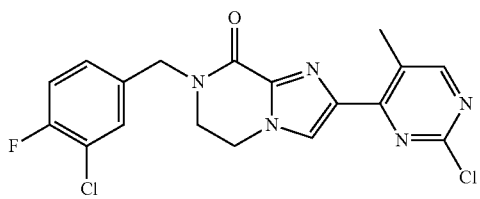 [SMILES: Cc1cnc(Cl)nc1-c1cn2c(n1)C(=O)N(Cc1ccc(F)c(Cl)c1)CC2]

NaH (68.3 mg, 1.71 mmol) was added to 2-(2-chloro-5-methylpyrimidin-4-yl)-6,7-dihydroimidazo[1,2-a]pyrazin-8(5H)-one (Intermediate 48; 150 mg, 0.57 mmol) in DMF (5 mL) at 25° C. under nitrogen. The resulting solution was then stirred at 25° C. for 30 minutes. 4-(bromomethyl)-2-chloro-1-fluorobenzene (254 mg, 1.14 mmol) was added at 25° C. and stirring continue for 2 hours. The reaction mixture was quenched with saturated aqueous NaHCO$_3$ (25 mL), the resulting precipitate was collected by filtration, washed with water (50 mL) and dried under vacuum to afford 7-(3-chloro-4-fluorobenzyl)-2-(2-chloro-5-methylpyrimidin-4-yl)-6,7-dihydroimidazo[1,2-a]pyrazin-8(5H)-one (Intermediate 48; 292 mg, >100%) as a yellow solid, which was used without further purification. $^1$H NMR (400 MHz, DMSO, 20.1° C.) δ 2.64 (3H, s), 3.74-3.82 (2H, m), 4.35-4.43 (2H, m), 4.70 (2H, s), 7.34-7.49 (2H, m), 7.60 (1H, ddd), 8.25 (1H, s), 8.61 (1H, s). m/z (ES+), [M+H]+=406.

Intermediate 48

2-(2-Chloro-5-methylpyrimidin-4-yl)-6,7-dihydroimidazo[1,2-a]pyrazin-8(5H)-one

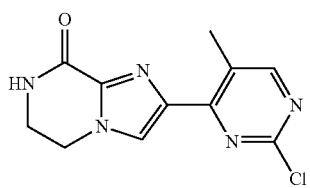 [SMILES: Cc1cnc(Cl)nc1-c1cn2c(n1)C(=O)NCC2]

NH$_3$ (7N in MeOH, 15 mL) was added to ethyl 1-(2-aminoethyl)-4-(2-chloro-5-methylpyrimidin-4-yl)-1H-imidazole-2-carboxylate dihydrochloride (Intermediate 21; 1.3 g, 3.40 mmol) at 20° C. under air and the resulting solution was stirred at 20° C. for 12 hours. The solvent was removed by distillation under vacuum, the resulting solid was slurried with water (50 mL), filtered and dried under vacuum to afford 2-(2-chloro-5-methylpyrimidin-4-yl)-6,7-dihydroimidazo[1,2-a]pyrazin-8(5H)-one (Intermediate 48; 0.80 g, 89%) as a white solid, which was used without further purification. $^1$H NMR (400 MHz, DMSO, 20.3° C.) δ 2.62 (3H, s), 3.61 (2H, ddd), 4.29-4.37 (2H, m), 8.26 (1H, s), 8.35 (1H, t), 8.59 (1H, d). m/z (ES+), [M+H]+=264.

Example 13

7-(3-Chlorobenzyl)-2-(5-methyl-2-((1-methyl-1H-pyrazol-5-yl)amino)pyrimidin-4-yl)-6,7-dihydroimidazo[1,2-a]pyrazin-8(5H)-one

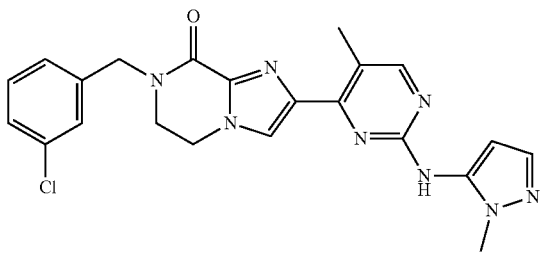 [SMILES: Cc1cnc(Nc2ccnn2C)nc1-c1cn2c(n1)C(=O)N(Cc1cccc(Cl)c1)CC2]

2nd Generation XantPhos precatalyst (62.0 mg, 0.07 mmol) was added to 2-(2-chloro-5-methylpyrimidin-4-yl)-7-(3-chlorobenzyl)-6,7-dihydroimidazo[1,2-a]pyrazin-8(5H)-one (Intermediate 49; 271 mg, 0.70 mmol), 1-methyl-1H-pyrazol-5-amine (136 mg, 1.40 mmol) and Cs$_2$CO$_3$ (569 mg, 1.75 mmol) in 1,4-dioxane (5 mL) at 25° C. under nitrogen. The resulting solution was stirred at 100° C. for 4 hours. The solvent was then removed by distillation under vacuum and the crude product was purified by flash silica chromatography, elution gradient 0 to 7% MeOH in DCM. Product containing fractions were evaporated to dryness to afford crude product. This crude product was further purified by preparative HPLC (XSelect CSH Prep C18 OBD column, 5μ silica, 19 mm diameter, 150 mm length), using decreasingly polar mixtures of water (containing 0.05% NH$_4$HCO$_3$) and MeCN as eluents. Fractions containing the desired compound were evaporated to dryness to afford 7-(3-chlorobenzyl)-2-(5-methyl-2-((1-methyl-1H-pyrazol-5-yl)amino)pyrimidin-4-yl)-6,7-dihydroimidazo[1,2-a]pyrazin-8(5H)-one (Example 13; 43.5 mg, 13.9%) as a white solid. $^1$H NMR (400 MHz, CDCl$_3$, 20.1° C.) δ 2.69 (3H, s), 3.68-3.76 (2H, m), 3.81 (3H, s), 4.29 (2H, dd), 4.80 (2H, s), 6.31 (1H, d), 7.06 (1H, s), 7.25-7.29 (1H, m), 7.30-7.34 (2H, m), 7.36-7.39 (1H, m), 7.49 (1H, d), 7.73 (1H, s), 8.29 (1H, s). m/z (ES+), [M+H]+=449.

Intermediate 49

2-(2-Chloro-5-methylpyrimidin-4-yl)-7-(3-chlorobenzyl)-6,7-dihydroimidazo[1,2-a]pyrazin-8(5H)-one

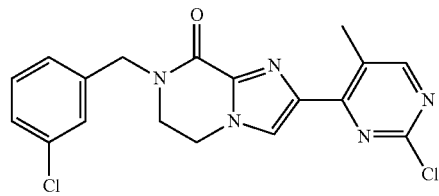 [SMILES: Cc1cnc(Cl)nc1-c1cn2c(n1)C(=O)N(Cc1cccc(Cl)c1)CC2]

NaH (68.3 mg, 1.71 mmol) was added to 2-(2-chloro-5-methylpyrimidin-4-yl)-6,7-dihydroimidazo[1,2-a]pyrazin-8(5H)-one (Intermediate 48; 150 mg, 0.57 mmol) in DMF (5 mL) at 25° C. under nitrogen. The resulting solution was stirred at 25° C. for 30 minutes. 1-(bromomethyl)-3-chlorobenzene (234 mg, 1.14 mmol) was added and the resulting solution was stirred at 25° C. for 2 hours. The reaction mixture was quenched with saturated NaHCO₃ (25 mL), the resulting precipitate was collected by filtration, washed with water (50 mL) and dried under vacuum to afford 2-(2-chloro-5-methylpyrimidin-4-yl)-7-(3-chlorobenzyl)-6,7-dihydroimidazo[1,2-a]pyrazin-8(5H)-one (Intermediate 49; 271 mg) as a yellow solid, which was used without further purification. ¹H NMR (400 MHz, CDCl₃, 20.1° C.) δ 2.64 (3H, s), 3.74-3.82 (2H, m), 4.36-4.44 (2H, m), 4.72 (2H, s), 7.39-7.48 (4H, m), 8.26 (1H, s), 8.61 (1H, s). m/z (ES+) [M+H]+=388.

Example 14

7-(3-(Difluoromethyl)benzyl)-2-(5-methyl-2-((1-methyl-1H-pyrazol-5-yl)amino)pyrimidin-4-yl)-6,7-dihydroimidazo[1,2-a]pyrazin-8(5H)-one

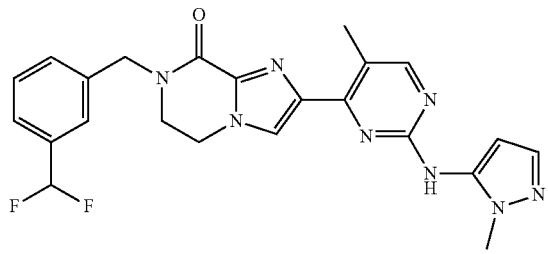 [SMILES: Cc1cnc(Nc2ccnn2C)nc1-c1cn2c(n1)C(=O)N(Cc1cccc(C(F)F)c1)CC2]

2nd Generation XantPhos precatalyst (61.6 mg, 0.07 mmol) was added to 2-(2-chloro-5-methylpyrimidin-4-yl)-7-(3-(difluoromethyl)benzyl)-6,7-dihydroimidazo[1,2-a]pyrazin-8(5H)-one (Intermediate 50; 280 mg, 0.69 mmol), 1-methyl-1H-pyrazol-5-amine (135 mg, 1.39 mmol) and Cs₂CO₃ (565 mg, 1.73 mmol) in 1,4-dioxane (5 mL) at 25° C. under nitrogen. The resulting solution was stirred at 100° C. for 4 hours. The solvent was then removed by distillation under vacuum. The crude product was purified by flash silica chromatography, elution gradient 0 to 7% MeOH in DCM. Compound containing fractions were evaporated to dryness to afford impure product. This impure product was purified further by preparative HPLC (XSelect CSH Prep C18 OBD column, 5μ silica, 19 mm diameter, 150 mm length), using decreasingly polar mixtures of water (containing 0.05% NH₄HCO₃) and MeCN as eluents. Fractions containing the desired compound were evaporated to dryness to afford 7-(3-(difluoromethyl)benzyl)-2-(5-methyl-2-((1-methyl-1H-pyrazol-5-yl)amino)pyrimidin-4-yl)-6,7-dihydroimidazo[1,2-a]pyrazin-8(5H)-one (Example 14; 14; 69.6 mg, 21.6%) as a white solid. ¹H NMR (400 MHz, CDCl₃, 20.2° C.) δ 2.70 (3H, s), 3.68-3.76 (2H, m), 3.81 (3H, s), 4.24-4.32 (2H, m), 4.88 (2H, s), 6.31 (1H, d), 6.66 (1H, t), 6.98 (1H, s), 7.43-7.56 (5H, m), 7.73 (1H, s), 8.30 (1H, s). m/z (ES+), [M+H]+=465.

Intermediate 50

2-(2-Chloro-5-methylpyrimidin-4-yl)-7-(3-(difluoromethyl)benzyl)-6,7-dihydroimidazo[1,2-a]pyrazin-8(5H)-one

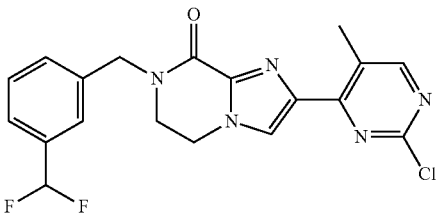 [SMILES: Cc1cnc(Cl)nc1-c1cn2c(n1)C(=O)N(Cc1cccc(C(F)F)c1)CC2]

NaH (68.3 mg, 1.71 mmol) was added to 2-(2-chloro-5-methylpyrimidin-4-yl)-6,7-dihydroimidazo[1,2-a]pyrazin-8 (5H)-one (150 mg, 0.57 mmol) in DMF (5 mL) at 25° C. under nitrogen and the resulting solution was stirred at 25° C. for 30 minutes. 1-(bromomethyl)-3-(difluoromethyl)benzene (251 mg, 1.14 mmol) was added and the resulting solution was stirred at 25° C. for 2 hours. The reaction mixture was quenched with saturated NaHCO₃ (25 mL) and the resulting precipitate was collected by filtration, washed with water (50 mL) and dried under vacuum to afford 2-(2-chloro-5-methylpyrimidin-4-yl)-7-(3-(difluoromethyl) benzyl)-6,7-dihydroimidazo[1,2-a]pyrazin-8(5H)-one (Intermediate 50; 280 mg) as a yellow solid, which was used without further purification. ¹H NMR (400 MHz, DMSO, 19.9° C.) δ 2.64 (3H, s), 3.74-3.82 (2H, m), 4.36-4.44 (2H, m), 4.79 (2H, s), 7.06 (1H, td), 7.49-7.56 (4H, m), 8.26 (1H, s), 8.61 (1H, s).

Example 15

7-((6-(Difluoromethyl)pyridin-2-yl)methyl)-2-(5-methyl-2-((1-methyl-1H-pyrazol-5-yl)amino)pyrimidin-4-yl)-6,7-dihydroimidazo[1,2-a]pyrazin-8(5H)-one

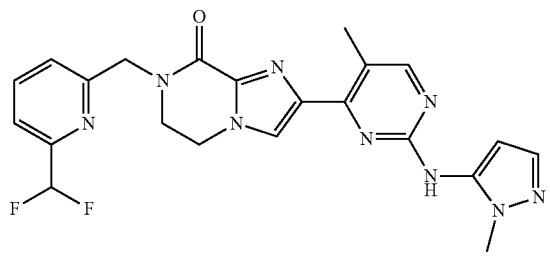 [SMILES: Cc1cnc(Nc2ccnn2C)nc1-c1cn2c(n1)C(=O)N(Cc1cccc(C(F)F)n1)CC2]

3rd Generation BrettPhos precatalyst (22.95 mg, 0.03 mmol) was added to 2-(2-chloro-5-methylpyrimidin-4-yl)-7-((6-(difluoromethyl)pyridin-2-yl)methyl)-6,7-dihydroimidazo[1,2-a]pyrazin-8(5H)-one (Intermediate 51; 205 mg, 0.51 mmol), 1-methyl-1H-pyrazol-5-amine (123 mg, 1.27 mmol) and Cs₂CO₃ (330 mg, 1.01 mmol) in 1,4-dioxane (8 mL) at 25° C. under nitrogen and the resulting mixture was stirred at 100° C. for 8 hours. The solvent was then removed under reduced pressure. The crude product was purified by flash silica chromatography, elution gradient 0 to 6% MeOH in DCM. Compound containing fractions were evaporated to dryness to afford a yellow residue. This residue was purified further by preparative HPLC (XSelect CSH Prep C18 OBD column, 5μ silica, 19 mm diameter, 150 mm length), using decreasingly polar mixtures of water (containing 0.03% NH₃) and MeCN as eluents. Fractions containing the desired compound were evaporated to dryness to afford 7-((6-(difluoromethyl)pyridin-2-yl)methyl)-2-(5-methyl-2-((1-methyl-1H-pyrazol-5-yl)amino)pyrimidin-4-yl)-6,7-dihydroimidazo[1,2-a]pyrazin-8(5H)-one (Example 15; 122 mg, 51.8%) as a white solid. $^1$H NMR (400 MHz, DMSO, 20° C.) δ 2.50 (3H, s), 3.70 (3H, s), 3.87-3.95 (2H, m), 4.42-4.50 (2H, m), 4.87 (2H, s), 6.30 (1H, d), 6.95 (1H, t), 7.33 (1H, d), 7.61 (2H, t), 7.94 (1H, s), 8.00 (1H, t), 8.32 (1H, s), 9.24 (1H, s). m/z (ES+), [M+H]+=466.

Intermediate 51

2-(2-Chloro-5-methylpyrimidin-4-yl)-7-((6-(difluoromethyl)pyridin-2-yl)methyl)-6,7-dihydroimidazo[1,2-a]pyrazin-8(5H)-one

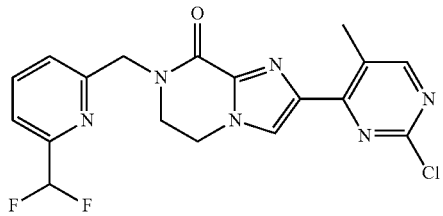 [SMILES: Cc1cnc(Cl)nc1-c1cn2c(n1)C(=O)N(Cc1cccc(C(F)F)n1)CC2]

6-(Difluoromethyl)picolinaldehyde (Intermediate 39; 123 mg, 0.78 mmol) was added to ethyl 1-(2-aminoethyl)-4-(2-chloro-5-methylpyrimidin-4-yl)-1H-imidazole-2-carboxylate dihydrochloride (Intermediate 21; 200 mg, 0.52 mmol), DIPEA (0.274 mL, 1.57 mmol) and AcOH (0.090 mL, 1.57 mmol) in DCM (10 mL) at 25° C. under nitrogen. After stirring at 25° C. for 1 hour, sodium triacetoxyborohydride (332 mg, 1.57 mmol) was added and the resulting mixture was stirred at 25° C. for 1 hour and then heated at 50° C. for 3 hours. The reaction mixture was quenched with saturated NaHCO₃ (20 mL), extracted with DCM (2×75 mL), the combined organic phases were dried over Na₂SO₄, filtered and evaporated to afford a yellow residue. The crude product was purified by flash silica chromatography, elution gradient 0 to 5% MeOH in DCM. Pure fractions were evaporated to dryness to afford 2-(2-chloro-5-methylpyrimidin-4-yl)-7-((6-(difluoromethyl)pyridin-2-yl)methyl)-6,7-dihydroimidazo[1,2-a]pyrazin-8(5H)-one (Intermediate 51; 205 mg, 97%) as a yellow solid. $^1$H NMR (400 MHz, CDCl₃, 20° C.) δ 2.74 (3H, d), 3.95-4.04 (2H, m), 4.27-4.39 (2H, m), 4.94 (2H, s), 6.43-6.73 (1H, m), 7.57 (2H, d), 7.84 (1H, t), 7.96 (1H, s), 8.42 (1H, s). m/z (ES+), [M+H]+=405.

Example 16

(R)-7-((6-(Difluoromethyl)pyridin-2-yl)methyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one

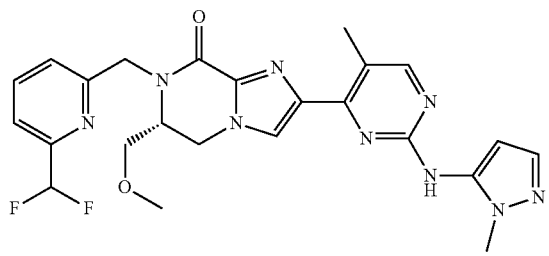 [SMILES: COC[C@H]1Cn2cc(-c3nc(Nc4ccnn4C)ncc3C)nc2C(=O)N1Cc1cccc(C(F)F)n1]

3rd Generation BrettPhos precatalyst (30.3 mg, 0.03 mmol) was added to (R)-2-(2-chloro-5-methylpyrimidin-4-yl)-7-((6-(difluoromethyl)pyridin-2-yl)methyl)-6-(methoxymethyl)-6,7-dihydroimidazo[1,2-a]pyrazin-8(5H)-one (Intermediate 52; 150 mg, 0.33 mmol), 1-methyl-1H-pyrazol-5-amine (81 mg, 0.84 mmol) and Cs₂CO₃ (218 mg, 0.67 mmol) in 1,4-dioxane (8 mL) at 25° C. under nitrogen and the resulting mixture was stirred at 120° C. for 8 hours. The solvent was then removed under reduced pressure. The resulting residue was purified by flash silica chromatography, elution gradient 0 to 6% MeOH in DCM to afford a yellow residue. This residue was purified further by preparative HPLC (XSelect CSH Prep C18 OBD column, 5μ silica, 19 mm diameter, 150 mm length), using decreasingly polar mixtures of water (containing 0.03% NH₃) and MeCN as eluents. Fractions containing the desired compound were evaporated to dryness to afford (R)-7-((6-(difluoromethyl)pyridin-2-yl)methyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (Example 16; 27 mg, 15.9%) as a white solid. $^1$H NMR (400 MHz, DMSO, 25° C.) δ 2.50 (3H, s), 3.20 (3H, s), 3.34-3.42 (1H, m), 3.52 (1H, dd), 3.71 (3H, s), 4.15 (1H, s), 4.59 (3H, d), 5.24 (1H, d), 6.28-6.33 (1H, m), 6.97 (1H, t), 7.34 (1H, d), 7.59-7.66 (2H, m), 7.95-8.04 (2H, m), 8.32 (1H, s), 9.21 (1H, s). m/z (ES+), [M+H]+=510.

Intermediate 52

(R)-2-(2-Chloro-5-methylpyrimidin-4-yl)-7-((6-(difluoromethyl)pyridin-2-yl)methyl)-6-(methoxymethyl)-6,7-dihydroimidazo[1,2-a]pyrazin-8(5H)-one

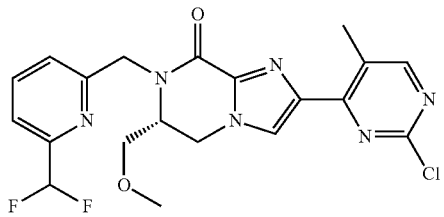 [SMILES: COC[C@H]1Cn2cc(-c3nc(Cl)ncc3C)nc2C(=O)N1Cc1cccc(C(F)F)n1]

A solution of (R)-ethyl 4-(2-chloro-5-methylpyrimidin-4-yl)-1-(2-(((6-(difluoromethyl)pyridin-2-yl)methyl)amino)-3-methoxypropyl)-1H-imidazole-2-carboxylate (Intermediate 53; 360 mg, 0.73 mmol) in NH₃ in MeOH (20 mL, 140.00 mmol) was stirred at 25° C. for 48 hours. The volatiles were then removed under reduced pressure. The crude product was purified by flash silica chromatography, elution gradient 0 to 5% MeOH in DCM. Pure fractions were evaporated to dryness to afford (R)-2-(2-chloro-5-methylpyrimidin-4-yl)-7-((6-(difluoromethyl)pyridin-2-yl)methyl)-6-(methoxymethyl)-6,7-dihydroimidazo[1,2-a]pyrazin-8(5H)-one (Intermediate 52; 300 mg, 92%) as a yellow solid. m/z (ES+), [M+H]+=449.

Intermediate 53

(R)-Ethyl 4-(2-chloro-5-methylpyrimidin-4-yl)-1-(2-(((6-(difluoromethyl)pyridin-2-yl)methyl)amino)-3-methoxypropyl)-1H-imidazole-2-carboxylate

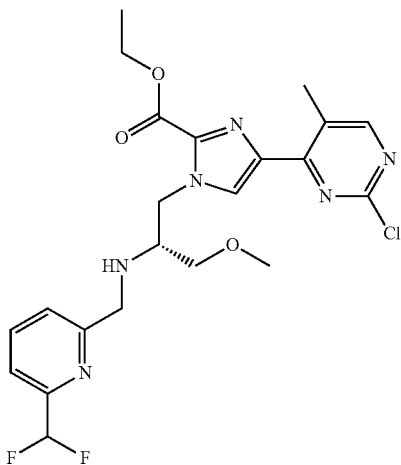 [SMILES: CCOC(=O)c1nc(-c2nc(Cl)ncc2C)cn1C[C@H](COC)NCc1cccc(C(F)F)n1]

6-(Difluoromethyl)picolinaldehyde (442 mg, 2.81 mmol) was added to (R)-ethyl 1-(2-amino-3-methoxypropyl)-4-(2-chloro-5-methylpyrimidin-4-yl)-1H-imidazole-2-carboxylate dihydrochloride (Intermediate 54; 400 mg, 0.94 mmol) in DCM (20 mL) at 25° C. under nitrogen. After stirring at 40° C. for 3 hours, sodium triacetoxyborohydride (596 mg, 2.81 mmol) was added and the resulting mixture was stirred at 25° C. for 3 hours. The reaction mixture was quenched with saturated NaHCO$_3$ (20 mL), extracted with DCM (2×50 mL), the organic layer was dried over Na$_2$SO$_4$, filtered and evaporated to afford yellow residue. The crude product was purified by flash silica chromatography, elution gradient 0 to 5% MeOH in DCM. Pure fractions were evaporated to dryness to afford (R)-ethyl 4-(2-chloro-5-methylpyrimidin-4-yl)-1-(2-(((6-(difluoromethyl)pyridin-2-yl)methyl)amino)-3-methoxypropyl)-1H-imidazole-2-carboxylate (Intermediate 53; 360 mg, 78%) as a yellow solid. m/z (ES+), [M+H]+=495.

Intermediate 54

(R)-Ethyl 1-(2-amino-3-methoxypropyl)-4-(2-chloro-5-methylpyrimidin-4-yl)-1H-imidazole-2-carboxylate dihydrochloride

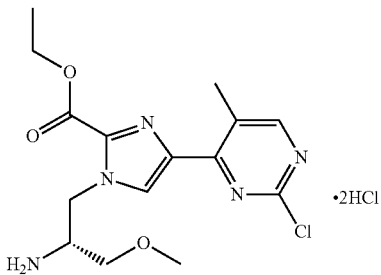 [SMILES: CCOC(=O)c1nc(-c2nc(Cl)ncc2C)cn1C[C@@H](N)COC]

A solution of (R)-ethyl 1-(2-((tert-butoxycarbonyl)amino)-3-methoxypropyl)-4-(2-chloro-5-methylpyrimidin-4-yl)-1H-imidazole-2-carboxylate (Intermediate 55; 1 g, 2.20 mmol) in 1,4-dioxane/HCl (20 mL) was stirred at 25° C. overnight. The precipitate was collected by filtration, washed with EtOAc (20 mL) and dried under vacuum to afford (R)-ethyl 1-(2-amino-3-methoxypropyl)-4-(2-chloro-5-methylpyrimidin-4-yl)-1H-imidazole-2-carboxylate (Intermediate 54; 0.80 g, 85%) as a white solid. $^1$H NMR (400 MHz, DMSO, 22° C.) δ 1.36 (3H, t), 2.64 (3H, s), 3.48-3.66 (5H, m), 3.85 (1H, s), 4.39 (2H, q), 4.64-4.79 (2H, m), 8.36 (2H, s), 8.41 (1H, s), 8.62-8.67 (1H, m). m/z (ES+), [M+H]+=354.

Intermediate 55

(R)-Ethyl 1-(2-((tert-butoxycarbonyl)amino)-3-methoxypropyl)-4-(2-chloro-5-methylpyrimidin-4-yl)-1H-imidazole-2-carboxylate

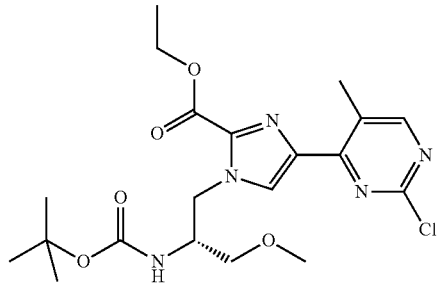 [SMILES: CCOC(=O)c1nc(-c2nc(Cl)ncc2C)cn1C[C@H](COC)NC(=O)OC(C)(C)C]

1M HCl (20 mL, 20.00 mmol) was added to (R)-(tert-butoxycarbonyl)(1-(4-(2-chloro-5-methylpyrimidin-4-yl)-2-(ethoxycarbonyl)-1H-imidazol-1-yl)-3-methoxypropan-2-yl)sulfamic acid (Intermediate 56; 5 g, 9.36 mmol) in EtOH (20 mL) at 25° C. under air and the resulting mixture was stirred at 50° C. for 20 minutes. The reaction mixture was quenched with saturated NaHCO$_3$ (50 mL), extracted with DCM (3×100 mL), the organic phases were dried over Na$_2$SO$_4$, filtered and evaporated to afford yellow residue. The crude product was purified by flash silica chromatography, elution gradient 0 to 30% EtOAc in petroleum ether. Pure fractions were evaporated to dryness to afford (R)-ethyl 1-(2-((tert-butoxycarbonyl)amino)-3-methoxypropyl)-4-(2-chloro-5-methylpyrimidin-4-yl)-1H-imidazole-2-carboxylate (Intermediate 55; 1.0 g, 23.53%) as a yellow solid. $^1$H NMR (400 MHz, CDCl$_3$, 22° C.) δ 1.32 (9H, s), 1.47 (3H, t), 2.71 (3H, s), 3.40 (3H, s), 3.51 (2H, qd), 4.24 (1H, d), 4.41-4.57 (3H, m), 4.73 (1H, dd), 5.11 (1H, d), 7.98 (1H, s), 8.41 (1H, s).

Intermediate 56

(R)-(tert-Butoxycarbonyl)(1-(4-(2-chloro-5-methyl-pyrimidin-4-yl)-2-(ethoxycarbonyl)-1H-imidazol-1-yl)-3-methoxypropan-2-yl)sulfamic acid

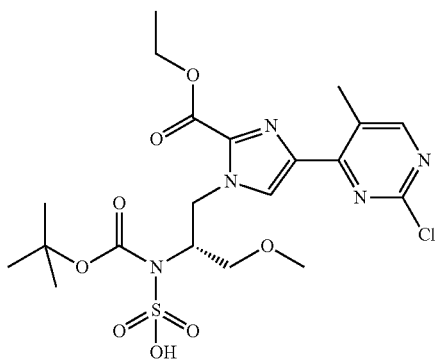 [SMILES: CCOC(=O)c1nc(-c2nc(Cl)ncc2C)cn1C[C@H](COC)N(C(=O)OC(C)(C)C)S(=O)(=O)O]

(S)-tert-Butyl 4-(methoxymethyl)-1,2,3-oxathiazolidine-3-carboxylate 2,2-dioxide (Intermediate 57; 3.26 g, 12.19 mmol) was added portionwise to ethyl 4-(2-chloro-5-methylpyrimidin-4-yl)-1H-imidazole-2-carboxylate (Intermediate 23; 2.5 g, 9.37 mmol), $K_2CO_3$ (3.89 g, 28.12 mmol) and 18-crown-6 (0.496 g, 1.87 mmol) in 1,4-dioxane (30 mL) at 100° C. under nitrogen and the resulting mixture was stirred at 100° C. for 12 hours. The reaction mixture was then filtered and washed with DCM and the solvent was removed under reduced pressure to afford the desired product (R)-(tert-butoxycarbonyl)(1-(4-(2-chloro-5-methylpyrimidin-4-yl)-2-(ethoxycarbonyl)-1H-imidazol-1-yl)-3-methoxypropan-2-yl)sulfamic acid (5.00 g, 100%) as a yellow oil, which was used directly in the next stage. m/z (ES+), [M+H]+=534.

Intermediate 57

(S)-tert-Butyl 4-(methoxymethyl)-1,2,3-oxathiazolidine-3-carboxylate 2,2-dioxide

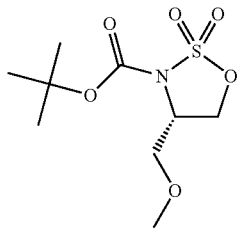 [SMILES: COC[C@H]1COS(=O)(=O)N1C(=O)OC(C)(C)C]

To a solution of (4S)-tert-butyl 4-(methoxymethyl)-1,2,3-oxathiazolidine-3-carboxylate 2-oxide (Intermediate 58; 3.34 g, 13.29 mmol) in acetonitrile (30 mL) at 0° C. under nitrogen was added sequentially sodium metaperiodate (3.13 g, 14.62 mmol), ruthenium(III) chloride (0.276 g, 1.33 mmol) and water (30.0 mL) and then stirred at 0° C. for 3 hours. The reaction mixture was diluted with water (100 mL) and filtered to remove insoluble inorganic salts. The resulting solution was extracted with ether (2×100 mL), washed with brine (2×100 mL) and dried over $MgSO_4$ to give (S)-tert-butyl 4-(methoxymethyl)-1,2,3-oxathiazolidine-3-carboxylate 2,2-dioxide (Intermediate 57; 2.86 g, 80%) as an oil. $^1$H NMR (500 MHz, $CDCl_3$, 27° C.) 1.56 (9H, s), 3.41 (3H, s), 3.59 (1H, t), 3.66 (1H, ddd), 4.38 (1H, dddd), 4.52-4.67 (2H, m). m/z: ES+[M+H]+ 268.

Alternative preparation of Intermediate 57:

A solution of sodium metaperiodate (95 g, 444.49 mmol) and ruthenium chloride (0.349 g, 1.33 mmol) in water (800 mL) was added to a solution of tert-butyl (4S)-4-(methoxymethyl)-1,2,3-oxathiazolidine-3-carboxylate 2-oxide (Intermediate 58; 111.7 g, 444.49 mmol) in acetonitrile (800 mL) at 10° C. The reaction was shown to be complete by $^1$H NMR immediately after the addition. The reaction mixture was diluted with MTBE (1000 mL) and the layers were separated. The organic layer was washed water (2×500 mL) and concentrated to afford (S)-tert-butyl 4-(methoxymethyl)-1,2,3-oxathiazolidine-3-carboxylate 2,2-dioxide (Intermediate 57; 115 g, 95%) as an oil. $^1$H NMR (400 MHz, MeOD) δ 1.54 (s, 9H), 3.40 (s, 3H), 3.61 (d, 2H), 4.46 (qd, 1H), 4.60 (dd, 1H), 4.68 (dd, 1H).

Intermediate 58

(4S)-tert-Butyl 4-(methoxymethyl)-1,2,3-oxathiazolidine-3-carboxylate 2-oxide

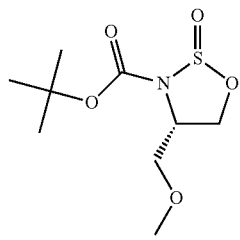 [SMILES: COC[C@H]1COS(=O)N1C(=O)OC(C)(C)C]

Imidazole (1.629 g, 23.92 mmol) was added in one portion to thionyl chloride (1.75 mL, 23.92 mmol) and triethylamine (3.33 mL, 23.92 mmol) in DCM (100 mL) and cooled to −78° C. under nitrogen. The resulting solution was stirred for 20 minutes. A solution of (R)-tert-butyl (1-hydroxy-3-methoxypropan-2-yl)carbamate (Intermediate 59; 4.91 g, 23.92 mmol) in DCM (26.7 mL) was added dropwise over 10 minutes. The resulting solution was stirred at −78° C. for 3 hours and then allowed to warm to room temperature. To the reaction mixture was added water (100 mL), and then extracted with DCM (2×100 mL). The organics were combined and washed with brine (100 mL), dried over $MgSO_4$ and evaporated to afford a crude product. The crude product was purified by flash silica chromatography, eluting with 10% $Et_2O$ in DCM. Pure fractions were evaporated to dryness to afford (4S)-tert-butyl 4-(methoxymethyl)-1,2,3-oxathiazolidine-3-carboxylate 2-oxide (Intermediate 58; 3.34 g, 55.6%) as a colourless oil and as a 2:1 mixture of diastereomers. $^1$H NMR (500 MHz, $CDCl_3$, 27° C.) 1.55-1.58 (9H, d), 3.31 (0.5H, t), 3.41 (3H, s), 3.52-3.63 (1H, m), 3.90 (0.5 H, dd), 4.17-4.4 (1H, m), 4.64-4.92 (1H, m), 4.94-5.07 (1H, m). m/z: ES+[M+H]+ 252.

Alternative preparation of Intermediate 58:

To a solution of 1H-imidazole (672 g, 9.76 mol) in dichloromethane (5 L) was added triethylamine (568 g, 5.61 mol) and the resulting solution was cooled to −60° C. Thionyl chloride (377 g, 3.17 mol) was added dropwise to the mixture maintaining a temperature below −50° C. (2 h). (R)-tert-Butyl (1-hydroxy-3-methoxypropan-2-yl)carbamate (Intermediate 59; 500 g, 2.44 mol) dissolved in dichloromethane (5 L) was then added dropwise over the course of 4 to 5 hours keeping the temperature below −55° C. throughout the addition. Once all the starting material is added, the reaction was left to warm to room temperature overnight.

The reaction mixture was then poured into water (~3 L), the layers separated, and the aqueous layer extracted with DCM (1 L). The combined organic layers were dried over MgSO4, and the mixture filtered through a plug of silica (2 Kg) eluting with dichloromethane, and concentrated under reduced pressure to give an oil. This oil was placed under high vacuum with stirring to remove residual dichloromethane to give (4S)-tert-butyl 4-(methoxymethyl)-1,2,3-oxathiazolidine-3-carboxylate 2-oxide (Intermediate 58; 489 g, 80%) as an oil and as a 36:64 mixture of diastereomers.

Intermediate 59

(R)-tert-Butyl (1-hydroxy-3-methoxypropan-2-yl)carbamate

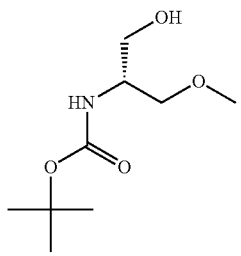

iso-Butyl chloroformate (0.599 mL, 4.56 mmol) was added dropwise to (S)-2-((tert-butoxycarbonyl)amino)-3-methoxypropanoic acid (1 g, 4.56 mmol) and N-methylmorpholine (0.501 mL, 4.56 mmol) in THF (6 mL) and cooled to 0° C. over a period of 15 minutes under nitrogen. The resulting suspension was stirred at 0° C. for a further 15 minutes. Sodium borohydride (0.500 g, 13.23 mmol) dissolved in water (1.2 mL) was added slowly to the reaction at 0° C. The reaction was stirred for 30 minutes before being diluted with EtOAc (50 mL) and neutralised with aqueous HCl (2M). Water was added (50 mL) and the organic layer was separated, washed with brine (50 mL) and dried over MgSO$_4$. The evaporation of the solvent gave a crude product which was purified by flash silica chromatography, elution gradient 0 to 50% EtOAc in heptane. Pure fractions were evaporated to dryness to afford (R)-tert-butyl (1-hydroxy-3-methoxypropan-2-yl)carbamate (Intermediate 59; 0.510 g, 54.5%) as a colourless oil. $^1$H NMR (500 MHz, CDCl$_3$, 27° C.) 1.45 (9H, s), 3.36 (3H, s), 3.5-3.62 (2H, m), 3.64-3.73 (1H, m), 3.74-3.84 (2H, m), 5.16 (1H, s). m/z: ES+[M+Na]+ 228.

Example 17

(R)-7-(3-Chlorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one

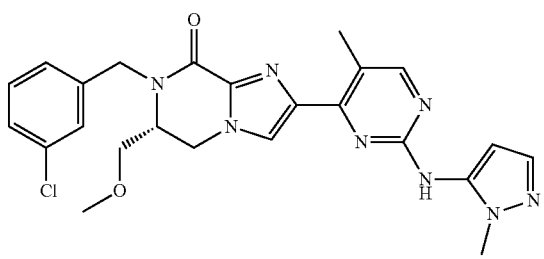 [SMILES: COC[C@H]1Cn2cc(-c3nc(Nc4ccnn4C)ncc3C)nc2C(=O)N1Cc1cccc(Cl)c1]

2nd Generation XantPhos precatalyst (30.8 mg, 0.03 mmol) was added to (R)-2-(2-chloro-5-methylpyrimidin-4-yl)-7-(3-chlorobenzyl)-6-(methoxymethyl)-6,7-dihydroimidazo[1,2-a]pyrazin-8(5H)-one (Intermediate 60; 150 mg, 0.35 mmol), 1-methyl-1H-pyrazol-5-amine (84 mg, 0.87 mmol) and Cs$_2$CO$_3$ (226 mg, 0.69 mmol) in 1,4-dioxane (5 mL) at 25° C. under nitrogen. The resulting mixture was stirred at 100° C. for 8 hours. The solvent was then removed under reduced pressure. The crude product was purified by flash silica chromatography, elution gradient 0 to 6% MeOH in DCM. Product containing fractions were evaporated to dryness to afford a yellow residue. This residue was purified further by preparative HPLC (XSelect CSH Prep C18 OBD column, 5µ silica, 19 mm diameter, 150 mm length), using decreasingly polar mixtures of water (containing 0.03% NH$_3$) and MeCN as eluents. Fractions containing the product were evaporated to dryness to afford (R)-7-(3-chlorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (Example 17; 34.0 mg, 19.9%) as a white solid. $^1$H NMR (400 MHz, DMSO, 24° C.) δ 2.51 (3H, s), 3.18 (3H, s), 3.29 (1H, s), 3.40 (1H, dd), 3.70 (3H, s), 4.04 (1H, s), 4.39-4.57 (3H, m), 5.09 (1H, d), 6.30 (1H, d), 7.31-7.50 (5H, m), 7.94 (1H, s), 8.32 (1H, s), 9.21 (1H, s). m/z (ES+), [M+H]+=493.

Intermediate 60

(R)-2-(2-Chloro-5-methylpyrimidin-4-yl)-7-(3-chlorobenzyl)-6-(methoxymethyl)-6,7-dihydroimidazo[1,2-a]pyrazin-8(5H)-one

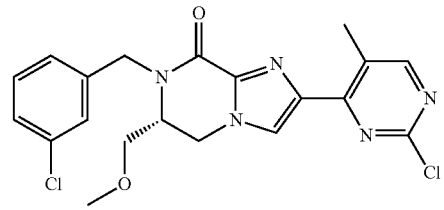 [SMILES: COC[C@H]1Cn2cc(-c3nc(Cl)ncc3C)nc2C(=O)N1Cc1cccc(Cl)c1]

1-(Bromomethyl)-3-chlorobenzene (187 mg, 0.91 mmol) was added to (R)-2-(2-chloro-5-methylpyrimidin-4-yl)-6-(methoxymethyl)-6,7-dihydroimidazo[1,2-a]pyrazin-8(5H)-one (Intermediate 61; 140 mg, 0.45 mmol) and NaH (54.6 mg, 1.36 mmol) in DMF (5 mL) at 25° C. under nitrogen and the resulting mixture was stirred at 25° C. for 12 hours. The reaction mixture was quenched with water (25 mL) and extracted with EtOAc (3×25 mL). The combined organic phases were washed with brine, dried over Na$_2$SO$_4$, filtered and evaporated to afford yellow residue. The crude product was purified by flash silica chromatography, elution gradient 0 to 5% MeOH in DCM. Pure fractions were evaporated to dryness to afford (R)-2-(2-chloro-5-methylpyrimidin-4-yl)-7-(3-chlorobenzyl)-6-(methoxymethyl)-6,7-dihydroimidazo[1,2-a]pyrazin-8(5H)-one (Intermediate 60; 150 mg, 76%) as a yellow solid. $^1$H NMR (400 MHz, CDCl$_3$, 25° C.) δ 2.81 (3H, s), 3.30 (4H, s), 3.41 (1H, s), 3.84 (1H, s), 4.17-4.28 (2H, m), 4.43 (1H, d), 5.44 (1H, d), 7.33 (2H, d), 7.40 (2H, s), 7.97 (1H, s), 8.04 (1H, s). m/z (ES+), [M+H]+=432.

109

Intermediate 61

(R)-2-(2-Chloro-5-methylpyrimidin-4-yl)-6-(methoxymethyl)-6,7-dihydroimidazo[1,2-a]pyrazin-8(5H)-one

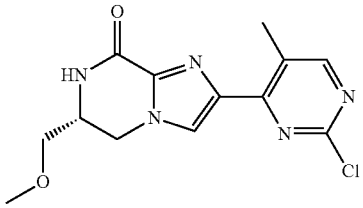 [SMILES: COC[C@H]1Cn2cc(-c3nc(Cl)ncc3C)nc2C(=O)N1]

A solution of (R)-ethyl 1-(2-amino-3-methoxypropyl)-4-(2-chloro-5-methylpyrimidin-4-yl)-1H-imidazole-2-carboxylate dihydrochloride (Intermediate 54; 400 mg, 0.94 mmol) in NH$_3$ in MeOH (15 mL, 105.00 mmol) was stirred at 25° C. overnight. The solvent was then removed under reduced pressure. The crude product was purified by flash silica chromatography, elution gradient 0 to 5% MeOH in DCM. Pure fractions were evaporated to dryness to afford (R)-2-(2-chloro-5-methylpyrimidin-4-yl)-6-(methoxymethyl)-6,7-dihydroimidazo[1,2-a]pyrazin-8(5H)-one (Intermediate 61; 280 mg, 97%) as a white solid. $^1$H NMR (400 MHz, CDCl$_3$, 23° C.) δ 2.78 (3H, s), 3.43 (3H, s), 3.49-3.58 (2H, m), 4.16-4.33 (2H, m), 4.37 (1H, dd), 6.56 (1H, s), 8.01 (1H, s), 8.45 (1H, s). m/z (ES+), [M+H]+=308.

Alternative preparation of Intermediate 61:

A solution of tert-butyl (S)-4-(methoxymethyl)-1,2,3-oxathiazolidine-3-carboxylate 2,2-dioxide (Intermediate 57; 105 g, 383.60 mmol) in acetone (500 mL) was added to a stirred suspension of ethyl 4-(2-chloro-5-methylpyrimidin-4-yl)-1H-imidazole-2-carboxylate (Intermediate 23; 93 g, 348.73 mmol) and K$_2$CO$_3$ (57.8 g, 418.47 mmol) in a mixture of acetone (500 mL) and 1,4 dioxane (500 mL) at room temperature. The resulting mixture was stirred at 25° C. for 16 hours. The reaction mixture was filtered and the filtrate was concentrated to 500 mL. To the concentrated solution, HCl in iso-propylalchol (5-6N, 500 mL, 2500 mmol) was added and stirred at 25° C. for 24 hours. Et$_3$N (486 mL, 3487.26 mmol) was then added to the mixture and stirred at 55° C. for 16 hours. The reaction mixture was quenched with water (1500 mL) and resulting solid was filtered. The solid cake was washed with a water (400 mL) and 1:1 mixture of acetone/water (200 mL×2) to afford (R)-2-(2-chloro-5-methylpyrimidin-4-yl)-6-(methoxymethyl)-6,7-dihydroimidazo [1,2-a]pyrazin-8(5H)-one (82 g, 76%) as a solid. $^1$H NMR (400 MHz, DMSO, 20° C.) δ 2.62 (s, 3H), 3.27 (s, 3H), 3.39 (dd, 2H), 3.99 (s, 1H), 4.30 (dd, 1H), 4.43 (dd, 1H), 8.26 (s, 1H), 8.42 (d, 1H), 8.59 (s, 1H). m/z (ES+), [M+H]+=308.

Example 18

(R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one

110

2nd Generation XantPhos precatalyst (0.784 g, 0.86 mmol) was added to (R)-2-(2-chloro-5-methylpyrimidin-4-yl)-7-(3,4-difluorobenzyl)-6-(methoxymethyl)-6,7-dihydroimidazo[1,2-a]pyrazin-8(5H)-one (Intermediate 62; 7.5 g, 17.29 mmol), 1-methyl-1H-pyrazol-5-amine (4.20 g, 43.22 mmol) and Cs$_2$CO$_3$ (11.27 g, 34.58 mmol) in 1,4-dioxane (200 mL) at 25° C. under nitrogen. The resulting mixture was stirred at 100° C. for 8 hours. The solvent was then removed under reduced pressure. The crude product was purified by flash silica chromatography, elution gradient 0 to 6% MeOH in DCM. Product containing fractions were evaporated to dryness to afford a residue. This residue was purified further by C18-flash chromatography, elution gradient 5 to 50% MeCN in water (0.1% NH$_4$HCO$_3$). Pure fractions were evaporated to dryness to afford (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (Example 18; 5.50 g, 64.3%) as a solid. (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one was determined to be amorphous by XRPD.

Alternative preparation of Example 18:

To a mixture of (R)-2-(2-chloro-5-methylpyrimidin-4-yl)-7-(3,4-difluorobenzyl)-6-(methoxymethyl)-6,7-dihydroimidazo[1,2-a]pyrazin-8(5H)-one (Intermediate 62; 104.7 g, 225.64 mmol), 1-methyl-1H-pyrazol-5-amine (33.5 g, 338.47 mmol) in 2-methyl tetrahydrofuran (1200 mL) and Cs$_2$CO$_3$ (147 g, 451.29 mmol) in water (120 mL) were added 2'-(dicyclohexylphosphanyl)-N,N-dimethyl-[1,1'-biphenyl]-2-amine (7.10 g, 18.05 mmol) and Pd$_2$(dba)$_3$ (8.27 g, 9.03 mmol) at 25° C. under nitrogen. The resulting mixture was degassed 3 times under nitrogen and then stirred at 70° C. for 24 hours. The reaction mixture was cooled to room temperature and the layers were separated. The organic layer was washed successively with water (500 mL), aqueous citric acid (1N, 600 mL) and water (200 mL). Silicycle (Si—SH, 150 g) was added to the organic layer at 40° C. and stirred for 20 hours. After filtration the filtrate was concentrated and the residue was purified by SFC chromatography using a Kromasil DIOL column, elution gradient 25% EtOH/NH$_3$ 100/0.5 in CO$_2$, 140 bar. Pure fractions were evaporated to dryness to afford (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (Example 18; 72.6 g, 65%) as a solid. $^1$H NMR (500 MHz, DMSO) δ 2.51 (3H, s), 3.17 (3H, s), 3.30 (1H, dd), 3.39 (1H, dd), 3.69 (3H, s), 4.03 (1H, dtd), 4.38 (1H, d), 4.44 (1H, dd), 4.51 (1H, dd), 5.08 (1H, d), 6.30 (1H, d), 7.22-7.28 (1H, m), 7.33 (1H, d), 7.41 (1H, dt), 7.47 (1H, ddd), 7.93 (1H, s), 8.31 (1H, s), 9.21 (1H, s). m/z (ES+), [M+H]+=495.

Example 18a

Preparation of (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct Form 1

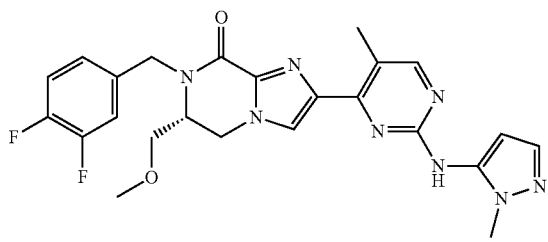 [SMILES: COC[C@H]1Cn2cc(-c3nc(Nc4ccnn4C)ncc3C)nc2C(=O)N1Cc1ccc(F)c(F)c1]

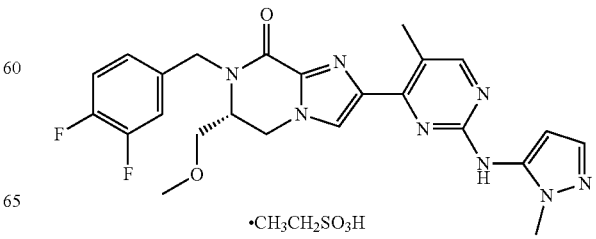

·CH$_3$CH$_2$SO$_3$H

Figure 2:
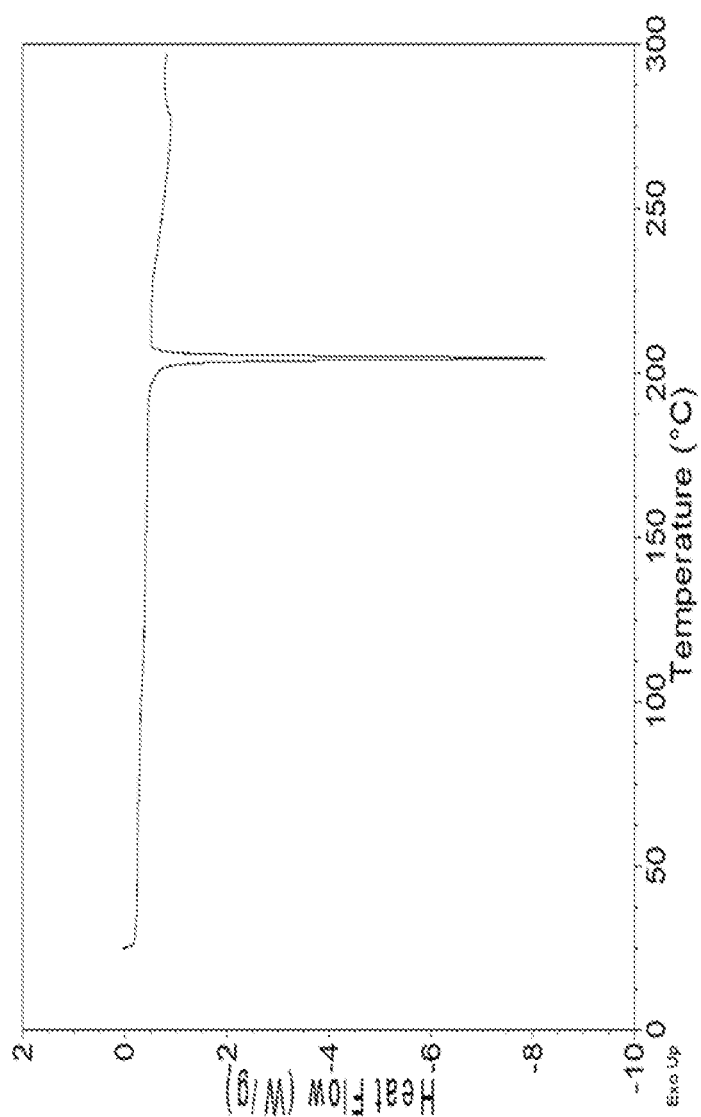
FIG. 2 shows the DSC Thermogram of (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Ethanesulfonic acid adduct Form 1 (Example 18a).

To a hot solution of (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (Example 18; 114 g, 200.56 mmol) in MeCN (500 mL) at 55° C. was added a solution of ethanesulfonic acid (17.02 mL, 210.59 mmol) in acetonitrile (100 mL). The reaction mixture was slowly cooled to 5° C. over 24 hours, the resulting solid was filtered and washed with cold MeCN (200 mL) to afford the ethanesulfonic acid adduct Form 1 of (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Form 1 (Example 18a; 119 g, 98%) as a solid. The adduct was determined by $^1$H NMR to be a 1:1 molar ratio of ethanesulfonic acid:(R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one. $^1$H NMR (400 MHz, DMSO, 24° C.) δ 1.08 (3H, t), 2.44-2.49 (2H, m), 2.51 (3H, s), 3.16 (3H, s), 3.32 (1H, dd), 3.41 (1H, dd), 3.76 (3H, s), 3.97-4.12 (1H, m), 4.32-4.62 (3H, m), 5.08 (1H, d), 6.48 (1H, d), 7.17-7.30 (1H, m), 7.34-7.52 (2H, m), 7.55 (1H, d), 8.04 (1H, s), 8.39 (1H, s), 9.67 (1H, s). (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one ethanesulfonic acid adduct Form 1 was determined to be crystalline by XRPD (FIG. 1) and had a melting point of 203.8° C. (onset) (FIG. 2).

Intermediate 62

(R)-2-(2-Chloro-5-methylpyrimidin-4-yl)-7-(3,4-difluorobenzyl)-6-(methoxymethyl)-6,7-dihydroimidazo[1,2-a]pyrazin-8(5H)-one

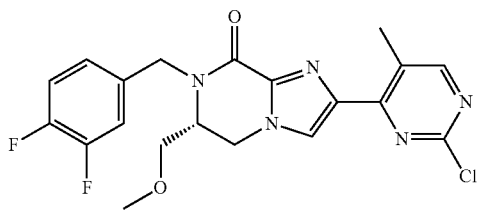 [SMILES: COC[C@H]1Cn2cc(-c3nc(Cl)ncc3C)nc2C(=O)N1Cc1ccc(F)c(F)c1]

4-(Bromomethyl)-1,2-difluorobenzene (6.05 g, 29.25 mmol) was added to (R)-2-(2-chloro-5-methylpyrimidin-4-yl)-6-(methoxymethyl)-6,7-dihydroimidazo[1,2-a]pyrazin-8(5H)-one (Intermediate 61; 6 g, 19.50 mmol) and NaH (2 g, 50. mmol) in DMF (80 mL) at 25° C. under nitrogen. The resulting mixture was stirred at 25° C. for 2 hours. The reaction mixture was quenched with saturated NaHCO$_3$ (400 mL), extracted with EtOAc (3×250 mL), the organic layers were washed with brine, dried over Na$_2$SO$_4$, filtered and evaporated to afford a yellow residue. The crude product was purified by flash silica chromatography, elution gradient 0 to 5% MeOH in DCM. Pure fractions were evaporated to dryness to afford (R)-2-(2-chloro-5-methylpyrimidin-4-yl)-7-(3,4-difluorobenzyl)-6-(methoxymethyl)-6,7-dihydroimidazo[1,2-a]pyrazin-8(5H)-one (Intermediate 62; 8.00 g, 95%) as a light yellow solid. $^1$H NMR (300 MHz, CDCl$_3$) δ 2.76 (3H, s), 3.25-3.35 (1H, m), 3.28 (3H, s), 3.35-3.42 (1H, m), 3.78-3.85 (1H, m), 4.18-4.26 (2H, m), 4.42 (1H, d), 5.34 (1H, d), 7.08-7.30 (3H, m), 7.95 (1H, s), 8.43 (1H, s). m/z (ES+), [M+H]+=434.

Alternative preparation of Intermediate 62:

Cs$_2$CO$_3$ (115 g, 354.44 mmol) was added to (R)-2-(2-chloro-5-methylpyrimidin-4-yl)-6-(methoxymethyl)-6,7-dihydroimidazo[1,2-a]pyrazin-8(5H)-one (Intermediate 61: 79.5 g, 253.17 mmol) in MeCN (800 mL) at 25° C. under nitrogen. The resulting mixture was heated to 40° C. and MeCN (100 mL) was distilled off. 4-(Bromomethyl)-1,2-difluorobenzene (64.2 g, 303.80 mmol) was added at 60° C. and stirred at 60-70° C. for 20 hours. The reaction mixture was concentrated to 500 mL and diluted with EtOAc (1000 mL) and water (500 mL). The layers were separated and the organic layer was washed water (2×500 mL) and the volatiles removed under reduced pressure. The residue was stirred in a mixture of MTBE (120 mL) and Heptane (480 mL) at 40° C., the resulting solid was filtered and washed with heptane (250 mL) to afford (R)-2-(2-chloro-5-methylpyrimidin-4-yl)-7-(3,4-difluorobenzyl)-6-(methoxymethyl)-6,7-dihydroimidazo[1,2-a]pyrazin-8(5H)-one (100 g, 91%) as a solid. $^1$H NMR (400 MHz, DMSO, 24° C.) δ 2.37 (3H, s), 3.04 (3H, s), 3.11-3.19 (1H, m), 3.28 (1H, dd), 3.92 (1H, m), 4.27 (1H, d), 4.35 (2H d), 4.95 (1H, d), 7.06-7.22 (1H, m), 7.22-7.48 (2H, m), 8.13 (1H, s), 8.47 (s, 1H). m/z (ES+), [M+H]+=434.

Example 19

(S)-7-(3-Chlorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one

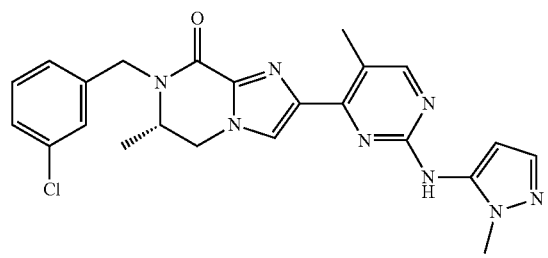 [SMILES: Cc1cnc(Nc2ccnn2C)nc1-c1cn2c(n1)C(=O)N(Cc1cccc(Cl)c1)[C@@H](C)C2]

2nd Generation XantPhos precatalyst (33.1 mg, 0.04 mmol) was added to (S)-2-(2-chloro-5-methylpyrimidin-4-yl)-7-(3-chlorobenzyl)-6-methyl-6,7-dihydroimidazo[1,2-a]pyrazin-8(5H)-one (Intermediate 63; 150 mg, 0.37 mmol), 1-methyl-1H-pyrazol-5-amine (91 mg, 0.93 mmol) and Cs$_2$CO$_3$ (243 mg, 0.75 mmol) in 1,4-dioxane (5 mL) at 25° C. under nitrogen. The resulting mixture was stirred at 100° C. for 4 hours. The solvent was then removed under reduced pressure. The crude product was purified by flash silica chromatography, elution gradient 0 to 5% MeOH in DCM. Pure fractions were evaporated to dryness to afford a yellow residue. This residue was purified further by preparative HPLC (XSelect CSH Prep C18 OBD column, 5μ silica, 19 mm diameter, 150 mm length), using decreasingly polar mixtures of water (containing 0.03% NH$_3$) and MeCN as eluents. Fractions containing the desired compound were evaporated to dryness to afford (S)-7-(3-chlorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one (Example 19; 71.0 mg, 41.1%) as a white solid. $^1$H NMR (400 MHz, DMSO, 24° C.) 61.14 (3H, d), 2.53 (3H, s), 3.70 (3H, s), 4.00 (1H, s), 4.30-4.48 (3H, m), 5.07 (1H, d), 6.30 (1H, d), 7.31-7.45 (4H, m), 7.48 (1H, s), 7.93 (1H, s), 8.33 (1H, s), 9.22 (1H, s). m/z (ES+), [M+H]+=463.

Intermediate 63

(S)-2-(2-Chloro-5-methylpyrimidin-4-yl)-7-(3-chlorobenzyl)-6-methyl-6,7-dihydroimidazo[1,2-a]pyrazin-8(5H)-one

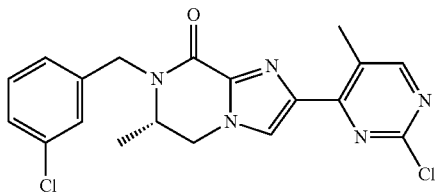 [SMILES: Cc1cnc(Cl)nc1-c1cn2c(n1)C(=O)N(Cc1cccc(Cl)c1)[C@@H](C)C2]

1-(Bromomethyl)-3-chlorobenzene (1332 mg, 6.48 mmol) was added to (S)-2-(2-chloro-5-methylpyrimidin-4-yl)-6-methyl-6,7-dihydroimidazo[1,2-a]pyrazin-8(5H)-one (Intermediate 64; 300 mg, 1.08 mmol) and NaH (259 mg, 6.48 mmol) in DMF (10 mL) at 25° C. under nitrogen. The resulting mixture was stirred at 25° C. for 2 hours. The reaction mixture was quenched with water (25 mL), extracted with EtOAc (2×25 mL), the organic layers were washed with brine and dried over Na$_2$SO$_4$, filtered and evaporated to afford a yellow residue. The crude product was purified by flash silica chromatography, elution gradient 10 to 60% EtOAc in petroleum ether. Pure fractions were evaporated to dryness to afford (S)-2-(2-chloro-5-methylpyrimidin-4-yl)-7-(3-chlorobenzyl)-6-methyl-6,7-dihydroimidazo[1,2-a]pyrazin-8(5H)-one (Intermediate 63; 300 mg, 69.0%) as a white solid. $^1$H NMR (400 MHz, CDCl$_3$, 22° C.) δ 1.24-1.34 (3H, m), 2.81 (3H, s), 3.84-3.92 (1H, m), 4.03-4.19 (2H, m), 4.37 (1H, dd), 5.45 (1H, d), 7.27 (1H, d), 7.30-7.34 (2H, m), 7.38 (1H, s), 7.99 (1H, s), 8.45 (1H, s). m/z (ES+), [M+H]+=402.

Intermediate 64

(S)-2-(2-Chloro-5-methylpyrimidin-4-yl)-6-methyl-6,7-dihydroimidazo[1,2-a]pyrazin-8(5H)-one

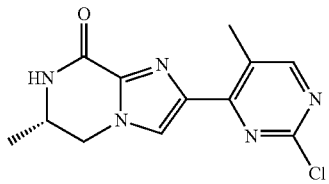 [SMILES: Cc1cnc(Cl)nc1-c1cn2c(n1)C(=O)N[C@@H](C)C2]

A solution of (S)-ethyl 1-(2-aminopropyl)-4-(2-chloro-5-methylpyrimidin-4-yl)-1H-imidazole-2-carboxylate dihydrochloride (Intermediate 65; 2.8 g, 7.77 mmol) in NH$_3$ (7N in MeOH, 20 mL, 140 mmol) was stirred at 25° C. overnight. The solvent was removed under reduced pressure to afford the desired product (S)-2-(2-chloro-5-methylpyrimidin-4-yl)-6-methyl-6,7-dihydroimidazo[1,2-a]pyrazin-8(5H)-one (2.1 g, 97%) as a white solid, which was used in the next step without purification. m/z (ES+), [M+H]+=278.

Intermediate 65

(S)-Ethyl 1-(2-aminopropyl)-4-(2-chloro-5-methylpyrimidin-4-yl)-1H-imidazole-2-carboxylate dihydrochloride

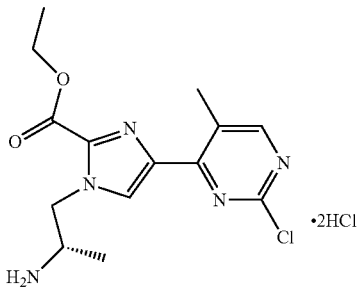 [SMILES: CCOC(=O)c1nc(-c2nc(Cl)ncc2C)cn1C[C@H](C)N]

A solution of (S)-ethyl 1-(2-((tert-butoxycarbonyl)amino)propyl)-4-(2-chloro-5-methylpyrimidin-4-yl)-1H-imidazole-2-carboxylate (Intermediate 66; 3.4 g, 8.02 mmol) in 33% HCl (gas) in EtOH (20 mL) was stirred at 25° C. overnight. The solvent was removed under reduced pressure to afford the desired product (S)-ethyl 1-(2-aminopropyl)-4-(2-chloro-5-methylpyrimidin-4-yl)-1H-imidazole-2-carboxylate dihydrochloride (Intermediate 65; 2.80 g, 97%) as a white solid. $^1$H NMR (400 MHz, DMSO, 24° C.) δ 1.28 (3H, d), 1.35 (3H, t), 2.64 (3H, s), 3.74 (1H, s), 4.39 (2H, q), 4.58-4.76 (2H, m), 8.37 (2H, s), 8.47 (1H, s), 8.61-8.67 (1H, m). m/z (ES+), [M+H]+=324.

Intermediate 66

(S)-Ethyl 1-(2-((tert-butoxycarbonyl)amino)propyl)-4-(2-chloro-5-methylpyrimidin-4-yl)-1H-imidazole-2-carboxylate

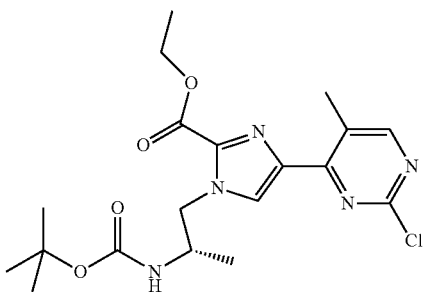 [SMILES: CCOC(=O)c1nc(-c2nc(Cl)ncc2C)cn1C[C@H](C)NC(=O)OC(C)(C)C]

1M HCl (20 mL, 20.00 mmol) was added to (S)-(tert-butoxycarbonyl)(1-(4-(2-chloro-5-methylpyrimidin-4-yl)-2-(ethoxycarbonyl)-1H-imidazol-1-yl)propan-2-yl)sulfamic acid (Intermediate 67; 5 g, 9.92 mmol) in EtOH (20 mL) at 25° C. under air. The resulting mixture was stirred at 50° C. for 20 minutes. The reaction mixture was quenched with saturated NaHCO$_3$ (50 mL), extracted with DCM (3×100 mL), the organic layer was dried over Na$_2$SO$_4$, filtered and evaporated to afford a yellow residue. The crude product was purified by flash silica chromatography, elution gradient 0 to 30% EtOAc in petroleum ether. Pure fractions were evaporated to dryness to afford (S)-ethyl 1-(2-((tert-butoxycarbonyl)amino)propyl)-4-(2-chloro-5-methylpyrimidin-4- yl)-1H-imidazole-2-carboxylate (Intermediate 66; 3.40 g, 81%) as a yellow solid. $^1$H NMR (400 MHz, CDCl$_3$, 24° C.) δ 1.27 (3H, dd), 1.35 (9H, s), 1.48 (3H, t), 2.72 (3H, s), 4.09-4.18 (1H, m), 4.47 (3H, qd), 4.64 (2H, dd), 8.01 (1H, s), 8.42 (1H, s). m/z (ES+), [M+H]+=424.

Intermediate 67

(S)-(tert-Butoxycarbonyl)(1-(4-(2-chloro-5-methylpyrimidin-4-yl)-2-(ethoxycarbonyl)-1H-imidazol-1-yl)propan-2-yl)sulfamic acid

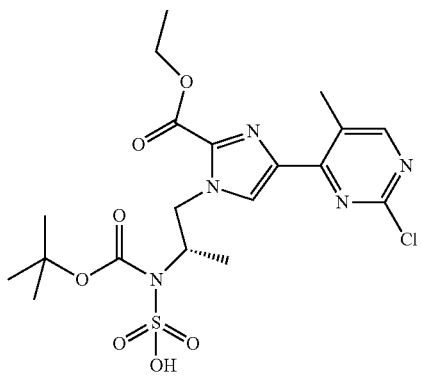 [SMILES: CCOC(=O)c1nc(-c2nc(Cl)ncc2C)cn1C[C@H](C)N(C(=O)OC(C)(C)C)S(=O)(=O)O]

(S)-tert-Butyl 4-methyl-1,2,3-oxathiazolidine-3-carboxylate 2,2-dioxide (Intermediate 12; 3.34 g, 14.06 mmol) was added portionwise to ethyl 4-(2-chloro-5-methylpyrimidin-4-yl)-1H-imidazole-2-carboxylate (Intermediate 23; 3 g, 11.25 mmol) and K$_2$CO$_3$ (3.11 g, 22.50 mmol) in acetonitrile (3 mL) at 80° C. under nitrogen. The resulting mixture was stirred at 85° C. for 4 hours. The reaction mixture was filtered and washed with MeCN, the solvent was removed under reduced pressure to afford the desired product (S)-(tert-butoxycarbonyl)(1-(4-(2-chloro-5-methylpyrimidin-4-yl)-2-(ethoxycarbonyl)-1H-imidazol-1-yl)propan-2-yl)sulfamic acid (5.00 g, 88%) as a yellow oil. m/z (ES+), [M+H]+=504.

Example 20

(S)-7-(3,4-Difluorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one

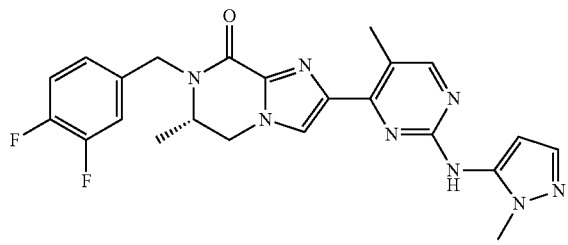 [SMILES: Cc1cnc(Nc2ccnn2C)nc1-c1cn2c(n1)C(=O)N(Cc1ccc(F)c(F)c1)[C@@H](C)C2]

(S)-2-(2-chloro-5-methylpyrimidin-4-yl)-7-(3,4-difluorobenzyl)-6-methyl-6,7-dihydroimidazo[1,2-a]pyrazin-8(5H)-one (Intermediate 68; 189 mg, 0.47 mmol), 1-methyl-1H-pyrazol-5-amine (91 mg, 0.94 mmol), Cs$_2$CO$_3$ (457 mg, 1.40 mmol) and 3rd Generation BrettPhos precatalyst (42.4 mg, 0.05 mmol) in 1,4-dioxane (5 mL) was stirred under an atmosphere of nitrogen at 110° C. for 8 hours. The solvent was removed by distillation under vacuum. The crude product was purified by flash silica chromatography, elution gradient 4 to 5% MeOH in DCM. Pure fractions were evaporated to dryness to afford a yellow solid. The solid was purified further by preparative HPLC (XSelect CSH Prep C18 OBD column, 5μ silica, 19 mm diameter, 150 mm length), using decreasingly polar mixtures of water (containing 0.01% NH$_4$HCO$_3$) and MeCN as eluents. Fractions containing the desired compound were evaporated to dryness to afford (S)-7-(3,4-difluorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one (Example 20; 63.8 mg, 29.3%) as a white solid. $^1$H NMR (400 MHz, DMSO, 24.8° C.) δ 1.14 (3H, d), 2.53 (3H, d), 3.70 (3H, s), 3.95-4.03 (1H, m), 4.29-4.38 (2H, m), 4.44 (1H, dd), 5.06 (1H, d), 6.30 (1H, d), 7.27 (1H, s), 7.34 (1H, d), 7.37-7.53 (2H, m), 7.93 (1H, s), 8.33 (1H, d), 9.21 (1H, s). m/z (ES+), [M+H]+=465.

Intermediate 68

(S)-2-(2-Chloro-5-methylpyrimidin-4-yl)-7-(3,4-difluorobenzyl)-6-methyl-6,7-dihydroimidazo[1,2-a]pyrazin-8(5H)-one

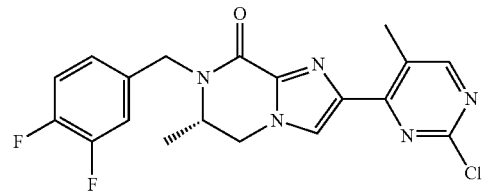 [SMILES: Cc1cnc(Cl)nc1-c1cn2c(n1)C(=O)N(Cc1ccc(F)c(F)c1)[C@@H](C)C2]

NaH (108 mg, 2.70 mmol) was added to (S)-2-(2-chloro-5-methylpyrimidin-4-yl)-6-methyl-6,7-dihydroimidazo[1,2-a]pyrazin-8(5H)-one (Intermediate 64; 250 mg, 0.90 mmol) in DMF (5 mL) at 0° C. under nitrogen. The resulting solution was stirred at 0° C. for 30 minutes. 4-(Bromomethyl)-1,2-difluorobenzene (373 mg, 1.80 mmol) was then added and the resulting solution was stirred at 20° C. for 12 hours. The reaction mixture was quenched with water (15 mL), extracted with EtOAc (4×10 mL). The organic layers were combined and washed with water (3×20 mL), brine (20 mL). The organic layers were dried over Na$_2$SO$_4$, filtered and evaporated to afford yellow oil. The crude product was purified by flash silica chromatography, elution gradient 0 to 3% MeOH in DCM. Pure fractions were evaporated to dryness to afford (S)-2-(2-chloro-5-methylpyrimidin-4-yl)-7-(3,4-difluorobenzyl)-6-methyl-6,7-dihydroimidazo[1,2-a]pyrazin-8(5H)-one (Intermediate 68; 189 mg, 52%) as a yellow solid. m/z (ES+), [M+H]+=404.

Example 21

(S)-7-(3-(Difluoromethyl)benzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one

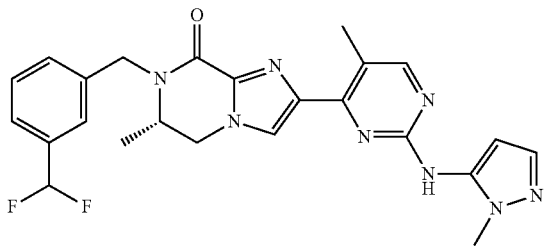 [SMILES: Cc1cnc(Nc2ccnn2C)nc1-c1cn2c(n1)C(=O)N(Cc1cccc(C(F)F)c1)[C@@H](C)C2]

BrettPhos 3rd generation precatalyst (12.44 mg, 0.02 mmol) was added to $Cs_2CO_3$ (304 mg, 0.93 mmol), 1-methyl-1H-pyrazol-5-amine (91 mg, 0.93 mmol) and (S)-2-(2-chloro-5-methylpyrimidin-4-yl)-7-(3-(difluoromethyl)benzyl)-6-methyl-6,7-dihydroimidazo[1,2-a]pyrazin-8(5H)-one (Intermediate 69; 130 mg, 0.31 mmol) in 1,4-dioxane (5 mL) under nitrogen. The resulting mixture was stirred at 100° C. for 4 hours. The solvent was then removed under reduced pressure. The crude product was purified by flash silica chromatography, elution gradient 0 to 6% MeOH in DCM. Pure fractions were evaporated to dryness to afford a residue. This residue was purified further by preparative HPLC (XSelect CSH Prep C18 OBD column, 5μ silica, 19 mm diameter, 150 mm length), using decreasingly polar mixtures of water (containing 0.1% Formic acid) and MeCN as eluents. Fractions containing the desired compound were evaporated to dryness to afford (S)-7-(3-(difluoromethyl)benzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one (Example 21; 85 mg, 57.1%) as a white solid. $^1$H NMR (300 MHz, DMSO, 23° C.) δ 1.12 (3H, s), 2.40 (3H, s), 3.70 (3H, s), 3.90-4.10 (1H, m), 4.36-4.44 (3H, m), 5.14 (1H, d), 6.29 (1H, d), 7.04 (1H, t), 7.33 (1H, d), 7.50-7.59 (4H, m), 7.93 (1H, s), 8.32 (1H, s), 9.21 (1H, s). m/z (ES+), [M+H]+=479.

Intermediate 69

(S)-2-(2-Chloro-5-methylpyrimidin-4-yl)-7-(3-(difluoromethyl)benzyl)-6-methyl-6,7-dihydroimidazo[1,2-a]pyrazin-8(5H)-one

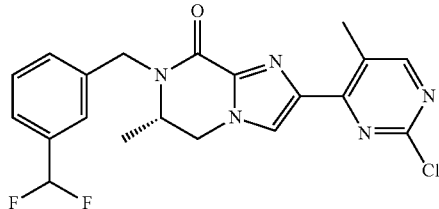

1-(Bromomethyl)-3-(difluoromethyl)benzene (207 mg, 0.94 mmol) was added to (S)-2-(2-chloro-5-methylpyrimidin-4-yl)-6-methyl-6,7-dihydroimidazo[1,2-a]pyrazin-8(5H)-one (Intermediate 64; 130 mg, 0.47 mmol) and NaH (56.2 mg, 1.40 mmol) in DMF (3 mL). The resulting mixture was stirred at 25° C. for 18 hours. The reaction mixture was poured into saturated $NaHCO_3$ (50 mL), extracted with EtOAc (2×50 mL), the organic layer was dried over $Na_2SO_4$, filtered and evaporated to afford crude. The crude product was purified by flash silica chromatography, elution gradient 0 to 4% MeOH in DCM. Pure fractions were evaporated to dryness to afford (S)-2-(2-chloro-5-methylpyrimidin-4-yl)-7-(3-(difluoromethyl)benzyl)-6-methyl-6,7-dihydroimidazo[1,2-a]pyrazin-8(5H)-one (130 mg, 66.5%) as a pale yellow oil. m/z (ES+), [M+H]+=418.

Example 22

(S)-7-(3,5-Difluorobenzyl)-6-methyl-2-(5-methyl-2-((1-methyl-1H-pyrazol-5-L)amino)pyrimidin-4-yl)-6,7-dihydroimidazo[1,2-a]pyrazin-8(5H)-one

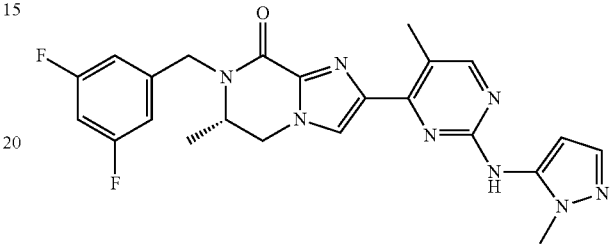

Brettphos 3rd generation precatalyst (12.88 mg, 0.02 mmol) was added to 1-methyl-1H-pyrazol-5-amine (94 mg, 0.97 mmol), (S)-2-(2-chloro-5-methylpyrimidin-4-yl)-7-(3,5-difluorobenzyl)-6-methyl-6,7-dihydroimidazo[1,2-a]pyrazin-8(5H)-one (Intermediate 70; 130 mg, 0.32 mmol) and $Cs_2CO_3$ (315 mg, 0.97 mmol) in 1,4-dioxane (5 mL) under nitrogen. The resulting mixture was stirred at 100° C. for 4 hours. The solvent was then removed under reduced pressure. The crude product was purified by flash silica chromatography, elution gradient 0 to 7% MeOH in DCM. Pure fractions were evaporated to dryness to afford a residue. The crude product was purified further by preparative HPLC (XSelect CSH Prep C18 OBD column, 5μ silica, 19 mm diameter, 150 mm length), using decreasingly polar mixtures of water (containing 0.1% Formic acid) and MeCN as eluents. Fractions containing the desired compound were evaporated to dryness to afford (S)-7-(3,5-difluorobenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one (Example 22; 60 mg, 40.1%) as a white solid. $^1$H NMR (300 MHz, DMSO, 23° C.) δ 1.15 (3H, d), 2.60 (3H, s), 3.70 (3H, s), 3.90-4.10 (1H, m), 4.32-4.38 (2H, m), 4.46-4.52 (1H, dd), 5.08 (1H, d), 6.29 (1H, d), 7.12-7.18 (3H, m), 7.33 (1H, s), 7.93 (1H, s), 8.32 (1H, s), 9.21 (1H, s). m/z (ES+), [M+H]+=465.

Intermediate 70

(S)-2-(2-Chloro-5-methylpyrimidin-4-yl)-7-(3,5-difluorobenzyl)-6-methyl-6,7-dihydroimidazo[1,2-a]pyrazin-8(5H)-one

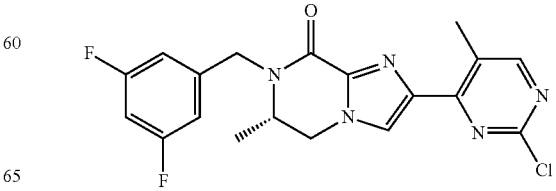

1-(Bromomethyl)-3,5-difluorobenzene (194 mg, 0.94 mmol) was added to (S)-2-(2-chloro-5-methylpyrimidin-4-yl)-6-methyl-6,7-dihydroimidazo[1,2-a]pyrazin-8(5H)-one (Intermediate 64; 130 mg, 0.47 mmol) and NaH (37.4 mg, 0.94 mmol) in DMF (3 mL) and the resulting mixture was stirred at 25° C. for 18 hours. The reaction mixture was poured into saturated NaHCO$_3$ (50 mL), extracted with EtOAc (2×50 mL), the organic layers were dried over Na$_2$SO$_4$, filtered and evaporated to afford crude product. The crude product was purified by flash silica chromatography, elution gradient 0 to 4% MeOH in DCM. Pure fractions were evaporated to dryness to afford (S)-2-(2-chloro-5-methylpyrimidin-4-yl)-7-(3,5-difluorobenzyl)-6-methyl-6,7-dihydroimidazo[1,2-a]pyrazin-8(5H)-one (Intermediate 70; 130 mg, 68.8%) as a pale yellow oil. $^1$H NMR (400 MHz, DMSO, 20° C.) δ 1.15 (3H, d), 2.64 (3H, s), 4.02 (1H, s), 4.26-4.42 (2H, m), 4.47-4.57 (1H, m), 5.09 (1H, d), 7.15 (3H, d), 8.27 (1H, s), 8.61 (1H, s). m/z (ES+), [M+H]+=404.

Example 23

(S)-7-(3-Methoxybenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one

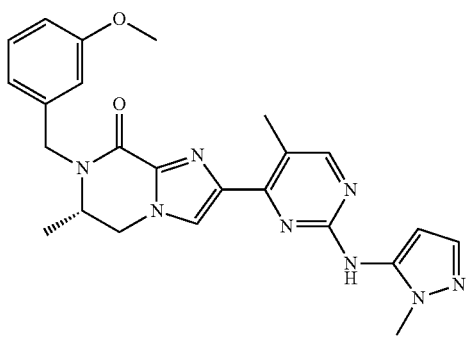 [SMILES: COc1cccc(CN2C(=O)c3nc(-c4nc(Nc5ccnn5C)ncc4C)cn3C[C@@H]2C)c1]

(S)-2-(2-Chloro-5-methylpyrimidin-4-yl)-7-(3-methoxybenzyl)-6-methyl-6,7-dihydroimidazo[1,2-a]pyrazin-8(5H)-one (Intermediate 71; 193 mg, 0.49 mmol), 1-methyl-1H-pyrazol-5-amine (94 mg, 0.97 mmol), Cs$_2$CO$_3$ (474 mg, 1.46 mmol) and 3rd Generation BrettPhos precatalyst (44.0 mg, 0.05 mmol) in 1,4-dioxane (5 mL) was stirred under an atmosphere of nitrogen at 120° C. for 8 hours. The solvent was then removed by distillation under vacuum. The crude product was purified by flash silica chromatography, elution gradient 3 to 5% MeOH in DCM, compound containing fractions were evaporated to dryness to afford a yellow solid. This solid was purified further by preparative HPLC (XSelect CSH Prep C18 OBD column, 5µ silica, 19 mm diameter, 150 mm length), using decreasingly polar mixtures of water (containing 0.01% NH$_4$HCO$_3$) and MeCN as eluents. Fractions containing the desired compound were evaporated to dryness to afford (S)-7-(3-methoxybenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one (Example 23; 81 mg, 36.2%) as a white solid. $^1$H NMR (400 MHz, DMSO, 22.4° C.) δ 1.12 (3H, d), 2.53 (3H, d), 3.70 (3H, s), 3.76 (3H, s), 3.90-3.99 (1H, m), 4.25-4.44 (3H, m), 5.09 (1H, d), 6.31 (1H, d), 6.87 (1H, ddd), 6.92-7.00 (2H, m), 7.29 (1H, t), 7.34 (1H, d), 7.93 (1H, s), 8.33 (1H, d), 9.22 (1H, s). m/z (ES+), [M+H]+=459.

Intermediate 71

(S)-2-(2-Chloro-5-methylpyrimidin-4-yl)-7-(3-methoxybenzyl)-6-methyl-6,7-dihydroimidazo[1,2-a]pyrazin-8(5H)-one

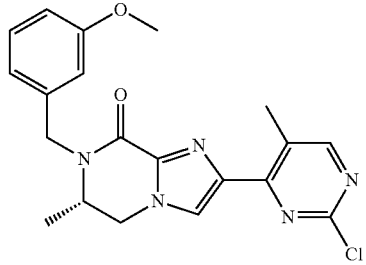 [SMILES: COc1cccc(CN2C(=O)c3nc(-c4nc(Cl)ncc4C)cn3C[C@@H]2C)c1]

Batch 1: NaH (8.64 mg, 0.22 mmol) was added to (S)-2-(2-chloro-5-methylpyrimidin-4-yl)-6-methyl-6,7-dihydroimidazo[1,2-a]pyrazin-8(5H)-one (Intermediate 64; 20 mg, 0.07 mmol) in DMF (1 mL) at 25° C. under nitrogen. The resulting solution was stirred at 25° C. for 30 minutes. 1-(bromomethyl)-3-methoxybenzene (29.0 mg, 0.14 mmol) was added to reaction mixture and the resulting solution was stirred at 25° C. for 2 hours. Batch 2: NaH (56.2 mg, 1.40 mmol) was added to (S)-2-(2-chloro-5-methylpyrimidin-4-yl)-6-methyl-6,7-dihydroimidazo[1,2-a]pyrazin-8(5H)-one (130 mg, 0.47 mmol) in DMF (3 mL) at 20° C. under nitrogen. The resulting solution was stirred at 20° C. for 30 minutes. 1-(bromomethyl)-3-methoxybenzene (188 mg, 0.94 mmol) was added to reaction mixture and the resulting solution was stirred at 20° C. for 2 hours. The 2 batches of material were combined and the following procedure applied to the combined batches: The reaction mixture was quenched with saturated NaHCO$_3$ (15 mL) and extracted with EtOAc (3×15 mL). The organic layers were combined and washed with water (2×15 mL), brine (15 mL), the organic layer was dried over Na$_2$SO$_4$, filtered and evaporated to afford yellow oil. The crude product was purified by flash silica chromatography, elution gradient 3 to 4% MeOH in DCM. Pure fractions were evaporated to dryness to afford (S)-2-(2-chloro-5-methylpyrimidin-4-yl)-7-(3-methoxybenzyl)-6-methyl-6,7-dihydroimidazo[1,2-a]pyrazin-8(5H)-one (Intermediate 71; 193 mg, 89%) as a yellow oil. $^1$H NMR (400 MHz, CDCl$_3$, 23.0° C.) δ 1.29 (3H, d), 2.81 (3H, s), 3.80-3.93 (4H, m), 3.98-4.13 (1H, m), 4.34 (1H, dd), 5.32 (1H, s), 5.50 (1H, d), 6.84-6.99 (3H, m), 7.31 (1H, d), 7.97 (1H, s), 8.45 (1H, s). m/z (ES+), [M+H]+=398.

Example 24

(S)-7-(4-Fluoro-3-methoxybenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one

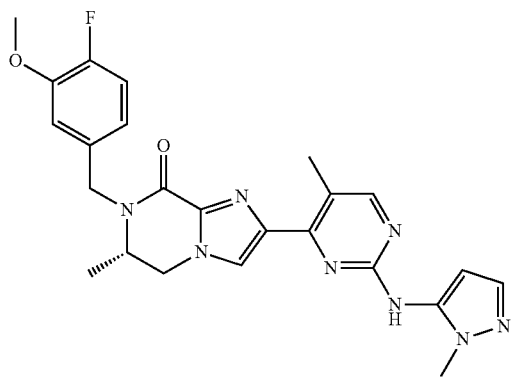 [SMILES: COc1cc(CN2C(=O)c3nc(-c4nc(Nc5ccnn5C)ncc4C)cn3C[C@@H]2C)ccc1F]

(S)-2-(2-Chloro-5-methylpyrimidin-4-yl)-7-(4-fluoro-3-methoxybenzyl)-6-methyl-6,7-dihydroimidazo[1,2-a]pyrazin-8(5H)-one (Intermediate 72; 205 mg, 0.49 mmol), 1-methyl-1H-pyrazol-5-amine (96 mg, 0.99 mmol), Cs₂CO₃ (482 mg, 1.48 mmol) and 3rd Generation BrettPhos precatalyst (44.7 mg, 0.05 mmol) in 1,4-dioxane (5 mL) was stirred under an atmosphere of nitrogen at 120° C. for 8 hours. The solvent was then removed by distillation under vacuum. The crude product was purified by flash silica chromatography, elution gradient 3 to 5% MeOH in DCM. Pure fractions were evaporated to dryness to afford a yellow solid. This solid was purified further by preparative HPLC (XSelect CSH Prep C18 OBD column, 5μ silica, 19 mm diameter, 150 mm length), using decreasingly polar mixtures of water (containing 0.01% NH₄HCO₃) and MeCN as eluents. Fractions containing the desired compound were evaporated to dryness to afford (S)-7-(4-fluoro-3-methoxybenzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one (Example 24; 59.0 mg, 25.1%) as a white solid. ¹H NMR (400 MHz, DMSO, 22.3° C.) δ 1.13 (3H, d), 2.53 (3H, d), 3.70 (3H, s), 3.85 (3H, s), 3.95 (1H, dd), 4.23-4.44 (3H, m), 5.10 (1H, d), 6.31 (1H, d), 6.96 (1H, ddd), 7.14-7.24 (2H, m), 7.34 (1H, d), 7.93 (1H, s), 8.33 (1H, d), 9.22 (1H, s). m/z (ES+), [M+H]+=477.

Intermediate 72

(S)-2-(2-Chloro-5-methylpyrimidin-4-yl)-7-(4-fluoro-3-methoxybenzyl)-6-methyl-6,7-dihydroimidazo[1,2-a]pyrazin-8(5H)-one

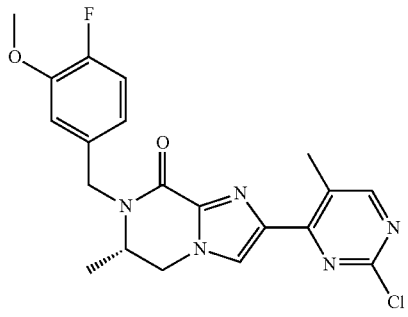 [SMILES: COc1cc(CN2C(=O)c3nc(-c4nc(Cl)ncc4C)cn3C[C@@H]2C)ccc1F]

Batch 1: NaH (56.2 mg, 1.40 mmol) was added to (S)-2-(2-chloro-5-methylpyrimidin-4-yl)-6-methyl-6,7-dihydroimidazo[1,2-a]pyrazin-8(5H)-one (130 mg, 0.47 mmol) in DMF (3 mL) at 20° C. under nitrogen. The resulting solution was stirred at 20° C. for 30 minutes. 4-(bromomethyl)-1-fluoro-2-methoxybenzene (205 mg, 0.94 mmol) was added to reaction mixture and the resulting solution was stirred at 20° C. for 2 hours. Batch 2: NaH (8.64 mg, 0.22 mmol) was added to (S)-2-(2-chloro-5-methylpyrimidin-4-yl)-6-methyl-6,7-dihydroimidazo[1,2-a]pyrazin-8(5H)-one (20 mg, 0.07 mmol) in DMF (1 mL) at 20° C. under nitrogen. The resulting solution was stirred at 20° C. for 30 minutes. 4-(bromomethyl)-1-fluoro-2-methoxybenzene (31.6 mg, 0.14 mmol) was added to reaction mixture and the resulting solution was stirred at 20° C. for 2 hours. The 2 batches of material were combined and the following procedure applied to the combined batches: The reaction mixture was quenched with saturated NaHCO₃ (15 mL) and extracted with EtOAc (3×15 mL). The organic layers were combined and washed with water (2×15 mL), brine (15 mL) and the organic layers was dried over Na₂SO₄, filtered and evaporated to afford yellow oil. The crude product was purified by flash silica chromatography, elution gradient 3 to 4% MeOH in DCM. Pure fractions were evaporated to dryness to afford (S)-2-(2-chloro-5-methylpyrimidin-4-yl)-7-(4-fluoro-3-methoxybenzyl)-6-methyl-6,7-dihydroimidazo[1,2-a]pyrazin-8(5H)-one (205 mg, 91%) as a yellow oil. m/z (ES+), [M+H]+=416.

Example 25

(S)-7-((6-(Difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one

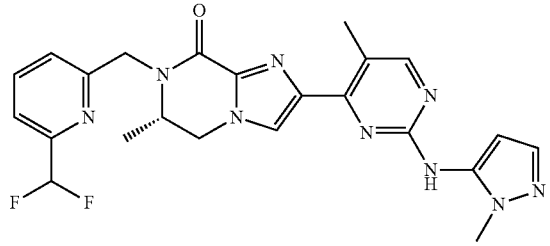 [SMILES: Cc1cnc(Nc2ccnn2C)nc1-c1cn2c(n1)C(=O)N(Cc1cccc(C(F)F)n1)[C@@H](C)C2]

3rd Generation BrettPhos precatalyst (0.541 g, 0.60 mmol) was added to Cs₂CO₃ (11.67 g, 35.81 mmol), 1-methyl-1H-pyrazol-5-amine (3.48 g, 35.81 mmol) and (S)-2-(2-chloro-5-methylpyrimidin-4-yl)-7-((6-(difluoromethyl)pyridin-2-yl)methyl)-6-methyl-6,7-dihydroimidazo[1,2-a]pyrazin-8(5H)-one (Intermediate 73; 5 g, 11.94 mmol) in 1,4-dioxane (100 mL). The resulting mixture was stirred at 100° C. for 4 hours. The reaction mixture was then filtered and the solvent was removed under reduced pressure. The crude product was purified by flash silica chromatography, elution gradient 0 to 6% MeOH in DCM. Pure fractions were evaporated to dryness to afford a residue. This residue was purified further by C18-flash chromatography, elution gradient 5 to 40% MeCN in water (contained 0.1% NH₄CO₃). Pure fractions were evaporated to dryness to afford (S)-7-((6-(difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one (Example 25; 3.50 g, 61.1%) as a white solid. ¹H NMR (300 MHz, DMSO, 23° C.) δ 1.19 (3H, d), 2.45 (3H, s), 2.61 (3H, s), 3.70 (3H, s), 4.03-4.17 (1H, m), 4.33-4.41 (1H, dd), 4.45-4.520 (2H, m), 5.22 (1H, d), 6.30 (1H, d), 6.97 (1H, t), 7.34 (1H, d), 7.60-7.69 (2H, m), 7.96 (1H, s), 7.97-8.02 (1H, t), 8.33 (1H, s), 9.23 (1H, s); m/z (ES+), [M+H]+=480.

Intermediate 73

(S)-2-(2-Chloro-5-methylpyrimidin-4-yl)-7-((6-(difluoromethyl)pyridin-2-yl)methyl)-6-methyl-6,7-dihydroimidazo[1,2-a]pyrazin-8(5H)-one

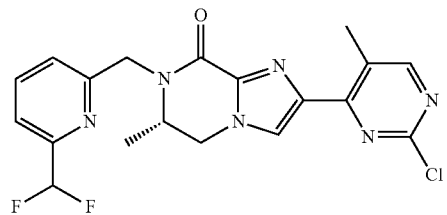 [SMILES: Cc1cnc(Cl)nc1-c1cn2c(n1)C(=O)N(Cc1cccc(C(F)F)n1)[C@@H](C)C2]

Sodium acetate (2.047 g, 24.95 mmol) was added to (S)-ethyl 4-(2-chloro-5-methylpyrimidin-4-yl)-1-(2-(((6-(difluoromethyl)pyridin-2-yl)methyl)amino)propyl)-1H-imidazole-2-carboxylate (Intermediate 74; 5.8 g, 12.48 mmol) in ethanol (absolute, 99.5%, 100 mL). The resulting mixture was stirred at 70° C. for 18 hours. The solvent was then removed under reduced pressure. The crude product was purified by flash silica chromatography, elution gradient 0 to 5% MeOH in DCM. Pure fractions were evaporated to dryness to afford (S)-2-(2-chloro-5-methylpyrimidin-4-yl)-7-((6-(difluoromethyl)pyridin-2-yl)methyl)-6-methyl-6,7-dihydroimidazo[1,2-a]pyrazin-8(5H)-one (Intermediate 73; 5.00 g, 96%) as a pale yellow solid. m/z (ES+), [M+H]+=419.

Intermediate 74

(S)-Ethyl 4-(2-chloro-5-methylpyrimidin-4-yl)-1-(2-(((6-(difluoromethyl)pyridin-2-yl)methyl)amino)propyl)-1H-imidazole-2-carboxylate

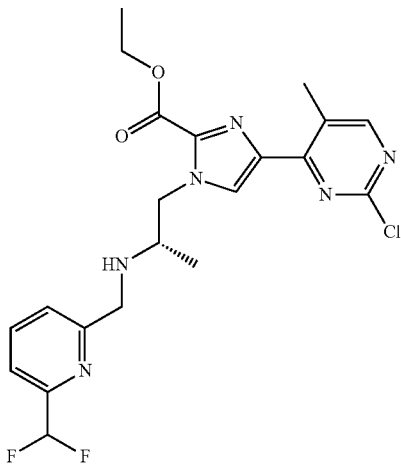

Sodium triacetoxyborohydride (9.62 g, 45.37 mmol) was added to DIPEA (7.92 mL, 45.37 mmol), (S)-ethyl 1-(2-aminopropyl)-4-(2-chloro-5-methylpyrimidin-4-yl)-1H-imidazole-2-carboxylate dihydrochloride (Intermediate 65; 6 g, 15.12 mmol), 6-(difluoromethyl)picolinaldehyde (3 g, 19.09 mmol) and acetic acid (2.60 mL, 45.37 mmol) in DCM (100 mL). The resulting mixture was stirred at 25° C. for 1 hours. The reaction mixture was poured into saturated NaHCO$_3$ (300 mL) and extracted with DCM (2×150 mL). The organic phases were dried over Na$_2$SO$_4$ and the volatiles removed under reduced pressure. The crude product was purified by flash silica chromatography, elution gradient 0 to 5% MeOH in DCM. Pure fractions were evaporated to dryness to afford (S)-ethyl 4-(2-chloro-5-methylpyrimidin-4-yl)-1-(2-(((6-(difluoromethyl)pyridin-2-yl)methyl)amino)propyl)-1H-imidazole-2-carboxylate (Intermediate 74; 5.8 g, 82%) as a pale yellow oil. m/z (ES+), [M+H]+=465.

Example 26

(S)-6-methyl-2-(5-methyl-2-((1-methyl-1H-pyrazol-5-yl)amino)pyrimidin-4-yl)-7-((2-(trifluoromethyl)pyrimidin-4-yl)methyl)-6,7-dihydroimidazo[1,2-a]pyrazin-8(5H)-one

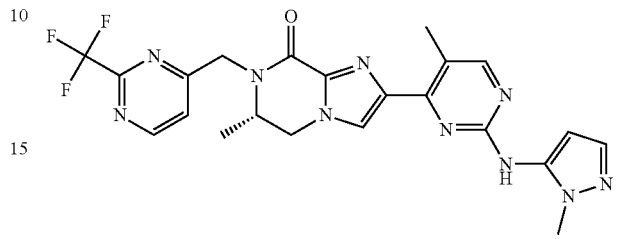

(S)-2-(2-chloro-5-methylpyrimidin-4-yl)-6-methyl-7-((2-(trifluoromethyl)pyrimidin-4-yl)methyl)-6,7-dihydroimidazo[1,2-a]pyrazin-8(5H)-one (Intermediate 75; 60 mg, 0.14 mmol), 1-methyl-1H-pyrazol-5-amine (39.9 mg, 0.41 mmol), Cs$_2$CO$_3$ (134 mg, 0.41 mmol) and 3rd Generation BrettPhos precatalyst (12.42 mg, 0.01 mmol) in 1,4-dioxane (2.5 mL) were stirred under an atmosphere of nitrogen at 120° C. for 8 hours. The solvent was then removed by distillation under vacuum. The crude product was purified by flash silica chromatography, elution gradient 0 to 5% MeOH in DCM. Pure fractions were evaporated to dryness to afford a yellow solid. This solid was purified further by preparative HPLC (XSelect CSH Prep C18 OBD column, 5μ silica, 19 mm diameter, 150 mm length), using decreasingly polar mixtures of water (containing 0.01% NH$_4$HCO$_3$) and MeCN as eluents. Fractions containing the desired compound were evaporated to dryness to afford (S)-6-methyl-2-(5-methyl-2-((1-methyl-1H-pyrazol-5-yl)amino)pyrimidin-4-yl)-7-((2-(trifluoromethyl)pyrimidin-4-yl)methyl)-6,7-dihydroimidazo[1,2-a]pyrazin-8(5H)-one (Example 26; 21 mg, 30.7%) as a light yellow solid. $^1$H NMR (400 MHz, CDCl$_3$, 25.5° C.) δ 1.44 (3H, d), 2.74 (3H, s), 3.88 (3H, s), 4.21 (1H, dd), 4.30 (1H, t), 4.42 (1H, d), 4.63 (1H, dd), 5.48 (1H, d), 6.38 (1H, d), 7.52 (1H, d), 7.68 (1H, d), 8.09 (1H, s), 8.31 (1H, s), 8.53 (1H, s), 8.90 (1H, d). m/z (ES+), [M+H]+=499.

Intermediate 75

(S)-2-(2-Chloro-5-methylpyrimidin-4-yl)-6-methyl-7-((2-(trifluoromethyl)pyrimidin-4-yl)methyl)-6,7-dihydroimidazo[1,2-a]pyrazin-8(5H)-one

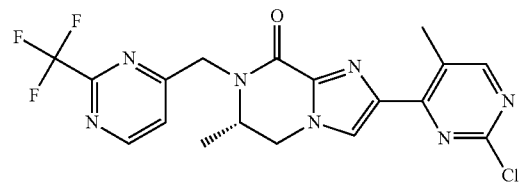 [SMILES: Cc1cnc(Cl)nc1-c1cn2c(n1)C(=O)N(Cc1ccnc(C(F)(F)F)n1)[C@@H](C)C2]

NH$_3$ (7N in MeOH, 10 mL) was added to (S)-ethyl 4-(2-chloro-5-methylpyrimidin-4-yl)-1-(2-(((2-(trifluoromethyl)pyrimidin-4-yl)methyl)amino)propyl)-1H-imidazole-2-carboxylate (Intermediate 76; 100 mg, 0.21 mmol) at 20°

C. under air. The resulting solution was stirred at 50° C. for 16 hours. The solvent was then removed by distillation under vacuum. The crude product was purified by flash silica chromatography, elution gradient 0 to 6% MeOH in DCM. Pure fractions were evaporated to dryness to afford (S)-2-(2-chloro-5-methylpyrimidin-4-yl)-6-methyl-7-((2-(trifluoromethyl)pyrimidin-4-yl)methyl)-6,7-dihydroimidazo[1,2-a]pyrazin-8(5H)-one (Intermediate 75; 60 mg, 66.3%) as a colourless oil. m/z (ES+), [M+H]+=438.

Intermediate 76

(S)-Ethyl 4-(2-chloro-5-methylpyrimidin-4-yl)-1-(2-(((2-(trifluoromethyl)pyrimidin-4-yl)methyl)amino)propyl)-1H-imidazole-2-carboxylate

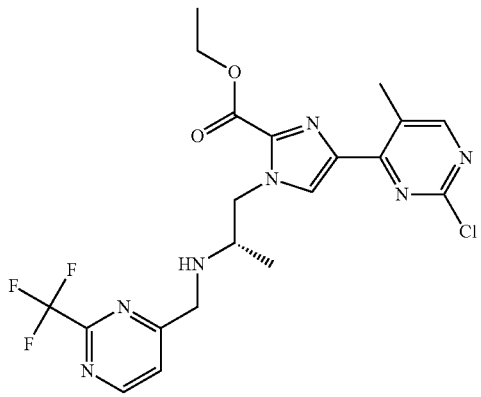 [SMILES: CCOC(=O)c1nc(-c2nc(Cl)ncc2C)cn1C[C@H](C)NCc1ccnc(C(F)(F)F)n1]

2-(Trifluoromethyl)pyrimidine-4-carbaldehyde (147 mg, 0.83 mmol) was added to (S)-ethyl 1-(2-aminopropyl)-4-(2-chloro-5-methylpyrimidin-4-yl)-1H-imidazole-2-carboxylate dihydrochloride (Intermediate 65; 250 mg, 0.69 mmol) in DCM (10 mL) under air. The resulting solution was stirred at 40° C. for 12 hours. Sodium triacetoxyborohydride (441 mg, 2.08 mmol) was added and the resulting solution was stirred at 20° C. for 12 hour. The reaction was quenched with water (5 mL), and extracted with DCM (5×10 mL). The organic phases were dried over Na₂SO₄, filtered and evaporated to afford yellow oil. The crude product was purified by flash silica chromatography, elution gradient 2 to 4% MeOH in DCM. Pure fractions were evaporated to dryness to afford (S)-ethyl 4-(2-chloro-5-methylpyrimidin-4-yl)-1-(2-(((2-(trifluoromethyl)pyrimidin-4-yl)methyl)amino)propyl)-1H-imidazole-2-carboxylate (Intermediate 76; 110 mg, 32.8%) as a colourless oil. m/z (ES+), [M+H]+=484.

Example 27

(S)-6-Methyl-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one

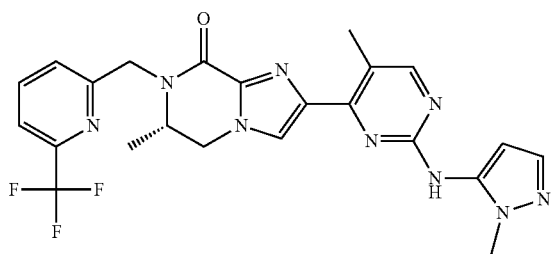 [SMILES: Cc1cnc(Nc2ccnn2C)nc1-c1cn2c(n1)C(=O)N(Cc1cccc(C(F)(F)F)n1)[C@@H](C)C2]

3rd Generation BrettPhos precatalyst (11.90 mg, 0.01 mmol) was added to 1-methyl-1H-pyrazol-5-amine (87 mg, 0.89 mmol), Cs₂CO₃ (291 mg, 0.89 mmol) and (S)-2-(2-chloro-5-methylpyrimidin-4-yl)-6-methyl-7-((6-(trifluoromethyl)pyridin-2-yl)methyl)-6,7-dihydroimidazo[1,2-a]pyrazin-8(5H)-one (Intermediate 77; 130 mg, 0.30 mmol) in 1,4-dioxane (5 mL) under nitrogen. The resulting mixture was stirred at 100° C. for 4 hours. The solvent was then removed under reduced pressure. The crude product was purified by flash silica chromatography, elution gradient 0 to 6% MeOH in DCM, product containing fraction were evaporated to afford a solid. This solid was purified further by preparative HPLC (XSelect CSH Prep C18 OBD column, 5μ silica, 19 mm diameter, 150 mm length), using decreasingly polar mixtures of water (containing 0.1% Formic acid) and MeCN as eluents. Fractions containing the desired compound were evaporated to dryness to afford (S)-6-methyl-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one (Example 27; 100 mg, 67.5%) as a white solid. ¹H NMR (300 MHz, DMSO, 23° C.) δ 1.20 (3H, d), 2.56 (3H, s), 3.70 (3H, s), 4.05-4.18 (1H, m), 4.37-4.41 (1H, m), 451-4.60 (2H, m), 5.212 (1H, d), 6.30 (1H, d), 7.34 (1H, d), 7.76-7.83 (2H, m), 7.96 (1H, s), 8.06-8.11 (1H, m), 8.32 (1H, s). m/z (ES+), [M+H]+=498.

Intermediate 77

(S)-2-(2-Chloro-5-methylpyrimidin-4-yl)-6-methyl-7-((6-(trifluoromethyl)pyridin-2-yl)methyl)-6,7-dihydroimidazo[1,2-a]pyrazin-8(5H)-one

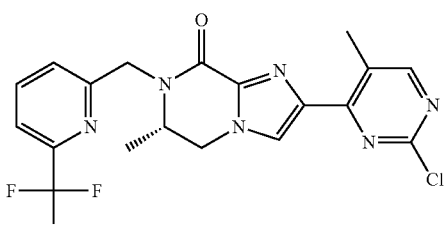

(S)-Ethyl 4-(2-chloro-5-methylpyrimidin-4-yl)-1-(2-(((6-(trifluoromethyl)pyridin-2-yl)methyl)amino)propyl)-1H-imidazole-2-carboxylate (Intermediate 78; 140 mg, 0.29 mmol) was added to NH₃ (7N in MeOH) solution (10 mL) and the resulting mixture was stirred at 50° C. for 5 hours. The solvent was removed under reduced pressure. This afforded (S)-2-(2-chloro-5-methylpyrimidin-4-yl)-6-methyl-7-((6-(trifluoromethyl)pyridin-2-yl)methyl)-6,7-dihydroimidazo[1,2-a]pyrazin-8(5H)-one (Intermediate 77; 110 mg, 87%) as white solid. m/z (ES+), [M+H]+=437.

Intermediate 78

(S)-Ethyl 4-(2-chloro-5-methylpyrimidin-4-yl)-1-(2-(((6-(trifluoromethyl)pyridin-2-yl)methyl)amino)propyl)-1H-imidazole-2-carboxylate

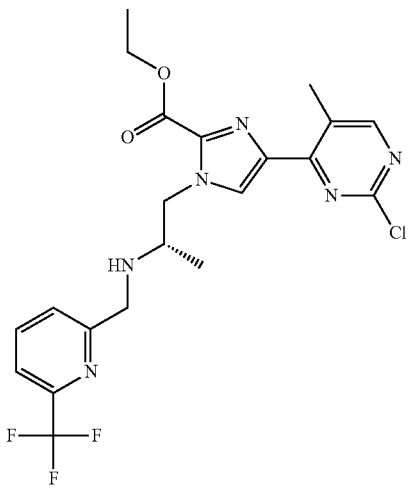 [SMILES: CCOC(=O)c1nc(-c2nc(Cl)ncc2C)cn1C[C@H](C)NCc1cccc(C(F)(F)F)n1]

6-(Trifluoromethyl)picolinaldehyde (110 mg, 0.63 mmol) was added to (S)-ethyl 1-(2-aminopropyl)-4-(2-chloro-5-methylpyrimidin-4-yl)-1H-imidazole-2-carboxylate dihydrochloride (Intermediate 64; 250 mg, 0.63 mmol) in DCM (15 mL) and the resulting mixture was stirred at 40° C. for 4 hours. After being cooled to room temperature, sodium triacetoxyborohydride (267 mg, 1.26 mmol) was added and the reaction stirred for 1 hour. The reaction was then quenched with saturated NaHCO$_3$ (50 mL) and extracted with DCM (2×50 mL). The organic layers were dried over Na$_2$SO$_4$, filtered and evaporated to afford pale yellow oil. The crude product was purified by flash silica chromatography, elution gradient 0 to 5% MeOH in DCM. Pure fractions were evaporated to dryness to afford (S)-ethyl 4-(2-chloro-5-methylpyrimidin-4-yl)-1-(2-(((6-(trifluoromethyl)pyridin-2-yl)methyl)amino)propyl)-1H-imidazole-2-carboxylate (Intermediate 78; 140 mg, 46%) as a pale yellow oil. m/z (ES+), [M+H]+=483.

Example 28

(S)-7-(3-(Difluoromethoxy)benzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one

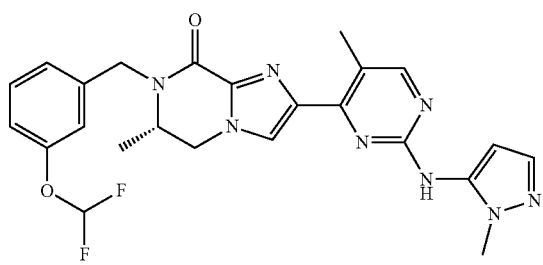 [SMILES: Cc1cnc(Nc2ccnn2C)nc1-c1cn2c(n1)C(=O)N(Cc1cccc(OC(F)F)c1)[C@@H](C)C2]

3rd Generation BrettPhos precatalyst (11.99 mg, 0.01 mmol) was added to 1-methyl-1H-pyrazol-5-amine (87 mg, 0.90 mmol), (S)-2-(2-chloro-5-methylpyrimidin-4-yl)-7-(3-(difluoromethoxy)benzyl)-6-methyl-6,7-dihydroimidazo[1,2-a]pyrazin-8(5H)-one (Intermediate 79, 130 mg, 0.30 mmol) in 1,4-dioxane (5 mL) under nitrogen and the resulting mixture was stirred at 100° C. for 4 hours. The solvent was then removed under reduced pressure. The crude product was purified by flash silica chromatography, elution gradient 0 to 7% MeOH in DCM, compound containing fractions were evaporated to afford a solid. This solid was purified further by preparative HPLC (XSelect CSH Prep C18 OBD column, 5μ silica, 19 mm diameter, 150 mm length), using decreasingly polar mixtures of water (containing 0.1) and MeCN as eluents. Fractions containing the desired compound were evaporated to dryness to afford (S)-7-(3-(difluoromethoxy)benzyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one (Example 28; 80 mg, 54%) as a white solid. $^1$H NMR (300 MHz, DMSO, 23° C.) δ 1.11 (3H, d), 2.60 (3H, s), 3.70 (3H, s), 3.90-4.10 (1H, m), 4.31-4.45 (3H, m), 5.10 (1H, d), 6.29 (1H, d), 7.00-7.50 (4H, m), 7.92 (1H, s), 7.83 (1H, s), 8.21 (1H, s), 8.32 (1H, s), 9.21 (1H, s). m/z (ES+), [M+H]+=495.

Intermediate 79

(S)-2-(2-Chloro-5-methylpyrimidin-4-yl)-7-(3-(difluoromethoxy)benzyl)-6-methyl-6,7-dihydroimidazo[1,2-a]pyrazin-8(5H)-one

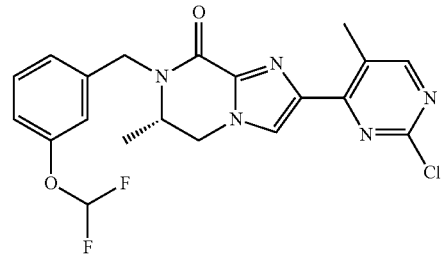 [SMILES: Cc1cnc(Cl)nc1-c1cn2c(n1)C(=O)N(Cc1cccc(OC(F)F)c1)[C@@H](C)C2]

3-(Difluoromethoxy)benzaldehyde (108 mg, 0.63 mmol) was added to (S)-ethyl 1-(2-aminopropyl)-4-(2-chloro-5-methylpyrimidin-4-yl)-1H-imidazole-2-carboxylate dihydrochloride (Intermediate 64; 250 mg, 0.63 mmol) in DCM (15 mL) and the resulting mixture was stirred at 40° C. for 4 hours. Sodium triacetoxyborohydride (267 mg, 1.26 mmol) was then added and the reaction stirred for a further 1 hour. The reaction mixture was then poured into saturated NaHCO$_3$ (50 mL) and extracted with DCM (2×50 mL). The combined organic phases were dried over Na$_2$SO$_4$, filtered and evaporated to afford crude. The crude product was purified by flash silica chromatography, elution gradient 0 to 5% MeOH in DCM. Pure fractions were evaporated to dryness to afford a white solid. This solid was then treated with NH$_3$ (7N in MeOH, 15.00 mL) and heated for 5 hour at 50° C. The volatiles were then removed under reduced pressure to afford (S)-2-(2-chloro-5-methylpyrimidin-4-yl)-7-(3-(difluoromethoxy)benzyl)-6-methyl-6,7-dihydroimidazo[1,2-a]pyrazin-8(5H)-one (130 mg, 47.5%) as light yellow oil. m/z (ES+), [M+H]+=434.

Example 29

(S)-6-Methyl-2-(5-methyl-2-((1-methyl-1H-pyrazol-5-yl)amino)pyrimidin-4-yl)-7-((4-(trifluoromethyl)pyridin-2-yl)methyl)-6,7-dihydroimidazo[1,2-a]pyrazin-8(5H)-one

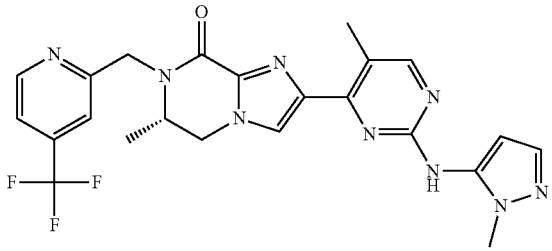 [SMILES: Cc1cnc(Nc2ccnn2C)nc1-c1cn2c(n1)C(=O)N(Cc1cc(C(F)(F)F)ccn1)[C@@H](C)C2]

3rd Generation BrettPhos precatalyst (31.1 mg, 0.03 mmol) was added to (S)-2-(2-chloro-5-methylpyrimidin-4-yl)-6-methyl-7-((4-(trifluoromethyl)pyridin-2-yl)methyl)-6,7-dihydroimidazo[1,2-a]pyrazin-8(5H)-one (Intermediate 80; 300 mg, 0.69 mmol), 1-methyl-1H-pyrazol-5-amine (167 mg, 1.72 mmol) and Cs$_2$CO$_3$ (448 mg, 1.37 mmol) in 1,4-dioxane (8 mL) at 25° C. under nitrogen. The resulting mixture was stirred at 100° C. for 8 hours. The solvent was then removed under reduced pressure. The crude product was purified by flash silica chromatography, elution gradient 0 to 6% MeOH in DCM. Compound containing fractions were evaporated to dryness to afford a yellow residue. This residue was purified further by preparative HPLC (XSelect CSH Prep C18 OBD column, 5μ silica, 19 mm diameter, 150 mm length), using decreasingly polar mixtures of water (containing 0.03% NH$_3$) and MeCN as eluents. Fractions containing the desired compound were evaporated to dryness to afford (S)-6-methyl-2-(5-methyl-2-((1-methyl-1H-pyrazol-5-yl)amino)pyrimidin-4-yl)-7-((4-(trifluoromethyl)pyridin-2-yl)methyl)-6,7-dihydroimidazo[1,2-a]pyrazin-8(5H)-one (Example 28; 141 mg, 41.3%) as a white solid. $^1$H NMR (400 MHz, DMSO, 20° C.) δ 1.21 (3H, d), 2.52 (3H, s), 3.71 (3H, s), 4.13 (1H, dd), 4.37 (1H, dd), 4.52 (1H, dd), 4.58 (1H, d), 5.26 (1H, d), 6.31 (1H, d), 7.34 (1H, d), 7.71 (1H, d), 7.82 (1H, s), 7.95 (1H, s), 8.33 (1H, s), 8.84 (1H, d), 9.24 (1H, s). m/z (ES+), [M+H]+=498.

Intermediate 80

(S)-2-(2-Chloro-5-methylpyrimidin-4-yl)-6-methyl-7-((4-(trifluoromethyl)pyridin-2-yl)methyl)-6,7-dihydroimidazo[1,2-a]pyrazin-8(5H)-one

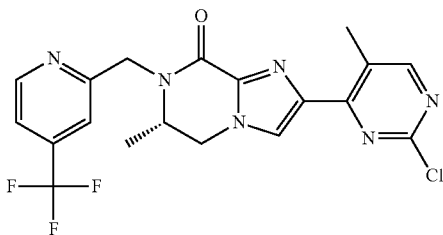 [SMILES: Cc1cnc(Cl)nc1-c1cn2c(n1)C(=O)N(Cc1cc(C(F)(F)F)ccn1)[C@@H](C)C2]

4-(Trifluoromethyl)picolinaldehyde (136 mg, 0.78 mmol) was added to (S)-ethyl 1-(2-aminopropyl)-4-(2-chloro-5-methylpyrimidin-4-yl)-1H-imidazole-2-carboxylate dihydrochloride (Intermediate 64; 280 mg, 0.71 mmol), DIPEA (0.37 mL, 2.12 mmol) and AcOH (0.121 mL, 2.12 mmol) in DCM (10 mL) at 25° C. under nitrogen. After stirring at 25° C. for 1 hour, sodium triacetoxyborohydride (449 mg, 2.12 mmol) was added and the resulting mixture was stirred at 25° C. for 2 hours and then heated at 50° C. for 8 hours. The reaction mixture was quenched with saturated NaHCO$_3$ (20 mL) and extracted with DCM (2×75 mL). The combined organic layer was dried over Na$_2$SO$_4$, filtered and evaporated to afford yellow residue. The crude product was purified by flash silica chromatography, elution gradient 0 to 5% MeOH in DCM. Pure fractions were evaporated to dryness to afford (S)-2-(2-chloro-5-methylpyrimidin-4-yl)-6-methyl-7-((4-(trifluoromethyl)pyridin-2-yl)methyl)-6,7-dihydroimidazo[1,2-a]pyrazin-8(5H)-one (Intermediate 80; 300 mg, 97%) as a yellow solid. $^1$H NMR (400 MHz, CDCl$_3$, 20° C.) δ 1.60 (3H, s), 2.79 (3H, s), 4.07-4.20 (1H, m), 4.26 (1H, s), 4.36-4.45 (1H, m), 4.50 (1H, dd), 5.54 (1H, d), 7.49 (1H, d), 7.72 (1H, s), 8.00 (1H, s), 8.45 (1H, s), 8.75 (1H, d).

Example 30

(S)-6-Methyl-2-(5-methyl-2-((1-methyl-1H-pyrazol-5-yl)amino)pyrimidin-4-yl)-7-((2-(trifluoromethyl)pyridin-4-yl)methyl)-6,7-dihydroimidazo[1,2-a]pyrazin-8(5H)-one

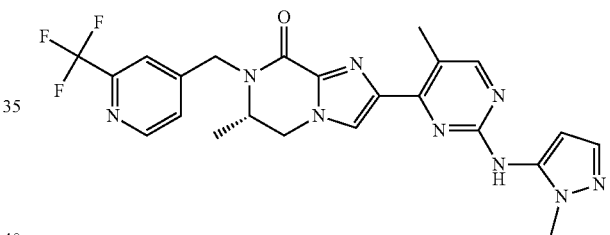

3rd Generation BrettPhos precatalyst (31.1 mg, 0.03 mmol) was added to (S)-2-(2-chloro-5-methylpyrimidin-4-yl)-6-methyl-7-((2-(trifluoromethyl)pyridin-4-yl)methyl)-6,7-dihydroimidazo[1,2-a]pyrazin-8(5H)-one (Intermediate 81; 300 mg, 0.69 mmol), 1-methyl-1H-pyrazol-5-amine (167 mg, 1.72 mmol) and Cs$_2$CO$_3$ (448 mg, 1.37 mmol) in 1,4-dioxane (8 mL) at 25° C. under nitrogen. The resulting mixture was stirred at 100° C. for 5 hours. The solvent was then removed under reduced pressure. The crude product was purified by flash silica chromatography, elution gradient 0 to 6% MeOH in DCM. Compound containing fractions were evaporated to dryness to afford a yellow residue. This residue was purified further by preparative HPLC (XSelect CSH Prep C18 OBD column, 5μ silica, 19 mm diameter, 150 mm length), using decreasingly polar mixtures of water (containing 0.03% NH$_3$) and MeCN as eluents. Fractions containing the desired compound were evaporated to dryness to afford (S)-6-methyl-2-(5-methyl-2-((1-methyl-1H-pyrazol-5-yl)amino)pyrimidin-4-yl)-7-((2-(trifluoromethyl)pyridin-4-yl)methyl)-6,7-dihydroimidazo[1,2-a]pyrazin-8(5H)-one (Example 30; 200 mg, 58.5%) as a white solid. $^1$H NMR (300 MHz, DMSO, 23° C.) δ 1.18 (3H, d), 2.61 (3H, s), 3.70 (3H, s), 4.00-4.13 (1H, m), 4.30-4.40 (1H, d), 4.45-4.60 (2H, m), 5.18 (1H, d), 6.30 (1H, s), 6.20 (1H, d), 7.73 (1H, d), 7.91 (1H, s), 7.96 (1H, s), 8.33 (1H, s), 8.73 (1H, d), 9.23 (1H, s). m/z (ES+), [M+H]+=498.

Intermediate 81

(S)-2-(2-Chloro-5-methylpyrimidin-4-yl)-6-methyl-7-((2-(trifluoromethyl)pyridin-4-yl)methyl)-6,7-dihydroimidazo[1,2-a]pyrazin-8(5H)-one

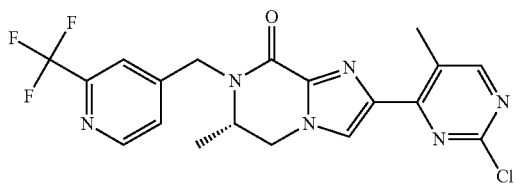 [SMILES: Cc1cnc(Cl)nc1-c1cn2c(n1)C(=O)N(Cc1ccnc(C(F)(F)F)c1)[C@@H](C)C2]

2-(Trifluoromethyl)isonicotinaldehyde (170 mg, 0.97 mmol) was added to (S)-ethyl 1-(2-aminopropyl)-4-(2-chloro-5-methylpyrimidin-4-yl)-1H-imidazole-2-carboxylate dihydrochloride (Intermediate 64; 350 mg, 0.88 mmol), DIPEA (0.462 mL, 2.65 mmol) and AcOH (0.152 mL, 2.65 mmol) in DCM (15 mL) at 25° C. under nitrogen. After stirring at 25° C. for 1 hour, sodium triacetoxyborohydride (561 mg, 2.65 mmol) was added and the resulting mixture was stirred at 25° C. for 1 hour and heated at 50° C. for 18 hours. The reaction mixture was quenched with saturated NaHCO$_3$ (50 mL) and extracted with DCM (2×75 mL). The organic phases were dried over Na$_2$SO$_4$, filtered and evaporated to afford yellow residue. The crude product was purified by flash silica chromatography, elution gradient 0 to 5% MeOH in DCM. Pure fractions were evaporated to dryness to afford (S)-2-(2-chloro-5-methylpyrimidin-4-yl)-6-methyl-7-((2-(trifluoromethyl)pyridin-4-yl)methyl)-6,7-dihydroimidazo[1,2-a]pyrazin-8(5H)-one (320 mg, 83%) as a yellow oil. m/z (ES+), [M+H]+=437.

Example 31

(S)-7-((4-(Difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one

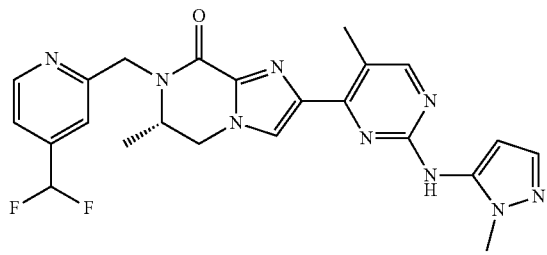 [SMILES: Cc1cnc(Nc2ccnn2C)nc1-c1cn2c(n1)C(=O)N(Cc1cc(C(F)F)ccn1)[C@@H](C)C2]

3rd Generation BrettPhos precatalyst (51.9 mg, 0.06 mmol) was added to (S)-2-(2-chloro-5-methylpyrimidin-4-yl)-7-((4-(difluoromethyl)pyridin-2-yl)methyl)-6-methyl-6,7-dihydroimidazo[1,2-a]pyrazin-8(5H)-one (Intermediate 82; 240 mg, 0.57 mmol), 1-methyl-1H-pyrazol-5-amine (111 mg, 1.15 mmol) and Cs$_2$CO$_3$ (373 mg, 1.15 mmol) in 1,4-dioxane (5 mL) at 25° C. under nitrogen. The resulting solution was stirred at 120° C. for 8 hours. The solvent was then removed by distillation under vacuum. The crude product was purified by flash silica chromatography, elution gradient 4 to 6% MeOH in DCM. Product containing fractions were evaporated to dryness to afford a solid. This solid was purified further by preparative HPLC (XSelect CSH Prep C18 OBD column, 5μ silica, 19 mm diameter, 150 mm length), using decreasingly polar mixtures of water (containing 0.05% NH$_4$HCO$_3$) and MeCN as eluents. Fractions containing the desired compound were evaporated to dryness to afford (S)-7-((4-(difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one (Example 31; 92 mg, 33.5%) as a white solid. $^1$H NMR (400 MHz, CDCl$_3$, 20.2° C.) δ 1.36 (3H, d), 2.69 (3H, s), 3.82 (3H, s), 4.09 (1H, dd), 4.22 (1H, tt), 4.37-4.49 (2H, m), 5.50 (1H, d), 6.31 (1H, d), 6.64 (1H, t), 7.01 (1H, s), 7.36-7.43 (1H, m), 7.50 (1H, d), 7.61 (1H, s), 7.75 (1H, s), 8.29 (1H, s), 8.69 (1H, d). m/z (ES+), [M+H]+=480.

Intermediate 82

(S)-2-(2-Chloro-5-methylpyrimidin-4-yl)-7-((4-(difluoromethyl)pyridin-2-yl)methyl)-6-methyl-6,7-dihydroimidazo[1,2-a]pyrazin-8(5H)-one

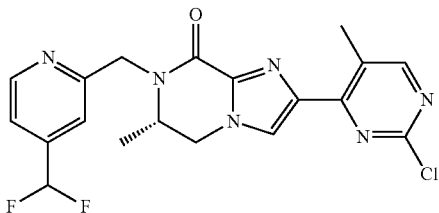 [SMILES: Cc1cnc(Cl)nc1-c1cn2c(n1)C(=O)N(Cc1cc(C(F)F)ccn1)[C@@H](C)C2]

4-(Difluoromethyl)picolinaldehyde (Intermediate 83; 154 mg, 0.98 mmol) was added to (S)-ethyl 1-(2-aminopropyl)-4-(2-chloro-5-methylpyrimidin-4-yl)-1H-imidazole-2-carboxylate dihydrochloride (Intermediate 64; 300 mg, 0.76 mmol), DIPEA (0.396 mL, 2.27 mmol) and AcOH (0.130 mL, 2.27 mmol) in DCM (10 mL) at 25° C. under nitrogen. After stirring at 25° C. for 0.5 hour, sodium triacetoxyborohydride (481 mg, 2.27 mmol) was added and the reaction stirred at 25° C. for 0.5 hour and heated at 50° C. for 12 hours. The reaction mixture was quenched with saturated NaHCO$_3$ (20 mL) and extracted with DCM (2×75 mL). The organic phases ere dried over Na$_2$SO$_4$, filtered and evaporated to afford a yellow residue. The crude product was purified by flash silica chromatography, elution gradient 3 to 4% MeOH in DCM. Pure fractions were evaporated to dryness to afford (S)-2-(2-chloro-5-methylpyrimidin-4-yl)-7-((4-(difluoromethyl)pyridin-2-yl)methyl)-6-methyl-6,7-dihydroimidazo[1,2-a]pyrazin-8(5H)-one (Intermediate 82; 240 mg, 76%) as a yellow solid. $^1$H NMR (400 MHz, CDCl$_3$, 20.5° C.) δ 1.37 (3H, d), 2.79 (3H, d), 4.10 (1H, dd), 4.25 (1H, tdd), 4.35-4.53 (2H, m), 5.50 (1H, d), 6.64 (1H, t), 7.33-7.47 (1H, m), 7.61 (1H, s), 7.99 (1H, s), 8.44 (1H, d), 8.69 (1H, dd). m/z (ES+), [M+H]+=419.

Intermediate 83

4-(Difluoromethyl)picolinaldehyde

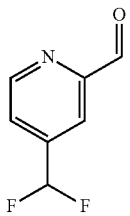

LiAlH₄ (0.274 g, 7.22 mmol) was added to 4-(difluoromethyl)-N-methoxy-N-methylpicolinamide (Intermediate 84; 1.2 g, 5.55 mmol) in THF (10 mL) cooled to −78° C. under nitrogen. The resulting solution was stirred at −78° C. for 20 minutes. EtOAc (1 mL) was added, then the reaction quenched with water (0.3 mL) at −78° C. 15% NaOH aqueous solution (1.5 mL), further water (0.3 mL) was added and the resulting solids removed by filtration. The filtrate was dried over Na₂SO₄, filtered and evaporated to afford 4-(difluoromethyl)picolinaldehyde (Intermediate 83; 1.09 g) as a green oil. The product was used in the next step directly without further purification. m/z (ES+), [M+H]+=158.

Intermediate 84

4-(Difluoromethyl)-N-methoxy-N-methylpicolinamide

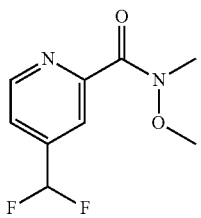

Trimethylaluminum (2M in n-hexane, 40.1 mL, 80.15 mmol) was added to N,O-dimethylhydroxylamine hydrochloride (6.25 g, 64.12 mmol) in DCM (80 mL) at 0° C. over a period of 20 minutes under nitrogen. The resulting solution was stirred at 0° C. for 20 minutes. Methyl 4-(difluoromethyl)picolinate (Intermediate 85; 3.0 g, 16.03 mmol) in DCM (20 mL) was added to reaction mixture at 0° C. and the resulting solution was stirred at 0° C. for 2 hours. The reaction mixture was quenched with 2M NaOH (50 mL) at 0° C. and extracted with DCM (3×100 mL). The organic phases were dried over Na₂SO₄, filtered and evaporated to afford yellow oil. The crude product was purified by flash silica chromatography, elution gradient 30 to 40% EtOAc in petroleum ether. Pure fractions were evaporated to dryness to afford 4-(difluoromethyl)-N-methoxy-N-methylpicolinamide (Intermediate 84; 2.47 g, 71.3%) as a yellow oil. ¹H NMR (400 MHz, MeOD, 20.3° C.) δ 3.42 (3H, s), 3.73 (3H, s), 6.94 (1H, t), 7.65-7.72 (1H, m), 8.75-8.82 (1H, m). m/z (ES+), [M+H]+=217.

Intermediate 85

Methyl 4-(difluoromethyl)picolinate

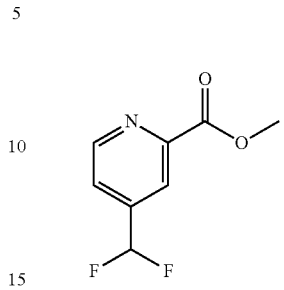

2-Chloro-4-(difluoromethyl)pyridine (Intermediate 86; 6.9 g, 42.19 mmol), potassium acetate (8.28 g, 84.38 mmol) and Pd(dppf)Cl₂ (1.543 g, 2.11 mmol) in MeOH (150 mL) were stirred under an atmosphere of CO at 10 atm at 70° C. for 24 hours. The mixture was then filtered and the filtrate was evaporated under reduced pressure. The crude product was purified by flash silica chromatography, elution gradient 20 to 30% EtOAc in petroleum ether. Pure fractions were evaporated to dryness to afford methyl 4-(difluoromethyl)picolinate (Intermediate 85; 6.30 g, 80%) as a yellow oil. ¹H NMR (400 MHz, MeOD, 20.1° C.) δ 4.03 (3H, s), 6.98 (1H, t), 7.79-7.86 (1H, m), 8.30 (1H, dd), 8.86 (1H, dd). m/z (ES+), [M+H]+=188.

Intermediate 86

2-Chloro-4-(difluoromethyl)pyridine

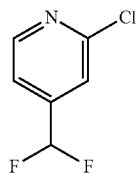

DAST (20.53 mL, 155.42 mmol) was added dropwise to 2-chloroisonicotinaldehyde (10 g, 70.64 mmol) in DCM (150 mL) at 0° C. over a period of 10 minutes under nitrogen. The temperature was increased to room temperature and stirred for 12 hours. The reaction mixture was quenched and adjusted to pH 7-8 with saturated NaHCO₃ at 0° C. The aqueous phase was extracted with DCM (3×150 mL), the organic phases dried over Na₂SO₄, filtered and evaporated to afford yellow oil. The crude product was purified by flash silica chromatography, elution gradient 5 to 10% EtOAc in petroleum ether. Pure fractions were evaporated to dryness to afford 2-chloro-4-(difluoromethyl)pyridine (Intermediate 86; 7.00 g, 60.6%) as a yellow oil. ¹H NMR (400 MHz, CDCl₃, 20.5° C.) δ6.65 (1H, t), 7.38 (1H, dd), 7.49 (1H, s), 8.55 (1H, dd). m/z (ES+), [M+H]+=164.

Example 32

(S)-6-Methyl-2-(5-methyl-2-((1-methyl-1H-pyrazol-5-yl)amino)pyrimidin-4-yl)-7-((6-(trifluoromethyl)pyrimidin-4-yl)methyl)-6,7-dihydroimidazo[1,2-a]pyrazin-8(5H)-one

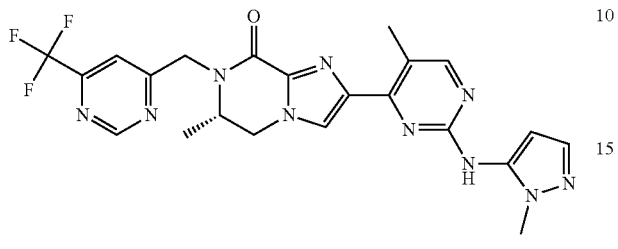

3rd Generation BrettPhos precatalyst (12.42 mg, 0.01 mmol) was added to (S)-2-(2-chloro-5-methylpyrimidin-4-yl)-6-methyl-7-((6-(trifluoromethyl)pyrimidin-4-yl)methyl)-6,7-dihydroimidazo[1,2-a]pyrazin-8(5H)-one (Intermediate 87; 120 mg, 0.27 mmol), 1-methyl-1H-pyrazol-5-amine (66.5 mg, 0.69 mmol) and $Cs_2CO_3$ (179 mg, 0.55 mmol) in 1,4-dioxane (4 mL) at 25° C. under nitrogen. The resulting mixture was stirred at 100° C. for 8 hours. The solvent was then removed under reduced pressure. The crude product was purified by flash silica chromatography, elution gradient 0 to 6% MeOH in DCM. Pure fractions were evaporated to dryness to afford a yellow residue. This residue was purified further by preparative HPLC (XSelect CSH Prep C18 OBD column, 5μ silica, 19 mm diameter, 150 mm length), using decreasingly polar mixtures of water (containing 0.03% $NH_3$) and MeCN as eluents. Fractions containing the desired compound were evaporated to dryness to afford (S)-6-methyl-2-(5-methyl-2-((1-methyl-1H-pyrazol-5-yl)amino)pyrimidin-4-yl)-7-((6-(trifluoromethyl)pyrimidin-4-yl)methyl)-6,7-dihydroimidazo[1,2-a]pyrazin-8(5H)-one (Example 32; 60 mg, 43.9%) as a white solid. $^1$H NMR (300 MHz, DMSO) δ 1.25 (d, 3H), 3.71 (s, 3H), 4.14-4.21 (m, 1H), 4.34-4.46 (m, 1H), 4.56-4.71 (m, 2H), 5.27 (d, 1H), 6.32 (d, 1H), 7.35 (d, 1H), 7.98 (s, 1H), 8.13 (d, 1H), 8.34 (s, 1H), 9.24 (s, 1H), 9.41 (s, 1H). m/z (ES+), [M+H]+=499.

Intermediate 87

(S)-2-(2-Chloro-5-methylpyrimidin-4-yl)-6-methyl-7-((6-(trifluoromethyl)pyrimidin-4-yl)methyl)-6,7-dihydroimidazo[1,2-a]pyrazin-8(5H)-one

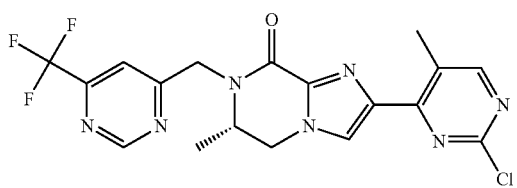 [SMILES: Cc1cnc(Cl)nc1-c1cn2c(n1)C(=O)N(Cc1cc(C(F)(F)F)ncn1)[C@@H](C)C2]

Sodium acetate (212 mg, 2.58 mmol) was added to (S)-ethyl 4-(2-chloro-5-methylpyrimidin-4-yl)-1-(2-(((6-(trifluoromethyl)pyrimidin-4-yl)methyl)amino)propyl)-1H-imidazole-2-carboxylate (Intermediate 88; 250 mg, 0.52 mmol) in EtOH (5 mL) and the resulting mixture was stirred at 80° C. for 20 hours. The solvent was then removed under reduced pressure. The crude product was purified by flash silica chromatography, elution gradient 0 to 5% MeOH in DCM. Pure fractions were evaporated to dryness to afford (S)-2-(2-chloro-5-methylpyrimidin-4-yl)-6-methyl-7-((6-(trifluoromethyl)pyrimidin-4-yl)methyl)-6,7-dihydroimidazo[1,2-a]pyrazin-8(5H)-one (Intermediate 87; 120 mg, 53.1%) as a pale yellow solid. $^1$H NMR (300 MHz, $CDCl_3$, 20.5° C.) δ 1.45 (d, 3H), 2.79 (s, 3H), 4.43 (d, 1H), 4.15-4.25 (m 1H), 4.60 (dd, 1H), 5.50 (d, 1H), 7.82 (d, 1H), 8.03 (s, 1H), 8.46 (s, 1H), 9.34 (s, 1H). m/z (ES+), [M+H]+=438.

Intermediate 88

(S)-Ethyl 4-(2-chloro-5-methylpyrimidin-4-yl)-1-(2-(((6-(trifluoromethyl)pyrimidin-4-yl)methyl)amino)propyl)-1H-imidazole-2-carboxylate

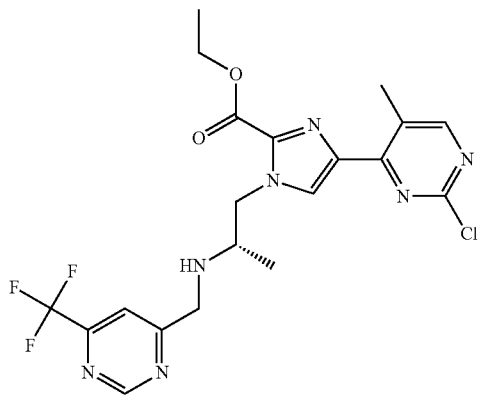 [SMILES: CCOC(=O)c1nc(-c2nc(Cl)ncc2C)cn1C[C@H](C)NCc1cc(C(F)(F)F)ncn1]

$Cp_2ZrHCl$ (492 mg, 1.91 mmol) was added to N-methoxy-N-methyl-6-(trifluoromethyl)pyrimidine-4-carboxamide (Intermediate 89; 300 mg, 1.28 mmol) in THF (10 mL) under nitrogen. The resulting mixture was stirred at 25° C. for 20 minutes and then used directly. Sodium triacetoxyborohydride (385 mg, 1.81 mmol), acetic acid (0.104 mL, 1.81 mmol), (S)-ethyl 1-(2-aminopropyl)-4-(2-chloro-5-methylpyrimidin-4-yl)-1H-imidazole-2-carboxylate dihydrochloride (Intermediate 64; 240 mg, 0.60 mmol) and DIPEA (0.317 mL, 1.81 mmol) in DCM (15 mL) were added and the resulting mixture was stirred at 25° C. for 1 hour. Further sodium triacetoxyborohydride (385 mg, 1.81 mmol) was added and stirred for a further 1 hour. The reaction mixture was then poured into saturated $NaHCO_3$ (75 mL) and extracted with DCM (3×25 mL). The organic phases were dried over $Na_2SO_4$, filtered and evaporated. The crude product was purified by flash silica chromatography, elution gradient 0 to 5% DCM in MeOH. Pure fractions were evaporated to dryness to afford (S)-ethyl 4-(2-chloro-5-methylpyrimidin-4-yl)-1-(2-(((6-(trifluoromethyl)pyrimidin-4-yl)methyl)amino)propyl)-1H-imidazole-2-carboxylate (Intermediate 88; 250 mg, 85%) as a pale yellow solid. m/z (ES+), [M+H]+=484.

Intermediate 89

N-Methoxy-N-methyl-6-(trifluoromethyl)pyrimidine-4-carboxamide

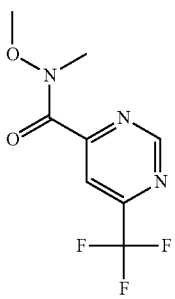 [SMILES: CON(C)C(=O)c1cc(C(F)(F)F)ncn1]

Trimethylaluminum (2M in n-hexane, 72.8 mL, 145.54 mmol) was added dropwise to N,O-dimethylhydroxylamine hydrochloride (10.65 g, 109.16 mmol) in DCM (150 mL) at 0° C. over a period of 20 minutes under nitrogen. The resulting solution was stirred at 0° C. for 20 minutes. Methyl 6-(trifluoromethyl)pyrimidine-4-carboxylate (Intermediate 90; 7.5 g, 36.39 mmol) in DCM (70 mL) was added dropwise to reaction mixture at 0° C. The reaction mixture was then stirred for 1 hour at 0° C. The reaction was quenched with 2M NaOH (100 mL) and extracted with DCM (3×150 mL). The organic phases were dried over Na$_2$SO$_4$, filtered and evaporated to afford yellow oil. The crude product was purified by flash silica chromatography, elution gradient 0 to 25% EtOAc in petroleum ether. Pure fractions were evaporated to dryness to afford N-methoxy-N-methyl-6-(trifluoromethyl)pyrimidine-4-carboxamide (Intermediate 89; 5.63 g, 65.8%) as a yellow oil. $^1$H NMR (400 MHz, CDCl$_3$, 20.2° C.) δ 3.42 (3H, s), 3.79 (3H, s), 7.90 (1H, s), 9.41-9.47 (1H, m). m/z (ES+), [M+H]+=236.

Intermediate 90

Methyl 6-(trifluoromethyl)pyrimidine-4-carboxylate

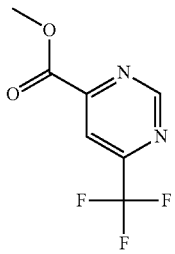

4-Chloro-6-(trifluoromethyl)pyrimidine (10 g, 54.79 mmol), potassium acetate (10.75 g, 109.57 mmol) and Pd(dppf)Cl$_2$ (2.00 g, 2.74 mmol) in MeOH (300 mL) were stirred under an atmosphere of CO at 10 atm and 70° C. for 6 hours. The mixture was filtered and the filtrate was evaporated under reduced pressure. The crude product was purified by flash silica chromatography, elution gradient 0 to 20% EtOAc in petroleum ether. Pure fractions were evaporated to dryness to afford methyl 6-(trifluoromethyl)pyrimidine-4-carboxylate (Intermediate 90; 7.86 g, 69.6%) as a yellow solid. $^1$H NMR (400 MHz, CDCl$_3$, 20.3° C.) δ 4.11 (3H, s), 8.37 (1H, d), 9.55-9.61 (1H, m). m/z (ES+), [M+H]+=207.

Example 33

7-(3,4-Difluorobenzyl)-2-(5-methyl-2-((1-methyl-1H-pyrazol-5-yl)amino)pyrimidin-4-yl)-6,7-dihydroimidazo[1,2-a]pyrazin-8(5H)-one

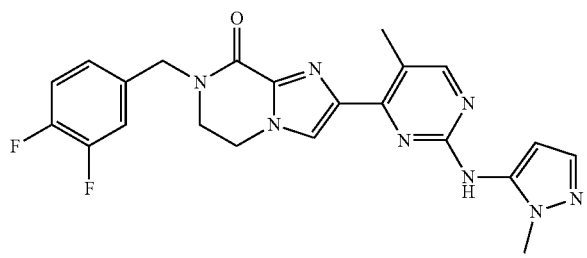 [SMILES: Cc1cnc(Nc2ccnn2C)nc1-c1cn2c(n1)C(=O)N(Cc1ccc(F)c(F)c1)CC2]

2nd Generation XantPhos precatalyst (78 mg, 0.09 mmol) was added to 2-(2-chloro-5-methylpyrimidin-4-yl)-7-(3,4-difluorobenzyl)-6,7-dihydroimidazo[1,2-a]pyrazin-8(5H)-one (Intermediate 91; 340 mg, 0.87 mmol), 1-methyl-1H-pyrazol-5-amine (169 mg, 1.74 mmol) and Cs$_2$CO$_3$ (568 mg, 1.74 mmol) in 1,4-dioxane (5 mL) at 25° C. under nitrogen. The resulting solution was stirred at 100° C. for 12 hours. The solvent was then removed by distillation under vacuum. The crude product was purified by flash silica chromatography, elution gradient 3 to 5% MeOH in DCM. Pure fractions were evaporated to dryness to afford a solid. This solid was purified further by preparative HPLC (XSelect CSH Prep C18 OBD column, 5μ silica, 19 mm diameter, 150 mm length), using decreasingly polar mixtures of water (containing 0.05% NH$_4$HCO$_3$) and MeCN as eluents. Fractions containing the desired compound were evaporated to dryness to afford 7-(3,4-difluorobenzyl)-2-(5-methyl-2-((1-methyl-1H-pyrazol-5-yl)amino)pyrimidin-4-yl)-6,7-dihydroimidazo[1,2-a]pyrazin-8(5H)-one (Example 33; 89 mg, 22.6%) as a white solid. $^1$H NMR (400 MHz, CDCl$_3$, 20.1° C.) δ 2.68 (3H, d), 3.68-3.76 (2H, m), 3.80 (3H, s), 4.25-4.33 (2H, m), 4.77 (2H, s), 6.29 (1H, d), 6.90 (1H, s), 7.07-7.28 (3H, m), 7.49 (1H, d), 7.69 (1H, s), 8.29 (1H, d). m/z (ES+), [M+H]+=451.

Intermediate 91

2-(2-Chloro-5-methylpyrimidin-4-yl)-7-(3,4-difluorobenzyl)-6,7-dihydroimidazo[1,2-a]pyrazin-8(5H)-one

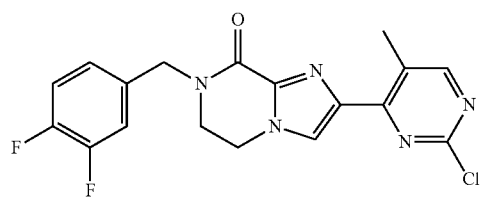

NaH (91 mg, 2.28 mmol) was added to 2-(2-chloro-5-methylpyrimidin-4-yl)-6,7-dihydroimidazo[1,2-a]pyrazin-8

(5H)-one (Intermediate 48; 200 mg, 0.76 mmol) in DMF (5 mL) at 25° C. under nitrogen. The resulting solution was stirred at 25° C. for 30 minutes. 4-(bromomethyl)-1,2-difluorobenzene (314 mg, 1.52 mmol) was added and the resulting solution was stirred at 25° C. for 12 hours. The reaction mixture was poured into water (50 mL), the precipitate was collected by filtration, washed with water (50 mL) and dried under vacuum to afford 2-(2-chloro-5-methylpyrimidin-4-yl)-7-(3,4-difluorobenzyl)-6,7-dihydroimidazo[1,2-a]pyrazin-8(5H)-one (Intermediate 91; 340 mg) as a yellow solid, which was used directly with further purification. $^1$H NMR (400 MHz, DMSO, 19.9° C.) δ 2.64 (3H, s), 3.74-3.82 (2H, m), 4.36-4.44 (2H, m), 4.70 (2H, s), 7.37-7.51 (3H, m), 8.26 (1H, s), 8.61 (1H, s). m/z (ES+), [M+H]+=390.

Example 34

Preparation of (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one adipic acid adduct, Form 1

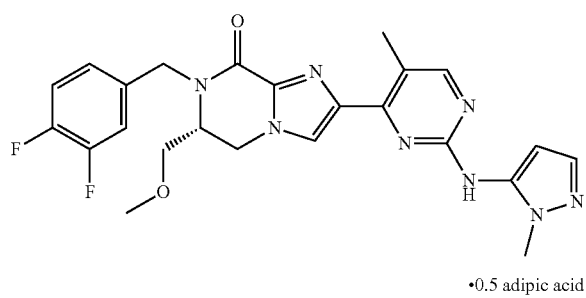 [SMILES: COC[C@H]1Cn2cc(-c3nc(Nc4ccnn4C)ncc3C)nc2C(=O)N1Cc1ccc(F)c(F)c1]

Figure 3:
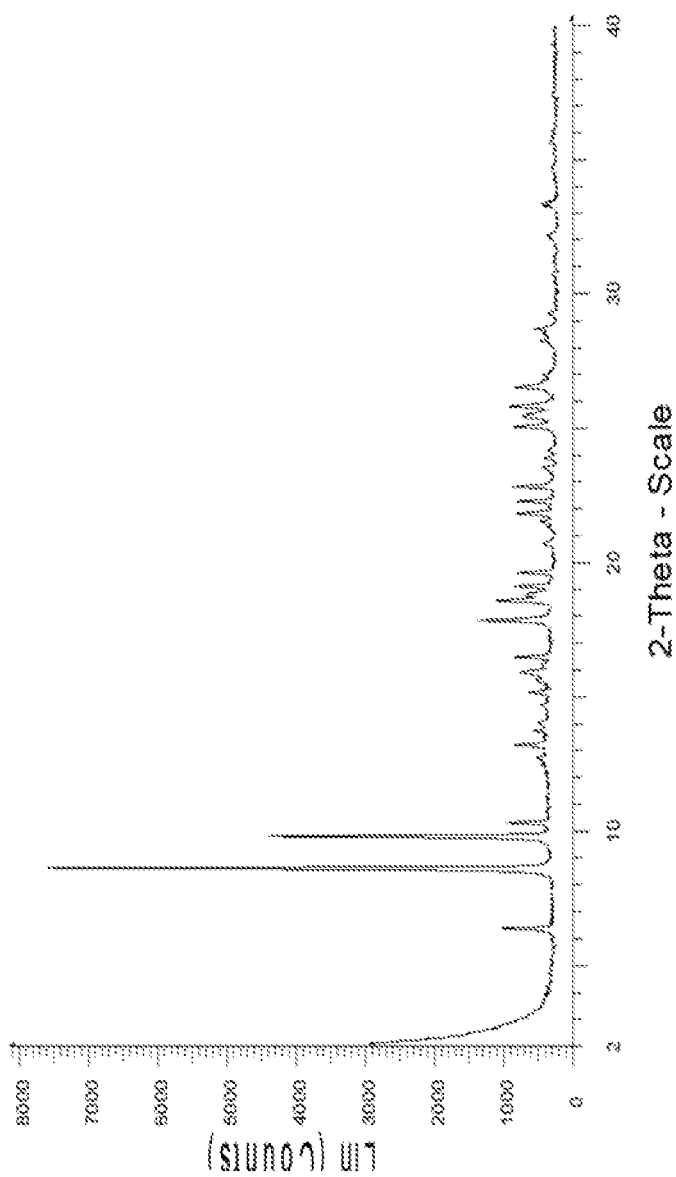
FIG. 3 shows the X-Ray Powder Diffraction Pattern of (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct Form 1 (Example 34).
Figure 4:
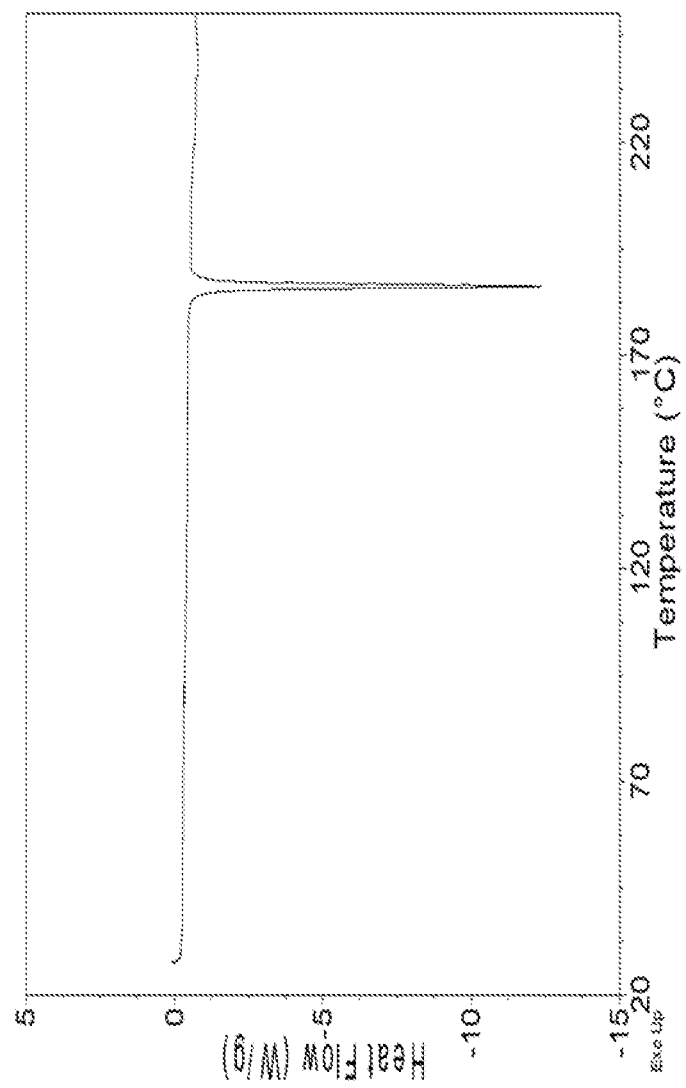
FIG. 4 shows the DSC Thermogram of (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one Adipic acid adduct Form 1 (Example 34).
Figure 5:
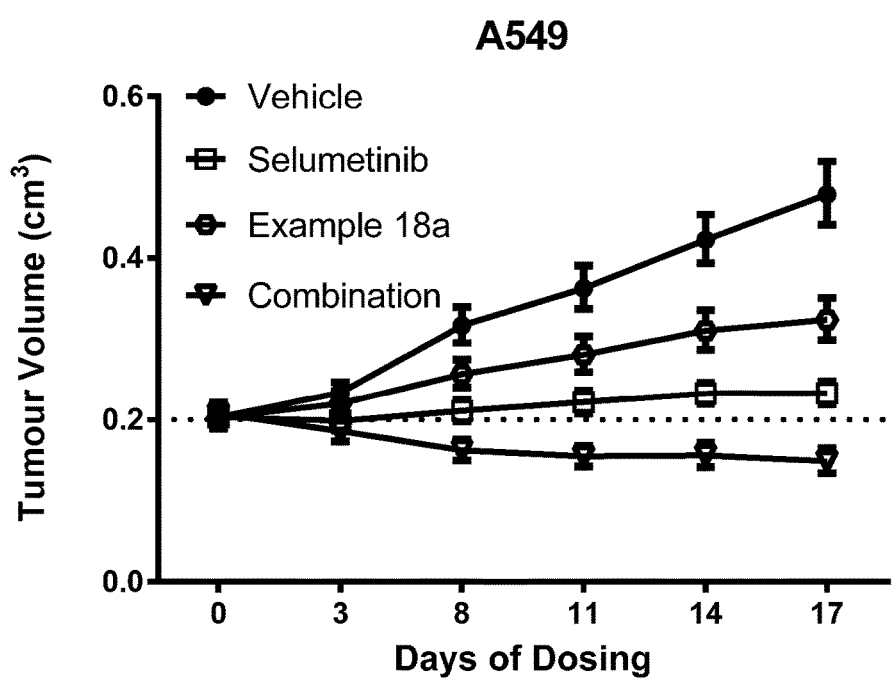
FIG. 5 shows Tumour Growth Inhibition by Example 18a in combination with selumetinib (ARRY-142886) in A549 xenograft model.
Figure 6:
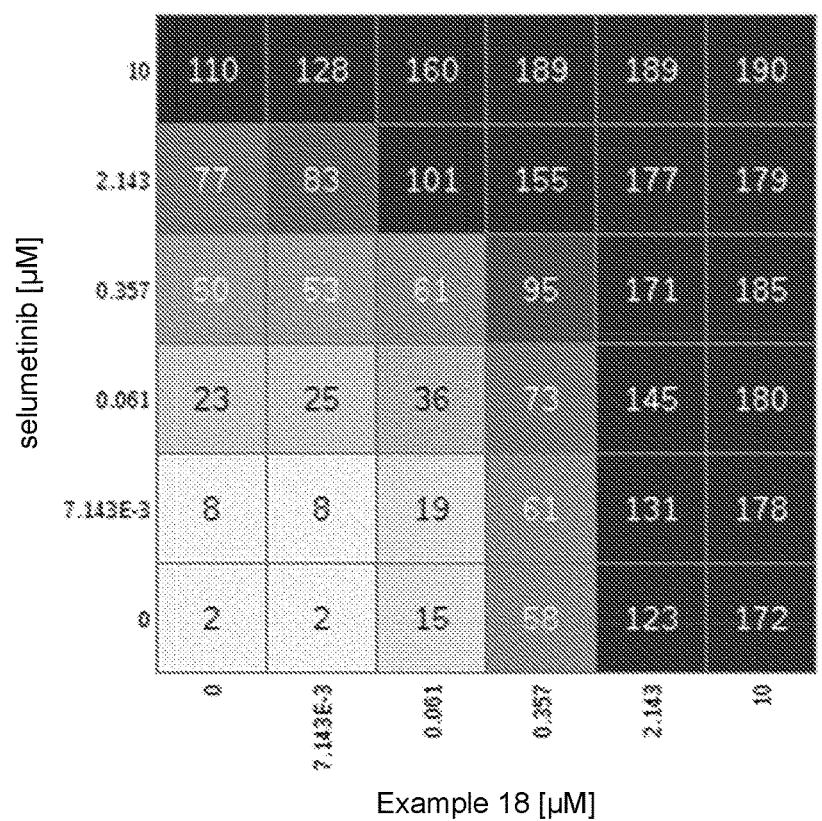
FIG. 6: Cell Growth Inhibition in KRAS-mutant Non-Small Cell Lung Cancer (NSCLC) A549 cell line by Example 18 in combination with selumetinib (ARRY-142886). Dose matrix representing percent growth inhibition values taken from the fitted dose response curves.
Figure 7:
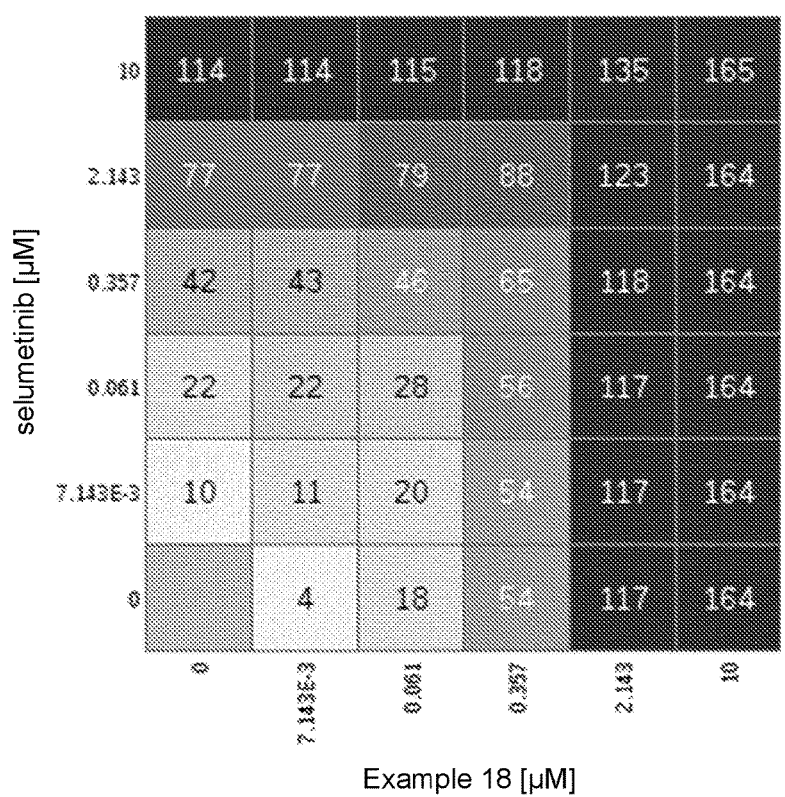
FIG. 7: Cell Growth Inhibition in KRAS-mutant Non-Small Cell Lung Cancer (NSCLC) A549 cell line by Example 18 in combination with selumetinib (ARRY-142886). Loewe model of additivity calculated from the monotherapy dose response curves.
Figure 8:
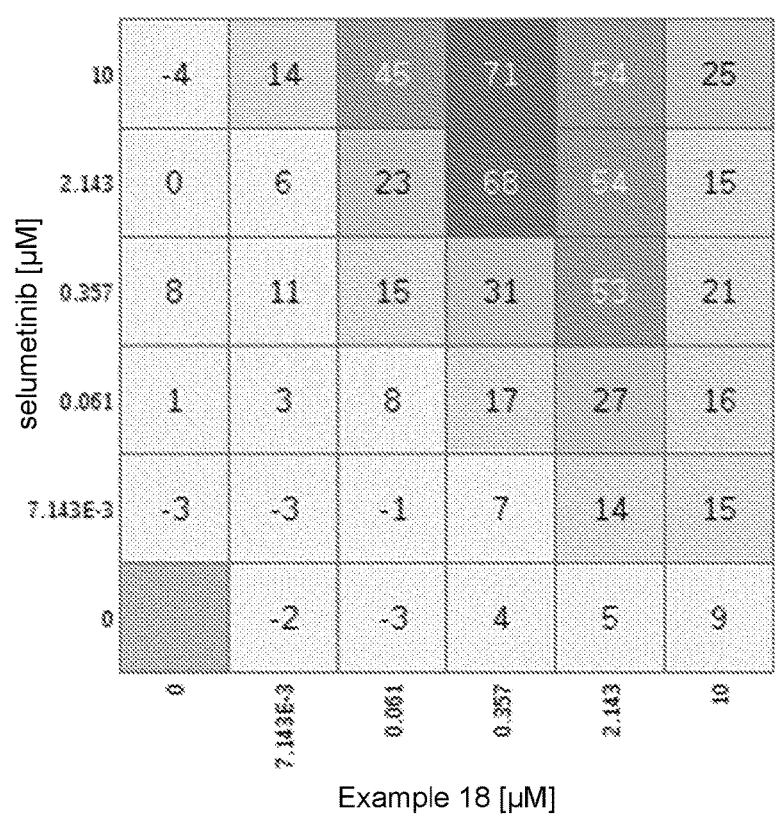
FIG. 8: Cell Growth Inhibition in KRAS-mutant Non-Small Cell Lung Cancer (NSCLC) A549 cell line by Example 18 in combination with selumetinib (ARRY-142886). Excess heatmap (synergy) calculated by subtracting the Loewe model of additivity data from the fitted data.
Figure 9:
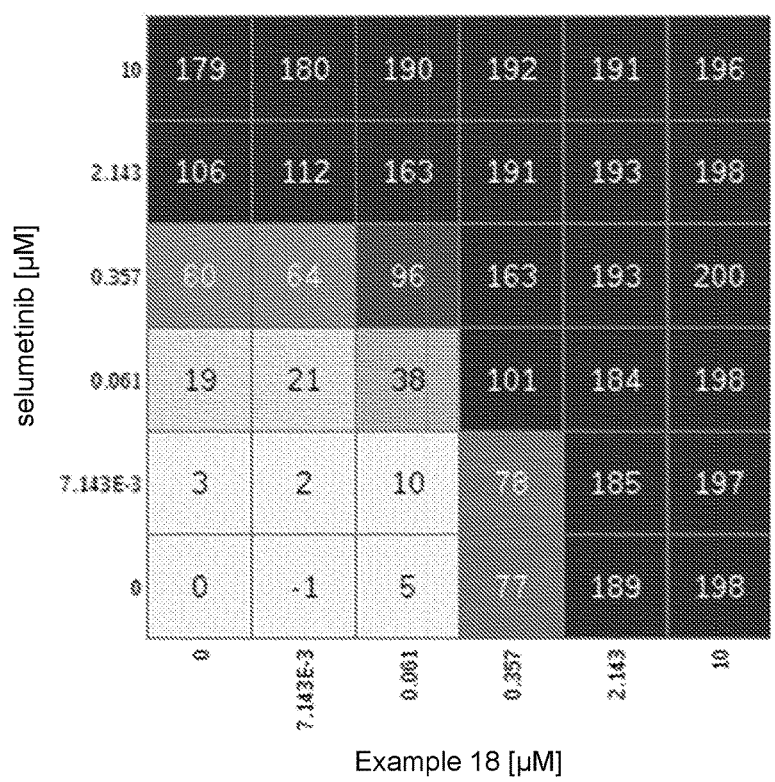
FIG. 9: Cell Growth Inhibition in KRAS-mutant Non-Small Cell Lung Cancer (NSCLC) H2122 cell line by Example 18 in combination with selumetinib (ARRY-142886). Dose matrix representing percent growth inhibition values taken from the fitted dose response curves.
Figure 10:
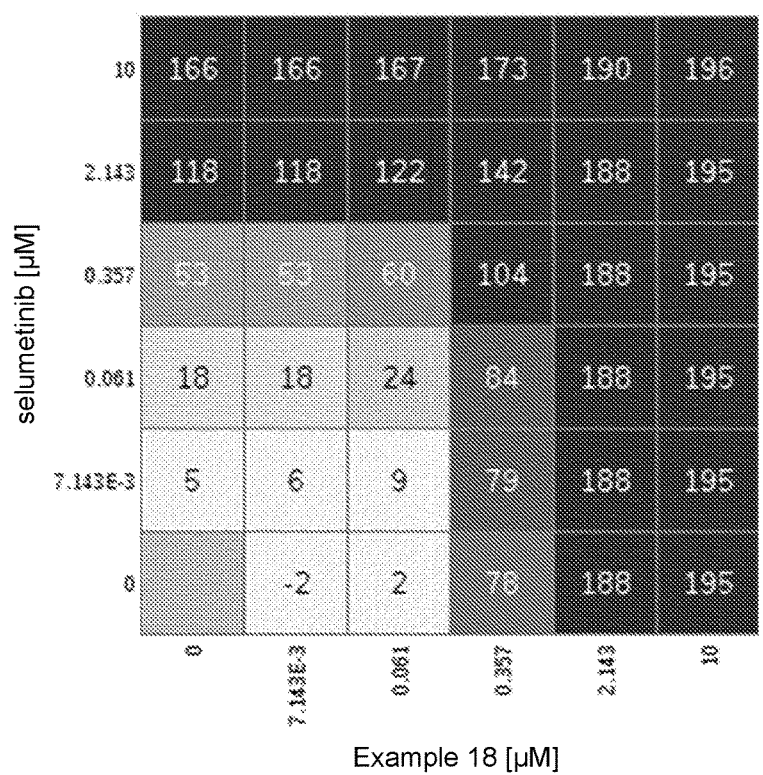
FIG. 10: Cell Growth Inhibition in KRAS-mutant Non-Small Cell Lung Cancer (NSCLC) H2122 cell line by Example 18 in combination with selumetinib (ARRY-142886). Loewe model of additivity calculated from the monotherapy dose response curves.
Figure 11:
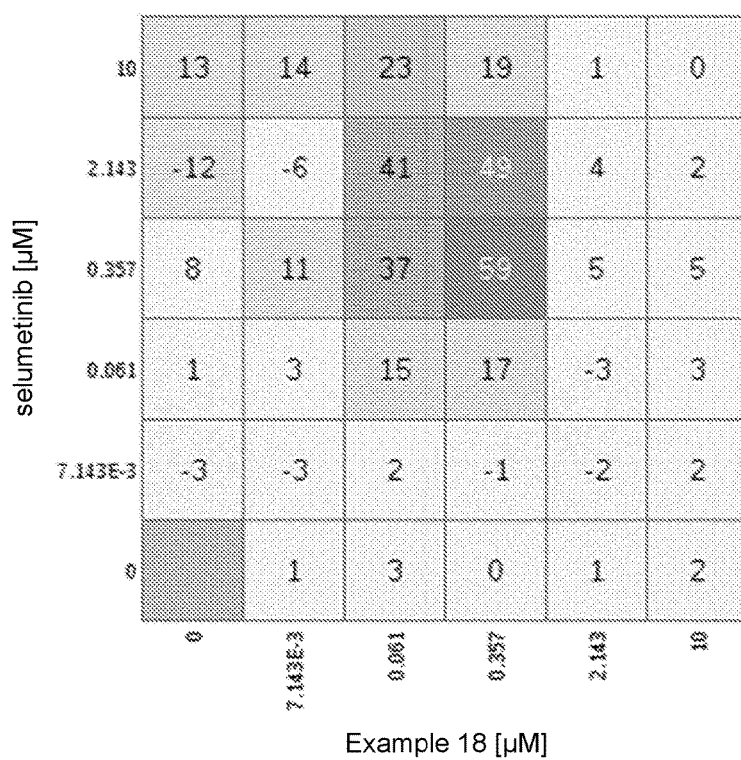
FIG. 11: Cell Growth Inhibition in KRAS-mutant Non-Small Cell Lung Cancer (NSCLC) H2122 cell line by Example 18 in combination with selumetinib (ARRY-142886). Excess heatmap (synergy) calculated by subtracting the Loewe model of additivity data from the fitted data.
Figure 12:
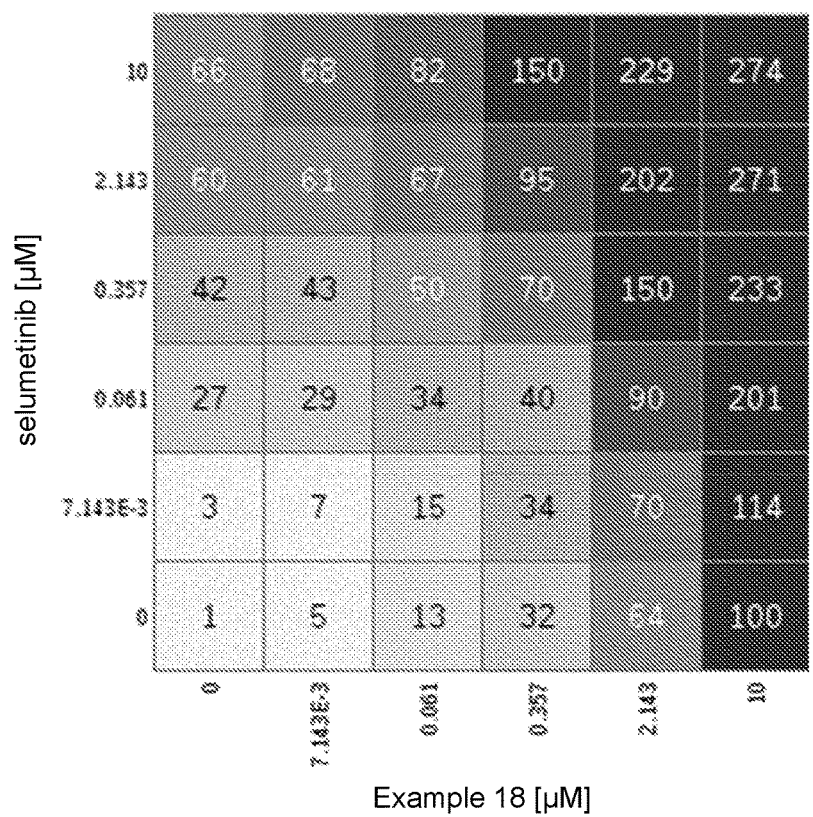
FIG. 12: Cell Growth Inhibition in KRAS-mutant Non-Small Cell Lung Cancer (NSCLC) H2009 cell line by Example 18 in combination with selumetinib (ARRY-142886). Dose matrix representing percent growth inhibition values taken from the fitted dose response curves.
Figure 13:
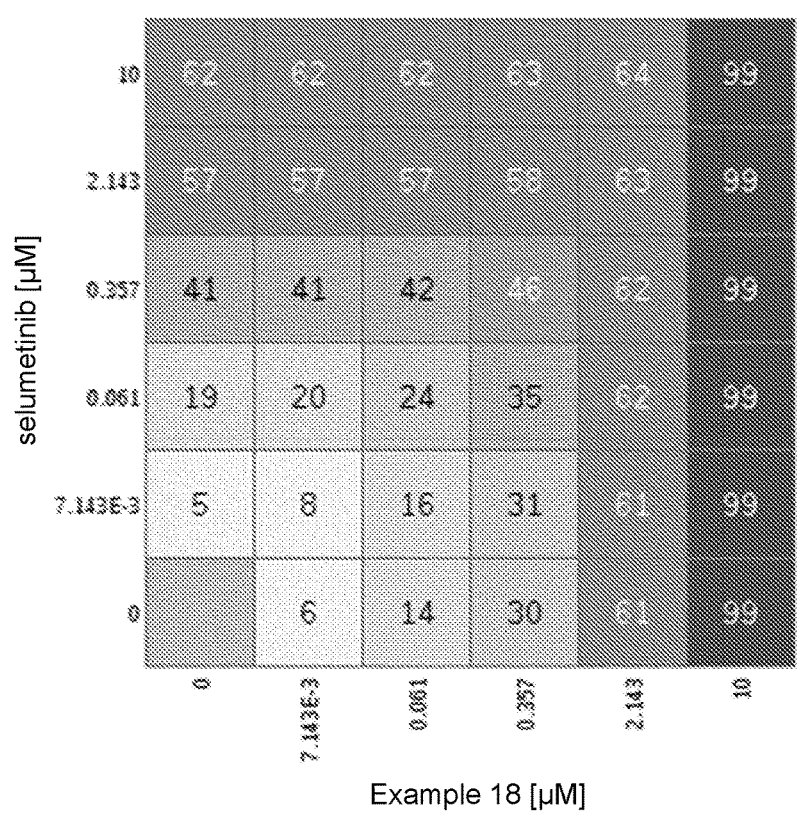
FIG. 13: Cell Growth Inhibition in KRAS-mutant Non-Small Cell Lung Cancer (NSCLC) H2009 cell line by Example 18 in combination with selumetinib (ARRY-142886). Loewe model of additivity calculated from the monotherapy dose response curves.
Figure 14:
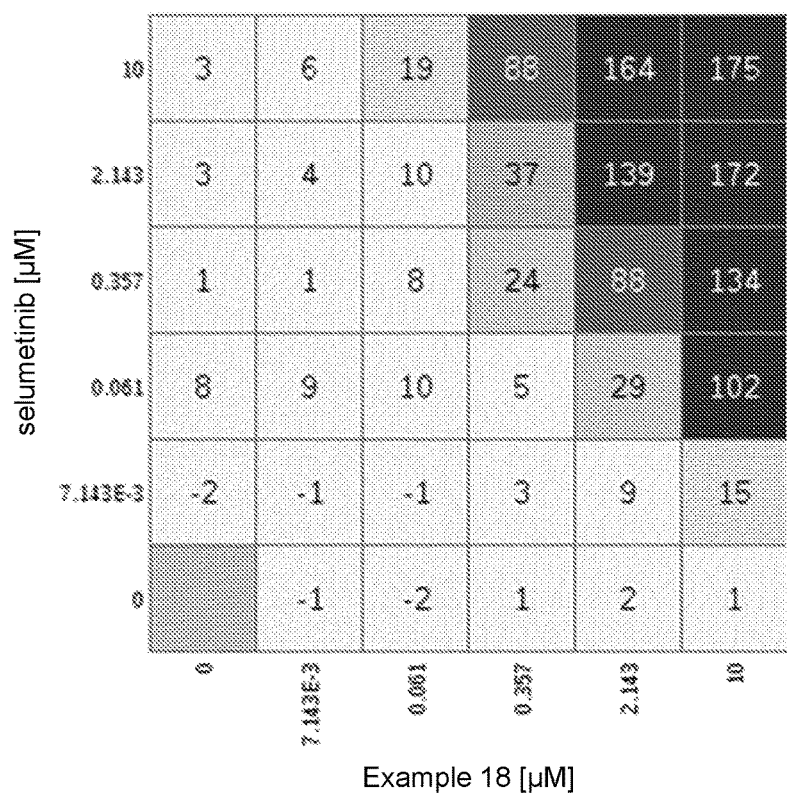
FIG. 14: Cell Growth Inhibition in KRAS-mutant Non-Small Cell Lung Cancer (NSCLC) H2009 cell line by Example 18 in combination with selumetinib (ARRY-142886). Excess heatmap (synergy) calculated by subtracting the Loewe model of additivity data from the fitted data.
Figure 15:
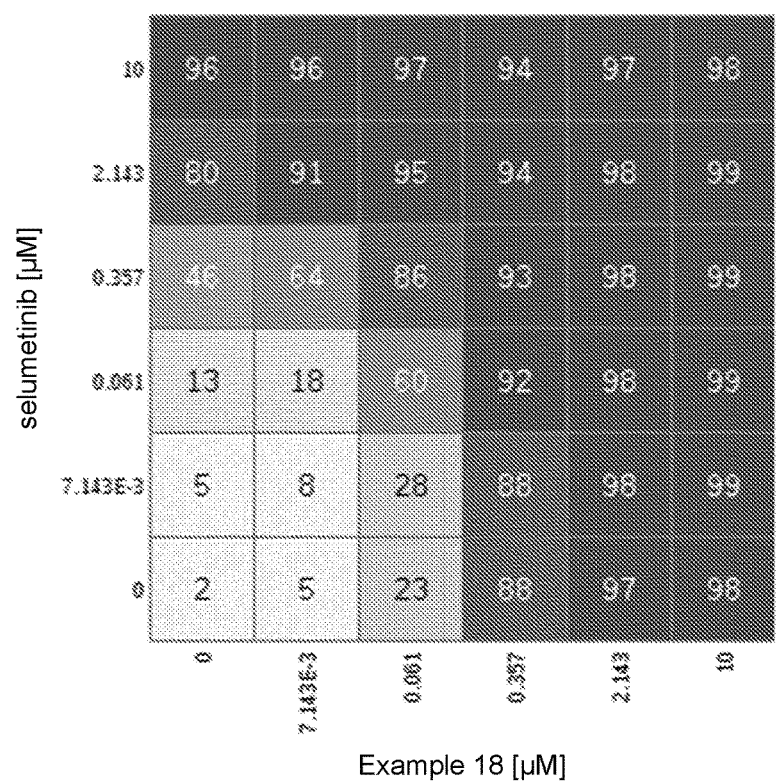
FIG. 15: Cell Growth Inhibition in KRAS-mutant Non-Small Cell Lung Cancer (NSCLC) Calu6 cell line by Example 18 in combination with selumetinib (ARRY-142886). Dose matrix representing percent growth inhibition values taken from the fitted dose response curves.
Figure 16:
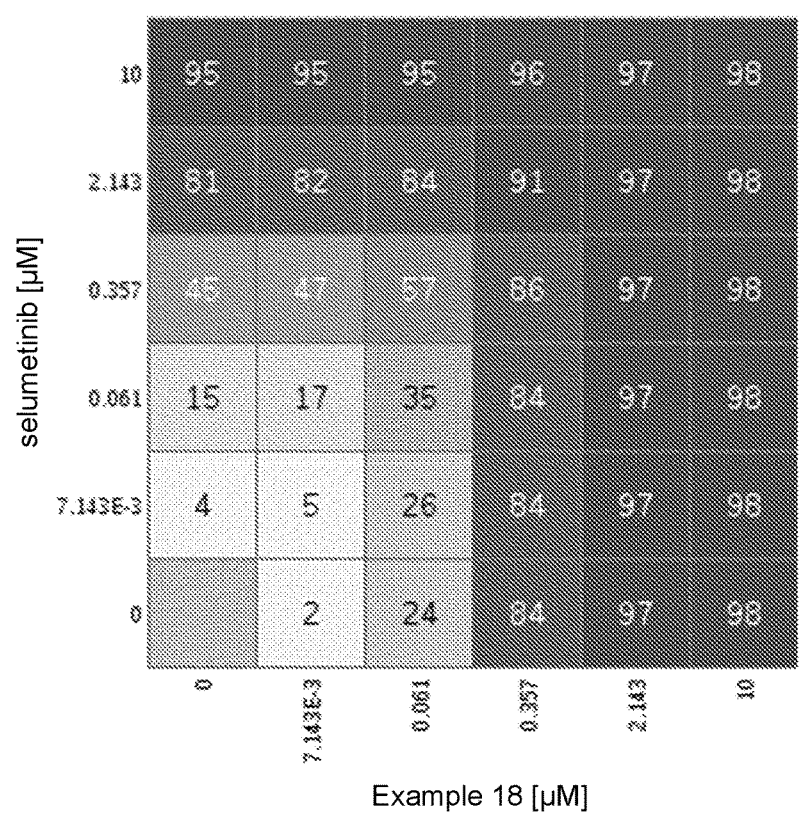
FIG. 16: Cell Growth Inhibition in KRAS-mutant Non-Small Cell Lung Cancer (NSCLC) Calu6 cell line by Example 18 in combination with selumetinib (ARRY-142886). Loewe model of additivity calculated from the monotherapy dose response curves.
Figure 17:
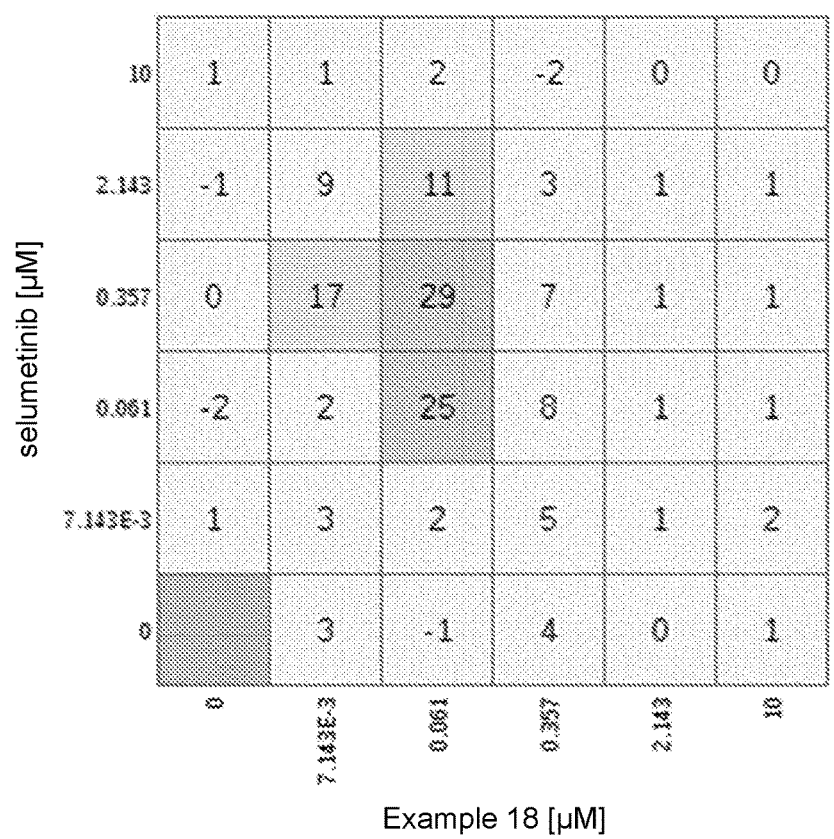
FIG. 17: Cell Growth Inhibition in KRAS-mutant Non-Small Cell Lung Cancer (NSCLC) Calu6 cell line by Example 18 in combination with selumetinib (ARRY-142886). Excess heatmap (synergy) calculated by subtracting the Loewe model of additivity data from the fitted data.

•0.5 adipic acid 50 mg of (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (Example 18) was dissolved in approximately 0.5 mL of methanol. A heat gun was used to aid dissolution. 16 mg of adipic acid was dissolved in approximately 0.5 ml of methanol. A heat gun was used to aid dissolution. The (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one solution was then slowly added to the adipic acid solution. This remained as a solution. A magnetic stirrer bar was added and the solution allowed to stir at ambient temperature. A precipitate was seen after approximately 15 minutes. Further volumes of methanol were added until a free flowing precipitate was achieved and the precipitate was allowed to stir overnight. The precipitate was then filtered to afford (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one adipic acid adduct (Example 34), Form 1, in a 1:2 molar ratio of adipic acid:(R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one as determined by $^1$H NMR. $^1$H NMR (500 MHz, Methanol-d$_4$, 27° C.) δ 8.24 (1H, s), 7.82 (1H, s), 7.41 (1H, d), 7.35 (1H, ddd), 7.28-7.20 (3H, m), 6.31 (1H, d), 5.18 (1H, d), 4.52-4.39 (3H, m), 4.03-4.00 (1H, m), 3.73 (3H, s), 3.46-3.43 (1H, m), 3.39-3.35 (1H, m), 3.23 (3H, s), 2.53 (3H, s), 2.30 (2H, m), 1.63 (2H, m), exchangebale carboxylic acid protons not observed. The sample was analysed by XRPD (see FIG. 3) and DSC (see FIG. 4). (R)-7-(3,4-Difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one adipic acid adduct Form 1 was determined to be crystalline by XRPD and had a melting point of 185.4° C. (onset).

Example 35

Preparation of the Ethanesulfonic acid adduct of (S)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one

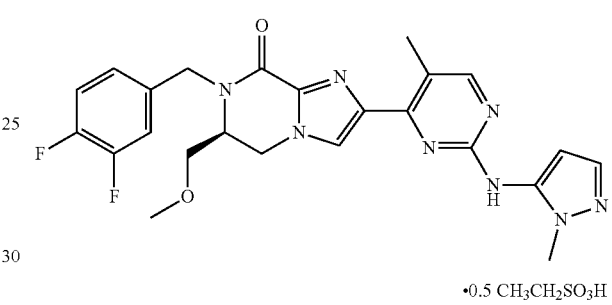

•0.5 CH$_3$CH$_2$SO$_3$H (S)-2-(2-chloro-5-methylpyrimidin-4-yl)-7-(3,4-difluorobenzyl)-6-(methoxymethyl)-6,7-dihydroimidazo[1,2-a]pyrazin-8(5H)-one (Intermediate 35a; 2.2 g, 5.07 mmol), 1-methyl-1H-pyrazol-5-amine (0.754 g, 7.61 mmol) and cesium carbonate (3.30 g, 10.14 mmol) were dissolved in 2-MeTHF (25 mL) and water (2.5 mL) and degassed with nitrogen. 2'-(dicyclohexylphosphanyl)-N,N-dimethyl-[1,1'-biphenyl]-2-amine (0.160 g, 0.41 mmol) and Pd$_2$dba$_3$ (0.186 g, 0.20 mmol) were added and the mixture further degassed with nitrogen. The reaction was then heated at 80° C. for 24 hours. The reaction was cooled to ambient temperature and further 2'-(dicyclohexylphosphanyl)-N,N-dimethyl-[1,1'-biphenyl]-2-amine (0.160 g, 0.41 mmol) and Pd$_2$dba$_3$ (0.186 g, 0.20 mmol) were added and the reaction degassed with nitrogen. The reaction was then stirred at 80° C. for 16 hours. Silicycle (1.2 g, SiliaMetS Thiol) was added and the reaction cooled to ambient temperature. The reaction mixture was filtered through celite washing with EtOAc. The reaction was extracted with ethyl acetate, washed with aqueous citric acid (0.5 M) and saturated sodium bicarbonate. The volatiles were then removed under reduced pressure. Purification by preparative supercritical fluid chromatography (Kromasil DIOL column, 250 mm×50 mm, 10 um, mobile phase 25% EtOH/NH$_3$ 100/0.5 in CO$_2$, 140 bar) afforded (S)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (1.38 g) which was used without further purification in the next stage. (S)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (1.3 g, 1.93 mmol) from the previous step was dissolved in acetonitrile (2 mL) and heated to 66° C. Ethanesulfonic acid (0.22 mL, 2.63 mmol) in acetonitrile (2 mL) was then added. The reaction was then stirred at ambient temperature for 1 hour. A precipitate was observed. Further acetonitrile (3 mL) was added and the precipitate filtered, washed with acetonitrile (3 mL) and dried under vacuum for 66 hours to afford the ethanesulfonic adduct of (S)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (0.41 g). The filtrate was evaporated under reduced pressure and acetonitrile (3 mL) and MTBE (2 mL) were added. The resulting precipitate was filtered and dried under vacuum to afford further ethanesulfonic adduct of (S)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (0.73 g). The 2 batches were combined to afford the ethanesulfonic acid adduct of (S)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (Example 35; 1.14 g, 72%) in a 1:2 molar ratio of ethane suflonic acid:(S)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one as determined by ¹H NMR. ¹H NMR (500 MHz, DMSO, 27° C.) 1.08 (1.5H, t), 2.42 (1H, q), 2.52 (3H, m), 3.18 (3H, s), 3.32 (1H, dd), 3.41 (1H, dd), 3.73 (3H, s), 4.05 (1H, dtd), 4.39 (1H, d), 4.43-4.56 (2H, m), 5.09 (1H, d), 6.38 (1H, d), 7.19-7.32 (1H, m), 7.38-7.45 (2H, m), 7.48 (1H, ddd), 7.98 (1H, s), 8.36 (1H, d), 9.38 (1H, s). m/z (ES+) [M+H]+ 495.

Intermediate 35a (S)-2-(2-Chloro-5-methylpyrimidin-4-yl)-7-(3,4-difluorobenzyl)-6-(methoxymethyl)-6,7-dihydroimidazo[1,2-a]pyrazin-8(5H)-one

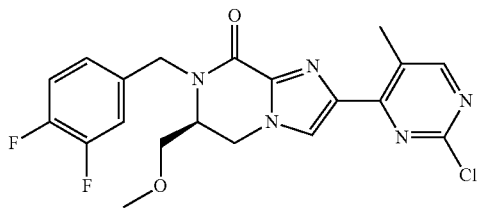

(S)-2-(2-chloro-5-methylpyrimidin-4-yl)-6-(methoxymethyl)-6,7-dihydroimidazo[1,2-a]pyrazin-8(5H)-one (Intermediate 35b; 1.8 g, 5.85 mmol) and Cs₂CO₃ (2.67 g, 8.19 mmol) were slurried in acetronitrile (20 mL) and heated to 70° C. under nitrogen. 4-(bromomethyl)-1,2-difluorobenzene (1.48 g, 7.02 mmol) in acetonitrile (3 mL) was added via syringe to the slurry and the reaction was stirred at 70° C. for 23 hours. The volatiles were then removed under reduced pressure and ethyl acetate (30 mL) and then water (20 mL) was added to the residue. The phases were separated the aqueous phase was extracted with ethyl acetate (2×20 mL). The organic phases were combined and the volatiles removed under reduced pressure. The resulting solid was suspended in heptane/MTBE (4:1, 30 mL) and stirred at 50° C. for 2 hours. The solid was filtered off and dried under reduced pressure to afford (S)-2-(2-chloro-5-methylpyrimidin-4-yl)-7-(3,4-difluorobenzyl)-6-(methoxymethyl)-6,7-dihydroimidazo[1,2-a]pyrazin-8(5H)-one (Intermediate 35a; 2.36 g, 93%) as a solid. ¹H NMR (400 MHz, CDCl₃, 25° C.) δ 2.77 (3H, s), 3.28 (4H, s), 3.38 (1H, dd), 3.81 (1H, m), 4.22 (2H, m), 4.41 (1H, dd), 5.37 (1H, d), 7.10-7.26 (3H, m), 7.94 (1H, s), 8.42 (1H, s). m/z (ES+), [M+H]+=434.

Intermediate 35b (S)-2-(2-chloro-5-methylpyrimidin-4-yl)-6-(methoxymethyl)-6,7-dihydroimidazo[1,2-a]pyrazin-8(5H)-one

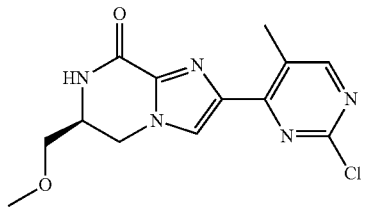 [SMILES: COC[C@@H]1Cn2cc(-c3nc(Cl)ncc3C)nc2C(=O)N1]

Ethyl 4-(2-chloro-5-methylpyrimidin-4-yl)-1H-imidazole-2-carboxylate (Intermediate 23; 2 g, 7.42 mmol) and K₂CO₃ (1.23 g, 8.91 mmol) were suspended in 1,4-dioxane (20 mL) and acetone (20 mL). tert-Butyl (R)-4-(methoxymethyl)-1,2,3-oxathiazolidine-3-carboxylate 2,2-dioxide (Intermediate 35c; 2.18 g, 8.17 mmol) in acetone (15 mL) was added at ambient temperature for 3 days. The mixture was filtered through celite and the solids rinsed with acetone (15 mL). The filtrate was then concentrated to a total volume of (10 mL). A solution of HCl (5M in isopropanol, 10.39 mL) was added and the reaction stirred at ambient temperature for 16 hours. Triethylamine (10.33 mL, 74.24 mmol) was added slowly followed by isopropanol (15 mL) to afford a suspension. The reaction was then heated at 50° C. for 3 hours. Water (40 mL) was added which resulted in a fine suspension. The suspension was stirred at 50° C. for 30 minutes and then at ambient temperature for 16 hours. The precipitate was then filtered, and washed with 50% acetone in water (2×25 mL) and dried under reduced pressure at 40° C. for 4 days to afford (S)-2-(2-chloro-5-methylpyrimidin-4-yl)-6-(methoxymethyl)-6,7-dihydroimidazo[1,2-a]pyrazin-8(5H)-one (Intermediate 35b; 1.95 g, 85%) as a solid. ¹H NMR (400 MHz, DMSO, 20° C.) δ 2.61 (s, 3H), 3.26 (s, 3H), 3.33-3.45 (m, 2H), 3.99 (br s, 1H), 4.30 (dd, 1H), 4.44 (dd, 1H), 8.26 (s, 1H), 8.42 (d, 1H), 8.58 (s, 1H). m/z (ES+), [M+H]+=308. Intermediate 35c is made in an analogous manner to Intermediate 57 starting from (S)-tert-butyl (1-hydroxy-3-methoxypropan-2-yl)carbamate Intermediate 35c tert-Butyl (R)-4-(methoxymethyl)-1,2,3-oxathiazolidine-3-carboxylate 2,2-dioxide

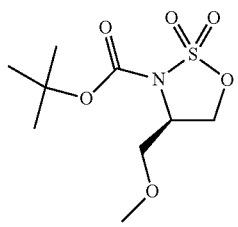 [SMILES: COC[C@@H]1COS(=O)(=O)N1C(=O)OC(C)(C)C]

¹H NMR (400 MHz, MeOD) δ 1.54 (s, 9H), 3.40 (s, 3H), 3.61 (d, 2H), 4.46 (qd, 1H), 4.60 (dd, 1H), 4.68 (dd, 1H). m/z: ES+[M+H]+ 268.

Example 36

(R)-6-Methyl-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one

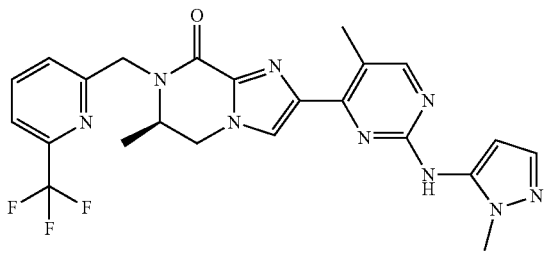

(R)-2-(2-Chloro-5-methylpyrimidin-4-yl)-6-methyl-7-((6-(trifluoromethyl)pyridin-2-yl)methyl)-6,7-dihydroimidazo[1,2-a]pyrazin-8(5H)-one (Intermediate 91; 187 mg, 0.43 mmol), 1-methyl-1H-pyrazol-5-amine (104 mg, 1.07 mmol), Cs₂CO₃ (279 mg, 0.86 mmol) and 2nd Generation XantPhos precatalyst (38.0 mg, 0.04 mmol) in 1,4-dioxane (5 mL) was stirred under an atmosphere of nitrogen at 110° C. for 16 hours. The solvent was removed by distillation under vacuum. The crude product was purified by flash silica chromatography, elution gradient 3 to 5% MeOH in DCM. The product was further purified by preparative HPLC (XSelect CSH Prep C18 OBD column, 5µ silica, 19 mm diameter, 150 mm length), using decreasingly polar mixtures of water (containing 0.01% NH₄HCO₃) and MeCN as eluents. Fractions containing the desired compound were evaporated to dryness to afford (R)-6-methyl-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one (112 mg, 52.6%) as a white solid. ¹H NMR (400 MHz, DMSO, 20.9° C.) δ 1.22 (3H, d), 2.52 (3H, s), 3.35 (1H, s), 3.71 (3H, s), 4.13 (1H, ddd), 4.40 (1H, dd), 4.51-4.63 (2H, m), 5.22 (1H, d), 6.31 (1H, d), 7.34 (1H, d), 7.78 (1H, d), 7.84 (1H, d), 7.97 (1H, s), 8.10 (1H, t), 8.33 (1H, d), 9.24 (1H, s). m/z (ES+), [M+H]+=498.

Intermediate 92

(R)-2-(2-chloro-5-methylpyrimidin-4-yl)-6-methyl-7-((6-(trifluoromethyl)pyridin-2-yl)methyl)-6,7-dihydroimidazo[1,2-a]pyrazin-8(5H)-one

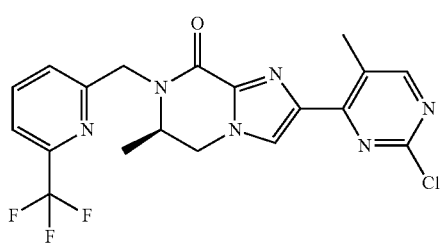 [SMILES: Cc1cnc(Cl)nc1-c1cn2c(n1)C(=O)N(Cc1cccc(C(F)(F)F)n1)[C@H](C)C2]

6-(Trifluoromethyl)picolinaldehyde (126 mg, 0.72 mmol) was added to (R)-ethyl 1-(2-aminopropyl)-4-(2-chloro-5-methylpyrimidin-4-yl)-1H-imidazole-2-carboxylate dihydrochloride (Intermediate 93; 260 mg, 0.66 mmol), DIPEA (0.343 mL, 1.97 mmol) and AcOH (0.113 mL, 1.97 mmol) in DCM (10 mL) at 25° C. under nitrogen. The resulting solution was stirred at 25° C. for 20 minutes. Sodium triacetoxyborohydride (417 mg, 1.97 mmol) was added to the reaction mixture and the resulting solution was stirred at 25° C. for 1 hour and then at 50° C. for 12 hours. The reaction mixture was poured into water (10 mL), extracted with DCM (3×15 mL), the organic layer was dried over Na₂SO₄, filtered and evaporated to afford a yellow oil. The crude product was purified by flash silica chromatography, elution gradient 3 to 4% MeOH in DCM. Pure fractions were evaporated to dryness to afford (R)-2-(2-chloro-5-methylpyrimidin-4-yl)-6-methyl-7-((6-(trifluoromethyl)pyridin-2-yl)methyl)-6,7-dihydroimidazo[1,2-a]pyrazin-8(5H)-one (Intermediate 92; 187 mg, 65.3%) as a colourless oil. m/z (ES+), [M+H]+=437.

Intermediate 93

(R)-Ethyl 1-(2-aminopropyl)-4-(2-chloro-5-methylpyrimidin-4-yl)-1H-imidazole-2-carboxylate dihydrochloride

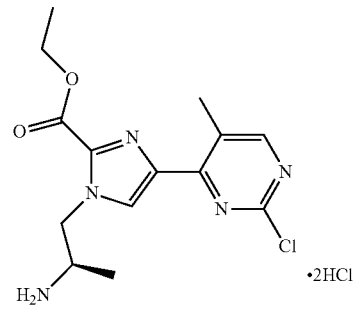 [SMILES: CCOC(=O)c1nc(-c2nc(Cl)ncc2C)cn1C[C@@H](C)N]

Intermediate 93 was prepared in an analogous manner to Intermediate 65, using (R)-tert-butyl 4-methyl-1,2,3-oxathiazolidine-3-carboxylate 2,2-dioxide. Intermediate 93 exhibited the following analytical data. ¹H NMR (400 MHz, DMSO, 22° C.) δ 1.27 (3H, d), 1.36 (3H, t), 2.64 (3H, s), 3.57 (3H, s), 3.74 (1H, s), 4.33-4.44 (2H, m), 4.58-4.75 (2H, m), 8.33 (3H, s), 8.47 (1H, s), 8.64 (1H, s). m/z (ES+), [M+H]+=324.

Example 37

(R)-7-((6-(Difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one

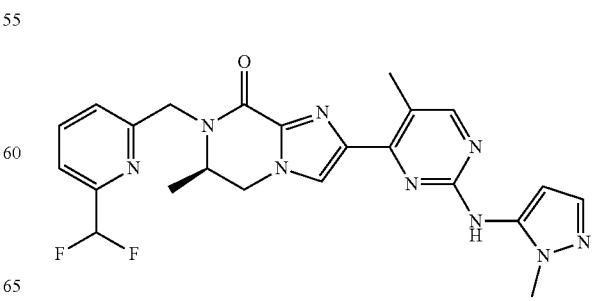

3rd Generation BrettPhos precatalyst (60.6 mg, 0.07 mmol) was added to (R)-2-(2-chloro-5-methylpyrimidin-4-yl)-7-((6-(difluoromethyl)pyridin-2-yl)methyl)-6-methyl-6,7-dihydroimidazo[1,2-a]pyrazin-8(5H)-one (Intermediate 94; 280 mg, 0.67 mmol), 1-methyl-1H-pyrazol-5-amine (162 mg, 1.67 mmol) and Cs₂CO₃ (436 mg, 1.34 mmol) in 1,4-dioxane (10 mL) at 25° C. under nitrogen. The resulting mixture was stirred at 100° C. for 8 hours. The solvent was then removed under reduced pressure. The crude product was purified by flash silica chromatography, elution gradient 0 to 6% MeOH in DCM. Pure fractions were evaporated to dryness to afford a yellow residue. The residue was further purified by preparative HPLC (XSelect CSH Prep C18 OBD column, 5µ silica, 19 mm diameter, 150 mm length), using decreasingly polar mixtures of water (containing 0.03% NH₃) and MeCN as eluents. Fractions containing the desired compound were evaporated to dryness to afford (R)-7-((6-(difluoromethyl)pyridin-2-yl)methyl)-6-methyl-2-(5-methyl-2-((1-methyl-1H-pyrazol-5-yl)amino)pyrimidin-4-yl)-6,7-dihydroimidazo[1,2-a]pyrazin-8(5H)-one (Example 37; 119 mg, 37.1%) as a solid. ¹H NMR (400 MHz, DMSO, 20° C.) δ 1.20 (3H, d), 2.51 (3H, s), 3.70 (3H, s), 4.10 (1H, d), 4.34-4.43 (1H, m), 4.47-4.61 (2H, m), 5.21 (1H, d), 6.30 (1H, d), 6.97 (1H, t), 7.34 (1H, d), 7.59-7.66 (2H, m), 7.94-8.04 (2H, m), 8.33 (1H, s), 9.23 (1H, s). m/z (ES+) [M+H]+ 480.

Intermediate 94

(R)-2-(2-Chloro-5-methylpyrimidin-4-yl)-7-((6-(difluoromethyl)pyridin-2-yl)methyl)-6-methyl-6,7-dihydroimidazo[1,2-a]pyrazin-8(5H)-one

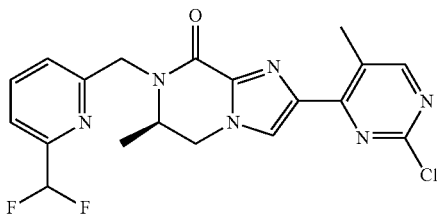 [SMILES: Cc1cnc(Cl)nc1-c1cn2c(n1)C(=O)N(Cc1cccc(C(F)F)n1)[C@H](C)C2]

6-(Difluoromethyl)picolinaldehyde (214 mg, 1.36 mmol) was added to (R)-ethyl 1-(2-aminopropyl)-4-(2-chloro-5-methylpyrimidin-4-yl)-1H-imidazole-2-carboxylate dihydrochloride (Intermediate 93; 270 mg, 0.68 mmol), DIPEA (0.357 mL, 2.04 mmol) and AcOH (0.117 mL, 2.04 mmol) in DCM (10 mL) at 25° C. under nitrogen. After stirring at 25° C. for 1 hour, sodium triacetoxyborohydride (433 mg, 2.04 mmol) was added and the resulting mixture was stirred at 25° C. for 1 hour and heated at 50° C. for 5 hours. The reaction mixture was quenched with saturated NaHCO₃ (20 mL) and extracted with DCM (2×75 mL). The organic layer was dried over Na₂SO₄, filtered and evaporated to afford a yellow residue. The crude product was purified by flash silica chromatography, elution gradient 0 to 5% MeOH in DCM. Pure fractions were evaporated to dryness to afford (R)-2-(2-chloro-5-methylpyrimidin-4-yl)-7-((6-(difluoromethyl)pyridin-2-yl)methyl)-6-methyl-6,7-dihydroimidazo[1,2-a]pyrazin-8(5H)-one (Intermediate 94; 280 mg, 98%) as a yellow solid. ¹H NMR (400 MHz, DMSO, 20° C.) δ 1.21 (3H, d), 2.64 (3H, d), 4.09-4.16 (1H, m), 4.35 (1H, dd), 4.49-4.64 (2H, m), 5.22 (1H, d), 6.82-7.12 (1H, m), 7.60-7.68 (2H, m), 7.95-8.05 (1H, m), 8.30 (1H, s), 8.61 (1H, s). m/z (ES+) [M+H]+ 419.

Example 38

(R)-7-(3-(Difluoromethyl)benzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one

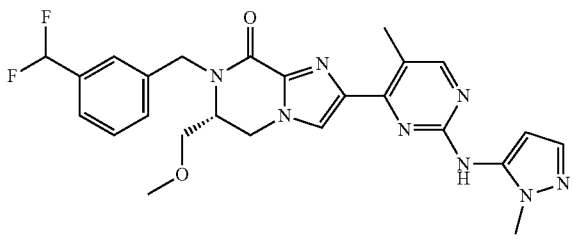 [SMILES: COC[C@H]1Cn2cc(-c3nc(Nc4ccnn4C)ncc3C)nc2C(=O)N1Cc1cccc(C(F)F)c1]

(R)-2-(2-Chloro-5-methylpyrimidin-4-yl)-7-(3-(difluoromethyl)benzyl)-6-(methoxymethyl)-6,7-dihydroimidazo[1,2-a]pyrazin-8(5H)-one (Intermediate 95; 288 mg, 0.64 mmol), 1-methyl-1H-pyrazol-5-amine (68.7 mg, 0.71 mmol), cesium carbonate (419 mg, 1.29 mmol) and BrettPhos 3rd generation pre-catalyst (29.1 mg, 0.03 mmol) were suspended in tert-butanol (6 mL) and de-gassed for 10 minutes. The reaction was heated to 80° C. for 18 hours under nitrogen. The reaction was then diluted with ethyl acetate (75 mL) and washed with saturated aqueous sodium bicarbonate (25 mL), dried (sodium sulfate) and concentrated in vacuo to give a brown gum. The crude product was purified by preparative HPLC (Waters XBridge Prep C18 OBD column, 5µ silica, 30 mm diameter, 100 mm length), using decreasingly polar mixtures of water (containing 1% NH₃) and MeCN as eluents. Fractions containing the desired compound were evaporated to dryness to afford (R)-7-(3-(difluoromethyl)benzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (Example 38; 88 mg, 26.9%) as a white solid. ¹H NMR (500 MHz, DMSO, 30° C.) 2.53 (2H, s), 3.19 (1H, d), 3.33 (3H, d), 3.40 (1H, dd), 3.71 (3H, d), 4.03 (1H, q), 4.09 (1H, q), 4.4-4.57 (3H, m), 5.17 (1H, d), 6.31 (1H, d), 7.05 (1H, t), 7.34 (1H, d), 7.5-7.56 (2H, m), 7.56-7.63 (2H, m), 7.95 (1H, s), 8.33 (1H, s), 9.20 (1H, s). m/z ES+[M+H]+ 509.

Intermediate 95

(R)-2-(2-Chloro-5-methylpyrimidin-4-yl)-7-(3-(difluoromethyl)benzyl)-6-(methoxymethyl)-6,7-dihydroimidazo[1,2-a]pyrazin-8(5H)-one

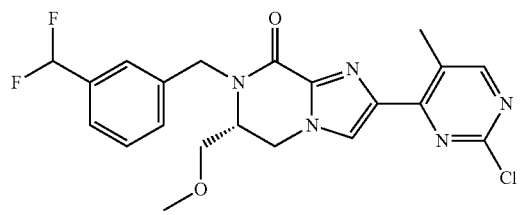 [SMILES: COC[C@H]1Cn2cc(-c3nc(Cl)ncc3C)nc2C(=O)N1Cc1cccc(C(F)F)c1]

Sodium hydride (60% dispersion) (28.6 mg, 0.71 mmol) was added to (R)-2-(2-chloro-5-methylpyrimidin-4-yl)-6-(methoxymethyl)-6,7-dihydroimidazo[1,2-a]pyrazin-8(5H)- one (Intermediate 61; 200 mg, 0.65 mmol) in DMF (15 mL) under nitrogen. The resulting suspension was stirred at 20° C. for 30 minutes. 1-(Chloromethyl)-3-(difluoromethyl)benzene (126 mg, 0.71 mmol) was added followed by tetrabutylammonium iodide (24.01 mg, 0.06 mmol) and the resulting solution stirred at 20° C. for 18 hours. It was diluted with saturated aqueous ammonium chloride (30 mL) and extracted with ethyl acetate (2×70 mL). The combined organics were dried (sodium sulfate) and concentrated in vacuo to give (R)-2-(2-chloro-5-methylpyrimidin-4-yl)-7-(3-(difluoromethyl)benzyl)-6-(methoxymethyl)-6,7-dihydroimidazo[1,2-a]pyrazin-8(5H)-one (Intermediate 95; 321 mg, >100%) as a gum which was used in the next step without further purification. $^1$H NMR (400 MHz, DMSO, 30° C.) 2.64 (3H, s), 3.17 (3H, s), 3.40 (2H, dd), 3.99-4.11 (1H, m), 4.4-4.59 (3H, m), 5.15 (1H, d), 7.03 (1H, t), 7.5-7.53 (2H, m), 7.59 (1H, d), 7.96 (1H, s), 8.25 (1H, s), 8.59 (1H, s). m/z ES+[M+H]+ 448.

Example 39

(R)-6-(Methoxymethyl)-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one

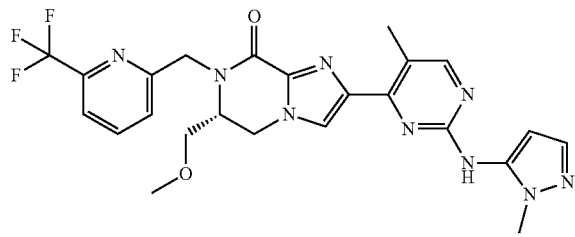 [SMILES: COC[C@H]1Cn2cc(-c3nc(Nc4ccnn4C)ncc3C)nc2C(=O)N1Cc1cccc(C(F)(F)F)n1]

(R)-2-(2-Chloro-5-methylpyrimidin-4-yl)-6-(methoxymethyl)-7-((6-(trifluoromethyl)pyridin-2-yl)methyl)-6,7-dihydroimidazo[1,2-a]pyrazin-8(5H)-one (Intermediate 96; 201 mg, 0.43 mmol), 1-methyl-1H-pyrazol-5-amine (46.0 mg, 0.47 mmol), cesium carbonate (281 mg, 0.86 mmol) and BrettPhos 3rd generation pre-catalyst (19.51 mg, 0.02 mmol) were suspended in tert-butanol (5 mL) and de-gassed for 10 minutes. The reaction was heated to 80° C. for 18 hours under nitrogen. The reaction was then diluted with ethyl acetate (75 mL) and washed with saturated aqueous sodium bicarbonate (25 mL), dried (sodium sulfate) and concentrated in vacuo to give a brown gum. The crude product was purified by preparative HPLC (Waters XBridge Prep C18 OBD column, 5μ silica, 30 mm diameter, 100 mm length), using decreasingly polar mixtures of water (containing 1% NH$_3$) and MeCN as eluents. Fractions containing the desired compound were evaporated to dryness to afford (R)-6-(methoxymethyl)-2-(5-methyl-2-((1-methyl-1H-pyrazol-5-yl)amino)pyrimidin-4-yl)-7-((6-(trifluoromethyl)pyridin-2-yl)methyl)-6,7-dihydroimidazo[1,2-a]pyrazin-8(5H)-one (Example 39; 68 mg, 29.9%) as a solid. $^1$H NMR (500 MHz, DMSO, 30° C.) 3.18 (1H, d), 3.20 (3H, d), 3.32 (3H, s), 3.39 (1H, dd), 3.54 (1H, dd), 3.71 (3H, d), 4.51-4.63 (2H, m), 4.66 (1H, d), 5.24 (1H, d), 6.31 (1H, d), 7.34 (1H, dd), 7.78 (1H, d), 7.83 (1H, d), 7.98 (1H, s), 8.09 (1H, t), 8.33 (1H, s), 9.20 (1H, s). m/z ES+[M+H]+ 528.

Intermediate 96

(R)-2-(2-chloro-5-methylpyrimidin-4-yl)-6-(methoxymethyl)-7-((6-(trifluoromethyl)pyridin-2-yl)methyl)-6,7-dihydroimidazo[1,2-a]pyrazin-8(5H)-one

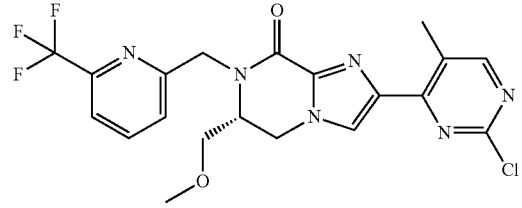 [SMILES: COC[C@H]1Cn2cc(-c3nc(Cl)ncc3C)nc2C(=O)N1Cc1cccc(C(F)(F)F)n1]

Sodium hydride (60% dispersion) (19.16 mg, 0.48 mmol) was added to (R)-2-(2-chloro-5-methylpyrimidin-4-yl)-6-(methoxymethyl)-6,7-dihydroimidazo[1,2-a]pyrazin-8(5H)-one (Intermediate 61; 134 mg, 0.44 mmol) in DMF (10 mL) under nitrogen. The resulting suspension was stirred at 20° C. for 30 minutes. 2-(Bromomethyl)-6-(trifluoromethyl)pyridine (115 mg, 0.48 mmol) was added and the resulting solution stirred at 20° C. for 18 hours. The reaction was quenched with saturated aqueous ammonium chloride (30 mL) and extracted with ethyl acetate (2×70 mL). The combined organics were dried (sodium sulfate) and concentrated in vacuo to give (R)-2-(2-chloro-5-methylpyrimidin-4-yl)-6-(methoxymethyl)-7-((6-(trifluoromethyl)pyridin-2-yl)methyl)-6,7-dihydroimidazo[1,2-a]pyrazin-8(5H)-one (Intermediate 96; 203 mg, 100%) as a gum. $^1$H NMR (400 MHz, DMSO, 30° C.) 2.63 (3H, s), 3.20 (3H, s), 3.37-3.42 (1H, m), 3.54 (1H, dd), 4.20 (1H, dt), 4.56 (2H, d), 4.67 (1H, d), 5.23 (1H, d), 7.80 (2H, dd), 8.09 (1H, t), 8.29 (1H, s), 8.59 (1H, d). m/z ES+[M+H]+ 467.

Example 40

(R)-7-(3,5-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one

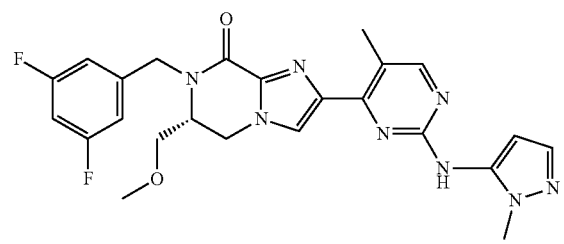 [SMILES: COC[C@H]1Cn2cc(-c3nc(Nc4ccnn4C)ncc3C)nc2C(=O)N1Cc1cc(F)cc(F)c1]

(R)-2-(2-Chloro-5-methylpyrimidin-4-yl)-7-(3,5-difluorobenzyl)-6-(methoxymethyl)-6,7-dihydroimidazo[1,2-a]pyrazin-8(5H)-one (Intermediate 97; 280 mg, 0.65 mmol), 1-methyl-1H-pyrazol-5-amine (68.9 mg, 0.71 mmol), cesium carbonate (421 mg, 1.29 mmol) and BrettPhos 3rd generation pre-catalyst (29.3 mg, 0.03 mmol) were suspended in tert-butanol (6 mL) and de-gassed for 10 minutes. The reaction was heated to 80° C. for 18 hours under nitrogen. The reaction mixture was diluted with ethyl acetate (75 mL) and washed with saturated aqueous sodium bicarbonate (25 mL), dried (sodium sulfate) and concentrated in vacuo to give a brown gum. The crude product was purified by preparative HPLC (Waters XBridge Prep C18 OBD column, 5µ silica, 30 mm diameter, 100 mm length), using decreasingly polar mixtures of water (containing 1% NH$_3$) and MeCN as eluents. Fractions containing the desired compound were evaporated to dryness to afford (R)-7-(3,5-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (Example 40; 80 mg, 25.1%) as an off white solid. $^1$H NMR (500 MHz, DMSO, 30° C.) 2.52 (3H, s), 3.19 (1H, s), 3.19 (3H, s), 3.35 (1H, dd), 3.43 (1H, dd), 3.71 (3H, s), 4.43 (1H, d), 4.48-4.57 (2H, m), 5.12 (1H, d), 6.30 (1H, d), 7.15 (3H, td), 7.34 (1H, d), 7.94 (1H, s), 8.32 (1H, s), 9.18 (1H, s). m/z ES+[M+H]+ 495.

Intermediate 97 was made in an analagous manner to Intermediate 96, using Intermediate 61 and 1-(bromomethyl)-3,5-difluorobenzene.

Intermediate 97

(R)-2-(2-chloro-5-methylpyrimidin-4-yl)-7-(3,5-difluorobenzyl)-6-(methoxymethyl)-6,7-dihydroimidazo[1,2-a]pyrazin-8(5H)-one

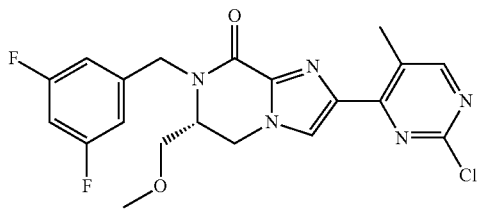 [SMILES: COC[C@H]1Cn2cc(-c3nc(Cl)ncc3C)nc2C(=O)N1Cc1cc(F)cc(F)c1]

$^1$H NMR (400 MHz, DMSO, 30° C.) 2.64 (3H, s), 3.18 (3H, s), 3.44 (2H, dd), 4.08 (1H, dd), 4.4-4.59 (3H, m), 5.10 (1H, d), 7.13 (3H, dt), 8.25 (1H, s), 8.56-8.62 (1H, m). m/z ES+[M+H]+ 434.

Example 41

(R)-7-(3-Methoxybenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one

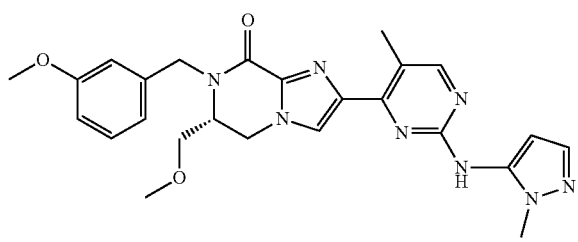 [SMILES: COC[C@H]1Cn2cc(-c3nc(Nc4ccnn4C)ncc3C)nc2C(=O)N1Cc1cccc(OC)c1]

(R)-2-(2-Chloro-5-methylpyrimidin-4-yl)-7-(3-methoxybenzyl)-6-(methoxymethyl)-6,7-dihydroimidazo[1,2-a] pyrazin-8(5H)-one (Intermediate 98; 164 mg, 0.38 mmol), 1-methyl-1H-pyrazol-5-amine (40.9 mg, 0.42 mmol), cesium carbonate (250 mg, 0.77 mmol) and BrettPhos 3rd generation pre-catalyst (17.37 mg, 0.02 mmol) were suspended in tert-butanol (5 mL) and de-gassed for 10 minutes. The reaction was heated to 80° C. for 18 hours under nitrogen. The reaction was diluted with ethyl acetate (75 mL) and washed with saturated aqueous sodium bicarbonate (25 mL), dried (sodium sulfate) and concentrated in vacuo to give a brown gum. The crude product was purified by preparative HPLC (Waters XBridge Prep C18 OBD column, 5µ silica, 30 mm diameter, 100 mm length), using decreasingly polar mixtures of water (containing 1% NH$_3$) and MeCN as eluents. Fractions containing the desired compound were evaporated to dryness to afford (R)-7-(3-methoxybenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (Example 41; 58.0 mg, 31%) as an off white solid. $^1$H NMR (500 MHz, DMSO, 30° C.) 2.53 (3H, s), 3.18 (3H, d), 3.19 (1H, d), 3.38 (1H, dd), 3.70 (3H, s), 3.76 (3H, s), 3.95-4.02 (1H, m), 4.33-4.43 (2H, m), 4.49-4.55 (1H, m), 5.12 (1H, d), 6.30 (1H, d), 6.88 (1H, dd), 6.98 (2H, s), 7.27-7.31 (1H, m), 7.34 (1H, d), 7.93 (1H, s), 8.29-8.36 (1H, m), 9.18 (1H, s). m/z ES+ [M+H]+ 489.

Intermediate 98 was made in an analagous manner to Intermediate 96, using Intermediate 61 and 1-(bromomethyl)-3-methoxybenzene.

Intermediate 98

(R)-2-(2-chloro-5-methylpyrimidin-4-yl)-7-(3-methoxybenzyl)-6-(methoxymethyl)-6,7-dihydroimidazo[1,2-a]pyrazin-8(5H)-one

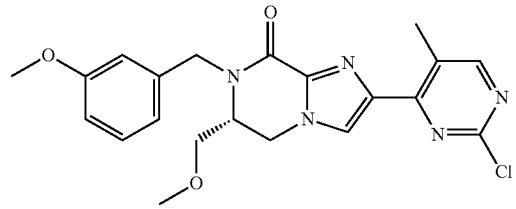 [SMILES: COC[C@H]1Cn2cc(-c3nc(Cl)ncc3C)nc2C(=O)N1Cc1cccc(OC)c1]

$^1$H NMR (400 MHz, DMSO, 30° C.) 2.64 (3H, s), 3.17 (3H, s), 3.37-3.42 (2H, m), 3.76 (3H, s), 3.98 (1H, s), 4.33-4.45 (2H, m), 4.49 (1H, d), 5.04-5.19 (1H, m), 6.88 (1H, d), 6.97 (2H, d), 7.29 (1H, t), 8.24 (1H, s), 8.60 (1H, s). m/z ES+[M+H]+ 428.

The invention claimed is:

1. A method of treating cancer comprising administering to a subject in need thereof an effective amount of (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one, and selumetinib (ARRY-142886).

2. The method of claim 1, wherein the cancer has a KRAS mutation.

3. The method of claim 1, wherein the cancer is non-small cell lung cancer.

* * * * *